(12) United States Patent
Desir et al.

(10) Patent No.: US 10,273,311 B2
(45) Date of Patent: Apr. 30, 2019

(54) COMPOSITIONS TO REGULATE RENALASE IN THE TREATMENT OF DISEASES AND DISORDERS

(71) Applicant: Yale University, New Haven, CT (US)

(72) Inventors: Gary Desir, Woodbridge, CT (US); Abigail Hunt, Alameda, CA (US); Jessica O-Rear, Redwood City, CA (US); Peter Flynn, San Francisco, CA (US)

(73) Assignee: YALE UNIVERSITY, New Haven, CT (US)

( * ) Notice: Subject to any disclaimer, the term of this patent is extended or adjusted under 35 U.S.C. 154(b) by 77 days.

(21) Appl. No.: 15/321,015

(22) PCT Filed: Jun. 26, 2015

(86) PCT No.: PCT/US2015/037971
§ 371 (c)(1),
(2) Date: Dec. 21, 2016

(87) PCT Pub. No.: WO2015/200790
PCT Pub. Date: Dec. 30, 2015

(65) Prior Publication Data
US 2017/0226228 A1    Aug. 10, 2017

Related U.S. Application Data

(60) Provisional application No. 62/017,487, filed on Jun. 26, 2014.

(51) Int. Cl.
*C07K 16/40* (2006.01)
*G01N 33/573* (2006.01)
*A61K 39/395* (2006.01)
*A61K 39/00* (2006.01)

(52) U.S. Cl.
CPC ........ *C07K 16/40* (2013.01); *A61K 39/39558* (2013.01); *C12Y 106/03* (2013.01); *G01N 33/573* (2013.01); *A61K 2039/505* (2013.01); *C07K 2317/34* (2013.01); *C07K 2317/51* (2013.01); *C07K 2317/515* (2013.01); *C07K 2317/565* (2013.01); *C07K 2317/73* (2013.01); *C07K 2317/76* (2013.01); *C07K 2317/92* (2013.01); *G01N 2333/90209* (2013.01)

(58) Field of Classification Search
CPC .................................................... C07K 16/40
See application file for complete search history.

(56) References Cited

U.S. PATENT DOCUMENTS

| 7,700,740 B2 | 4/2010 | Garcia-Martinez et al. |
| 2005/0033031 A1 | 2/2005 | Couto |
| 2009/0022659 A1 | 1/2009 | Olson et al. |
| 2013/0273023 A1 | 10/2013 | Xu et al. |
| 2013/0283461 A1 | 10/2013 | Abad et al. |

FOREIGN PATENT DOCUMENTS

| WO | 2010006214 | 1/2010 |
| WO | 2014/014899 A1 | 1/2014 |

OTHER PUBLICATIONS

Ara et al., 2009, "Interleukin-6 in the bone marrow microenvironment promotes the growth and survival of neuroblastoma cells." Cancer Res. 69(1):329-37.
Armesilla et al., 2004, "Novel Functional Interaction between the Plasma Membrane Ca2+ Pump 4b and the Proapoptotic Tumor Suppressor Ras-associated Factor 1 (RASSF1)." Journal of Biological Chemistry. 279(30):31318-28.
Beaupre et al., 2015, "Metabolic Function for Human Renalase: Oxidation of Isomeric Forms of B-NAD(P)H that Are Inhibitory to Primary Metabolism." Biochemistry. 54(3):795-806.
Cartwright et al., 2007, "Plasma Membrane Calcium ATPase and Its Relationship to Nitric Oxide Signaling in the Heart." Annals of the New York Academy of Sciences. 1099(1):247-53.
Catlett-Falcone et al., 1999, "Constitutive Activation of Stat3 Signaling Confers Resistance to Apoptosis in Human U266 Myeloma Cells." Immunity. 10(1):105-15.
Corcoran et al., 2011, "STAT3 plays a critical role in KRAS-induced pancreatic tumorigenesis." Cancer Res. 71(14):5020-9.
Dankort et al., 2009, "BRAF(V600E) cooperates with Pten silencing to elicit metastatic melanoma." Nature genetics. 41:544-52.
Desir et al., 2012, "Renalase Lowers Ambulatory Blood Pressure by Metabolizing Circulating Adrenaline." J Am Heart Assoc. 1(e):e002634.
Desir et al., 2012, "Human renalase: a review of its biology, function, and implications for hypertension." J Am Soc Hypertens. 6(6):417-26.
Emeagi et al., 2013, "Downregulation of Stat3 in melanoma: reprogramming the immune microenvironment as an anticancer therapeutic strategy." Gene therapy. 20:1085-92.
Farzaneh-Far et al., 2010, "A Functional Polymorphism in Renalase (Glu37Asp) Is Associated with Cardiac Hypertrophy, Dysfunction, and Ischemia: Data from the Heart and Soul Study." PLoS One. 5(10):e13496.
Gould et al., 2009, "Melanoma Prognostic Model Using Tissue Microarrays and Genetic Algorithms." Journal of Clinical Oncology, 27(34):5772-5780.
Gray-Schopfer et al., 2007, "Melanoma biology and new targeted therapy." Nature. 445:851-7.
Guo et al., 2014, "Renalase: its role as a cytokine, and an update on its association with type 1 diabetes and ischemic stroke." Curr Opin Nephrol Hypertens. 23(5):513-8.
Hao et al., 2012, "Macrophages in TumorMicroenvironments and the Progression of Tumors." Clinical and Developmental Immunology. 2012:11.
Hidalgo et al., 2012, "New insights into pancreatic cancer biology." Annals of Oncology. 23(suppl 10):x135-x8.

(Continued)

*Primary Examiner* — Prema M Mertz
(74) *Attorney, Agent, or Firm* — Riverside Law LLP

(57) ABSTRACT

The invention provides compositions and methods for binding and inhibiting renalase. In one embodiment, the renalase binding molecule inhibits renalase activity. Thus, in diseases and conditions where a reduction of renalase activity is beneficial, such inhibitory renalase binding molecules act as therapeutics.

8 Claims, 67 Drawing Sheets
Specification includes a Sequence Listing.

(56) References Cited

OTHER PUBLICATIONS

Jones et al., 2008, "Core Signaling Pathways in Human Pancreatic Cancers Revealed by Global Genomic Analyses." Science. 321(5897):1801-6.
Jung et al., 2010, "Examination of the expanding pathways for the regulation of p21 expression and activity." Cellular Signalling. 22(7):1003-12.
Kortylewski et al., 2005, "Targeting STAT3 affects melanoma on multiple fronts." Cancer metastasis reviews. 24:315-27.
Lee et al., 2013, "Renalase Protects against Ischemic AKI." J Am Soc Nephrol. 24(3):445-55.
Lesinski et al., 2013, "The potential for targeting the STAT3 pathway as a novel therapy for melanoma." Future oncology. 9:925-7.
Li et al., 2008, "Catecholamines Regulate the Activity, Secretion, and Synthesis of Renalase." Circulation. 117(10):1277-82.
Lowe et al., 2014, "Increasing Incidence of Melanoma among Middle-Aged Adults: An Epidemiologic Study in Olmsted County, Minnesota" Mayo Clinic Proceedings. 89:52-9.
Momi et al., 2013, "Nicotine/Cigarette-smoke Promotes Metastasis of Pancreatic Cancer Through alpha7nAChR-mediated MUC4 Up-regulation." Oncogene. 32(11):1384-95.
Nolen et al., 2014, "Prediagnostic Serum Biomarkers as Early Detection Tools for Pancreatic Cancer in a Large Prospective Cohort Study." PLoS ONE. 9(4):e94928.
Oceandy et al., 2011, "Local signals with global impacts and clinical implications: Lessons from the plasma membrane calcium pump (PMCA4)." Biochimica et Biophysica Acta (BBA)—Molecular Cell Research. 1813(5):974-8.
Ono et al., 2000, "The p38 signal transduction pathway Activation and function." Cellular Signalling. 12(1):1-13.
Pinton et al., 2001, "The Ca2+ concentration of the endoplasmic reticulum is a key determinant of ceramide-induced apoptosis: significance for the molecular mechanism of Bcl-2 action." EMBO J. 20(11): 2690-2701.
Sonawane et al., 2014, "Transcriptional Regulation of the Novel Monoamine Oxidase Renalase: Crucial Roles of Transcription Factors Sp1, STAT3, and ZBP89." Biochemistry. 53(44):6878-6892.
Wang et al., 2008, "Identification, expression and tissue distribution of a renalase homologue from mouse." Mol Biol Rep. 35(4):613-20.
Wang et al., 2014, "Renalase Prevents AKI Independent of Amine Oxidase Activity." Journal of the American Society of Nephrology. 25:1226-1235.
Wang et al., 2015, "Identification of a Receptor for Extracellular Renalase." PLoS ONE. 10(4):e0122932.
Xu et al., 2005, "Renalase is a novel, soluble monoamine oxidase that regulates cardiac function and blood pressure." J Clin Invest. 115 (5):1275-80.
Yajima et al., 2012, "RAS/RAF/MEK/ERK and PI3K/PTEN/AKT Signaling in Malignant Melanoma Progression and Therapy." Dermatology research and practice. 2012:354191.
Yang et al., 2010, "The role of constitutively activated STAT3 in B16 melanoma cells." International journal of interferon, cytokine and mediator research : IJIM. 2010:1-7.
Yu et al., 2007, "Crosstalk between cancer and immune cells: role of STAT3 in the tumour microenvironment." Nat Rev Immunol. 7(1):41-51.
Yu et al., 2009, "STATs in cancer inflammation and immunity: a leading role for STAT3." Nat Rev Cancer. 9(11):798-809.

Figure 5A

```
atggacacgagggcccccactcagctgctggggctcctgctgctctggctcccaggtgcc
 M  D  T  R  A  P  T  Q  L  L  G  L  L  L  W  L  P  G  A
acattgcccaagtgctgacccagactgcatcgccgtgtctgcagctgtgggaggcaca
 T  F  A  Q  V  L  T  Q  T  A  S  P  V  S  A  A  V  G  G  T
gtcaccatcaattgccaggccagtcagagtgtttatgataacaacaacttagcctggtat
 V  T  I  N  C  Q  A  S  Q  S  V  Y  D  N  N  N  L  A  W  Y
cagcagaaaccagggcagcctcccaagcaactgatctatggtgcatccactctggcatct
 Q  Q  K  P  G  Q  P  P  K  Q  L  I  Y  G  A  S  T  L  A  S
gggtctcatcgcggttcaaaggcagtggatctgggacacagttcactctcaccatcagc
 G  V  S  R  F  K  G  S  G  S  G  T  Q  F  T  L  T  I  S
ggcgtgcagtgtgacgatgctgccacttactactgtctaggcgaatttagttgtagtagt
 G  V  Q  C  D  D  A  A  T  Y  Y  C  L  G  E  F  S  C  S  S
gctgattgttttgctttcggcggagggaccgaggtggtcgtcaaaggtgatccagttgca
 A  D  C  F  A  F  G  G  G  T  E  V  V  V  K  G  D  P  V  A
cctactgtcctcatcttcccaccatctgctgatcttgtggcaactggaacagtcaccatc
 P  T  V  L  I  F  P  P  S  A  D  L  V  A  T  G  T  V  T  I
gtgtgtgtggcgaataaatacttcccggatgtcaccgtcacctgggaggtggatggcacc
 V  C  V  A  N  K  Y  F  P  D  V  T  V  T  W  E  V  D  G  T
acccaaacaactggcatcgagaacagtaaaacaccgcagaattctgcagattgtacctac
 T  Q  T  T  G  I  E  N  S  K  T  P  Q  N  S  A  D  C  T  Y
aacctcagcagcactctgaccctgaccagcacacagtacaacagccacaagagtacacc
 N  L  S  S  T  L  T  L  T  S  T  Q  Y  N  S  H  K  E  Y  T
tgcaaggtgacccagggcacgacctcagtcgtccagagcttcaatagggtgactgttag
 C  K  V  T  Q  G  T  T  S  V  V  Q  S  F  N  R  G  D  -
```

Figure 5B

```
atggagactgggctgcgctggcttctcctggtcgctgtgctcaaaggtgtccagtgtcag
M  E  T  G  L  R  W  L  L  L  V  A  V  L  K  G  V  Q  C  Q tcggtggaggagtccggggggtcgcctggtcacgcctggaggatccctgacactcacctgc
S  V  E  E  S  G  G  R  L  V  T  P  G  G  S  L  T  L  T  C acagtctctggattctccctcagtgactatgcaataatctgggtccgccaggctccaggg
T  V  S  G  F  S  L  S  D  Y  A  I  I  W  V  R  Q  A  P  G aagggctggaatacatcgcaattattggtagtagtggtgacacattctacgcgacctgg
K  G  L  E  Y  I  A  I  I  G  S  S  G  D  T  F  Y  A  T  W gcgaaaggccgattcaccatctccaaaacctcgaccacggtggatctgaaaatgaccagt
A  K  G  R  F  T  I  S  K  T  S  T  V  D  L  K  M  T  S ctgacagccgcggacacggccacctatttctgtgcccacgttatgctggtactactgat
L  T  A  A  D  T  A  T  Y  F  C  A  P  R  Y  A  G  T  T  D tatcatgatgcttttgatccctggggcccaggcactttggtcacgtctcctcagggcaa
```

Figure 5C-i

Y H D A F D P W G P G T L V T V S S G Q
cctaaggctccatcagtcttcccactggccccctgctgcggggacacacccagctccacg
P K A P S V F P L A P C C G D T P S S T
gtgacctgggctgcctggtcaaagggtacctccccggagtcagtgaccgtgacctggaac
V T L G C L V K G Y L P E P V T V T W N
tcgggcaccctcaccaatggggtacgcacattccccgtccgtccggcagtcctcaggcctc
S G T L T N G V R T F P S V R Q S S G L
tactgctgagcagcgtggtgagcgtgacctcaagcagccagcccgtcacctgcaacgtg
Y S L S S V V S V T S S Q P V T C N V
gccacccagccaccaacaccaaagtggacaagaccgttgcgcctcgacatgcagcaag
A H P A T N T K V D K T V A P S T C S K
cccacgtgcccaccccctgaactcctgggggacccgtctgtcttcatcttccccccaaaa
P T C P P P E L L G G P S V F I F P P K
cccaaggacaccctcatgatctcacgcaccccccgaggtcacatgcgtggtggtggacgtg
P K D T L M I S R T P E V T C V V V D V
agccaggatgacccagaggtgcagttcacatggtacataaacaacgagcaggtgcgcacc
S Q D D P E V Q F T W Y I N N E Q V R T
gcccggccgccgctacgggagcagcagttcaacagcacgatccgcgtggtcagcaccctc
A R P P L R E Q Q F N S T I R V V S T L
cccatcgcgcaccaggactggctgaggggcaaggagttcaagtgcaaagtccacaacaag
P I A H Q D W L R G K E F K C K V H N K
gcactcccggcccccatcgagaaaaccatctccaaagccagagggcagcccctggagcg
A L P A P I E K T I S K A R G Q P L E P
aaggtctacaccatgggcccctcccgggaggagctgagcagcaggtcggtcagcctgacc
K V Y T M G P P R E E L S S R S V S L T
tgcatgatcaacggcttctacccttccgacatctcggtggagtgggagaagaacgggaag
C M I N G F Y P S D I S V E W E K N G K
gcagaggacaactacaagaccacgccggccgtgctggacagcgacggctcctacttcctc
A E D N Y K T T P A V L D S D G S Y F L
tacagcaagctctcagtgcccacgagtgagtggcagcggggcgacgtcttcacctgctcc
Y S K L S V P T S E W Q R G D V F T C S
gtgatgcacgaggccttgcacaaccactacacgcagaagtccatctcccgctctccgggt
V M H E A L H N H Y T Q K S I S R S P G
aaatga
K

Figure 5C-ii atggacacgaggggccccactcagctgctggggctcctgctgctctggctcccaggtgcc
M  D  T  R  A  P  T  Q  L  L  G  L  L  L  W  L  P  G  A agatgtgccgaagtagtgatgacccagactccagcctccatggaggcacctatgggaggc
R  C  A  E  V  V  M  T  Q  T  P  A  S  M  E  A  P  M  G  G acagtcaccatcaagtgccaggccagtcagaacatttacaactacttatcctggtatcag
T  V  T  I  K  C  Q  A  S  Q  N  I  Y  N  Y  L  S  W  Y  Q cagaaaccagggcagcctcccaagctcctagtctacaaggcctccactctgacttctggg
Q  K  P  G  Q  P  P  K  L  L  V  Y  K  A  S  T  L  T  S  G gtcccgtcgcgcttcaaaggcagtggatctgggacacagttcactctcaccatcagcgac
V  P  S  R  F  K  G  S  G  S  G  T  Q  F  T  L  T  I  S  D ctggagtgtgccgatgctgccacttactactgtcaaatcaattactctatttataatcat
L  E  C  A  D  A  A  T  Y  Y  C  Q  I  N  Y  S  I  Y  N  H tataatattattttggcggagggaccgaggtggtcgtcaaggtgatccagttgcacct
Y  N  I  I  F  G  G  G  T  E  V  V  K  G  D  P  V  A  P actgtcctcatcttcccaccatctgctgatcttgtggcaactggaacagtcaccatcgtg
T  V  L  I  F  P  P  S  A  D  L  V  A  T  G  T  V  T  I  V tgtgtggcgaataaatactttcccgatgtcaccgtcacctggaggtggatggcaccacc
C  V  A  N  K  Y  F  P  D  V  T  V  T  W  E  V  D  G  T  T caaacaactggcatcgagaacagtaaaacaccgcagaattctgcagattgtacctacaac
Q  T  T  G  I  E  N  S  K  T  P  Q  N  S  A  D  C  Y  N ctcagcagcactctgacactgaccagcacacagtacaacagccacaaagagtacacctgc
L  S  S  T  L  T  L  T  S  T  Q  Y  N  S  H  K  E  Y  T  C aaggtgacccagggcacgacctcagtcgtccagagcttcaatagggggtgactgttag
K  V  T  Q  G  T  T  S  V  V  Q  S  F  N  R  G  D  -

Figure 5D atggagactgggctgcgctggcttctcctggtggctgtgctcaaaggtgtccagtgtcag
M  E  T  G  L  R  W  L  L  L  V  A  V  L  K  G  V  Q  C  Q
tcggtgaaggagtccgagggaggtctcttcaagcaacggatacccctgacactcacctgc
S  V  K  E  S  E  G  G  L  F  K  P  T  D  I  L  T  C
acagtctctggattctccctcagtagctatggagtgacctgggtccgccaggctccaggg
T  V  S  G  F  <u>S  L  S  S  Y  G  V  T</u>  W  V  R  Q  A  P  G
aacgggctggagtggatcggattgattggtgatcgtggtactacgttctacgcgagctgg
N  G  L  E  W  I  G  <u>L  I  G  D  R  G  T  T  F  Y  A  S  W</u>
gcgaaaagccgatccaccatcaccagaaacaccaacctgaacacggtgactctgaaaatg
<u>A  K  S</u>  R  S  T  I  T  R  N  T  N  L  N  T  V  T  L  K  M
accaggctgacagccgcggacacggccacctatttctgtgcgagggggagtgggtatggt
T  R  L  T  A  A  D  T  A  T  Y  F  C  A  R  <u>G  S  G  Y  G</u>
gctcgcatctggggcccaggcaccctggtcaccgtctcctcatggcaacctaaggctcca
<u>A  R  I</u>  W  G  P  G  T  L  V  T  V  S  S  W  Q  P  K  A  P
tcagtcttcccactggcccctgctgcgggagacacaccagctccacggtgaccctgggc
S  V  F  P  L  A  P  C  C  G  D  T  P  S  T  V  T  L  G
tgcctggtcaagggctacctccoggagccagtgaccgtgacctggaactcgggcaccctc
C  L  V  K  G  Y  L  P  E  P  V  T  V  T  W  N  S  G  T  L
accaatggggtacgcaccttcccgtccgtccggcagtcctcaggcctctactccctgagc
T  N  G  V  R  T  F  P  S  V  R  Q  S  S  G  L  Y  S  L  S
agcgtggtgagcgtgacctcaagcagccagccgtcacctgcaacgtggcccaccagcc
S  V  V  S  V  T  S  S  Q  P  V  T  C  N  V  A  H  P  A
accaacaccaaagtggacaagaccgttgcgccctcgacatgcagcaagcccagtgccca
T  N  T  K  V  D  K  T  V  A  P  S  T  C  S  K  P  C  P
cccctgaactcctggggggaccgtctgtcttcatcttccccccaaaacccaaggacacc
P  P  E  L  L  G  G  P  S  V  F  I  F  P  P  K  P  K  D  T
ctcatgatctcacgcaccccgaggtcacatgcgtggtggtggacgtgagccaggatgac
L  M  I  S  R  T  P  E  V  T  C  V  V  V  D  V  S  Q  D  D
cccgaggtgcagttcacatggtacataaacaacgagcaggtgcgcaccgccggccgcg
P  E  V  Q  F  T  W  Y  I  N  N  E  Q  V  R  T  A  R  P
ctacgggagcagcagttcaacagcacgatccgcgtggtcagcaccctccccatcgcgcac
L  R  E  Q  Q  F  N  S  T  I  R  V  V  S  T  L  P  I  A  H
caggactggctgaggggcaaggagttcaagtgcaaagtccacaacaaggcactcccggcc
Q  D  W  L  R  G  K  E  F  K  C  K  V  H  N  K  A  L  P  A
cccatcgagaaaaccatctccaaagccagagggcagccctggagccgaaggtctacacc

Figure 5E-i

```
P  I  E  K  T  I  S  K  A  R  G  Q  P  L  E  P  K  V  Y  T
atgggcoctcccggaggagctgagcagcaggtcggtcagcctgacctgcatgatcaac
M  G  P  P  R  E  E  L  S  S  R  S  V  S  L  T  C  M  I  N
ggcttctacccttccgacatctcggtggagtgggagaagaacgggaaggcagaggacaac
G  F  Y  P  S  D  I  S  V  E  W  E  K  N  G  K  A  E  D  N
tacaagaccacgccggccgtgctggacagcgacggctcctacttcctgtacagcaagctc
Y  K  T  T  P  A  V  L  D  S  D  G  S  Y  F  L  Y  S  K  L
tcagtgcccacgagtgagtggcagcggggcgacgtcttcacctgctccgtgatgcacgag
S  V  P  T  S  E  W  Q  R  G  D  V  F  T  C  S  V  M  H  E
gccttgcacaaccactacacgcagaagtccatctcccgctctccgggtaaatga
A  L  H  N  H  Y  T  Q  K  S  I  S  R  S  P  G  K  -
```

Figure 5E-ii

```
atggacacgagggccccactcagctcctggggctcctgctgctctggctcccaggtgcc
 M  D  T  R  A  P  T  Q  L  L  G  L  L  L  W  L  P  G  A
acatttgcccaagtgctgacccagactccatcgctgtgtctgcagctgtggaggcaca
 T  F  A  Q  V  L  T  Q  T  P  S  A  V  S  A  A  V  G  G  T
gtcaccatcaattgccagtccagtcagagtgtttataagaacaactacttagcctggtat
 V  T  I  N  C  Q  S  S  Q  S  V  Y  K  N  N  Y  L  A  W  Y
cagcagaaaccagggcagcctcccaagctccttatctacgaaacatccaaactggcatct
 Q  Q  K  P  G  Q  P  P  K  L  L  I  Y  E  T  S  K  L  A  S
ggggtcccacgcggttcagcggcagtgggtctgggacacagttcactctcaccatcagc
 G  V  P  R  F  S  G  S  G  S  G  T  Q  F  T  L  T  I  S
agcgtgcagtgtgacgatgctgccacttactactgtcaaggcggttatagtggtgttgat
 S  V  Q  C  D  D  A  A  T  Y  Y  C  Q  G  G  Y  S  G  V  D
tttatggctttcggcggagggaccgaggtggtcgtcaaaggtgatccagttgcacctact
 F  M  A  F  G  G  G  T  E  V  V  V  K  G  D  P  V  A  P  T
gtcctcatcttcccaccatctgctgatcttgtggcaactggaacagtcaccatcgtgtgt
 V  L  I  F  P  P  S  A  D  L  V  A  T  G  T  V  T  I  V  C
gtggcgaataaatactttccgatgtcaccgtcacctgggaggtggatggcaccacccaa
 V  A  N  K  Y  F  P  D  V  T  V  T  W  E  V  D  G  T  T  Q
acaactggcatcgagaacagtaaaacaccgcagaattctgcagattgtacctacaacctc
 T  T  G  I  E  N  S  K  T  P  Q  N  S  A  D  C  T  Y  N  L
agcagcactctgacactgaccagcacacagtacaacagccacaagagtacactgcaag
 S  S  T  L  T  L  T  S  T  Q  Y  N  S  H  K  E  Y  T  C  K
gtgacccagggcacgacctcagtcgtccagagcttcaatagggtgactgttag
 V  T  Q  G  T  T  S  V  V  Q  S  F  N  R  G  D  C  -
```

Figure 5F

```
atggagactgggctgcgctggcttctcctggtcgctgtgctcaaaggtgtccagtgtcag
 M  E  T  G  L  R  W  L  L  L  V  A  V  L  K  G  V  Q  C  Q tcggtgaaggagtccgagggaggtctcttcaagccaacggataccctgacactcacctgc
 S  V  K  E  S  E  G  G  L  F  K  P  T  D  T  L  T  L  T  C acagtctctggattctccctcactacctatggagtgacctgggtccgccaggctccaggg
 T  V  S  G  F  S  L  T  T  Y  G  V  T  W  V  R  Q  A  P  G aatggactggagtggatcggattgattggtgatcgcggtaccacttactacgcgagctgg
 N  G  L  E  W  I  G  L  I  G  D  R  G  T  T  Y  Y  A  S  W gtgaatggccgatccaccatcaccagaaacaccaacctgaacacggtgactctgaaaatg
 V  N  G  R  S  T  I  T  R  N  T  N  L  N  T  V  T  L  K  M accaggctgacagccgcggacacggccacctatttctgtgcgaggggggagtggatatggt
 T  R  L  T  A  A  D  T  A  T  Y  F  C  A  R  G  S  G  Y  G gctcgcatctggggcccaggcaccctggtcaccgtcgcctcatggcaacctaaggctcca
 A  R  I  W  G  P  G  T  L  V  T  V  A  S  W  Q  P  K  A  P tcagtcttcccactggccccctgctgcggggacacaccagctccacggtgaccctgggc
 S  V  F  P  L  A  P  C  C  G  D  T  P  S  S  T  V  T  L  G tgcctggtcaaagggtacctcccggagccagtgaccgtgacctggaactcgggcaccctc
 C  L  V  K  G  Y  L  P  E  P  V  T  V  T  W  N  S  G  T  L accaatggggtacgcaccttcccgtccgtccggcagtcctcaggcctctactccctgagc
 T  N  G  V  R  T  F  P  S  V  R  Q  S  S  G  L  Y  S  L  S agcgtggtgagcgtgacctcaagcagccagcccgtcacctgcaacgtggcccacccagcc
 S  V  V  S  V  T  S  S  Q  P  V  T  C  N  V  A  H  P  A accaacaccaaagtggacaagaccgttgcgcctcgacatgcagcaagcccacgtgccca
 T  N  T  K  V  D  K  T  V  A  P  S  C  S  K  P  T  C  P
```

Figure 5G-i

```
cccctgaactcctgggggaccgtctgtcttcatcttccccccaaaacccaaggacacc
 P  P  E  L  L  G  G  P  S  V  F  I  F  P  P  K  P  K  D  T
ctcatgatctcacgcacccccgaggtcacatgcgtggtggtggacgtgagccaggatgac
 L  M  I  S  R  T  P  E  V  T  C  V  V  V  D  V  S  Q  D  D
cccgaggtgcagttcacatggtacataaacaacgagcaggtgcgcaccgcccggccgccg
 P  E  V  Q  F  T  W  Y  I  N  N  E  Q  V  R  T  A  R  P  P
ctacgggagcagcagttcaacagcacgatccgcgtggtcagcaccctccccatcgcgcac
 L  R  E  Q  Q  F  N  S  T  I  R  V  V  S  T  L  P  I  A  H
caggactggctgaggggcaaggagttcaagtgcaaagtccacaacaaggcactcccggcc
 Q  D  W  L  R  G  K  E  F  K  C  K  V  H  N  K  A  L  P  A
cccatcgagaaaaccatctccaaagccagagggcagcccctggagccgaaggtctacacc
 P  I  E  K  T  I  S  K  A  R  G  Q  P  L  E  P  K  V  Y  T
atgggccctccccgggagtagctgagcagcaggtcggtcagcctgacctgcatgatcaac
 M  G  P  P  R  E  E  L  S  S  R  S  V  S  L  T  C  M  I  N
ggcttctacccttccgacatctcggtggagtgggagaagaacgggaaggcagaggacaac
 G  F  Y  P  S  D  I  S  V  E  W  E  K  N  G  K  A  E  D  N
tacaagaccacgcctgccgtgctggacagcgacggctcctacttcctctacagcaagctc
 Y  K  T  T  P  A  V  L  D  S  D  G  S  Y  F  L  Y  S  K  L
tcagtgcccacgagtgagtggcagcggggcgacgtcttcacctgctccgtgatgcacgag
 S  V  P  T  S  E  W  Q  R  G  D  V  F  T  C  S  V  M  H  E
gccttgcacaaccactacacgcagaagtccatctcccgctctccgggtaaatga
 A  L  H  N  H  Y  T  Q  K  S  I  S  R  S  P  G  K  -
```

Figure 5G-ii

```
atggacacgagggcccccactcagctcctggggctcctgctgctctggctcccaggtgcc
 M  D  T  R  A  P  T  Q  L  L  G  L  L  L  W  L  P  G  A acatttgcccaagtgctgacccagactccatcccccatgtctgcagctctgggaggcaca
 T  F  A  Q  V  L  T  Q  T  P  S  P  M  S  A  A  L  G  G  T gtcaccatcaattgccagtccagtcagactgtttataacaataactacttatcctggtat
 V  T  I  N  C  Q  S  S  Q  T  V  Y  N  N  N  Y  L  S  W  Y cagcagaaaccagggcagcctcccaagctcctatctacgaaacatccaaactgtcatct
 Q  Q  K  P  G  Q  P  P  K  L  L  I  Y  E  T  S  K  L  S  S ggggtcccacgcggttcagcggcagtgggtctgggacacagttcactctcaccatcagc
 G  V  P  R  F  S  G  S  G  S  G  T  Q  F  T  L  T  I  S agcgtgcagtgtgacgatgctgccacttactactgtcaaggcggttatagtggtgttgat
 S  V  Q  C  D  D  A  A  T  Y  Y  C  Q  G  G  Y  S  G  V  D tttatggctttcggcggagggaccgaggtggtcgtcaaaggtgatccagttgcacctact
 F  M  A  F  G  G  G  T  E  V  V  V  K  G  D  P  V  A  P  T gtcctcatcttcccaccatctgctgatcttgtggcaactggaacagtcaccatcgtgtgt
 V  L  I  F  P  P  S  A  D  L  V  A  T  G  T  V  T  I  V  C gtggcgaataaatactttccgatgtcaccgtcacctgtgaggtggatggcaccacccaa
 V  A  N  K  Y  F  P  D  V  T  V  T  W  E  V  D  G  T  T  Q acaactggcatcgagaacagtaaaacaccgcagaattctgcagattgtacctacaacctc
 T  T  G  I  E  N  S  K  T  P  Q  N  S  A  D  C  T  Y  N  L agcagcactctgacactgaccagcacacagtacaacagccacaaagagtacacctgcaag
 S  S  T  L  T  L  T  S  T  Q  Y  N  S  H  K  E  Y  T  C  K gtgacccagggcacgacctcagtcgtccagagcttcaatagggGtgactgttag
 V  T  Q  G  T  T  S  V  V  Q  S  F  N  R  G  D  C  -
```

Figure 5H

```
atggagactgggctgcgctggcttctcctggtcgctgtgctcaaaggtgtccagtgtcag
 M  E  T  G  L  R  W  L  L  L  V  A  V  L  K  G  V  Q  C  Q
tcgctggaggagtccggggggtcgcctggtcacgcctgggacacccctgacactcacctgc
 S  L  E  E  S  G  G  R  L  V  T  P  G  T  P  L  T  L  T  C
acagtctctggattctccctcaataactaccacatatactgggtccgccaggctccagga
 T  V  S  G  F  S  L  N  N  Y  H  I  Y  W  V  R  Q  A  P  G
aaggggctggaatacatcggaatcattttcaatggtggcacatattacgcgagatggaca
 K  G  L  E  Y  I  G  I  I  F  N  G  G  T  Y  Y  A  R  W  T
aaggccgattcaccatctccaaaacctcgaccacggtggatctgaaaatgaccagtctg
 K  G  R  F  T  I  S  K  T  S  T  T  V  D  L  K  M  T  S  L
acaaccgaggacacggccacctatttctgtgccagagggggacggcatctggggcccaggc
 T  T  E  D  T  A  T  Y  F  C  A  R  G  D  G  I  W  G  P  G
accctggtcaccgtctccttagggcaacctaaggctccatcagtcttcccactggccccc
 T  L  V  T  V  S  L  G  Q  P  K  A  P  S  V  F  P  L  A  P
tgctgcggggacacacccagctccacggtgaccctgggctgcctggtcaagggtacctc
 C  C  G  D  T  P  S  S  T  V  T  L  G  C  L  V  K  G  Y  L
```

Figure 5I-i

```
ccggagccagtgaccgtgacctggaactcgggcaccctcaccaatggggtacgcacctc
 P  E  P  V  T  V  T  W  N  S  G  T  L  T  N  G  V  R  T  F
ccgtccgtccggcagtcctcaggcctctactcgctgagcagcgtggtgagcgtgacctca
 P  S  V  R  Q  S  S  G  L  Y  S  L  S  S  V  V  S  V  T  S
agcagccagcccgtcacctgcaacgtggcccacccagccaccaacaccaaagtggacaag
 S  S  Q  P  V  T  C  N  V  A  H  P  A  T  N  T  K  V  D  K
accgttgcgccctcgacatgcagcaagccacgtgcccacccctgaactcctgggggga
 T  V  A  P  S  T  C  S  K  P  T  C  P  P  P  E  L  L  G  G
ccgtctgtcttcatcttccccccaaaacccaaggacaccctcatgatctcacgcacccc
 P  S  V  F  I  F  P  P  K  P  K  D  T  L  M  I  S  R  T  P
gaggtcacatgcgtggtggtggacgtgagccaggatgaccccgaggtgcagttcacatgg
 E  V  T  C  V  V  V  D  V  S  Q  D  D  P  E  V  Q  F  T  W
tacataaacaacgagcaggtgcgcaccgcccggccgcgctacggagcagcagttcaac
 Y  I  N  N  E  Q  V  R  T  A  R  P  P  L  R  E  Q  Q  F  N
agcacgatccgcgtggtcagcaccctccccatcgcgcaccaggactggctgaggggcaag
 S  T  I  R  V  V  S  T  L  P  I  A  H  Q  D  W  L  R  G  K
gagttcaagtgcaaagtccacaacaaggcactcccggcccccatcgagaaaaccatctcc
 E  F  K  C  K  V  H  N  K  A  L  P  A  P  I  E  K  T  I  S
aaagccagagggcagcccctggagccgaaggtctacaccatgggccctcccgggaggag
 K  A  R  G  Q  P  L  E  P  K  V  Y  T  M  G  P  P  R  E  E
ctgagcagcaggtcggtcagcctgacctgcatgatcaacggcttctaccttccgacatc
 L  S  S  R  S  V  S  L  T  C  M  I  N  G  F  Y  P  S  D  I
tcggtggagtgggagaagaacggaaggcagaggacaactacaagaccaccgccggccgtg
 S  V  E  W  E  K  N  G  K  A  E  D  N  Y  K  T  T  P  A  V
ctggacagcgacggctcctacttcctctacagcaagctctcagtgccacgagtgagtgg
 L  D  S  D  G  S  Y  F  L  Y  S  K  L  S  V  P  T  S  E  W
cagcggggcgacgtcttcacctgctccgtgatgcacgaggccttgcacaaccactacacg
 Q  R  G  D  V  F  T  C  S  V  M  H  E  A  L  H  N  H  Y  T
cagaagtccatctcccgctctccgggtaaatga
 Q  K  S  I  S  R  S  P  G  K  -
```

Figure 5I-ii

```
atggacacgagggcccccactcagctgctggggctcctgctgctctggctcccaggtgcc
 M  D  T  R  A  P  T  Q  L  L  G  L  L  L  W  L  P  G  A
acatttgcccaagtgctgacccagactccagcctccgtgtctgcagctgtgggaggcaca
 T  F  A  Q  V  L  T  Q  T  P  A  S  V  S  A  A  V  G  G  T
gtcaccatcaattgccaggccagtcagagtgtttttaataacaactatttagcctggtat
 V  T  I  N  C  Q  A  S  Q  S  V  F  N  N  N  Y  L  A  W  Y
cagcagaaaccagggcagcctcccaagcgcctgatctattctgcatccactctggcgtct
 Q  Q  K  P  G  Q  P  P  K  R  L  I  Y  S  A  S  T  L  A  S
ggggtctcatcgcggttcaaaggcagtggatctgggacagaattcactctgaccatgagt
 G  V  S  S  R  F  K  G  S  G  S  G  T  E  F  T  L  T  M  S
ggcgtggagtgtgacgatgctgccacttactactgtcaggcagttttgattgtaatagt
 G  V  E  C  D  D  A  A  T  Y  Y  C  A  G  S  F  D  C  N  S
ggtgattgtgttgctttcggcggagggaccgaggtggtggtcaaggtgatccagttgca
 G  D  C  V  A  F  G  G  G  T  E  V  V  V  K  G  D  P  V  A
cctactgtcctcatcttcccaccagctgctgatcaggtggcaactggaacagtcaccatc
 P  T  V  L  I  F  P  P  A  A  D  Q  V  A  T  G  T  V  T  I
gtgtgtgtggcgaataaatactttcccgatgtcaccgtcacctgggaggtggatggcacc
 V  C  V  A  N  K  Y  F  P  D  V  T  V  T  W  E  V  D  G  T
acccaaacaactggcatcgagaacagtaaaacaccgcagaattctgcagattgtacctac
 T  Q  T  T  G  I  E  N  S  K  T  P  Q  N  S  A  D  C  T  Y
aacctcagcagcactctgacactgaccagcacacagtacaacagccacaaagagtacacc
 N  L  S  S  T  L  T  L  T  S  T  Q  Y  N  S  H  K  E  Y  T
tgcaaggtgacccagggcacgacctcagtcgtccagagcttcaataggggtgactgttag
 C  K  V  T  Q  G  T  T  S  V  V  Q  S  F  N  R  G  D  C  -
```

Figure 5J

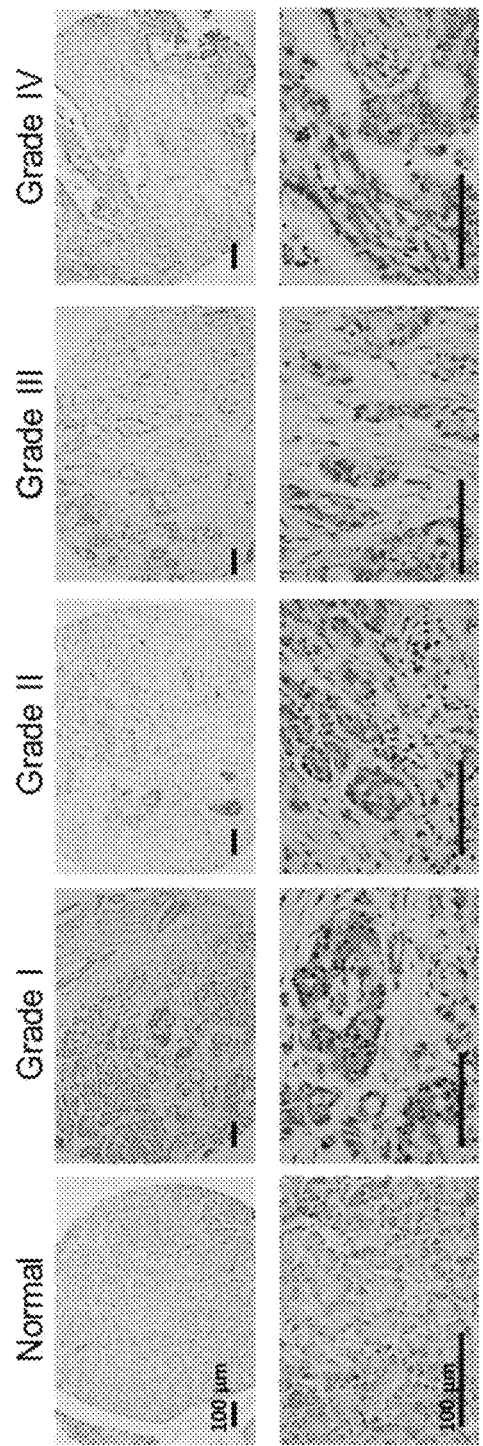
Figure 23C
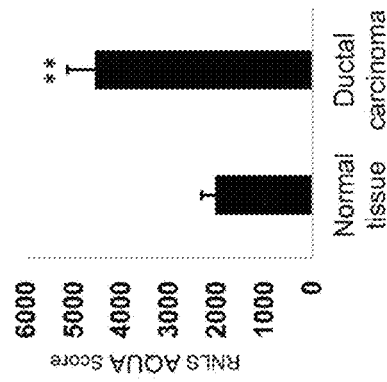
Figure 23D

SEQUENCE LISTING

<160> NUMBER OF SEQ ID NOS: 95

<210> SEQ ID NO 1
<211> LENGTH: 17
<212> TYPE: PRT
<213> ORGANISM: homo sapiens

<400> SEQUENCE: 1

Ala Val Trp Asp Lys Ala Asp Asp Ser Gly Gly Arg Met Thr Thr Ala
1               5                   10                  15

Cys

<210> SEQ ID NO 2
<211> LENGTH: 17
<212> TYPE: PRT
<213> ORGANISM: homo sapiens

<400> SEQUENCE: 2

Ala Val Trp Asp Lys Ala Glu Asp Ser Gly Gly Arg Met Thr Thr Ala
1               5                   10                  15

Cys

<210> SEQ ID NO 3
<211> LENGTH: 16
<212> TYPE: PRT
<213> ORGANISM: homo sapiens

<400> SEQUENCE: 3

Cys Thr Pro His Tyr Ala Lys Lys His Gln Arg Phe Tyr Asp Glu Leu
1               5                   10                  15

<210> SEQ ID NO 4
<211> LENGTH: 21
<212> TYPE: PRT
<213> ORGANISM: homo sapiens

```
<400> SEQUENCE: 4

Cys Ile Arg Phe Val Ser Ile Asp Asn Lys Lys Arg Asn Ile Glu Ser
1               5                   10                  15

Ser Glu Ile Gly Pro
            20

<210> SEQ ID NO 5
<211> LENGTH: 14
<212> TYPE: PRT
<213> ORGANISM: homo sapiens

<400> SEQUENCE: 5

Pro Gly Gln Met Thr Leu His His Lys Pro Phe Leu Ala Cys
1               5                   10

<210> SEQ ID NO 6
<211> LENGTH: 10
<212> TYPE: PRT
<213> ORGANISM: homo sapiens

<400> SEQUENCE: 6

Cys Val Leu Glu Ala Leu Lys Asn Tyr Ile
1               5                   10

<210> SEQ ID NO 7
<211> LENGTH: 9
<212> TYPE: PRT
<213> ORGANISM: homo sapiens

<400> SEQUENCE: 7

Pro Ser Ala Gly Val Ile Leu Gly Cys
1               5

<210> SEQ ID NO 8
<211> LENGTH: 342
<212> TYPE: PRT
<213> ORGANISM: homo sapiens

<400> SEQUENCE: 8

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
                20                  25                  30

Trp Asp Lys Ala Glu Asp Ser Gly Gly Arg Met Thr Thr Ala Cys Ser
            35                  40                  45

Pro His Asn Pro Gln Cys Thr Ala Asp Leu Gly Ala Gln Tyr Ile Thr
        50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
                100                 105                 110

Ser Ile Ile Lys His Tyr Leu Lys Glu Ser Gly Ala Glu Val Tyr Phe
            115                 120                 125

Arg His Arg Val Thr Gln Ile Asn Leu Arg Asp Asp Lys Trp Glu Val
        130                 135                 140

Ser Lys Gln Thr Gly Ser Pro Glu Gln Phe Asp Leu Ile Val Leu Thr
145                 150                 155                 160
```

```
Met Pro Val Pro Glu Ile Leu Gln Leu Gln Gly Asp Ile Thr Thr Leu
            165                 170                 175

Ile Ser Glu Cys Gln Arg Gln Leu Glu Ala Val Ser Tyr Ser Ser
        180                 185                 190

Arg Tyr Ala Leu Gly Leu Phe Tyr Glu Ala Gly Thr Lys Ile Asp Val
            195                 200                 205

Pro Trp Ala Gly Gln Tyr Ile Thr Ser Asn Pro Cys Ile Arg Phe Val
        210                 215                 220

Ser Ile Asp Asn Lys Lys Arg Asn Ile Glu Ser Glu Ile Gly Pro
225                 230                 235                 240

Ser Leu Val Ile His Thr Thr Val Pro Phe Gly Val Thr Tyr Leu Glu
            245                 250                 255

His Ser Ile Glu Asp Val Gln Glu Leu Val Phe Gln Gln Leu Glu Asn
        260                 265                 270

Ile Leu Pro Gly Leu Pro Gln Pro Ile Ala Thr Lys Cys Gln Lys Trp
        275                 280                 285

Arg His Ser Gln Val Thr Asn Ala Ala Ala Asn Cys Pro Gly Gln Met
        290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
            325                 330                 335

Ala Leu Lys Asn Tyr Ile
            340

<210> SEQ ID NO 9
<211> LENGTH: 459
<212> TYPE: PRT
<213> ORGANISM: oryctolagus cuniculus

<400> SEQUENCE: 9

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Phe Ala Val Gly Trp Val Arg Gln Ala Pro Gly Lys Gly Leu Glu
    50                  55                  60

Tyr Ile Gly Ile Ile Ser Ser Val Gly Ile Thr Arg Tyr Ala Ser Trp
65                  70                  75                  80

Ala Ala Gly Arg Phe Thr Ile Ser Lys Thr Ser Thr Val Asp Leu
            85                  90                  95

Lys Ile Thr Ser Pro Thr Thr Glu Asp Thr Ala Thr Tyr Phe Cys Ala
            100                 105                 110

Arg Tyr Gly Tyr Ser Gly Asp Val Asn Arg Leu Asp Leu Trp Gly Gln
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
            165                 170                 175

Trp Asn Ser Gly Thr Leu Thr Asn Gly Val Arg Thr Phe Pro Ser Val
        180                 185                 190
```

```
Arg Gln Ser Ser Gly Leu Tyr Ser Leu Ser Ser Val Ser Val Thr
            195                 200                 205
Ser Ser Ser Gln Pro Val Thr Cys Asn Val Ala His Pro Ala Thr Asn
    210                 215                 220
Thr Lys Val Asp Lys Thr Val Ala Pro Ser Thr Cys Ser Lys Pro Thr
225                 230                 235                 240
Cys Pro Pro Pro Glu Leu Leu Gly Gly Pro Ser Val Phe Ile Phe Pro
                245                 250                 255
Pro Lys Pro Lys Asp Thr Leu Met Ile Ser Arg Thr Pro Glu Val Thr
                260                 265                 270
Cys Val Val Val Asp Val Ser Gln Asp Asp Pro Glu Val Gln Phe Thr
            275                 280                 285
Trp Tyr Ile Asn Asn Glu Gln Val Arg Thr Ala Arg Pro Pro Leu Arg
        290                 295                 300
Glu Gln Gln Phe Asn Ser Thr Ile Arg Val Val Ser Thr Leu Pro Ile
305                 310                 315                 320
Ala His Gln Asp Trp Leu Arg Gly Lys Glu Phe Lys Cys Lys Val His
                325                 330                 335
Asn Lys Ala Leu Pro Ala Pro Ile Glu Lys Thr Ile Ser Lys Ala Arg
                340                 345                 350
Gly Gln Pro Leu Glu Pro Lys Val Tyr Thr Met Gly Pro Pro Arg Glu
            355                 360                 365
Glu Leu Ser Ser Arg Ser Val Ser Leu Thr Cys Met Ile Asn Gly Phe
        370                 375                 380
Tyr Pro Ser Asp Ile Ser Val Glu Trp Glu Lys Asn Gly Lys Ala Glu
385                 390                 395                 400
Asp Asn Tyr Lys Thr Thr Pro Ala Val Leu Asp Ser Asp Gly Ser Tyr
                405                 410                 415
Phe Leu Tyr Ser Lys Leu Ser Val Pro Thr Ser Glu Trp Gln Arg Gly
                420                 425                 430
Asp Val Phe Thr Cys Ser Val Met His Glu Ala Leu His Asn His Tyr
            435                 440                 445
Thr Gln Lys Ser Ile Ser Arg Ser Pro Gly Lys
    450                 455

<210> SEQ ID NO 10
<211> LENGTH: 239
<212> TYPE: PRT
<213> ORGANISM: oryctolagus cuniculus

<400> SEQUENCE: 10

Met Asp Thr Arg Ala Pro Thr Gln Leu Leu Gly Leu Leu Leu Leu Trp
1               5                   10                  15
Leu Pro Gly Ala Thr Phe Ala Gln Val Leu Thr Gln Thr Ala Ser Pro
            20                  25                  30
Val Ser Ala Ala Val Gly Gly Thr Val Thr Ile Asn Cys Gln Ala Ser
        35                  40                  45
Gln Ser Val Tyr Asp Asn Asn Asn Leu Ala Trp Tyr Gln Gln Lys Pro
    50                  55                  60
Gly Gln Pro Pro Lys Gln Leu Ile Tyr Gly Ala Ser Thr Leu Ala Ser
65                  70                  75                  80
Gly Val Ser Ser Arg Phe Lys Gly Ser Gly Ser Gly Thr Gln Phe Thr
                85                  90                  95
Leu Thr Ile Ser Gly Val Gln Cys Asp Asp Ala Ala Thr Tyr Tyr Cys
                100                 105                 110
```

```
Leu Gly Glu Phe Ser Cys Ser Ser Ala Asp Cys Phe Ala Phe Gly Gly
            115                 120                 125

Gly Thr Glu Val Val Lys Gly Asp Pro Val Ala Pro Thr Val Leu
130                 135                 140

Ile Phe Pro Pro Ser Ala Asp Leu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 11
<211> LENGTH: 7
<212> TYPE: PRT
<213> ORGANISM: oryctolagus cuniculus

<400> SEQUENCE: 11

Leu Ser Ser Phe Ala Val Gly
1               5

<210> SEQ ID NO 12
<211> LENGTH: 16
<212> TYPE: PRT
<213> ORGANISM: oryctolagus cuniculus

<400> SEQUENCE: 12

Ile Ile Ser Ser Val Gly Ile Thr Arg Tyr Ala Ser Trp Ala Ala Gly
1               5                   10                  15

<210> SEQ ID NO 13
<211> LENGTH: 12
<212> TYPE: PRT
<213> ORGANISM: oryctolagus cuniculus

<400> SEQUENCE: 13

Tyr Gly Tyr Ser Gly Asp Val Asn Arg Leu Asp Leu
1               5                   10

<210> SEQ ID NO 14
<211> LENGTH: 11
<212> TYPE: PRT
<213> ORGANISM: oryctolagus cuniculus

<400> SEQUENCE: 14

Ser Gln Ser Val Tyr Asp Asn Asn Leu Ala
1               5                   10

<210> SEQ ID NO 15
<211> LENGTH: 7
<212> TYPE: PRT
<213> ORGANISM: oryctolagus cuniculus

<400> SEQUENCE: 15

Gly Ala Ser Thr Leu Ala Ser
1               5
```

-continued

```
<210> SEQ ID NO 16
<211> LENGTH: 13
<212> TYPE: PRT
<213> ORGANISM: oryctolagus cuniculus

<400> SEQUENCE: 16

Leu Gly Glu Phe Ser Cys Ser Ser Ala Asp Cys Phe Ala
1               5                   10

<210> SEQ ID NO 17
<211> LENGTH: 461
<212> TYPE: PRT
<213> ORGANISM: oryctolagus cuniculus

<400> SEQUENCE: 17

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
                20                  25                  30

Gly Gly Ser Leu Thr Leu Thr Cys Thr Val Ser Gly Phe Ser Leu Ser
            35                  40                  45

Asp Tyr Ala Ile Ile Trp Val Arg Gln Ala Pro Gly Lys Gly Leu Glu
        50                  55                  60

Tyr Ile Ala Ile Ile Gly Ser Ser Gly Asp Thr Phe Tyr Ala Thr Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Pro Arg Tyr Ala Gly Thr Thr Asp Tyr His Asp Ala Phe Asp Pro Trp
        115                 120                 125

Gly Pro Gly Thr Leu Val Thr Val Ser Ser Gly Gln Pro Lys Ala Pro
130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Thr Cys Pro Pro Pro Glu Leu Leu Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320
```

```
Pro Ile Ala His Gln Asp Trp Leu Arg Gly Lys Glu Phe Lys Cys Lys
            325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
            355                 360                 365

Arg Glu Glu Leu Ser Ser Arg Ser Val Ser Leu Thr Cys Met Ile Asn
            370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Ala Val Leu Asp Ser Asp Gly
            405                 410                 415

Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
            435                 440                 445

His Tyr Thr Gln Lys Ser Ile Ser Arg Ser Pro Gly Lys
            450                 455                 460

<210> SEQ ID NO 18
<211> LENGTH: 238
<212> TYPE: PRT
<213> ORGANISM: oryctolagus cuniculus

<400> SEQUENCE: 18

Met Asp Thr Arg Ala Pro Thr Gln Leu Leu Gly Leu Leu Leu Leu Trp
1               5                   10                  15

Leu Pro Gly Ala Arg Cys Ala Glu Val Val Met Thr Gln Thr Pro Ala
            20                  25                  30

Ser Met Glu Ala Pro Met Gly Gly Thr Val Thr Ile Lys Cys Gln Ala
            35                  40                  45

Ser Gln Asn Ile Tyr Asn Tyr Leu Ser Trp Tyr Gln Gln Lys Pro Gly
            50                  55                  60

Gln Pro Pro Lys Leu Leu Val Tyr Lys Ala Ser Thr Leu Thr Ser Gly
65                  70                  75                  80

Val Pro Ser Arg Phe Lys Gly Ser Gly Ser Gly Thr Gln Phe Thr Leu
            85                  90                  95

Thr Ile Ser Asp Leu Glu Cys Ala Asp Ala Ala Thr Tyr Tyr Cys Gln
            100                 105                 110

Ile Asn Tyr Ser Ile Tyr Asn His Tyr Asn Ile Ile Phe Gly Gly Gly
            115                 120                 125

Thr Glu Val Val Val Lys Gly Asp Pro Val Ala Pro Thr Val Leu Ile
            130                 135                 140

Phe Pro Pro Ser Ala Asp Leu Val Ala Thr Gly Thr Val Thr Ile Val
145                 150                 155                 160

Cys Val Ala Asn Lys Tyr Phe Pro Asp Val Thr Val Thr Trp Glu Val
            165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
            195                 200                 205

Ser Thr Gln Tyr Asn Ser His Lys Glu Tyr Thr Cys Lys Val Thr Gln
            210                 215                 220

Gly Thr Thr Ser Val Val Gln Ser Phe Asn Arg Gly Asp Cys
225                 230                 235
```

<210> SEQ ID NO 19
<211> LENGTH: 7
<212> TYPE: PRT
<213> ORGANISM: oryctolagus cuniculus

<400> SEQUENCE: 19

Leu Ser Asp Tyr Ala Ile Ile
1               5

<210> SEQ ID NO 20
<211> LENGTH: 16
<212> TYPE: PRT
<213> ORGANISM: oryctolagus cuniculus

<400> SEQUENCE: 20

Ile Ile Gly Ser Ser Gly Asp Thr Phe Tyr Ala Thr Trp Ala Lys Gly
1               5                   10                  15

<210> SEQ ID NO 21
<211> LENGTH: 14
<212> TYPE: PRT
<213> ORGANISM: oryctolagus cuniculus

<400> SEQUENCE: 21

Arg Tyr Ala Gly Thr Thr Asp Tyr His Asp Ala Phe Asp Pro
1               5                   10

<210> SEQ ID NO 22
<211> LENGTH: 9
<212> TYPE: PRT
<213> ORGANISM: oryctolagus cuniculus

<400> SEQUENCE: 22

Ser Gln Asn Ile Tyr Asn Tyr Leu Ser
1               5

<210> SEQ ID NO 23
<211> LENGTH: 7
<212> TYPE: PRT
<213> ORGANISM: oryctolagus cuniculus

<400> SEQUENCE: 23

Lys Ala Ser Thr Leu Thr Ser
1               5

<210> SEQ ID NO 24
<211> LENGTH: 13
<212> TYPE: PRT
<213> ORGANISM: oryctolagus cuniculus

<400> SEQUENCE: 24

Gln Ile Asn Tyr Ser Ile Tyr Asn His Tyr Asn Ile Ile
1               5                   10

<210> SEQ ID NO 25
<211> LENGTH: 457
<212> TYPE: PRT
<213> ORGANISM: oryctolagus cuniculus

<400> SEQUENCE: 25

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

```
Thr Asp Thr Leu Thr Leu Thr Cys Thr Val Ser Gly Phe Ser Leu Ser
        35                  40                  45

Ser Tyr Gly Val Thr Trp Val Arg Gln Ala Pro Gly Asn Gly Leu Glu
 50                  55                  60

Trp Ile Gly Leu Ile Gly Asp Arg Gly Thr Thr Phe Tyr Ala Ser Trp
 65                  70                  75                  80

Ala Lys Ser Arg Ser Thr Ile Thr Arg Asn Thr Asn Leu Asn Thr Val
                 85                  90                  95

Thr Leu Lys Met Thr Arg Leu Thr Ala Ala Asp Thr Ala Thr Tyr Phe
             100                 105                 110

Cys Ala Arg Gly Ser Gly Tyr Gly Ala Arg Ile Trp Gly Pro Gly Thr
             115                 120                 125

Leu Val Thr Val Ser Ser Trp Gln Pro Lys Ala Pro Ser Val Phe Pro
        130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                 165                 170                 175

Ser Gly Thr Leu Thr Asn Gly Val Arg Thr Phe Pro Ser Val Arg Gln
             180                 185                 190

Ser Ser Gly Leu Tyr Ser Leu Ser Ser Val Val Ser Val Thr Ser Ser
             195                 200                 205

Ser Gln Pro Val Thr Cys Asn Val Ala His Pro Ala Thr Asn Thr Lys
        210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                 245                 250                 255

Pro Lys Asp Thr Leu Met Ile Ser Arg Thr Pro Glu Val Thr Cys Val
             260                 265                 270

Val Val Asp Val Ser Gln Asp Asp Pro Glu Val Gln Phe Thr Trp Tyr
             275                 280                 285

Ile Asn Asn Glu Gln Val Arg Thr Ala Arg Pro Pro Leu Arg Glu Gln
290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                 325                 330                 335

Ala Leu Pro Ala Pro Ile Glu Lys Thr Ile Ser Lys Ala Arg Gly Gln
             340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                 405                 410                 415

Tyr Ser Lys Leu Ser Val Pro Thr Ser Glu Trp Gln Arg Gly Asp Val
             420                 425                 430
```

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 26
<211> LENGTH: 237
<212> TYPE: PRT
<213> ORGANISM: oryctolagus cuniculus

<400> SEQUENCE: 26

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Gln Ser Val Tyr Lys Asn Asn Tyr Leu Ala Trp Tyr Gln Gln Lys Pro
    50                  55                  60

Gly Gln Pro Pro Lys Leu Leu Ile Tyr Glu Thr Ser Lys Leu Ala Ser
65                  70                  75                  80

Gly Val Pro Pro Arg Phe Ser Gly Ser Gly Ser Gly Thr Gln Phe Thr
                85                  90                  95

Leu Thr Ile Ser Ser Val Gln Cys Asp Asp Ala Ala Thr Tyr Tyr Cys
            100                 105                 110

Gln Gly Gly Tyr Ser Gly Val Asp Phe Met Ala Phe Gly Gly Gly Thr
        115                 120                 125

Glu Val Val Val Lys Gly Asp Pro Val Ala Pro Thr Val Leu Ile Phe
    130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 27
<211> LENGTH: 7
<212> TYPE: PRT
<213> ORGANISM: oryctolagus cuniculus

<400> SEQUENCE: 27

Leu Ser Ser Tyr Gly Val Thr
1               5

<210> SEQ ID NO 28
<211> LENGTH: 16
<212> TYPE: PRT
<213> ORGANISM: oryctolagus cuniculus -continued

<400> SEQUENCE: 28

Leu Ile Gly Asp Arg Gly Thr Thr Phe Tyr Ala Ser Trp Ala Lys Ser
1               5                   10                  15

<210> SEQ ID NO 29
<211> LENGTH: 8
<212> TYPE: PRT
<213> ORGANISM: oryctolagus cuniculus

<400> SEQUENCE: 29

Gly Ser Gly Tyr Gly Ala Arg Ile
1               5

<210> SEQ ID NO 30
<211> LENGTH: 11
<212> TYPE: PRT
<213> ORGANISM: oryctolagus cuniculus

<400> SEQUENCE: 30

Ser Gln Ser Val Tyr Lys Asn Asn Tyr Leu Ala
1               5                   10

<210> SEQ ID NO 31
<211> LENGTH: 7
<212> TYPE: PRT
<213> ORGANISM: oryctolagus cuniculus

<400> SEQUENCE: 31

Glu Thr Ser Lys Leu Ala Ser
1               5

<210> SEQ ID NO 32
<211> LENGTH: 11
<212> TYPE: PRT
<213> ORGANISM: oryctolagus cuniculus

<400> SEQUENCE: 32

Gln Gly Gly Tyr Ser Gly Val Asp Phe Met Ala
1               5                   10

<210> SEQ ID NO 33
<211> LENGTH: 457
<212> TYPE: PRT
<213> ORGANISM: oryctolagus cuniculus

<400> SEQUENCE: 33

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
                20                  25                  30

Thr Asp Thr Leu Thr Leu Thr Cys Thr Val Ser Gly Phe Ser Leu Thr
            35                  40                  45

Thr Tyr Gly Val Thr Trp Val Arg Gln Ala Pro Gly Asn Gly Leu Glu
        50                  55                  60

Trp Ile Gly Leu Ile Gly Asp Arg Gly Thr Thr Tyr Tyr Ala Ser Trp
65                  70                  75                  80

Val Asn Gly Arg Ser Thr Ile Thr Arg Asn Thr Asn Leu Asn Thr Val
                85                  90                  95

Thr Leu Lys Met Thr Arg Leu Thr Ala Ala Asp Thr Ala Thr Tyr Phe
            100                 105                 110

Cys Ala Arg Gly Ser Gly Tyr Gly Ala Arg Ile Trp Gly Pro Gly Thr
            115                 120                 125

Leu Val Thr Val Ala Ser Trp Gln Pro Lys Ala Pro Ser Val Phe Pro
130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 34
<211> LENGTH: 237
<212> TYPE: PRT
<213> ORGANISM: oryctolagus cuniculus

<400> SEQUENCE: 34

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

```
Met Ser Ala Leu Gly Gly Thr Val Thr Ile Asn Cys Gln Ser Ser
            35                  40                  45

Gln Thr Val Tyr Asn Asn Tyr Leu Ser Trp Tyr Gln Gln Lys Pro
 50                  55                  60

Gly Gln Pro Pro Lys Leu Leu Ile Tyr Glu Thr Ser Lys Leu Ser Ser
 65                  70                  75                  80

Gly Val Pro Pro Arg Phe Ser Gly Ser Gly Ser Gly Thr Gln Phe Thr
                 85                  90                  95

Leu Thr Ile Ser Ser Val Gln Cys Asp Asp Ala Ala Thr Tyr Tyr Cys
             100                 105                 110

Gln Gly Gly Tyr Ser Gly Val Asp Phe Met Ala Phe Gly Gly Thr
             115                 120                 125

Glu Val Val Val Lys Gly Asp Pro Val Ala Pro Thr Val Leu Ile Phe
 130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                 165                 170                 175

Gly Thr Thr Gln Thr Thr Gly Ile Glu Asn Ser Lys Thr Pro Gln Asn
                 180                 185                 190

Ser Ala Asp Cys Thr Tyr Asn Leu Ser Ser Thr Leu Thr Leu Thr Ser
             195                 200                 205

Thr Gln Tyr Asn Ser His Lys Glu Tyr Thr Cys Lys Val Thr Gln Gly
     210                 215                 220

Thr Thr Ser Val Val Gln Ser Phe Asn Arg Gly Asp Cys
225                 230                 235

<210> SEQ ID NO 35
<211> LENGTH: 7
<212> TYPE: PRT
<213> ORGANISM: oryctolagus cuniculus

<400> SEQUENCE: 35

Leu Thr Thr Tyr Gly Val Thr
1               5

<210> SEQ ID NO 36
<211> LENGTH: 16
<212> TYPE: PRT
<213> ORGANISM: oryctolagus cuniculus

<400> SEQUENCE: 36

Leu Ile Gly Asp Arg Gly Thr Thr Tyr Tyr Ala Ser Trp Val Asn Gly
1               5                  10                  15

<210> SEQ ID NO 37
<211> LENGTH: 8
<212> TYPE: PRT
<213> ORGANISM: oryctolagus cuniculus

<400> SEQUENCE: 37

Gly Ser Gly Tyr Gly Ala Arg Ile
1               5

<210> SEQ ID NO 38
<211> LENGTH: 11
<212> TYPE: PRT
<213> ORGANISM: oryctolagus cuniculus
```

```
<400> SEQUENCE: 38

Ser Gln Thr Val Tyr Asn Asn Asn Tyr Leu Ser
1               5                   10

<210> SEQ ID NO 39
<211> LENGTH: 7
<212> TYPE: PRT
<213> ORGANISM: oryctolagus cuniculus

<400> SEQUENCE: 39

Glu Thr Ser Lys Leu Ser Ser
1               5

<210> SEQ ID NO 40
<211> LENGTH: 10
<212> TYPE: PRT
<213> ORGANISM: oryctolagus cuniculus

<400> SEQUENCE: 40

Gln Gly Gly Tyr Ser Gly Val Asp Phe Met
1               5                   10

<210> SEQ ID NO 41
<211> LENGTH: 450
<212> TYPE: PRT
<213> ORGANISM: oryctolagus cuniculus

<400> SEQUENCE: 41

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
                20                  25                  30

Gly Thr Pro Leu Thr Leu Thr Cys Thr Val Ser Gly Phe Ser Leu Asn
            35                  40                  45

Asn Tyr His Ile Tyr Trp Val Arg Gln Ala Pro Gly Lys Gly Leu Glu
        50                  55                  60

Tyr Ile Gly Ile Ile Phe Asn Gly Gly Thr Tyr Tyr Ala Arg Trp Thr
65                  70                  75                  80

Lys Gly Arg Phe Thr Ile Ser Lys Thr Ser Thr Thr Val Asp Leu Lys
                85                  90                  95

Met Thr Ser Leu Thr Thr Glu Asp Thr Ala Thr Tyr Phe Cys Ala Arg
            100                 105                 110

Gly Asp Gly Ile Trp Gly Pro Gly Thr Leu Val Thr Val Ser Leu Gly
        115                 120                 125

Gln Pro Lys Ala Pro Ser Val Phe Pro Leu Ala Pro Cys Cys Gly Asp
    130                 135                 140

Thr Pro Ser Ser Thr Val Thr Leu Gly Cys Leu Val Lys Gly Tyr Leu
145                 150                 155                 160

Pro Glu Pro Val Thr Val Thr Trp Asn Ser Gly Thr Leu Thr Asn Gly
                165                 170                 175

Val Arg Thr Phe Pro Ser Val Arg Gln Ser Ser Gly Leu Tyr Ser Leu
            180                 185                 190

Ser Ser Val Val Ser Val Thr Ser Ser Gln Pro Val Thr Cys Asn
        195                 200                 205

Val Ala His Pro Ala Thr Asn Thr Lys Val Asp Lys Thr Val Ala Pro
    210                 215                 220

Ser Thr Cys Ser Lys Pro Thr Cys Pro Pro Glu Leu Leu Gly Gly
225                 230                 235                 240
```

```
Pro Ser Val Phe Ile Phe Pro Lys Pro Lys Asp Thr Leu Met Ile
                245                 250                 255

Ser Arg Thr Pro Glu Val Thr Cys Val Val Asp Val Ser Gln Asp
            260                 265                 270

Asp Pro Glu Val Gln Phe Thr Trp Tyr Ile Asn Asn Glu Gln Val Arg
        275                 280                 285

Thr Ala Arg Pro Pro Leu Arg Glu Gln Gln Phe Asn Ser Thr Ile Arg
    290                 295                 300

Val Val Ser Thr Leu Pro Ile Ala His Gln Asp Trp Leu Arg Gly Lys
305                 310                 315                 320

Glu Phe Lys Cys Lys Val His Asn Lys Ala Leu Pro Ala Pro Ile Glu
                325                 330                 335

Lys Thr Ile Ser Lys Ala Arg Gly Gln Pro Leu Glu Pro Lys Val Tyr
            340                 345                 350

Thr Met Gly Pro Pro Arg Glu Glu Leu Ser Ser Arg Ser Val Ser Leu
        355                 360                 365

Thr Cys Met Ile Asn Gly Phe Tyr Pro Ser Asp Ile Ser Val Glu Trp
    370                 375                 380

Glu Lys Asn Gly Lys Ala Glu Asp Asn Tyr Lys Thr Thr Pro Ala Val
385                 390                 395                 400

Leu Asp Ser Asp Gly Ser Tyr Phe Leu Tyr Ser Lys Leu Ser Val Pro
                405                 410                 415

Thr Ser Glu Trp Gln Arg Gly Asp Val Phe Thr Cys Ser Val Met His
            420                 425                 430

Glu Ala Leu His Asn His Tyr Thr Gln Lys Ser Ile Ser Arg Ser Pro
        435                 440                 445

Gly Lys
    450

<210> SEQ ID NO 42
<211> LENGTH: 239
<212> TYPE: PRT
<213> ORGANISM: oryctolagus cuniculus

<400> SEQUENCE: 42

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
                20                  25                  30

Val Ser Ala Ala Val Gly Gly Thr Val Thr Ile Asn Cys Gln Ala Ser
            35                  40                  45

Gln Ser Val Phe Asn Asn Asn Tyr Leu Ala Trp Tyr Gln Gln Lys Pro
        50                  55                  60

Gly Gln Pro Pro Lys Arg Leu Ile Tyr Ser Ala Ser Thr Leu Ala Ser
65                  70                  75                  80

Gly Val Ser Ser Arg Phe Lys Gly Ser Gly Ser Gly Thr Glu Phe Thr
                85                  90                  95

Leu Thr Met Ser Gly Val Glu Cys Asp Asp Ala Ala Thr Tyr Tyr Cys
            100                 105                 110

Ala Gly Ser Phe Asp Cys Asn Ser Gly Asp Cys Val Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160
```

```
Val Cys Val Ala Asn Lys Tyr Phe Pro Asp Val Thr Val Thr Trp Glu
                165                 170                 175
Val Asp Gly Thr Thr Gln Thr Thr Gly Ile Glu Asn Ser Lys Thr Pro
            180                 185                 190
Gln Asn Ser Ala Asp Cys Thr Tyr Asn Leu Ser Ser Thr Leu Thr Leu
        195                 200                 205
Thr Ser Thr Gln Tyr Asn Ser His Lys Glu Tyr Thr Cys Lys Val Thr
    210                 215                 220
Gln Gly Thr Thr Ser Val Val Gln Ser Phe Asn Arg Gly Asp Cys
225                 230                 235
```

<210> SEQ ID NO 43
<211> LENGTH: 7
<212> TYPE: PRT
<213> ORGANISM: oryctolagus cuniculus

<400> SEQUENCE: 43

```
Leu Asn Asn Tyr His Ile Tyr
1               5
```

<210> SEQ ID NO 44
<211> LENGTH: 15
<212> TYPE: PRT
<213> ORGANISM: oryctolagus cuniculus

<400> SEQUENCE: 44

```
Ile Ile Phe Asn Gly Gly Thr Tyr Tyr Ala Arg Trp Thr Lys Gly
1               5                   10                  15
```

<210> SEQ ID NO 45
<211> LENGTH: 4
<212> TYPE: PRT
<213> ORGANISM: oryctolagus cuniculus

<400> SEQUENCE: 45

```
Gly Asp Gly Ile
1
```

<210> SEQ ID NO 46
<211> LENGTH: 11
<212> TYPE: PRT
<213> ORGANISM: oryctolagus cuniculus

<400> SEQUENCE: 46

```
Ser Gln Ser Val Phe Asn Asn Asn Tyr Leu Ala
1               5                   10
```

<210> SEQ ID NO 47
<211> LENGTH: 7
<212> TYPE: PRT
<213> ORGANISM: oryctolagus cuniculus

<400> SEQUENCE: 47

```
Ser Ala Ser Thr Leu Ala Ser
1               5
```

<210> SEQ ID NO 48
<211> LENGTH: 13
<212> TYPE: PRT
<213> ORGANISM: oryctolagus cuniculus

<400> SEQUENCE: 48

Ala Gly Ser Phe Asp Cys Asn Ser Gly Asp Cys Val Ala
1               5                   10

<210> SEQ ID NO 49
<211> LENGTH: 1029
<212> TYPE: DNA
<213> ORGANISM: homo sapiens

<400> SEQUENCE: 49

| | |
|---|---:|
| atggcgcagg tgctgatcgt gggcgccggg atgacaggaa gcttgtgcgc tgcgctgctg | 60 |
| aggaggcaga cgtccggtcc cttgtacctt gctgtgtggg acaaggctga ggactcaggg | 120 |
| ggaagaatga ctacagcctg cagtcctcat aatcctcagt gcacagctga cttgggtgct | 180 |
| cagtacatca cctgcactcc tcattatgcc aaaaaacacc aacgttttta tgatgaactg | 240 |
| ttagcctatg gcgttttgag gcctctaagc tcgcctattg aaggaatggt gatgaaagaa | 300 |
| ggagactgta actttgtggc acctcaagga atttcttcaa ttattaagca ttacttgaaa | 360 |
| gaatcaggtg cagaagtcta cttcagacat cgtgtgacac agatcaacct aagagatgac | 420 |
| aaatgggaag tatccaaaca aacaggctcc cctgagcagt ttgatcttat tgttctcaca | 480 |
| atgccagttc ctgagattct gcagcttcaa ggtgacatca ccaccttaat tagtgaatgc | 540 |
| caaaggcagc aactggaggc tgtgagctac tcctctcgat atgctctggg cctcttttat | 600 |
| gaagctggta cgaagattga tgtcccttgg gctgggcagt acatcaccag taatccctgc | 660 |
| atacgcttcg tctccattga taataagaag cgcaatatag agtcatcaga aattgggcct | 720 |
| tccctcgtga ttcacaccac tgtcccattt ggagttacac acttgaaaca cagcattgag | 780 |
| gatgtgcaag agttagtctt ccagcagctg gaaaacattt tgccgggttt gcctcagcca | 840 |
| attgctacca aatgccaaaa atggagacat tcacaggtta caaatgctgc tgccaactgt | 900 |
| cctggccaaa tgactctgca tcacaaacct ttccttgcat gtggagggga tggatttact | 960 |
| cagtccaact tgatggctg catcacttct gccctatgtg ttctggaagc tttaaagaat | 1020 |
| tatatttaa | 1029 |

<210> SEQ ID NO 50
<211> LENGTH: 315
<212> TYPE: PRT
<213> ORGANISM: homo sapiens

<400> SEQUENCE: 50

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
                20                  25                  30

Trp Asp Lys Ala Glu Asp Ser Gly Gly Arg Met Thr Thr Ala Cys Ser
            35                  40                  45

Pro His Asn Pro Gln Cys Thr Ala Asp Leu Gly Ala Gln Tyr Ile Thr
        50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
                100                 105                 110

```
Ser Ile Ile Lys His Tyr Leu Lys Glu Ser Gly Ala Glu Val Tyr Phe
            115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
                180                 185                 190

Arg Tyr Ala Leu Gly Leu Phe Tyr Glu Ala Gly Thr Lys Ile Asp Val
    195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
                260                 265                 270

Ile Leu Pro Gly Leu Pro Gln Pro Ile Ala Thr Lys Cys Gln Lys Trp
        275                 280                 285

Arg His Ser Gln Val Pro Ser Ala Gly Val Ile Leu Gly Cys Ala Lys
    290                 295                 300

Ser Pro Trp Met Met Ala Ile Gly Phe Pro Ile
305                 310                 315

<210> SEQ ID NO 51
<211> LENGTH: 945
<212> TYPE: DNA
<213> ORGANISM: homo sapiens

<400> SEQUENCE: 51
atggcgcagg tgctgatcgt gggcgccggg atgacaggaa gcttgtgcgc tgcgctgctg      60
aggaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctctttttat     600 gaagctggta cgaagattga tgtcccttgg gctgggcagt acatcaccag taatccctgc     660
atacgcttcg tctccattga taataagaag cgcaatatag agtcatcaga aattgggcct     720
tccctcgtga ttcacaccac tgtcccattt ggagttacat acttggaaca cagcattgag     780
gatgtgcaag agttagtctt ccagcagctg gaaaacattt tgccgggttt gcctcagcca     840
attgctacca atgccaaaaa atggagacat tcacaggtac aagtgctgg tgtgattcta     900 ggatgtgcga agagcccctg gatgatggcg attggatttc ccatc                    945
```

<210> SEQ ID NO 52
<211> LENGTH: 1380
<212> TYPE: DNA
<213> ORGANISM: oryctolagus cuniculus

<400> SEQUENCE: 52

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | caccCctgac | actcacctgc | 120 |
| acagtctctg | gattctccct | cagtagtttt | gcagtgggct | gggtccgcca | ggctccaggg | 180 |
| aaggggctgg | aatacatcgg | aatcattagt | agtgttggta | ttacacgcta | cgcgagctgg | 240 |
| gcggccggcc | gattcaccat | ctccaaaacc | tcgaccacgg | tggatctgaa | aatcaccagt | 300 |
| ccgacaaccg | aggacacggc | cacctatttt | tgtgccagat | atggttatag | tggtgatgtt | 360 |
| aatcggttgg | atctctgggg | ccagggcacc | ctggtcaccg | tctcctcagg | caacctaag | 420 |
| gctccatcag | tcttcccact | ggccccctgc | tgcggggaca | cacccagctc | cacggtgacc | 480 |
| ctgggctgcc | tggtcaaagg | gtacctcccg | gagccagtga | ccgtgacctg | gaactcgggc | 540 |
| accctcacca | tggggtacg | caccttcccg | tccgtccggc | agtcctcagg | cctctactcg | 600 |
| ctgagcagcg | tggtgagcgt | gacctcaagc | agccagcccg | tcacctgcaa | cgtggcccac | 660 |
| ccagccacca | acaccaaagt | ggacaagacc | gttgcgccct | cgacatgcag | caagcccacg | 720 |
| tgcccacccc | ctgaactcct | gggggaccc | tctgtcttca | tcttcccccc | aaaacccaag | 780 |
| gacaccctca | tgatctcacg | caccccCgag | gtcacatgcg | tggtggtgga | cgtgagccag | 840 |
| gatgaccccg | aggtgcagtt | cacatggtac | ataaacaacg | agcaggtgcg | caccgccCgg | 900 |
| ccgccgctac | gggagcagca | gttcaacagc | acgatccgcg | tggtcagcac | cctccccatc | 960 |
| gcgcaccagg | actggctgag | gggcaaggag | ttcaagtgca | aagtccacaa | caaggcactc | 1020 |
| ccggccccca | tcgagaaaac | catctccaaa | gccagagggc | agccCctgga | gccgaaggtc | 1080 |
| tacaccatgg | gccctcccCg | ggaggagctg | agcagcaggt | cggtcagcct | gacctgcatg | 1140 |
| atcaacggct | tctacccttc | cgacatctcg | gtggagtggg | agaagaacgg | gaaggcagag | 1200 |
| gacaactaca | agaccacgcc | ggccgtgctg | gacagcgacg | gctcctactt | cctctacagc | 1260 |
| aagctctcag | tgcccacgag | tgagtggcag | cggggcgacg | tcttcacctg | ctccgtgatg | 1320 |
| cacgaggcct | gcacaacca | ctacacgcag | aagtccatct | cccgctctcc | gggtaaatga | 1380 |

<210> SEQ ID NO 53
<211> LENGTH: 720
<212> TYPE: DNA
<213> ORGANISM: oryctolagus cuniculus

<400> SEQUENCE: 53

| | | | | | |
|---|---|---|---|---|---|
| atggacacga | gggcccccac | tcagctgctg | gggctcctgc | tgctctggct | cccaggtgcc | 60 |
| acatttgccc | aagtgctgac | ccagactgca | tcgcccgtgt | ctgcagctgt | gggaggcaca | 120 |
| gtcaccatca | attgccaggc | cagtcagagt | gtttatgata | caacaacctt | agcctggtat | 180 |
| cagcagaaac | cagggcagcc | tcccaagcaa | ctgatctatg | gtgcatccac | tctggcatct | 240 |
| ggggtctcat | cgcggttcaa | aggcagtgga | tctgggacac | agttcactct | caccatcagc | 300 |
| ggcgtgcagt | gtgacgatgc | tgccacttac | tactgtctag | gcgaatttag | ttgtagtagt | 360 |
| gctgattgtt | ttgctttcgg | cggagggacc | gaggtggtcg | tcaaaggtga | tccagttgca | 420 |
| cctactgtcc | tcatcttccc | accatctgct | gatcttgtgg | caactggaac | agtcaccatc | 480 |
| gtgtgtgtgg | cgaataaata | cttccccgat | gtcaccgtca | cctgggaggt | ggatggcacc | 540 |

```
acccaaacaa ctggcatcga gaacagtaaa acaccgcaga attctgcaga ttgtacctac      600
aacctcagca gcactctgac actgaccagc acacagtaca acagccacaa agagtacacc      660
tgcaaggtga cccagggcac gacctcagtc gtccagagct tcaatagggg tgactgttag      720
```

<210> SEQ ID NO 54
<211> LENGTH: 21
<212> TYPE: DNA
<213> ORGANISM: oryctolagus cuniculus

<400> SEQUENCE: 54

```
ctcagtagtt ttgcagtggg c                                                21
```

<210> SEQ ID NO 55
<211> LENGTH: 48
<212> TYPE: DNA
<213> ORGANISM: oryctolagus cuniculus

<400> SEQUENCE: 55

```
atcattagta gtgttggtat tacacgctac gcgagctggg cggccggc                   48
```

<210> SEQ ID NO 56
<211> LENGTH: 36
<212> TYPE: DNA
<213> ORGANISM: oryctolagus cuniculus

<400> SEQUENCE: 56

```
tatggttata gtggtgatgt taatcggttg gatctc                                36
```

<210> SEQ ID NO 57
<211> LENGTH: 33
<212> TYPE: DNA
<213> ORGANISM: oryctolagus cuniculus

<400> SEQUENCE: 57

```
agtcagagtg tttatgataa caacaactta gcc                                   33
```

<210> SEQ ID NO 58
<211> LENGTH: 21
<212> TYPE: DNA
<213> ORGANISM: oryctolagus cuniculus

<400> SEQUENCE: 58

```
ggtgcatcca ctctggcatc t                                                21
```

<210> SEQ ID NO 59
<211> LENGTH: 39
<212> TYPE: DNA
<213> ORGANISM: oryctolagus cuniculus

<400> SEQUENCE: 59

```
ctaggcgaat ttagttgtag tagtgctgat tgttttgct                             39
```

<210> SEQ ID NO 60
<211> LENGTH: 1386
<212> TYPE: DNA
<213> ORGANISM: oryctolagus cuniculus

<400> SEQUENCE: 60

```
atggagactg ggctgcgctg gcttctcctg gtcgctgtgc tcaaaggtgt ccagtgtcag      60
tcggtggagg agtccggggg tcgcctggtc acgcctggag gatccctgac actcacctgc     120
acagtctctg gattctcccc tcagtgacta tgcaataatct gggtccgcca ggctccaggg     180
```

| aaggggctgg | aatacatcgc | aattattggt | agtagtggtg | acacattcta | cgcgacctgg | 240 |
| gcgaaaggcc | gattcaccat | ctccaaaacc | tcgaccacgg | tggatctgaa | aatgaccagt | 300 |
| ctgacagccg | cggacacggc | cacctatttc | tgtgccccac | gttatgctgg | tactactgat | 360 |
| tatcatgatg | cttttgatcc | ctggggccca | ggcactttgg | tcaccgtctc | ctcagggcaa | 420 |
| cctaaggctc | catcagtctt | cccactggcc | ccctgctgcg | gggacacacc | cagctccacg | 480 |
| gtgaccctgg | gctgcctggt | caaagggtac | ctcccggagc | cagtgaccgt | gacctggaac | 540 |
| tcgggcaccc | tcaccaatgg | ggtacgcacc | ttcccgtccg | tccggcagtc | ctcaggcctc | 600 |
| tactcgctga | gcagcgtggt | gagcgtgacc | tcaagcagcc | agcccgtcac | ctgcaacgtg | 660 |
| gcccacccag | ccaccaacac | caaagtggac | aagaccgttg | cgcctcgac | atgcagcaag | 720 |
| cccacgtgcc | cacccctga | actcctgggg | ggaccgtctg | tcttcatctt | cccccccaaaa | 780 |
| cccaaggaca | ccctcatgat | ctcacgcacc | cccgaggtca | catgcgtggt | ggtggacgtg | 840 |
| agccaggatg | accccgaggt | gcagttcaca | tggtacataa | acaacgagca | ggtgcgcacc | 900 |
| gcccggccgc | cgctacggga | gcagcagttc | aacagcacga | tccgcgtggt | cagcaccctc | 960 |
| cccatcgcgc | accaggactg | gctgaggggc | aaggagttca | agtgcaaagt | ccacaacaag | 1020 |
| gcactcccgg | ccccatcga | gaaaaccatc | tccaaagcca | gagggcagcc | cctggagccg | 1080 |
| aaggtctaca | ccatgggccc | tccccgggag | gagctgagca | gcaggtcggt | cagcctgacc | 1140 |
| tgcatgatca | acggcttcta | cccttccgac | atctcggtgg | agtgggagaa | gaacgggaag | 1200 |
| gcagaggaca | actacaagac | cacgccggcc | gtgctggaca | cgacggctc | ctacttcctc | 1260 |
| tacagcaagc | tctcagtgcc | cacgagtgag | tggcagcggg | gcgacgtctt | cacctgctcc | 1320 |
| gtgatgcacg | aggccttgca | caaccactac | acgcagaagt | ccatctcccg | ctctccgggt | 1380 |
| aaatga | | | | | | 1386 |

<210> SEQ ID NO 61
<211> LENGTH: 717
<212> TYPE: DNA
<213> ORGANISM: oryctolagus cuniculus

<400> SEQUENCE: 61

| atggacacga | gggcccccac | tcagctgctg | gggctcctgc | tgctctggct | cccaggtgcc | 60 |
| agatgtgccg | aagtagtgat | gacccagact | ccagcctcca | tggaggcacc | tatgggaggc | 120 |
| acagtcacca | tcaagtgcca | ggccagtcag | aacatttaca | actacttatc | ctggtatcag | 180 |
| cagaaaccag | gcagcctcc | caagctccta | gtctacaagg | cctccactct | gacttctggg | 240 |
| gtcccgtcgc | gcttcaaagg | cagtggatct | gggacacagt | tcactctcac | catcagcgac | 300 |
| ctggagtgtg | ccgatgctgc | cacttactac | tgtcaaatca | attactctat | ttataatcat | 360 |
| tataatatta | ttttggcgg | agggaccgag | gtggtcgtca | agggtgatcc | agttgcacct | 420 |
| actgtcctca | tcttcccacc | atctgctgat | cttgtggcaa | ctggaacagt | caccatcgtg | 480 |
| tgtgtggcga | ataaatactt | tcccgatgtc | accgtcacct | gggaggtgga | tggcaccacc | 540 |
| caaacaactg | gcatcgagaa | cagtaaaaca | ccgcagaatt | ctgcagattg | tacctacaac | 600 |
| ctcagcagca | ctctgacact | gaccagcaca | cagtacaaca | gccacaaaga | gtacacctgc | 660 |
| aaggtgaccc | agggcacgac | ctcagtcgtc | cagagcttca | ataggggtga | ctgttag | 717 |

<210> SEQ ID NO 62
<211> LENGTH: 21
<212> TYPE: DNA
<213> ORGANISM: oryctolagus cuniculus

```
<400> SEQUENCE: 62
ctcagtgact atgcaataat c                                              21

<210> SEQ ID NO 63
<211> LENGTH: 48
<212> TYPE: DNA
<213> ORGANISM: oryctolagus cuniculus

<400> SEQUENCE: 63
attattggta gtagtggtga cacattctac gcgacctggg cgaaaggc                 48

<210> SEQ ID NO 64
<211> LENGTH: 42
<212> TYPE: DNA
<213> ORGANISM: oryctolagus cuniculus

<400> SEQUENCE: 64
cgttatgctg gtactactga ttatcatgat gcttttgatc cc                       42

<210> SEQ ID NO 65
<211> LENGTH: 27
<212> TYPE: DNA
<213> ORGANISM: oryctolagus cuniculus

<400> SEQUENCE: 65
agtcagaaca tttacaacta cttatcc                                        27

<210> SEQ ID NO 66
<211> LENGTH: 21
<212> TYPE: DNA
<213> ORGANISM: oryctolagus cuniculus

<400> SEQUENCE: 66
aaggcctcca ctctgacttc t                                              21

<210> SEQ ID NO 67
<211> LENGTH: 39
<212> TYPE: DNA
<213> ORGANISM: oryctolagus cuniculus

<400> SEQUENCE: 67
caaatcaatt actctattta taatcattat aatattatt                           39

<210> SEQ ID NO 68
<211> LENGTH: 1374
<212> TYPE: DNA
<213> ORGANISM: oryctolagus cuniculus

<400> SEQUENCE: 68
atggagactg ggctgcgctg gcttctcctg gtcgctgtgc tcaaaggtgt ccagtgtcag     60
tcggtgaagg agtccgaggg aggtctcttc aagccaacgg ataccctgac actcacctgc    120
acagtctctg gattctcccct cagtagctat ggagtgacct gggtccgcca ggctccaggg   180
aacgggctgg agtggatcgg attgattggt gatcgtggta ctacgttcta cgcgagctgg    240
gcgaaaagcc gatccaccat caccagaaac accaacctga acacggtgac tctgaaaatg    300
accaggctga cagccgcgga cacggccacc tatttctgtg cgaggggag tgggtatggt    360 gctcgcatct ggggcccagg caccctggtc accgtctcct catggcaacc taaggctcca    420
tcagtcttcc cactggcccc ctgctgcggg gacacaccca gctccacggt gaccctgggc    480
tgcctggtca aagggtacct cccggagcca gtgaccgtga cctggaactc gggcacccctc    540
```

```
accaatgggg tacgcacctt cccgtccgtc cggcagtcct caggcctcta ctcgctgagc      600
agcgtggtga gcgtgacctc aagcagccag cccgtcacct gcaacgtggc ccacccagcc      660
accaacacca aagtggacaa gaccgttgcg ccctcgacat gcagcaagcc cacgtgccca      720 cccctgaac tcctgggggg accgtctgtc ttcatcttcc ccaaaaacc caaggacacc       780 ctcatgatct cacgcacccc cgaggtcaca tgcgtggtgg tggacgtgag ccaggatgac      840
cccgaggtgc agttcacatg gtacataaac aacgagcagg tgcgcaccgc ccggccgccg      900
ctacgggagc agcagttcaa cagcacgatc cgcgtggtca gcaccctccc catcgcgcac      960
caggactggc tgaggggcaa ggagttcaag tgcaaagtcc acaacaaggc actcccggcc     1020
cccatcgaga aaaccatctc caaagccaga gggcagcccc tggagccgaa ggtctacacc     1080
atgggccctc cccggagga gctgagcagc aggtcggtca gcctgacctg catgatcaac     1140
ggcttctacc cttccgacat ctcggtggag tgggagaaga cgggaaggc agaggacaac     1200 tacaagacca cgccggccgt gctggacagc gacggctcct acttcctcta cagcaagctc     1260
tcagtgccca cgagtgagtg gcagcggggc gacgtcttca cctgctccgt gatgcacgag     1320
gccttgcaca accactacac gcagaagtcc atctcccgct ctccgggtaa atga           1374
```

<210> SEQ ID NO 69
<211> LENGTH: 714
<212> TYPE: DNA
<213> ORGANISM: oryctolagus cuniculus

<400> SEQUENCE: 69

```
atggacacga gggcccccac tcagctcctg gggctcctgc tgctctggct cccaggtgcc       60
acatttgccc aagtgctgac ccagactcca tcgcctgtgt ctgcagctgt gggaggcaca      120
gtcaccatca attgccagtc cagtcagagt gtttataaga caactacttt agcctggtat      180
cagcagaaac cagggcagcc tcccaagctc cttatctacg aaacatccaa actggcatct     240
ggggtcccac cgcggttcag cggcagtggg tctgggacac agttcactct caccatcagc      300
agcgtgcagt gtgacgatgc tgccacttac tactgtcaag gcggttatag tggtgttgat      360
tttatggctt cggcggagg gaccgaggtg gtcgtcaaag gtgatccagt tgcacctact     420
gtcctcatct tcccaccatc tgctgatctt gtggcaactg gaacagtcac catcgtgtgt     480
gtggcgaata atactttcc cgatgtcacc gtcacctggg aggtggatgg caccaccaa       540 acaactggca tcgagaacag taaaacaccg cagaattctg cagattgtac ctacaacctc     600
agcagcactc tgacactgac cagcacacag tacaacagcc acaaagagta cacctgcaag     660
gtgacccagg gcacgaccctc agtcgtccag agcttcaata gggggtgactg ttag         714
```

<210> SEQ ID NO 70
<211> LENGTH: 21
<212> TYPE: DNA
<213> ORGANISM: oryctolagus cuniculus

<400> SEQUENCE: 70

```
ctcagtagct atggagtgac c                                                21
```

<210> SEQ ID NO 71
<211> LENGTH: 48
<212> TYPE: DNA
<213> ORGANISM: oryctolagus cuniculus

<400> SEQUENCE: 71

```
ttgattggtg atcgtggtac tacgttctac gcgagctggg cgaaaagc                   48
```

<210> SEQ ID NO 72
<211> LENGTH: 24
<212> TYPE: DNA
<213> ORGANISM: oryctolagus cuniculus

<400> SEQUENCE: 72
gggagtgggt atggtgctcg catc						24

<210> SEQ ID NO 73
<211> LENGTH: 33
<212> TYPE: DNA
<213> ORGANISM: oryctolagus cuniculus

<400> SEQUENCE: 73
agtcagagtg tttataagaa caactactta gcc					33

<210> SEQ ID NO 74
<211> LENGTH: 21
<212> TYPE: DNA
<213> ORGANISM: oryctolagus cuniculus

<400> SEQUENCE: 74
gaaacatcca aactggcatc t							21

<210> SEQ ID NO 75
<211> LENGTH: 33
<212> TYPE: DNA
<213> ORGANISM: oryctolagus cuniculus

<400> SEQUENCE: 75
caaggcggtt atagtggtgt tgattttatg gct					33

<210> SEQ ID NO 76
<211> LENGTH: 1374
<212> TYPE: DNA
<213> ORGANISM: oryctolagus cuniculus

<400> SEQUENCE: 76
atggagactg ggctgcgctg gcttctcctg gtcgctgtgc tcaaaggtgt ccagtgtcag	60
tcggtgaagg agtccgaggg aggtctcttc aagccaacgg ataccctgac actcacctgc	120
acagtctctg gattctcccct cactacctat ggagtgacct gggtccgcca ggctccaggg	180
aatgggctgg agtggatcgg attgattggt gatcgcggta ccacttacta cgcgagctgg	240
gtgaatggcc gatccaccat caccagaaac accaacctga cacggtgac tctgaaaatg	300
accaggctga cagccgcgga cacggccacc tatttctgtg cgaggggag tggatatggt	360
gctcgcatct ggggcccagg caccctggtc accgtcgcct catggcaacc taaggctcca	420
tcagtcttcc cactggcccc ctgctgcggg gacacaccca gctccacggt gaccctgggc	480
tgcctggtca agggtacct cccggagcca gtgaccgtga cctggaactc gggcaccctc	540
accaatgggg tacgcacctt cccgtccgtc cggcagtcct caggcctcta ctcgctgagc	600
agcgtggtga gcgtgacctc aagcagccag cccgtcacct gcaacgtggc ccacccagcc	660
accaacacca agtggacaa gaccgttgcg cctcgacat gcagcaagcc cacgtgccca	720
cccctgaac tcctgggggg accgtctgtc ttcatcttcc ccccaaaacc caaggacacc	780
ctcatgatct cacgcacccc cgaggtcaca tgcgtggtgg tggacgtgag ccaggatgac	840
cccgaggtgc agttcacatg gtacataaac aacgagcagg tgcgcaccgc ccggcgccg	900
ctacgggagc agcagttcaa cagcacgatc cgcgtggtca gcaccctccc catcgcgcac	960

| | |
|---|---|
| caggactggc tgaggggcaa ggagttcaag tgcaaagtcc acaacaaggc actcccggcc | 1020 |
| cccatcgaga aaaccatctc caaagccaga gggcagcccc tggagccgaa ggtctacacc | 1080 |
| atgggccctc cccggggagga gctgagcagc aggtcggtca gcctgacctg catgatcaac | 1140 |
| ggcttctacc cttccgacat ctcggtggag tgggagaaga acgggaaggc agaggacaac | 1200 |
| tacaagacca cgccggccgt gctggacagc gacggctcct acttcctcta cagcaagctc | 1260 |
| tcagtgccca cgagtgagtg gcagcggggc gacgtcttca cctgctccgt gatgcacgag | 1320 |
| gccttgcaca accactacac gcagaagtcc atctcccgct ctccgggtaa atga | 1374 |

<210> SEQ ID NO 77
<211> LENGTH: 714
<212> TYPE: DNA
<213> ORGANISM: oryctolagus cuniculus

<400> SEQUENCE: 77

| | |
|---|---|
| atggacacga gggcccccac tcagctcctg gggctcctgc tgctctggct cccaggtgcc | 60 |
| acatttgccc aagtgctgac ccagactcca tcccccatgt ctgcagctct ggagggcaca | 120 |
| gtcaccatca attgccagtc cagtcagact gtttataaca ataactactt atcctggtat | 180 |
| cagcagaaac cagggcagcc tcccaagctc cttatctacg aaacatccaa actgtcatct | 240 |
| ggggtcccac cgcggttcag cggcagtggg tctgggacac agttcactct caccatcagc | 300 |
| agcgtgcagt gtgacgatgc tgccacttac tactgtcaag gcggttatag tggtgttgat | 360 |
| tttatggctt tcggcggagg gaccgaggtg gtcgtcaaag tgatccagt tgcacctact | 420 |
| gtcctcatct tcccaccatc tgctgatctt gtggcaactg gaacagtcac catcgtgtgt | 480 |
| gtggcgaata aatactttcc cgatgtcacc gtcacctggg aggtggatgg caccaccccaa | 540 |
| acaactggca tcgagaacag taaaacaccg cagaattctg cagattgtac ctacaacctc | 600 |
| agcagcactc tgacactgac cagcacacag tacaacagcc acaaagagta cacctgcaag | 660 |
| gtgacccagg gcacgacctc agtcgtccag agcttcaata ggggtgactg ttag | 714 |

<210> SEQ ID NO 78
<211> LENGTH: 21
<212> TYPE: DNA
<213> ORGANISM: oryctolagus cuniculus

<400> SEQUENCE: 78

| | |
|---|---|
| ctcactacct atggagtgac c | 21 |

<210> SEQ ID NO 79
<211> LENGTH: 48
<212> TYPE: DNA
<213> ORGANISM: oryctolagus cuniculus

<400> SEQUENCE: 79

| | |
|---|---|
| ttgattggtg atcgcggtac cacttactac gcgagctggg tgaatggc | 48 |

<210> SEQ ID NO 80
<211> LENGTH: 24
<212> TYPE: DNA
<213> ORGANISM: oryctolagus cuniculus

<400> SEQUENCE: 80

| | |
|---|---|
| gggagtggat atggtgctcg catc | 24 |

```
<210> SEQ ID NO 81
<211> LENGTH: 33
<212> TYPE: DNA
<213> ORGANISM: oryctolagus cuniculus

<400> SEQUENCE: 81
agtcagactg tttataacaa taactactta tcc                                    33

<210> SEQ ID NO 82
<211> LENGTH: 21
<212> TYPE: DNA
<213> ORGANISM: oryctolagus cuniculus

<400> SEQUENCE: 82
gaaacatcca aactgtcatc t                                                 21

<210> SEQ ID NO 83
<211> LENGTH: 30
<212> TYPE: DNA
<213> ORGANISM: oryctolagus cuniculus

<400> SEQUENCE: 83
ggcggttata gtggtgttga ttttatggct                                        30

<210> SEQ ID NO 84
<211> LENGTH: 1353
<212> TYPE: DNA
<213> ORGANISM: oryctolagus cuniculus

<400> SEQUENCE: 84
atggagactg gctgcgctg gcttctcctg gtcgctgtgc tcaaaggtgt ccagtgtcag         60
tcgctggagg agtccggggg tcgcctggtc acgcctggga caccctgac actcacctgc       120 acagtctctg gattctccct caataactac cacatatact gggtccgcca ggctccagga      180
aaggggctgg aatacatcgg aatcattttc aatggtggca catattacgc gagatggaca     240
aaaggccgat tcaccatctc caaaacctcg accacggtgg atctgaaaat gaccagtctg     300
acaaccgagg acacggccac ctatttctgt gccagagggg acggcatctg gggcccaggc     360
accctggtca ccgtctcctt agggcaacct aaggctccat cagtcttccc actggcccc     420 tgctgcgggg acacacccag ctccacggtg accctgggct gcctggtcaa agggtacctc     480
ccggagccag tgaccgtgac ctggaactcg ggcaccctca ccaatggggt acgcaccttc     540
ccgtccgtcc ggcagtcctc aggcctctac tcgctgagca gcgtggtgag cgtgacctca     600
agcagccagc ccgtcacctg caacgtggcc cacccagcca ccaacaccaa agtggacaag     660
accgttgcgc cctcgacatg cagcaagccc acgtgcccac ccctgaact  cctgggggga     720 ccgtctgtct tcatcttccc cccaaaaccc aaggacaccc tcatgatctc acgcaccccc     780
gaggtcacat gcgtggtggt ggacgtgagc caggatgacc ccgaggtgca gttcacatgg     840
tacataaaca cgagcaggt gcgcaccgcc cggccgccgc tacgggagca gcagttcaac     900
agcacgatcc gcgtggtcag caccctcccc atcgcgcacc aggactggct gaggggcaag     960
gagttcaagt gcaaagtcca acaaggca ctcccggccc ccatcgagaa aaccatctcc      1020
aaagccagag ggcagcccct ggagccgaag gtctacacca tgggccctcc ccgggaggag    1080
ctgagcagca ggtcggtcag cctgacctgc atgatcaacg gcttctaccc ttccgacatc    1140
tcggtggagt gggagaagaa cgggaaggca gaggacaact acaagaccac gccgccgtg    1200 ctggacagcg acggctccta cttcctctac agcaagctct cagtgcccac gagtgagtgg    1260
```

```
cagcggggcg acgtcttcac ctgctccgtg atgcacgagg ccttgcacaa ccactacacg    1320
cagaagtcca tctcccgctc tccgggtaaa tga                                 1353
```

<210> SEQ ID NO 85
<211> LENGTH: 720
<212> TYPE: DNA
<213> ORGANISM: oryctolagus cuniculus

<400> SEQUENCE: 85

```
atggacacga gggcccccac tcagctgctg gggctcctgc tgctctggct cccaggtgcc     60
acatttgccc aagtgctgac ccagactcca gcctccgtgt ctgcagctgt gggaggcaca    120
gtcaccatca attgccaggc cagtcagagt gttttaata caactatttt agcctggtat    180
cagcagaaac cagggcagcc tcccaagcgc ctgatctatt ctgcatccac tctggcgtct    240
ggggtctcat cgcggttcaa aggcagtgga tctgggacag aattcactct gaccatgagt    300
ggcgtggagt gtgacgatgc tgccacttac tactgtgcag gcagttttga ttgtaatagt    360
ggtgattgtg ttgctttcgg cggagggacc gaggtggtgg tcaagggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga gaacagtaaa acaccgcaga attctgcaga ttgtacctac    600
aacctcagca gcactctgac actgaccagc acacagtaca cagccacaa agagtacacc    660 tgcaaggtga cccagggcac gacctcagtc gtccagagct tcaatagggg tgactgttag    720
```

<210> SEQ ID NO 86
<211> LENGTH: 21
<212> TYPE: DNA
<213> ORGANISM: oryctolagus cuniculus

<400> SEQUENCE: 86

```
ctcaataact accacatata c                                               21
```

<210> SEQ ID NO 87
<211> LENGTH: 45
<212> TYPE: DNA
<213> ORGANISM: oryctolagus cuniculus

<400> SEQUENCE: 87

```
atcattttca atggtggcac atattacgcg agatggacaa aaggc                     45
```

<210> SEQ ID NO 88
<211> LENGTH: 12
<212> TYPE: DNA
<213> ORGANISM: oryctolagus cuniculus

<400> SEQUENCE: 88

```
ggggacggca tc                                                         12
```

<210> SEQ ID NO 89
<211> LENGTH: 33
<212> TYPE: DNA
<213> ORGANISM: oryctolagus cuniculus

<400> SEQUENCE: 89

```
agtcagagtg tttttaataa caactattta gcc                                  33
```

<210> SEQ ID NO 90
<211> LENGTH: 21
<212> TYPE: DNA
<213> ORGANISM: oryctolagus cuniculus

<400> SEQUENCE: 90
tctgcatcca ctctggcgtc t                                              21

<210> SEQ ID NO 91
<211> LENGTH: 39
<212> TYPE: DNA
<213> ORGANISM: oryctolagus cuniculus

<400> SEQUENCE: 91
gcaggcagtt ttgattgtaa tagtggtgat tgtgttgct                          39

<210> SEQ ID NO 92
<211> LENGTH: 342
<212> TYPE: PRT
<213> ORGANISM: homo sapiens

<400> SEQUENCE: 92

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

```
Ile Leu Pro Gly Leu Pro Gln Pro Ile Ala Thr Lys Cys Gln Lys Trp
            275                 280                 285

Arg His Ser Gln Val Thr Asn Ala Ala Ala Asn Cys Pro Gly Gln Met
        290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
            325                 330                 335

Ala Leu Lys Asn Tyr Ile
            340
```

<210> SEQ ID NO 93
<211> LENGTH: 1029
<212> TYPE: DNA
<213> ORGANISM: homo sapiens

<400> SEQUENCE: 93

```
atggcgcagg tgctgatcgt gggcgccggg atgacaggaa gcttgtgcgc tgcgctgctg      60
acgaggcaga cgtccggtcc cttgtacctt gctgtgtggg acaaggctga ggactcaggg    120
ggaagaatga ctacagcctg cagtcctcat aatcctcagt gcacagctga cttgggtgct    180
cagtacatca cctgcactcc tcattatgcc aaaaaacacc aacgttttta tgatgaactg    240
ttagcctatg gcgttttgag gcctctaagc tcgccattg aaggaatggt gatgaaagaa    300
ggagactgta actttgtggc acctcaagga atttcttcaa ttattaagca ttacttgaaa    360
gaatcaggtg cagaagtcta cttcagacat cgtgtgacac agatcaacct aagagatgac    420
aaatgggaag tatccaaaca acaggctccc ctgagcagtt tgatcttat tgttctcaca    480
atgccagttc ctgagattct gcagcttcaa ggtgacatca ccaccttaat tagtgaatgc    540
caaaggcagc aactggaggc tgtgagctac tcctctcgat atgctctggg cctcttttat    600
gaagctggta cgaagattga tgtcccttgg gctgggcagt acatcaccag taatccctgc    660
atacgcttcg tctccattga taataagaag cgcaatatag agtcatcaga aattgggcct    720
tccctcgtga ttcacaccac tgtcccattt ggagttacat acttggaaca cagcattgag    780
gatgtgcaag agttagtctt ccagcagctg gaaaacattt tgccgggttt gcctcagcca    840
attgctacca atgccaaaa atggagacat tcacaggtta caaatgctgc tgccaactgt    900
cctggccaaa tgactctgca tcacaaacct ttccttgcat gtggagggga tggatttact    960
cagtccaact tgatggctg catcacttct gccctatgtg ttctggaagc tttaaagaat   1020
tatatttaa                                                          1029
```

<210> SEQ ID NO 94
<211> LENGTH: 315
<212> TYPE: PRT
<213> ORGANISM: homo sapiens

<400> SEQUENCE: 94

```
Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60
```

| | | | | | | | | | | | | |
|---|---|---|---|---|---|---|---|---|---|---|---|---|
|Cys|Thr|Pro|His|Tyr|Ala|Lys|Lys|His|Gln|Arg|Phe|Tyr|Asp|Glu|Leu|
|65| | | |70| | | | |75| | | | |80| |

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Pro Ser Ala Gly Val Ile Leu Gly Cys Ala Lys
    290                 295                 300

Ser Pro Trp Met Met Ala Ile Gly Phe Pro Ile
305                 310                 315

<210> SEQ ID NO 95
<211> LENGTH: 945
<212> TYPE: DNA
<213> ORGANISM: homo sapiens

<400> SEQUENCE: 95

```
atggcgcagg tgctgatcgt gggcgccggg atgacaggaa gcttgtgcgc tgcgctgctg      60
acgaggcaga cgtccggtcc cttgtacctt gctgtgtggg acaaggctga ggactcaggg     120
ggaagaatga ctacagcctg cagtcctcat aatcctcagt gcacagctga cttgggtgct     180
cagtacatca cctgcactcc tcattatgcc aaaaaacacc aacgttttta tgatgaactg     240
ttagcctatg gcgttttgag gcctctaagc tcgcctattg aaggaatggt gatgaaagaa     300
ggagactgta actttgtggc acctcaagga atttcttcaa ttattaagca ttacttgaaa     360
gaatcaggtg cagaagtcta cttcagacat cgtgtgacac agatcaacct aagagatgac     420
aaatgggaag tatccaaaca aacaggctcc cctgagcagt ttgatcttat tgttctcaca     480
atgccagttc ctgagattct gcagcttcaa ggtgacatca ccaccttaat tagtgaatgc     540
caaaggcagc aactggaggc tgtgagctac tcctctcgat atgctctggg cctctttat     600
gaagctggta cgaagattga tgtcccttgg gctgggcagt acatcaccag taatccctgc     660
atacgcttcg tctccattga taataagaag cgcaatatag agtcatcaga aattgggcct     720
```

```
                                                   -continued
tccctcgtga ttcacaccac tgtcccattt ggagttacat acttggaaca cagcattgag      780
gatgtgcaag agttagtctt ccagcagctg gaaaacattt tgccgggttt gcctcagcca      840
attgctacca aatgccaaaa atggagacat tcacaggtac caagtgctgg tgtgattcta      900
ggatgtgcga agagccctg gatgatggcg attggatttc ccatc                      945
```

COMPOSITIONS TO REGULATE RENALASE IN THE TREATMENT OF DISEASES AND DISORDERS

STATEMENT REGARDING FEDERALLY SPONSORED RESEARCH OR DEVELOPMENT

This invention was made with Government support under Grant Nos. RC1DK086465, RC1DK086402, DK54021 and R01DK081037 awarded by the National Institutes of Health. The Government has certain rights in this invention

BACKGROUND OF THE INVENTION

Renalase (RNLS) is a protein produced predominantly in the kidney, heart, skeletal muscle, testes and to a lesser extent in other tissues (Xu et al., 2005 J Clin Invest. 115 (5):1275-80 and Wang et al., 2008 Mol Biol Rep. 35(4): 613-20). Two isoform variants of renalase have been described, Renalase-1 and Renalase-2. These two forms of renalase differ due to differential splicing of the final exon. Renalase has been described as a novel flavin adenine dinucleotide-containing monoamine oxidase with an activity that selectively deaminates the catecholamines epinephrine, norepinephrine and dopamine. A deficiency of renalase in the plasma of patients with end-stage renal disease, in comparasion to healthy individuals, has been described. Catecholamines play a major role in the maintenance and modulation of blood pressure, including in disease, through effects on cardiac output and vascular resistance. The infusion of a recombinant form of renalase into rats caused a decrease in cardiac contractility, heart rate, and blood pressure. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes.

A deficiency of renalase in the plasma of patients with end-stage renal disease, in comparison to healthy individuals, has been described. Patients with renal failure have been characterized with heightened levels of circulating catecholamines which correlate with hypertension and greater mortality through cardiovascular complications. Thus the protein renalase may play a role in the control and maintenance of catecholamine-induced changes in blood pressure and the deficiency of renalase observed in renal disease patients may be detrimental to outcomes. However, little is know about the role of renalase in cancer.

An essential feature of cancer is dysregulation of cell senescence and death. Renalase (RNLS) is a secreted flavoprotein that protects against ischemic and toxic cellular injury by signaling through the plasma membrane calcium ATPase PMCA4b to activate the PI3K/AKT, and MAPK pathways.

Skin cancer is a common human malignancy, and its incidence has been increasing in developed countries (Gray-Schopfer et al., 2007 Nature. 445:851-7; Lowe et al., 2014 Mayo Clinic Proceedings. 89:52-9; Lesinski et al., 2013 Future oncology. 9:925-7). Melanoma is the deadliest form of skin cancer, with low survival rates once it becomes unresectable (Lowe et al., 2014 Mayo Clinic Proceedings. 89:52-9). It is a molecularly heterogeneous disease and some of the key alterations in signaling pathways that participate in disease development and progression have been identified. The Ras/Raf/MEK/ERK and the PI3K/AKT signaling pathways play key roles in the pathogenesis of melanoma (Gray-Schopfer et al., 2007 Nature. 445:851-7; Lesinski et al., 2013 Future oncology. 9:925-7; Yajima et al., 2012 Dermatology research and practice. 2012:354191). Mutations in Ras, Raf, PI3K or PTEN (PI3K inhibitor) can lead to the sustained activation of ERK and AKT, which in turn promote cell survival and proliferation. Dankort et al. demonstrated this well with conditional melanocyte-specific expression of BRaf$^{V600E}$ in mice, none of whom developed melanoma, however, revealed 100% penetrance of melanoma development when combined with silencing of the Pten tumor suppressor gene (Dankort et al., 2009 Nature genetics. 41:544-52). The elucidation of these pathogenic pathways has facilitated the development of specific inhibitors that target hyper-activated kinases. While these agents have proven effective in the treatment of selective groups of patients with metastatic melanoma, their beneficial actions are often short lived, hence the pressing need for the identification of additional therapeutic targets.

RNLS expression is markedly increased in melanoma tumors, and specifically in CD163+ tumor associated macrophages (TAMs). In a cohort of patients with primary melanoma, disease-specific survival was inversely correlated with RNLS expression in the tumor mass, suggesting a pathogenic role for RNLS. Inhibition of RNLS signaling using siRNA, anti-RNLS antibodies, or a RNLS derived inhibitory peptide significantly decreases melanoma cells survival in vitro. Anti-RNLS therapy with a monoclonal antibody markedly inhibits melanoma tumor growth in a xenograft mouse model. Treatment with m28-RNLS (also known as 1D-28-4), caused a marked reduction in endogenous RNLS expression, and in total and phosphorylated STAT3 in CD163$^+$ TAMs. Increased apoptosis in tumor cells was temporally related to p38 MAPK mediated activation of the B-cell lymphoma 2 related protein Bax. Expression of the cell cycle inhibitor p21 increased and cell cycle arrest was documented. These results indicate that increased RNLS production by CD163$^+$ TAMs facilitates melanoma growth by activating STAT3, and that inhibition of RNLS signaling has potential therapeutic application in the management of melanoma.

Improved methods for the detection of renalase in bodily fluids and tissues may aid in the diagnosis and prognosis of renal disease, cardiovascular disease and/or cancer. However, the validation of renalase as a relevant biomarker requires highly selective reagents for its detection. Antibody-based technologies are widely used for the detection of biomarkers. To date there have been only a small number of reagent antibodies raised against renalase with no to minimal characterization.

Pancreatic cancer is one of the most lethal neoplasms, causing approximately 330,000 death globally and 40,000 in the US (World Cancer Report 2014. WHO Press; 2014). Pancreas cancer is difficult to detect, and most cases are diagnosed at a late stage (Nolen et al., 2014 PLoS ONE. 9(4):e94928). Although there has been some progress in the use of chemotherapy of this cancer, the disease remains extremely resistant to all drugs therapies (Hidalgo et al., 2010 New England Journal of Medicine. 362(17):1605-17). The overall 5 year survival for individuals with pancreatic cancer is <5% (Hidalgo et al., 2010 New England Journal of Medicine. 362(17):1605-17), and additional therapeutic targets are needed.

The development of pancreatic cancer relies on the stepwise accumulation of gene mutations (Jones et al., 2008 Science. 321(5897):1801-6), some of which cause abnormal MAPK, PI3K and JAK-STAT signaling. Progression from minimally dysplastic epithelium to dysplasia to invasive carcinoma reflects the stepwise accumulation of gene mutations that either activate oncogenes (e.g. KRAS2), or inactivate tumor suppressor genes 9e.g. CDKN2a/INK4a, TP53 and DPC4/SMaD4) (Hidalgo et al., 2012 Annals of Oncology. 23(suppl 10):x135-x8). Ninety-five, 90 and 75% of pancreatic tumors carry mutations in KRAS2, CDKN2a, and TP53, respectively. These mutations result in sustained and dysregulated proliferation that characterizes cancer growth. The mutational landscape and core signaling pathways in pancreatic ductal adenocarcinoma (PDAC) have been defined through a comprehensive genetic analysis of 24 advanced PDACs (Jones et al., 2008 Science. 321(5897): 1801-6). These data indicate that most PDACs contain a large number of genetic changes that are primarily point mutations, and which affect approximately 12 cell signaling pathways.

That study also identified five hundred and forty one genes overexpressed in PDAC by at least 10 fold in 90% of the tumors. This included a 2 to 4 fold increase in the recently characterized protein, renalase (RNLS), in tumors or in tumor derived cell lines. RNLS, a novel secreted flavo-protein (Xu et al., 2005 J Clin Invest. 115(5):1275-80; Desir et al., 2012 J Am Heart Assoc. 1(e002634; Desir et al., 2012 J Am Soc Hypertens. 6(6):417-26; Li et al., 2008 Circulation. 117(10):1277-82) with NADH oxidase activity, (Farzaneh-Far et al., 2010 PLoS One. 5(10):e13496; Beaupre et al., 2015 Biochemistry. 54(3):795-806) promotes cell and organ survival (Lee et al., 2013 J Am Soc Nephrol. 24(3):445-55) through a receptor-mediated process that is independent of its intrinsic enzymatic activities (Wang et al., 2014 Journal of the American Society of Nephrology. DOI: 10.1681/asn.2013060665). RNLS rapidly activates protein kinase B (AKT), the extracellular signal-regulated kinase (ERK), and the mitogen activated protein kinase (p38). Chemical inhibition of either ERK or AKT abrogated the protective effect of RNLS (Wang et al., 2014 Journal of the American Society of Nephrology. DOI:10.1681/asn.2013060665).

Accordingly, there exists a need for improved methods and compositions that bind renalase, such as antibodies, for the detection, diagnosis, prevention and treatment of diseases or disorders including renal disease, cardiovascular disease, and cancer. The present meets this need.

SUMMARY

The invention includes compositions comprising a renalase inhibitor, which may be a chemical compound, a protein, a peptide, a peptidomemetic, a renalase receptor, a renalase receptor fragment, an antibody, an antibody fragment, an antibody mimetic, a ribozyme, a small molecule chemical compound, an short hairpin RNA, an antisense nucleic acid molecule, siRNA, miRNA, a nucleic acid encoding an antisense nucleic acid molecule, a nucleic acid sequence encoding a protein. In some embodiments, the renalase inhibitor is a renalase binding molecule. In some embodiments, the renalase binding molecule is an antibody or binding portion thereof. In some embodiments, the renalase binding molecule that specifically binds to renalase with an affinity of at least $10^{-6}$M. In some embodiments, the renalase binding molecule specifically binds a peptide sequence selected from the group consisting of SEQ ID NO: 1-7. In some embodiments, the renalase is human renalase. In various embodiments, the antibody may be a monoclonal antibody, a polyclonal antibody, a single chain antibody, an immunoconjugate, a defucosylated antibody, and a bispecific antibody. In some embodiments, the immunoconjugate comprises a therapeutic agent or a detection moiety. In various embodiments, the antibody may be a humanized antibody, a chimeric antibody, a fully human antibody, an antibody mimetic. In one embodiment, the antibody comprises at least one selected from the group consisting of: a) the heavy chain CDR1 sequence selected from the group consisting of SEQ ID NO: 11 and SEQ ID NO: 19; b) the heavy chain CDR2 sequence selected from the group consisting of SEQ ID NO: 12 and SEQ ID NO: 20; c) the heavy chain CDR3 sequence selected from the group consisting of SEQ ID NO: 13 and SEQ ID NO: 21; d) the light chain CDR1 sequence selected from the group consisting of SEQ ID NO: 14 and SEQ ID NO: 22; e) the light chain CDR2 sequence selected from the group consisting of SEQ ID NO: 15 and SEQ ID NO: 23; f) the light chain CDR3 sequence selected from the group consisting of SEQ ID NO: 16 and SEQ ID NO: 24. In some embodiments, the antibody specifically binds a polypeptide comprising the amino acid sequence of SEQ ID NO: 4. In some embodiments, the antibody comprises at least one selected from the group consisting of: a) the heavy chain CDR1 sequence selected from the group consisting of SEQ ID NO: 27 and SEQ ID NO: 35; b) the heavy chain CDR2 sequence selected from the group consisting of SEQ ID NO: 28 and SEQ ID NO: 36; c) the heavy chain CDR3 sequence selected from the group consisting of SEQ ID NO: 29 and SEQ ID NO: 37; d) the light chain CDR1 sequence selected from the group consisting of SEQ ID NO: 30 and SEQ ID NO: 38; e) the light chain CDR2 sequence selected from the group consisting of SEQ ID NO: 31 and SEQ ID NO: 39; f) the light chain CDR3 sequence selected from the group consisting of SEQ ID NO: 32 and SEQ ID NO: 40. In some embodiments, the antibody specifically binds a polypeptide comprising the amino acid sequence of SEQ ID NO: 6. In some embodiments, the antibody comprises at least one selected from the group consisting of: a) the heavy chain CDR1 sequence SEQ ID NO: 43; b) the heavy chain CDR2 sequence SEQ ID NO: 44; c) the heavy chain CDR3 sequence SEQ ID NO: 45; d) the light chain CDR1 sequence SEQ ID NO: 46; e) the light chain CDR2 sequence SEQ ID NO: 47; f) the light chain CDR3 sequence SEQ ID NO: 48. In some embodiments, the antibody specifically binds a polypeptide comprising the amino acid sequence of SEQ ID NO: 7. In some embodiments, the antibody comprises a heavy chain sequence selected from the group consisting of SEQ ID NOs: 9, 17, 25, 33, and 41. In some embodiments, the antibody comprises a light chain sequence selected from the group consisting of SEQ ID NOs: 10, 18, 26, 34, and 42. In embodiment, the invention is a composition comprising an antibody that binds to renalase and competes with the binding of the antibody of claim 3 to renalase.

In another embodiment, the invention is a method of treating or preventing a disease or disorder associated with renalase in a subject, including the step of administering to the subject at least one renalase inhibitor. In some embodiments, the renalase inhibitor is administered to the subject in combination with a second therapeutic agent. In some embodiments, the disease or disorder associated with renalase is selected from the group consisting of renal disease, cardiovascular disease, cancer, and any combination thereof. In some embodiments, where the disease or disorder is cancer, the cancer is pancreatic cancer or melanoma.

In another embodiment, the invention is an isolated nucleic acid molecule encoding a renalase binding molecule, such as, but not limited to, an antibody. In another embodiment, the invention is an expression vector comprising a nucleic acid molecule encoding a renalase binding molecule, such as, but not limited to, an antibody. In another embodiment, the invention is a host cell comprising a nucleic acid molecule encoding a renalase binding molecule, such as, but not limited to, an antibody.

In another embodiment, the invention is a method of diagnosing a disease or disorder in a subject in need thereof, the method including the steps of determining the level of renalase in a biological sample of the subject, comparing the level of renalase in the biological sample of the subject with a comparator control, and diagnosing the subject with a disease or disorder when the level of renalase in the biological sample of subject is elevated when compared with the level of renalase of the comparator control. In one embodiment, the method includes the additional step of administering a treatment to the subject that was diagnosed as having a disease or disorder. In one embodiment, the level of renalase in the biological sample is determined by measuring the level of renalase mRNA in the biological sample. In one embodiment, the level of renalase in the biological sample is determined by measuring the level of renalase polypeptide in the biological sample. In one embodiment, the level of renalase polypeptide in the biological sample is determined using a renalase binding molecule. In one embodiment, the level of renalase in the biological sample is determined by measuring an activity (e.g., enzymatic activity, substrate binding activity, receptor binding activity, etc.) of renalase polypeptide in the biological sample. In one embodiment, the level of renalase in the biological sample is determined to be elevated when the level of renalase is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, by at least 1000%, when compared with a comparator control. In various embodiments, the comparator control is at least one selected from the group consisting of: a positive control, a negative control, a historical control, a historical norm, or the level of a reference molecule in the biological sample. In one embodiment, the disease or disorder is at least one selected from the group consisting renal disease, cardiovascular disease, cancer, and any combination thereof. In one embodiment, when the disease or disorder is cancer, and the cancer is pancreatic cancer or melanoma. In one embodiment, the subject is human.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A and 1B, is a series of images showing time course of renalase-dependent cell signaling. FIG. 1A shows human embryonic kidney cells (HK-2) incubated with renalase and activation of protein kinase B (AKT) and extracellular-signal regulated kinase (ERK) determined by Western blot analysis; representative blot is shown, (n=3); signals normalized to glyceraldehyde 3-phosphate dehydrogenase loading control (n=3); changes over baseline statistically significant at from 1 to 60 minutes for ERK, and AKT (T308) and at 30 minutes only for AKT (S473). FIG. 1B shows that renalase upregulates the anti-apoptotic molecule Bcl-2 in HK-2 cells and human umbilical vein endothelial cells (HUVEC).

FIG. 5, comprising FIGS. 5A through 5J, is a series of images showing sequences of antibodies that bind to renalase; complementarity determining regions (CDR) are underlined. FIGS. 5A and 5B show the sequences for 1D-28-4 heavy chain and light chain coding sequences, respectively. FIGS. 5C and 5D show the sequences for 1D-37-10 heavy chain and light chain coding sequences, respectively. FIGS. 5E and 5F show the sequences for 1F-26-1 heavy chain and light chain coding sequences, respectively. FIGS. 5G and 5H show the sequences for 1F-42-7 heavy chain and light chain coding sequences, respectively. FIGS. 5I and 5J show the sequences for 3A-5-2 heavy chain and light chain coding sequences, respectively.

FIG. 17, comprising FIG. 17A is an image showing RNLS expression detected using anti-RNLS-m28 for immunofluorescence staining of tissue microarrays of normal human skin (n=15), benign nevi (n=295), and malignant melanoma (n=264); representative result shown for each, blue color: nuclei, green color: melanocytes, and red color: RNLS. FIG. 17B is a chart depicting fluorescence intensity quantified using the AQUAnalysis™ software, Yale TMA: normal human skin (n=15), benign nevi (n=295), and malignant melanoma (n=264). FIG. 17C is a chart showing fluorescence intensity quantified using the AQUAnalysis™ software, US Biomax TMA: normal human skin (n=14), benign nevi (n=14), primary melanoma (n=35), and metastatic melanoma (n=11), *indicates p=0.009 and **indicates p<0.001. FIG. 17D depicts the Kaplan-Meier survival curve for melanoma-specific death; 119 serial primary melanomas collected from 1997 to 2004, tumors stratified into low and high RNLS expression by the median AQUA score=75,764.45, *indicates p=0.008.

FIG. 18, comprising FIG. 18A is a chart depicting A375.S2, MeWo, Skme15, and Skme128 cells serum-starved and then treated with BSA (30 ug/ml) or rRNLS (30 ug/ml), and cell viability measured 72 hrs later using the WST-1 assay; n=6, *indicates p<0.05 and indicates p<0.005. FIG. 18B is a chart depicting A375.S2 cells serum-starved for 24 hrs, then untreated or incubated with 30 ug/ml of either bovine serum albumin (BSA) or rRNLS for 3 days; total and live cell number were determined using trypan blue and an automated cell counter; n=6, indicates p<0.001.

FIG. 19, comprising FIG. 19A is a chart depicting relative cell viability after transient transfection of melanoma cells A375.S2 and SK-Me1-28 using a RNLS-specific siRNA, or a non-specific control siRNA, where cell viability was assessed 72 hrs later using the WST-1 assay; n=6, *indicates p=0.03 and **indicates p=0.003. FIG. 19B comprises two charts depicting relative cell viability: Left panel: Cells were treated with indicated antibodies for 72 hrs and cell viability was determined using WST-1; m28-RNLS (also known as 1D-28-4), m37-RNLS (also known as 1D-37-10): monoclonal antibodies raised against RNLS peptide RP220; Right panel: A375.S2 cells treated with increasing doses of m28-RNLS for 72 hrs and cell viability determined with a WST-1 assay; n=6, *indicates p<0.05 and indicates p<0.005. FIG. 19C comprises representative photos of A375.S2, SkMe128, and SkMe15 after 72 hrs incubation with either control rabbit IgG or m28-RNLS. FIG. 19D is a chart depicting relative cell viability, comprising amino acid (AA) sequence of RNLS peptide antagonist (RP220A). A375.S2 cells treated with the indicated concentrations of BSA or RP220A, and cell viability measured 72 hrs later using the WST-1 assay; n=6, indicates p<0.005.

FIG. 20, comprising FIGS. 20A and 20B, comprises a chart and two images showing that inhibition of RNLS signaling blocks melanoma growth in vivo.

FIG. 21, comprising FIG. 21A comprises a series of images showing xenograft tumors treated with either rabbit IgG as a negative control or with RNLS monoclonal Ab, and probed for RNLS, phosphorylated STAT3, and total STAT3 by immunofluorescence; phospho STAT3=p-$Y^{705}$-STAT3; representative result shown for each, blue color: nuclei, green color: RNLS, and red color: phospho STAT3 (left panel) or total STAT3 (right panel). FIG. 21B is an image showing xenograft tumors treated with either rabbit IgG as a negative control or with RNLS monoclonal Ab, and tumor cell lysates probed for RNLS, phosphorylated STAT3, total STAT3, and p21 by western blot; p-$Y^{705}$-STAT3: phosphorylation at tyrosine 705; representative study. FIG. 21C is a chart depicting quantification of STAT3 protein expression in samples shown in FIG. 21B; p-$Y^{705}$-STAT3 signals normalized to total STAT3, total STAT3 signals normalized to protein loading measurements; n=3, *indicates p<0.05 and **indicates p<0.005. FIG. 21D is a chart showing xenograft tumors (n=14 each) treated with either rabbit IgG as a negative control or with RNLS monoclonal Ab, and probed for human and mouse RNLS expression by qPCR, *indicates p<0.05. FIG. 21E comprises representative images of IHC staining of sections from A375.S2 xenografted tumors (n=14 each) treated with m28-RNLS or control rabbit IgG for TUNEL assay to mark apoptotic cells or cell cycle inhibitor p21; brown color: TUNEL or p21 positive cells, respectively. FIG. 21F is an image showing A375.S2 cells treated with anti-RNLS antibody or control goat IgG; time course of p38 phosphorylation and Bax expression assessed by western blot; p-p38=phosphorylated p38; Bax=bcl-2 like protein 4.

FIG. 22, comprising FIG. 22A comprises images showing: Top panel: Tissue microarray human melanoma samples examined by IF for coexpression of RNLS and the pan-macrophage marker CD68; blue color: nuclei, green color: RNLS, and red color: all macrophages; DAPI: nuclear stain, RNLS-CD68: merged RNLS and CD68 stains; Middle panel: Melanoma samples examined by IF for coexpression of RNLS and the alternatively activated macrophage (M2) marker CD163; blue color: nuclei, green color: RNLS, and red color: M2 macrophages; DAPI: nuclear stain, RNLS-CD163: merged RNLS and CD163 stains. Significant coexpression of RNLS and CD163 noted; Lower panel: Melanoma samples examined by IF for coexpression of RNLS and the classically activated macrophage (M1) marker CD86; blue color: nuclei, green color: RNLS, and red color: M1 macrophages; DAPI: nuclear stain, RNLS-CD163: merged RNLS and CD86 stains. No significant coexpression of RNLS and CD186 noted. FIG. 22B comprises two images showing xenograft tumors treated with either rabbit IgG as a negative control or with m28-RNLS, and probed for RNLS and M2 TAMs (CD163+ cells) by immunofluorescence; representative result shown for each, green color: M2 macrophages, and red color: RNLS. m28-RNLS treatment decreases CD163+ TAMs and RNLS expression. FIG. 22C depicts the proposed mechanism of action of m28-RNLS-TAM: tumor associated macrophages, CD163: alternatively activated macrophage (M2) marker, CD86: classically activated macrophage (M1) marker, RNLS: renalase, m28-RNLS: antirenalase monoclonal antibody, t-STAT3: total STAT3, p-STAT3: phosphorylated STAT3.

FIG. 23, comprising FIGS. 23A through 23E, is a series of images and charts showing RNLS expression in some cancers, and association with poor patient outcome in PDAC. FIG. 23A is a chart showing RNLS mRNA level measured by qPCR in cDNA arrays containing 182 human tumor samples (OriGene Technologies) from 15 different tumor types; *indicates p<0.05, **indicates p=0.0001. FIG. 23B is a chart showing RNLS mRNA level measured by qPCR in normal pancreas (n=6), pancreatic ductal adenocarcinomas (n=11), and pancreatic neuroendocrine tumors (n=23); *indicates p=0.05; indicates p=0.00017. FIG. 23C is an image showing RNLS protein expression detected by immunohistochemistry using m28-RNLS in normal human pancreatic tissue (left panel, n=90), ductal adenocarcinoma (Grades 1-4, n=20 each); representative result shown for each; RNLS protein stains brown. FIG. 23D shows RNLS expression detected using anti-RNLS-m28 for immunofluorescence staining of tissue microarray of normal human pancreatic tissue (left panel, n=90), ductal carcinoma (middle panel, n=90); representative result shown for each, and blue color: nuclei, green color: cytokeratin, and red color: RNLS; right panel: fluorescence intensity quantified using the AQUAnalysis™ software, normal human pancreatic tissue (n=90), ductal carcinoma (n=90), *indicates p=0.00013. FIG. 23E shows the Kaplan-Meier survival curve for survival rates; Biomax cohort of 69 PDACs stratified into low (n=35, RNLS AQUA score<median) and high (n=34, RNLS AQUA score>median) RNLS expression, *indicates p=0.0001.

FIG. 24, comprising FIG. 24A shows PDACC lines BxPC3, Panc1 and MiaPaCa2 are serum starved for 48 hrs, then incubated with 30 µg/ml of either bovine serum albumin (BSA) or rRNLS for 3 days; total and live cell number determined using trypan blue and an automated cell counter; n=4, **indicates p<0.0001. FIG. 24B is a chart depicting cell viability relative to control: MiaPaCa2 cell serum starved and then treated with BSA (30 µg/ml) or rRNLS (30 µg/ml), with and without pretreatment with MEK1 inhibitor U0126, and cell viability measured 72 hrs later using the WST-1 assay; n=6, *indicates p<0.005. FIG. 24C comprises an image and a chart showing that siRNA mediated inhibition of PMCA4b expression blocks RNLS mediated MAPK signaling; Left and middle panels: MiaPaCa2 cells transfected with either non-targeting or PMCA4b siRNA, maintained in serum free medium for 3 days and treated with either 25 µg of BSA or 25 of RNLS peptide RP-220 for the indicated time; RP-220 mediated ERK and STAT3 activation assessed by western blot and representative immunoblots are shown; p-ERK=phosphorylated ERK, p-Y$^{705}$-STAT3=phosphorylated STAT3, p-S727-STAT3=phosphorylated STAT3, BSA=bovine serum albumin, RP-220=RNLS peptide agonist; Right panel: quantification of phosphorylated ERK (p-ERK), signals normalized to glyceraldehyde 3-phosphate dehydrogenase (GAPDH) loading control; n=3, *=P<0.05.

FIG. 24D shows is a graph showing fluorescence activated cell sorting (FACS) analysis of MiaPaCa2 cells treated with BSA (30 µg/ml) or rRNLS (30 µg/ml), n=3.

FIG. 25, comprising FIG. 25A is a chart showing relative cell viability following transient transfection of Panc1 cells using a RNLS-specific siRNA, or a non-specific control siRNA, and cell viability assayed 96 h later using the WST-1 reagent; n=6, **indicates p<0.001. FIG. 25B is a chart showing relative cell viability when cells were treated with indicated antibodies for 72 hrs and cell viability determined using WST-1; m28-RNLS and m37-RNLS: monoclonal antibodies raised against RNLS peptide RP220, ab31291: Abcam polyclonal antibody raised against a partial sequence of RP-220; n=6, *indicates p<0.005. FIG. 25C shows representative photos of MiaPaCa2 cells after 3 days incubation with m28-RNLS, n=10. FIG. 25D is a chart showing tumor volume increase after athymic nude mice received subcutaneous injection of Panc1 cells transduced with RNLS shRNA (sh-RNLS) or control (sh-Control); tumor volume measured every 23 days for up to 30 days, n=6 each; *indicates p<0.05. FIG. 25E is chart showing tumor volume increase after nude mice were xenografted with BxPC3; tumor volume measured prior to treatment every 3-4 days with 2 mg/kg of either rabbit IgG as a negative control or with m28-RNLS, n=10, *indicates p<0.05.

FIG. 26, comprising FIG. 26A shows representative images of TUNEL staining of sections from BxPC3 xenografted tumors (n=14 each) treated with anti-m28-RNLS or control rabbit IgG; arrow: TUNEL positive cells. FIG. 26B is a chart depicting FACS analysis of Panc1 cells in culture treated with either m28-RNLS (30 µg/ml) or 100 µM etoposide (positive control) for 4 days; n=3, *indicates p<0.05. FIG. 26C is an image showing Panc1 cells treated with polyclonal ab31291 or with goat IgG as a negative control, and cells lysates probed for p38 and Bax activation by western blot. FIG. 26D shows representative images of IHC staining of sections from BxPC3 xenografted tumors (n=14 each) treated with anti-m28-RNLS or control rabbit IgG for cell proliferation marker ki67, and cell cycle inhibitor p21. FIG. 26E is a chart showing the effect of m28-RNLS on cell cycle of Panc1 cells determined by FACS analysis; green curve: no treatment, purple curve: rabbit IgG, red curve: m28-RNLS 30 µg/ml.

FIG. 27, comprising FIG. 27A is an image showing activation of STAT3 by RNLS in Panc1 cells; Panc1 cells in culture treated with either BSA or RNLS, and STAT3 phosphorylation assessed by western blot; p-Ser$^{727}$-STAT3: phosphorylation at serine 727, p-Y$^{705}$-STAT3: phosphorylation at tyrosine 705; representative study. FIG. 27B is a chart depicting the quantification of STAT3 phosphorylation with RNLS; signals normalized to total STAT3; n=3, *=P<0.05.

FIG. 27C is an image showing that m28-RNLS inhibits STAT3 phosphorylation; Panc1 cells in culture treated with either rabbit IgG or anti-RNLS monoclonal m28-RNLS for up to 4 days, and STAT3 phosphorylation assessed by western blot; p-Ser$^{727}$-STAT3: phosphorylation at serine 727, p-Y$^{705}$-STAT3: phosphorylation at tyrosine 705; GAPDH loading control; representative study. FIG. 27D is a chart showing the quantification of STAT3 phosphorylation with m28-RNLS; signals normalized to GAPDH loading control; n=3, *=P<0.05. FIG. 27E depicts the proposed mechanistic model for antitumor activity of m28-RNLS.

DETAILED DESCRIPTION OF THE INVENTION

Figure 1:
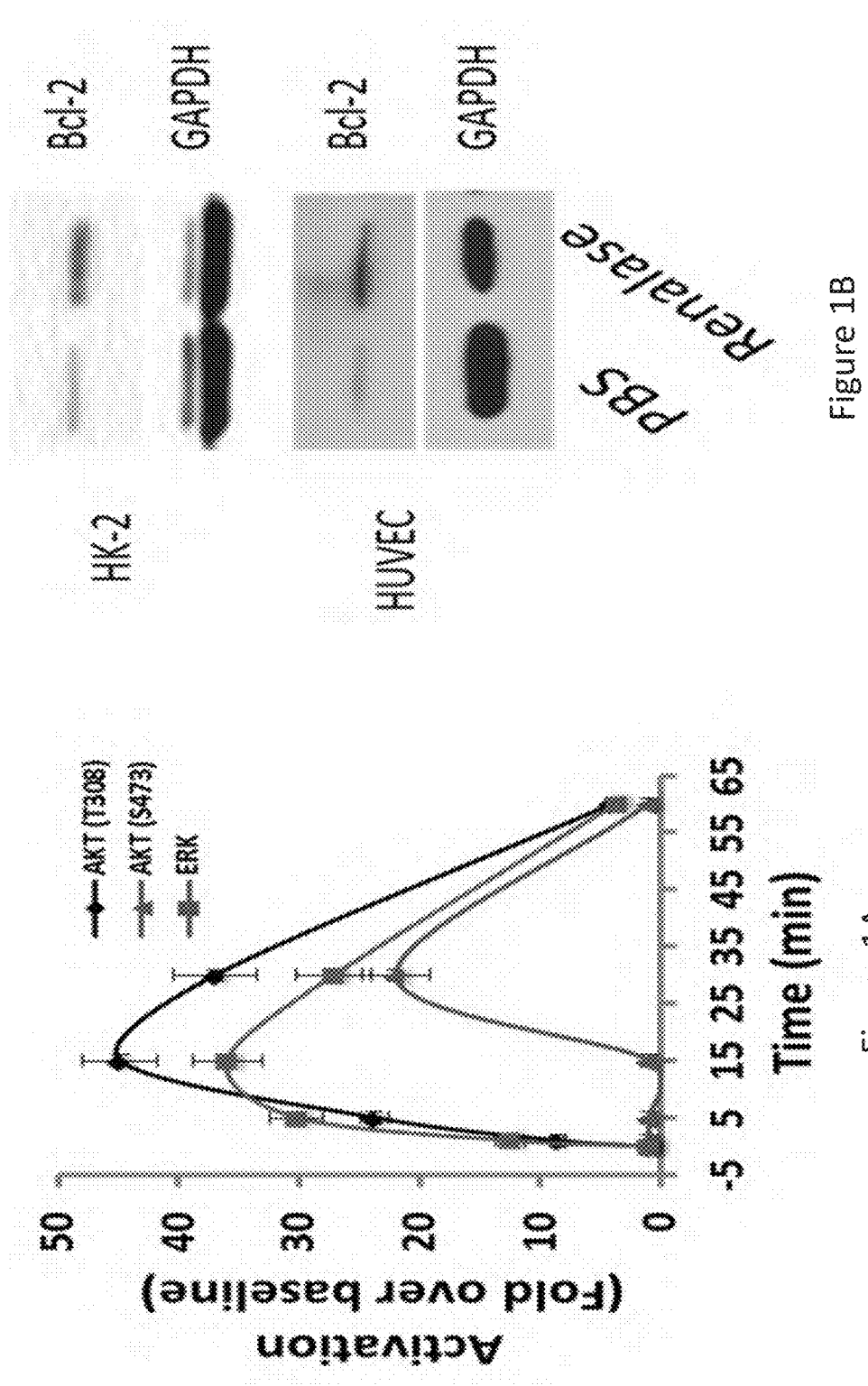
FIG. 1, comprising
Figure 2:
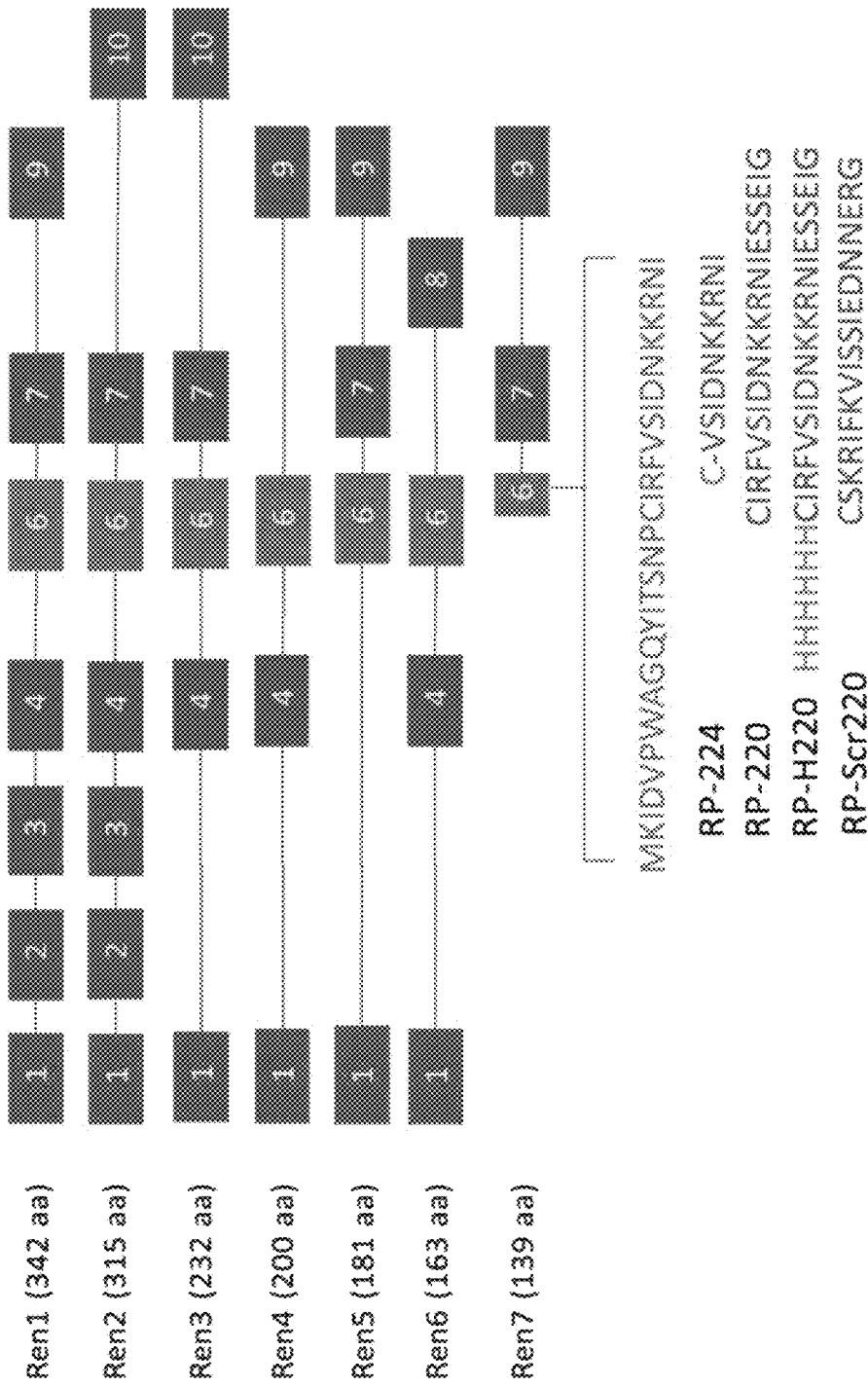
FIG. 2 is an image showing renalase isoforms Ren1-7: exons numbered from 1 to 10; RP-224, renalase peptide amino acid 224 233 of Ren1 or Ren2; RP-220, amino acids 220-239; RP-H220, histidine-tagged RP-220; RP-Scr220, scrambled RP-220.
Figure 3:
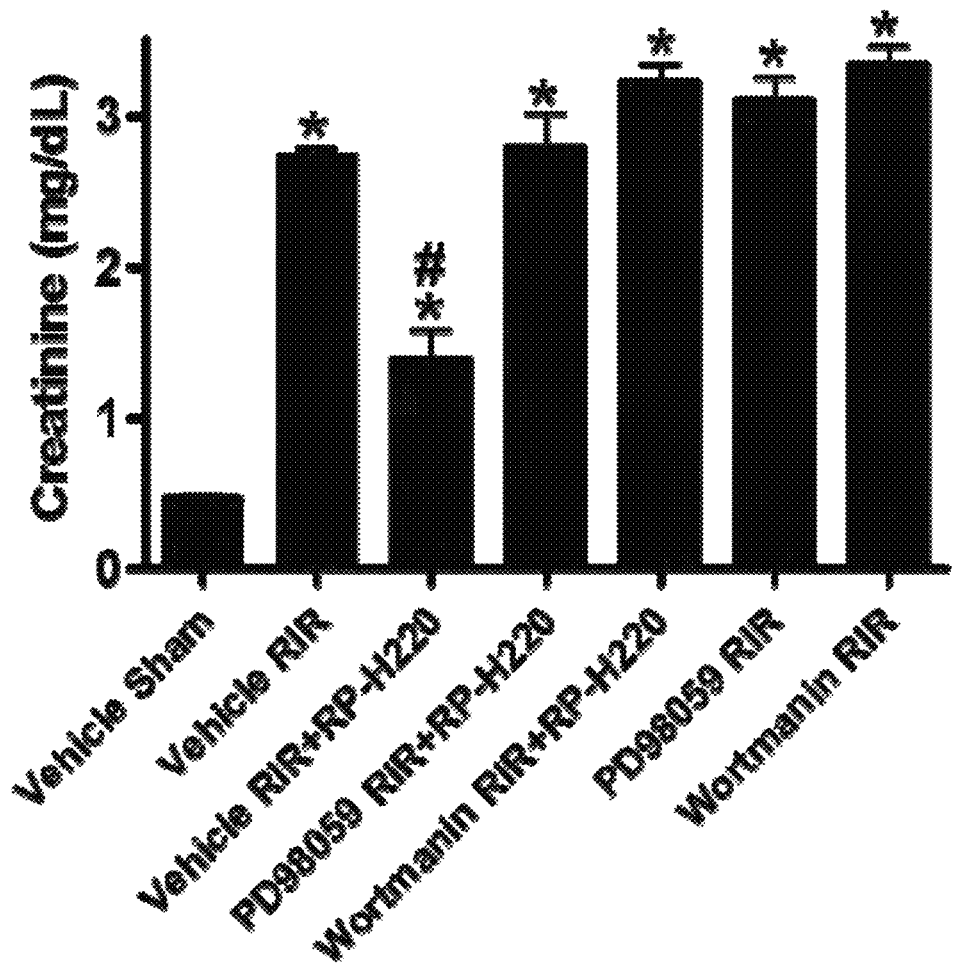
FIG. 3 is a chart showing that ERK or AKT inhibition abrogates protective effect of renalase peptide: WT mice subjected to sham surgery or to 30 minutes of renal ischemia and reperfusion; RP-H220 or vehicle (saline) injected 10 minutes before renal ischemia. ERK inhibitor PD98059 or the PI3K/AKT inhibitor wortmannin abrogated RP-H220's protective effect.

This invention relates to the inhibition of renalase using an inhibitor of renalase. In various embodiments, the invention is directed to compositions and methods for treating a renalase-associated pathology or renalase-associated condition in an individual by administering to a subject in need thereof an inhibitor of renalase. In various embodiments, the diseases and disorders diagnosable, preventable and treatable using the compositions and methods of the invention include acute renal failure (i.e., acute tubular necrosis, or ATN, an ischemic condition in the kidney), cardiovascular disease, and cancer.

In one embodiment, the invention broadly relates to the treatment, prevention, and diagnosis of cancer. In one embodiment, the present invention is directed to methods and compositions for diagnosis, treatment, inhibition, prevention, or reduction of cancer. In one embodiment, the invention provides compositions and methods for modulating one or more of the level, production, and activity of renalase. In the context of cancer and related diseases and disorders, the invention provides compositions and methods for decreasing one or more of the level, production, and activity of renalase. Some aspects of the invention provide methods and compositions for the treatment, prevention, diagnosis or prognosis of cancer metastasis.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), which are provided throughout this document.

The nomenclature used herein and the laboratory procedures used in analytical chemistry and organic syntheses described below are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, or ±10%, or ±5%, or ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

The term "analog" as used herein generally refers to compounds that are generally structurally similar to the compound of which they are an analog, or "parent" compound. Generally analogs will retain certain characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, more preferably at least about 80%-85% or about 86%-89%, and still more preferably at least about 90%, about 92%, about 94%, about 96%, about 98% or about 99% of the amino acids in a given amino acid sequence the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function.

The term "antibody," as used herein, refers to an immunoglobulin molecule which is able to specifically bind to a specific epitope of a binding partner molecule. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the binding specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the binding region and would be understood to be so by a skilled person. See for example Chothia et al., (1989) Conformations of immunoglobulin hypervariable regions; Nature 342, p 877-883.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific binding partner molecule, but does not substantially recognize or bind other molecules in a sample. For example, an antibody that specifically binds to a binding partner molecule from one species may also bind to that binding partner molecule from one or more species. But, such cross-species reactivity does not itself alter the classification of an antibody as specific. In another example, an antibody that specifically binds to binding partner molecule may also bind to different allelic forms of the binding partner molecule. However, such cross reactivity does not itself alter the classification of an antibody as specific.

In some instances, the terms "specific binding" or "specifically binding", can be used in reference to the interaction of an antibody, a protein, or a peptide with a second binding partner molecule, to mean that the interaction is dependent upon the presence of a particular structure (e.g., an antigenic determinant or epitope) on the binding partner molecule; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some instances, the terms "specific binding" and "specifically binding" refers to selective binding, wherein the antibody recognizes a sequence or conformational epitope important for the enhanced affinity of binding to the binding partner molecule.

As used herein, the term "neutralizing" refers to neutralization of biological activity of a renalase when a binding protein specifically binds the renalase. Preferably a neutralizing binding protein is a neutralizing antibody, the binding of which to renalase results in inhibition of a biological activity of renalase. Preferably the neutralizing binding protein binds renalase and reduces a biologically activity of renalase by at least about 20%, 40%, 60, 80%, 85% or more. In some embodiments, the renalase is human renalase.

The term "epitope" has its ordinary meaning of a site on binding partner molecule recognized by an antibody or a binding portion thereof or other binding molecule, such as, for example, an scFv. Epitopes may be molecules or segments of amino acids, including segments that represent a small portion of a whole protein or polypeptide. Epitopes may be conformational (i.e., discontinuous). That is, they may be formed from amino acids encoded by noncontiguous parts of a primary sequence that have been juxtaposed by protein folding.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer (e.g., melanoma), pancreatic cancer, colorectal cancer, renal cancer, liver cancer, brain cancer, lymphoma, leukemia, lung cancer, sarcoma and the like.

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

The term "high affinity" for binding domain polypeptides described herein refers to a dissociation constant (Kd) of at least about $10^{-6}$M, preferably at least about $10^{-7}$M, more preferably at least about $10^{-8}$M or stronger, more preferably at least about $10^{-9}$M or stronger, more preferably at least about $10^{-10}$ M or stronger, for example, up to $10^{-12}$ M or stronger. However, "high affinity" binding can vary for other binding domain polypeptides.

The term "inhibit," as used herein, means to suppress or block an activity or function, for example, about ten percent relative to a control value. Preferably, the activity is suppressed or blocked by 50% compared to a control value, more preferably by 75%, and even more preferably by 95%. "Inhibit," as used herein, also means to reduce the level of a molecule, a reaction, an interaction, a gene, an mRNA, and/or a protein's expression, stability, function or activity by a measurable amount or to prevent entirely. Inhibitors are compounds that, e.g., bind to, partially or totally block activity, decrease, prevent, delay activation, inactivate, desensitize, or down regulate a protein, a gene, and an mRNA stability, expression, function and activity, e.g., antagonists.

The terms "modulator" and "modulation" of a molecule of interest, as used herein in its various forms, is intended to encompass antagonism, agonism, partial antagonism and/or partial agonism of an activity associated the protease of interest. In various embodiments, "modulators" may inhibit or stimulate protease expression or activity. Such modulators include small molecules agonists and antagonists of a protease molecule, antisense molecules, ribozymes, triplex molecules, and RNAi polynucleotides, and others.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "conservative substitution," when describing a polypeptide, refers to a change in the amino acid composition of the polypeptide that does not substantially alter the activity of the polypeptide, i.e., substitution of amino acids with other amino acids having similar properties. Conservative substitution tables providing functionally similar amino acids are well known in the art. The following six groups each contain amino acids that are generally understood to represent conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W) (see also, Creighton, 1984, Proteins, W.H. Freeman and Company). In addition to the above-defined conservative substitutions, other modifications of amino acid residues can also result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, for example, often less than 5%, in an encoded sequence. Further, a conservatively modified variant can be made from a recombinant polypeptide by substituting a codon for an amino acid employed by the native or wild-type gene with a different codon for the same amino acid.

The term "RNA" as used herein is defined as ribonucleic acid. The term "recombinant DNA" as used herein is defined as DNA produced by joining pieces of DNA from different sources.

The term "recombinant polypeptide" as used herein is defined as a polypeptide produced by using recombinant DNA methods.

By "pharmaceutically acceptable" it is meant, for example, a carrier, diluent or excipient that is compatible with the other ingredients of the formulation and generally safe for administration to a recipient thereof. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

The terms "patient," "subject," "individual," and the like are used interchangeably herein, and refer to any animal, preferably a mammal, and most preferably a human, having a complement system, including a human in need of therapy for, or susceptible to, a condition or its sequelae. Thus, the individual may include, for example, dogs, cats, pigs, cows, sheep, goats, horses, rats, monkeys, and mice and humans.

The phrase "percent (%) identity" refers to the percentage of sequence similarity found in a comparison of two or more amino acid sequences. Percent identity can be determined electronically using any suitable software. Likewise, "similarity" between two polypeptides (or one or more portions of either or both of them) is determined by comparing the amino acid sequence of one polypeptide to the amino acid sequence of a second polypeptide. Any suitable algorithm useful for such comparisons can be adapted for application in the context of the invention.

A "therapeutic" treatment is a treatment administered to a subject who exhibits signs of pathology, for the purpose of diminishing or eliminating those signs.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to the inhibition of renalase using an inhibitor of renalase. In various embodiments, the invention is directed to compositions and methods for treating a renalase-associated disease or disorder in an individual by administering to a subject in need thereof an inhibitor of renalase. In some embodiments, the renalase inhibitor is a renalase binding molecule. In some embodiments, the renalase binding molecule is an antibody. In various embodiments, the diseases and disorders diagnosable, preventable and treatable using the compositions and methods of the invention include acute renal failure (i.e., acute tubular necrosis, or ATN, an ischemic condition in the kidney), cardiovascular disease, and cancer.

In one embodiment, the invention broadly relates to the treatment, prevention, and diagnosis of cancer. In one embodiment, the present invention is directed to methods and compositions for diagnosis, staging, treatment, inhibition, prevention, or reduction of cancer. In one embodiment, the invention provides compositions and methods for modulating one or more of the level, production, and activity of renalase. In the context of cancer and related diseases and disorders, the invention provides compositions and methods for decreasing one or more of the level, production, and activity of renalase. Some aspects of the invention provide methods and compositions for the treatment, prevention, diagnosis or prognosis of cancer metastasis.

Therapeutic Inhibitor Compositions and Methods of Use

In various embodiments, the present invention includes renalase inhibitor compositions and methods of treating or preventing a disease or disorder where a diminished level or activity of renalase is desired. One non-limiting example of a disease or disorder where a diminished level or activity of renalase is desired which can be treated or prevented with the compositions and methods of the invention includes cancer. In various embodiments, the renalase inhibitor compositions and methods of treatment or prevention of the invention diminish the amount of renalase polypeptide, the amount of renalase peptide fragment, the amount of renalase mRNA, the amount of renalase enzymatic activity, the amount of renalase substrate binding activity, the amount of renalase receptor binding activity, or a combination thereof.

It will be understood by one skilled in the art, based upon the disclosure provided herein, that a decrease in the level of renalase encompasses the decrease in renalase expression, including transcription, translation, or both, and also encompasses promoting the degradation of renalase, including at the RNA level (e.g., RNAi, shRNA, etc.) and at the protein level (e.g., Ubiquitination, etc.) The skilled artisan will also appreciate, once armed with the teachings of the present invention, that a decrease in the level of renalase includes a decrease in a renalase activity (e.g., enzymatic activity, substrate binding activity, receptor binding activity, etc.). Thus, decreasing the level or activity of renalase includes, but is not limited to, decreasing transcription, translation, or both, of a nucleic acid encoding renalase; and it also includes decreasing any activity of a renalase polypeptide, or peptide fragment thereof, as well. The renalase inhibitor compositions and methods of the invention can selectively inhibit renalase, or can inhibit both renalase and another molecule.

Inhibition of renalase can be assessed using a wide variety of methods, including those disclosed herein, as well as methods known in the art or to be developed in the future. That is, the routineer would appreciate, based upon the disclosure provided herein, that decreasing the level or activity of renalase can be readily assessed using methods that assess the level of a nucleic acid encoding renalase (e.g., mRNA), the level of a renalase polypeptide, or peptide fragment thereof, present in a biological sample, the level of renalase activity (e.g., enzymatic activity, substrate binding activity, receptor binding activity, etc.), or combinations thereof.

One skilled in the art, based upon the disclosure provided herein, would understand that the invention is useful in treating or preventing in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where renalase plays a role and where diminished renalase level or activity will promote a positive therapeutic outcome. In various embodiments, the disease or disorder treatable or preventable using the compounds and methods of the invention include acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

In another embodiment, the renalase inhibitor of the invention can be administered to a patient who is being treated with exogenous renalase, recombinant renalase, renalase fragment, and/or renalase activator, in order to control, titrate, diminish, or stabilize the level or activity of endogenous and/or exogenous renalase in the patient.

The renalase inhibitor compositions and methods of the invention that decrease the level or activity (e.g., enzymatic activity, substrate binding activity, receptor binding activity, etc.) of renalase, or a renalase fragment, include, but should not be construed as being limited to, a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. In some embodiments, the inhibitor is an allosteric inhibitor. One of skill in the art would readily appreciate, based on the disclosure provided herein, that a renalase inhibitor composition encompasses any chemical compound that decreases the level or activity of renalase, or a fragment thereof. Additionally, a renalase inhibitor composition encompasses a chemically modified compound, and derivatives, as is well known to one of skill in the chemical arts.

The renalase inhibitor compositions and methods of the invention that decrease the level or activity (e.g., enzymatic activity, substrate binding activity, receptor binding activity, etc.) of renalase, or a renalase fragment, include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to renalase. In some embodiments, the antibodies of the invention are bispecific antibodies, where the first specificity is to renalase and the second specificity is to a targeting molecule on a cell or tissue to guide the bispecific antibody to an anatomic location where the targeting molecule is present and where the renalase binding is desired. In some embodiments, the antibodies of the invention are bispecific antibodies, where the first specificity is to renalase and the second specificity is to a second binding partner molecule (i.e., payload) that is carried by the antibodies second specificity and deployed to an anatomic location where renalase binding is desired.

In some embodiments, the administration to the subject of the renalase inhibitor (e.g., renalase binding molecule) of the invention for the treatment of cancer, serves to initiate and/or supplement an immune response by the subject's immune system against the cancer. The subject's immune response against the cancer can be any host defense or response, including an innate immune response, a humoral immune response, a cell-mediated immune response, or a combination thereof.

Further, one of skill in the art, when equipped with this disclosure and the methods exemplified herein, would appreciate that a renalase inhibitor composition includes such inhibitors as discovered in the future, as can be identified by well-known criteria in the art of pharmacology, such as the physiological results of inhibition of renalase as described in detail herein and/or as known in the art. Therefore, the present invention is not limited in any way to any particular renalase inhibitor composition as exemplified or disclosed herein; rather, the invention encompasses those inhibitor compositions that would be understood by the routineer to be useful as are known in the art and as are discovered in the future.

Further methods of identifying and producing renalase inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, a renalase inhibitor can be synthesized chemically. Further, the routineer would appreciate, based upon the teachings provided herein, that a renalase inhibitor composition can be obtained from a recombinant organism. Compositions and methods for chemically synthesizing renalase inhibitors and for obtaining them from natural sources are well known in the art and are described in the art.

One of skill in the art will appreciate that an inhibitor can be administered as a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the level or activity of renalase can serve in the compositions and methods of the present invention to decrease the level or activity of renalase.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of renalase, or to diminish the amount of a molecule that causes an increase in the amount or activity of renalase, thereby decreasing the amount or activity of renalase.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing renalase, or of a gene expressing a protein that increases the level or activity of renalase, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168, 053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

Alternatively, inhibition of a gene expressing renalase, or of a gene expressing a protein that increases the level or activity of renalase, can be accomplished through the use of a short hairpin RNA or antisense RNA, including siRNA, miRNA, and RNAi. Given the nucleotide sequence of the molecule, one of ordinary skill in the art could synthesize such an short hairpin RNA or antisense RNA without undue experimentation, provided with the disclosure and references incorporated herein.

One of skill in the art will appreciate that inhibitors of renalase, or a renalase fragment, can be administered acutely (e.g., over a short period of time, such as a day, a week or a month) or chronically (e.g., over a long period of time, such as several months or a year or more). One of skill in the art will appreciate that inhibitors of renalase can be administered singly or in any combination with other agents. Further, renalase inhibitors can be administered singly or in any combination in a temporal sense, in that they may be administered concurrently, or before, and/or after each other. One of ordinary skill in the art will appreciate, based on the disclosure provided herein, that renalase inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of renalase, or renalase fragment, of the invention described herein can be administered alone or in combination with other inhibitors of other molecules associated with cancer.

It will be appreciated by one of skill in the art, when armed with the present disclosure including the methods detailed herein, that the invention is not limited to treatment of a disease or disorder, such as cancer, that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that a renalase inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject a renalase inhibitor composition as a preventative measure against the disease or disorder, including cancer. As more fully discussed elsewhere herein, methods of decreasing the level or activity of renalase encompass a wide plethora of techniques for decreasing not only renalase activity, but also for decreasing expression of a nucleic acid encoding renalase, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of renalase mediates, treats or prevents the disease, disorder or pathology. Methods for assessing whether a disease relates to the levels or activity of renalase are known in the art. Further, the invention encompasses treatment or prevention of such diseases discovered in the future.

The invention encompasses administration of an inhibitor of renalase to practice the methods of the invention; the skilled artisan would understand, based on the disclosure provided herein, how to formulate and administer the appropriate renalase inhibitor to a subject. However, the present invention is not limited to any particular method of administration or treatment regimen.

The invention provides compositions that bind to renalase. In one embodiment, the renalase binding agent inhibits renalase levels or activity. Thus, in diseases and conditions where a reduction of renalase activity would be beneficial, such inhibitory renalase binding agents can potentially act as therapeutics.

In some instances, in addition to its potential therapeutic role, renalase can be used as a diagnostic marker for diseases or disorders including, but not limited, to acute renal failure (i.e., acute tubular necrosis, or ATN, an ischemic condition in the kidney), cardiovascular disease, and cancer. Patients without a properly functioning kidney possess lower levels of renalase. Accordingly, also included in the invention are methods of diagnosing susceptibility to cardiovascular, heart, kidney, gastrointestinal, liver, lung, pancreas and mental and neurological related conditions, disorders and diseases, including cancer, based on the detection and/or quantitation of renalase using the renalase binding agents of the present invention. For example, cardiovascular conditions, disorders and diseases such as hypertension, asymptomatic left ventricular dysfunction, chronic congestive heart failure, myocardial infarction, cardiac rhythm disturbance, and atherosclerosis; mental conditions, disorders and diseases such as depression and anxiety; and heart conditions, disorders and diseases, such as pulmonary hypertension, can all be diagnosed, evaluated and monitored by determining renalase levels, such as renalase protein levels. For example, reduced levels of the renalase protein would be a diagnostic marker for a disorder associated with an increased sympathetic output. The compositions and methods of the present invention can be used to treat, prevent, reduce or ameliorate hypertension, including systolic hypertension, isolated systolic hypertension and diabetic hypertension. Moreover, the same benefit is anticipated for the more rare hypertensive disorder, pulmonary hypertension, as well as pancreatitis. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

The renalase inhibitor compositions of the invention that decrease the level or activity (e.g., enzymatic activity, substrate binding activity, receptor binding activity, etc.) of renalase include, but should not be construed as being limited to, a chemical compound, a protein, a peptide, a peptidomemetic, an antibody, an antibody fragment, an antibody mimetic, a ribozyme, a small molecule chemical compound, an short hairpin RNA, RNAi, an antisense nucleic acid molecule (e.g., siRNA, miRNA, etc.), a nucleic acid encoding an antisense nucleic acid molecule, a nucleic acid sequence encoding a protein, a renalase receptor, a renalase receptor fragment, or combinations thereof. In some embodiments, the inhibitor is an allosteric inhibitor. One of skill in the art would readily appreciate, based on the disclosure provided herein, that a renalase inhibitor composition encompasses a chemical compound that decreases the level or activity of renalase. Additionally, a renalase inhibitor composition encompasses a chemically modified compound, and derivatives, as is well known to one of skill in the chemical arts.

The renalase inhibitor compositions of the invention that decrease the level or activity (e.g., enzymatic activity, substrate binding activity, receptor binding activity, etc.) of renalase include antibodies, and fragments thereof. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to renalase. In some embodiments, the antibodies of the invention are bispecific antibodies, where the first specificity is to renalase and the second specificity is to a targeting molecule to guide the bispecific antibody to an anatomic location where the renalase binding is desired. In some embodiments, the antibodies of the invention are bispecific antibodies, where the first specificity is to renalase and the second specificity is to a second binding partner molecule that is carried and deployed to an anatomic location where renalase binding is desired.

Antibodies, including a renalase binding fragments thereof, of the present invention include, in certain embodiments, antibody amino acid sequences disclosed herein encoded by any suitable polynucleotide, or any isolated or formulated antibody. Further, antibodies of the present disclosure comprise antibodies having the structural and/or functional features of anti-renalase antibodies described herein. In one embodiment, the anti-renalase antibody binds renalase and, thereby partially or substantially alters at least one biological activity of renalase (e.g., enzymatic activity, substrate binding activity, receptor binding activity, etc.). In some embodiments, the renalase is human renalase.

In one embodiment, anti-renalase antibodies of the invention immunospecifically bind at least one specified epitope specific to the renalase protein, peptide, subunit, fragment, portion or any combination thereof and do not specifically bind to other polypeptides, other than renalase from other species. The at least one epitope can comprise at least one antibody binding region that comprises at least one portion of the renalase protein. The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In some embodiments, the invention includes compositions comprising an antibody that specifically binds to renalase (e.g., binding portion of an antibody). In one embodiment, the anti-renalase antibody is a polyclonal antibody. In another embodiment, the anti-renalase antibody is a monoclonal antibody. In some embodiments, the anti-renalase antibody is a chimeric antibody. In further embodiments, the anti-renalase antibody is a humanized antibody. In some embodiments, the renalase is human renalase. In some embodiments, the antibodies of the invention specifically bind to at least one of SEQ ID NOS:1-7, 8, 50, 92, 94, and fragments thereof.

The binding portion of an antibody comprises one or more fragments of an antibody that retain the ability to specifically bind to binding partner molecule (e.g., renalase). It has been shown that the binding function of an antibody can be performed by fragments of a full-length antibody. Examples of binding fragments encompassed within the term "binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "binding portion" of an antibody. These antibody fragments are obtained using conventional techniques known to those with skill in the art, and the fragments are screened for utility in the same manner as are intact antibodies. Binding portions can be produced by recombinant DNA techniques, or by enzymatic or chemical cleavage of intact immunoglobulins.

An antibody that binds to renalase of the invention is an antibody that inhibits, blocks, or interferes with at least one renalase activity (e.g., enzymatic activity, substrate binding activity, receptor binding activity, etc.), in vitro, in situ and/or in vivo. A suitable anti-renalase antibody, specified portion, or variant can also optionally affect at least one renalase activity or function, such as but not limited to, RNA, DNA or protein synthesis, protein release, renalase signaling, renalase cleavage, renalase activity, renalase receptor binding, renalase production and/or synthesis.

In one embodiment, antibodies of the invention bind renalase. In one embodiment, the antibodies specifically bind to renalase-1. In another embodiment, the antibodies specifically bind to renalase-2. In yet another embodiment, the antibodies specifically bind to both renalase-1 and renalase-2. In addition, epitope specific antibodies have been generated. Preferred antibodies of the invention include monoclonal antibodies 1C-22-1, 1D-28-4, 1D-37-10, 1F-26-1, 1F42-7 and 3A-5-2. Examples of dual specificity antibodies, e.g. antibodies that recognize renalase-1 and renalase-2 include antibodies 1C-22-1, 1D-28-4, 1D-37-10, and polyclonal antibodies as described in Table 1. Examples of renalase-type specific antibodies include 1F-26-1, 1F42-7, which are specific for renalase-1. 3A-5-2 is specific for renalase-2. Sequences encoding anti-renalase monoclonal antibodies are set forth in FIG. 5.

Figure 5A:
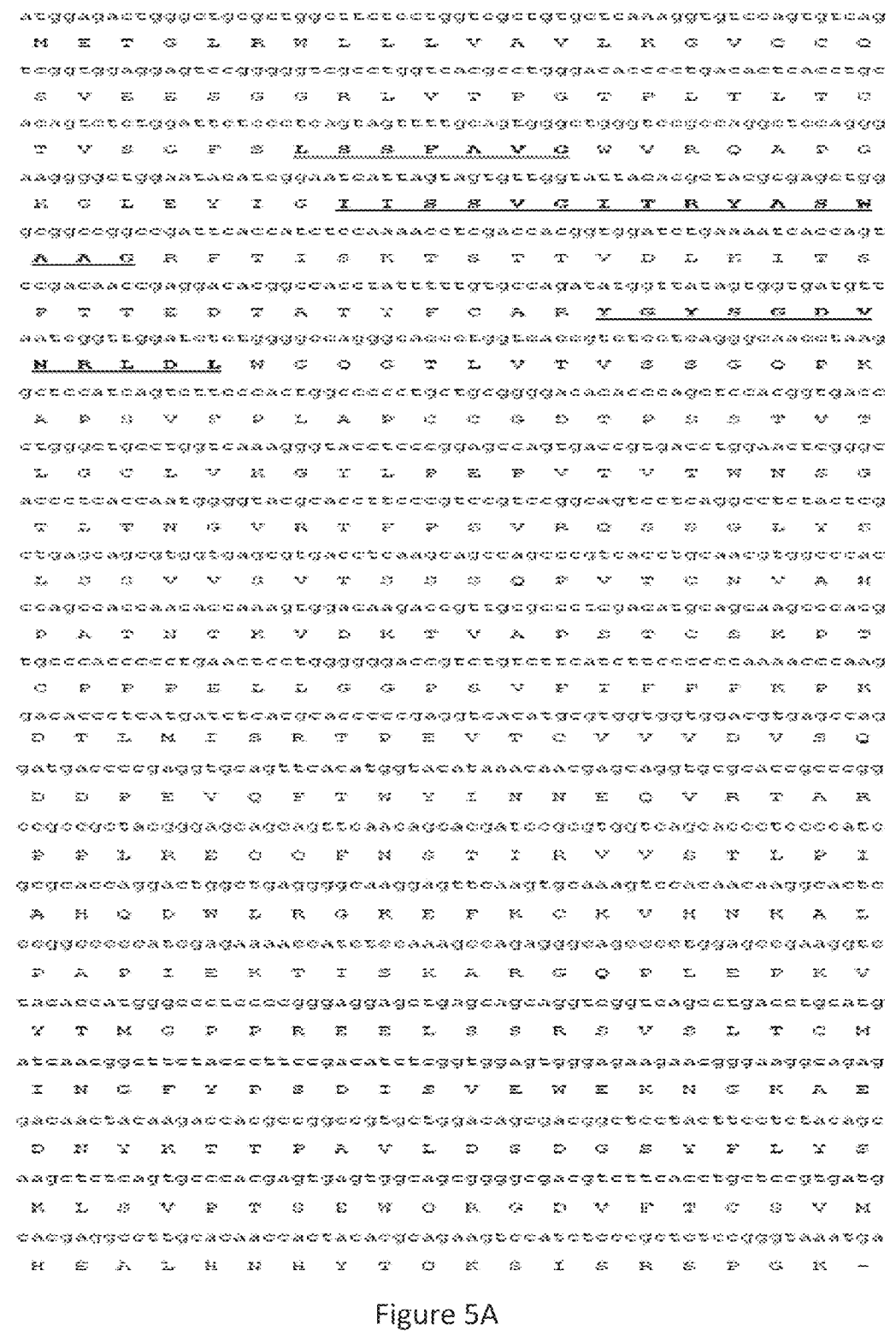

The nucleic acid (SEQ ID NO:52) and amino acid sequence (SEQ ID NO:9) of the heavy chain coding sequence of monoclonal antibody 1D-28-4 are found in FIG. 5. The nucleic acid (SEQ ID NO:53) and amino acid sequence (SEQ ID NO:10) of the light chain coding sequence of monoclonal antibody 1D-28-4 are found in FIG. 5.

The nucleic acid (SEQ ID NO:60) and amino acid sequence (SEQ ID NO:17) of the heavy chain coding sequence of monoclonal antibody 1D-37-10 are found in FIG. 5. The nucleic acid (SEQ ID NO:61) and amino acid sequence (SEQ ID NO:18) of the light chain coding sequence of monoclonal antibody 1D-37-10 are found in FIG. 5.

The nucleic acid (SEQ ID NO:68) and amino acid sequence (SEQ ID NO:25) of the heavy chain coding sequence of monoclonal antibody 1F-26-1 are found in FIG. 5. The nucleic acid (SEQ ID NO:69) and amino acid sequence (SEQ ID NO:26) of the light chain coding sequence of monoclonal antibody 1F-26-1 are found in FIG. 5.

The nucleic acid (SEQ ID NO:76) and amino acid sequence (SEQ ID NO:33) of the heavy chain coding sequence of monoclonal antibody 1F-42-7 are found in FIG. 5. The nucleic acid (SEQ ID NO:77) and amino acid sequence (SEQ ID NO:34) of the light chain coding sequence of monoclonal antibody 1F-42-7 are found in FIG. 5.

The nucleic acid (SEQ ID NO:84) and amino acid sequence (SEQ ID NO:41) of the heavy chain coding sequence of monoclonal antibody 3A-5-2 are found in FIG. 5. The nucleic acid (SEQ ID NO:85) and amino acid sequence (SEQ ID NO:42) of the light chain coding sequence of monoclonal antibody 3A-5-2 are found in FIG. 5.

The underlined sequences in each of the sequences incorporate CDR1, CDR2 and CDR3 sequences of each of the heavy and light chains.

Given that certain of the monoclonal antibodies can bind to the renalase protein, the VH and VL sequences can be "mixed and matched" to create other anti-renalase binding molecules of this disclosure. Renalase binding of such "mixed and matched" antibodies can be tested using the binding assays described above and in the Examples (e.g., immunoblot, Bia-Core, etc.). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence.

Accordingly, in one aspect, this disclosure provides an isolated monoclonal antibody, or binding portion thereof comprising: (a) a heavy chain variable region comprising an amino acid sequence selected from the group consisting of SEQ ID NOs: 9, 17, 25, 33 and 41; and (b) a light chain variable region comprising an amino acid sequence selected from the group consisting of SEQ ID NOs: 10, 18, 26, 34 and 42, wherein the antibody specifically binds a renalase protein.

Preferred heavy and light chain combinations include: (a) a heavy chain variable region comprising the amino acid sequence of SEQ ID NO: 9 and a light chain variable region comprising the amino acid sequence of SEQ ID NO: 10; or (b) a heavy chain variable region comprising the amino acid sequence of SEQ ID NO: 17 and a light chain variable region comprising the amino acid sequence of SEQ ID NO: 18; or (c) a heavy chain variable region comprising the amino acid sequence of SEQ ID NO: 25 and a light chain variable region comprising the amino acid sequence of SEQ ID NO: 26; or (d) a heavy chain variable region comprising the amino acid sequence of SEQ ID NO: 33 and a light chain variable region comprising the amino acid sequence of SEQ ID NO: 34; or (e) a heavy chain variable region comprising the amino acid sequence of SEQ ID NO: 41 and a light chain variable region comprising the amino acid sequence of SEQ ID NO: 42.

In another aspect, this disclosure provides antibodies that comprise the heavy chain and light chain CDR1s, CDR2s and CDR3s of 1D-28-4, 1D-37-10, 1F-26-1, 1F42-7 or 3A-5-2, or combinations thereof. The amino acid sequences of the VH CDR1s of 1D-28-4, 1D-37-10, 1F-26-1, 1F42-7 and 3A-5-2 incorporate the sequences shown in SEQ ID NOs: 11, 19, 27, 35, and 43, respectively. The amino acid sequences of the VH CDR2s 1D-28-4, 1D37-10, 1F-26-1, 1F42-7 or 3A-5-2 incorporate the sequences shown in SEQ ID NOs: 12, 20, 28, 36, and 44, respectively. The amino acid sequences of the VH CDR3s of 1D-28-4, 1D-3710, 1F-26-1, 1F42-7 or 3A-5-2 incorporate the sequences shown in SEQ ID NOs: 13, 21, 29, 37, and 45, respectively. The amino acid sequences of the VK CDR1s of 1D-28-4, 1D-37-10, 1F-26-1, 1F42-7 or 3A-5-2 incorporate the sequences shown in SEQ ID NOs: 14, 22, 30, 38, and 46, respectively. The amino acid sequences of the VK CDR2s of 1D-28-4, 1D-37-10, 1F26-1, 1F42-7 or 3A-5-2 incorporate the sequences shown in SEQ ID NOs: 15, 23, 31, 39 and 47. The amino acid sequences of the VKCDR3s of 1D-28-4, 1D-37-10, 1F-26-1, 1F42-7 or 3A-5-2 incorporate the sequences shown in SEQ ID NOs: 16, 24, 32, 40 and 48, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to renalase family members and that binding specificity is provided primarily by the CDR1, CDR2, and CDR3 regions, the VH CDR1, CDR2, and CDR3 sequences and VL CDR1, CDR2, and CDR3 sequences can be "mixed and matched" (i.e., CDRs from different antibodies can be mixed and match, although each antibody must contain a VH CDR1, CDR2, and CDR3 and a VL CDR1, CDR2, and CDR3) to create other anti-renalase binding molecules of this disclosure. renalase binding of such "mixed and matched" antibodies can be tested using the binding assays described above and in the Examples (e.g., immunoblot, Biacore® analysis, etc). Preferably, when VH CDR sequences are mixed and matched, the CDR1, CDR2 and/or CDR3 sequence from a particular VH sequence is replaced with a structurally similar CDR sequence(s). Likewise, when VL CDR sequences are mixed and matched, the CDR1, CDR2 and/or CDR3 sequence from a particular VL sequence preferably is replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences disclosed herein for monoclonal antibodies 1D-28-4, 1D-37-10, 1F-26-1, 1F42-7 or 3A-5-2.

Accordingly, in another aspect, the invention provides an isolated monoclonal antibody, or binding portion thereof comprising at least one selected from: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44; (c) a heavy chain variable region CDR3 comprising an amino acid sequence selected from the group consisting of SEQ ID NOs: 13, 21, 29, 37, and 45; (d) a light chain variable region CDR1 comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48; wherein the antibody specifically binds an renalase.

In another embodiment, the antibody comprises at least one of the CDRs selected from: (a) a heavy chain variable region CDR1 comprising SEQ ID NO: 11; (b) a heavy chain variable region CDR2 comprising SEQ ID NO: 12; (c) a heavy chain variable region CDR3 comprising SEQ ID NO: 13; (d) a light chain variable region CDR1 comprising SEQ ID NO: 14; (e) a light chain variable region CDR2 comprising SEQ ID NO: 15; and (f) a light chain variable region CDR3 comprising SEQ ID NO: 16.

In another embodiment, the antibody comprises at least one of the CDRs selected from: (a) a heavy chain variable region CDR1 comprising SEQ ID NO: 19; (b) a heavy chain variable region CDR2 comprising SEQ ID NO: 20; (c) a heavy chain variable region CDR3 comprising SEQ ID NO: 21; (d) a light chain variable region CDR1 comprising SEQ ID NO: 22; (e) a light chain variable region CDR2 comprising SEQ ID NO: 23; and (f) a light chain variable region CDR3 comprising SEQ ID NO: 24.

In another embodiment, the antibody comprises at least one of the CDRs selected from: (a) a heavy chain variable region CDR1 comprising SEQ ID NO: 27; (b) a heavy chain variable region CDR2 comprising SEQ ID NO: 28; (c) a heavy chain variable region CDR3 comprising SEQ ID NO: 29; (d) a light chain variable region CDR1 comprising SEQ ID NO: 30; (e) a light chain variable region CDR2 comprising SEQ ID NO:31; and (f) a light chain variable region CDR3 comprising SEQ ID NO: 32.

In another other embodiment, the antibody comprises at least one of the CDRs selected from: (a) a heavy chain variable region CDR1 comprising SEQ ID NO: 35; (b) a heavy chain variable region CDR2 comprising SEQ ID NO: 36; (c) a heavy chain variable region CDR3 comprising SEQ ID NO: 37; (d) a light chain variable region CDR1 comprising SEQ ID NO: 38; (e) a light chain variable region CDR2 comprising SEQ ID NO: 39; and (f) a light chain variable region CDR3 comprising SEQ ID NO: 40.

In another embodiment, the antibody comprises at least one of the CDRs selected from: (a) a heavy chain variable region CDR1 comprising SEQ ID NO: 43; (b) a heavy chain variable region CDR2 comprising SEQ ID NO: 44; (c) a heavy chain variable region CDR3 comprising SEQ ID NO: 45; (d) a light chain variable region CDR1 comprising SEQ ID NO: 46; (e) a light chain variable region CDR2 comprising SEQ ID NO: 47; and (f) a light chain variable region CDR3 comprising SEQ ID NO: 48.

The foregoing isolated anti-renalase antibody CDR sequences establish a novel family of renalase binding proteins, isolated in accordance with this invention, and comprising polypeptides that include the CDR sequences listed. To generate and to select CDR's of the invention having renalase binding and/or renalase detection and/or renalase neutralization activity, standard methods known in the art for generating binding proteins of the present invention and assessing the renalase and/or renalase binding and/or detection and/or neutralizing characteristics of those binding protein may be used, including but not limited to those specifically described herein.

Preferably, renalase binding molecules (e.g., antibodies, etc.) of the present invention, exhibit a high capacity to detect and bind renalase in a complex mixture of salts, compounds and other polypeptides, e.g., as assessed by any one of several in vitro and in vivo assays known in the art. The skilled artisan will understand that the renalase binding molecules (e.g., antibodies, etc.) described herein as useful in the methods of diagnosis and treatment and prevention of disease, are also useful in procedures and methods of the invention that include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, a protein chip assay, separation and purification processes, and affinity chromatography (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

More preferably, the renalase binding molecules (e.g., antibodies, etc.) of the present invention, exhibit a high capacity to reduce or to neutralize renalase activity (e.g., enzymatic activity, substrate binding activity, receptor binding activity, etc.) as assessed by any one of several in vitro and in vivo assays known in the art. For example, these renalase binding molecules (e.g., antibodies, etc.) neutralize renalase-associated or renalase-mediated disease or disorder. Preferably, renalase binding molecules (e.g., antibodies, etc.) of the present invention, also exhibit a high capacity to reduce or to neutralize renalase activity. In some embodiments, the renalase is human renalase.

As used herein, a renalase binding molecule (e.g., antibody, etc.) that "specifically binds to a renalase protein" is intended to refer to a renalase binding molecule (e.g., antibody, etc.) that binds to a renalase protein of any animal. In some embodiments, that antibody binds to human renalase. Preferably, the a renalase binding molecule (e.g., antibody, etc.) binds to a renalase protein with a KD of $1\times10^{-6}$ M or less, more preferably $1\times10^{-7}$ M or less, more preferably $1\times10^{-8}$ M or less, more preferably $5\times10^{-9}$ M or less, more preferably $1\times10^{-9}$ M or less or even more preferably $3\times10^{-10}$ M or less. The term "does not substantially bind" to a protein or cells, as used herein, means does not bind or does not bind with a high affinity to the protein or cells, i.e., binds to the protein or cells with a KD of greater than $1\times10^{6}$ M or more, more preferably $1\times10^{5}$ M or more, more preferably $1\times10^{4}$ M or more, more preferably $1\times10^{3}$ M or more, even more preferably $1\times10^{2}$ M or more. The term "KD", as used herein, is intended to refer to the dissociation constant, which is obtained from the ratio of Kd to Ka (i.e., Kd/Ka) and is expressed as a molar concentration (M). KD values for a renalase binding molecule (e.g., antibody, etc.) can be determined using methods well established in the art. A preferred method for determining the KD of a binding molecule (e.g., antibody, etc.) is by using surface plasmon resonance, preferably using a biosensor system such as a Biacore® system.

As used herein, the term "high affinity" for an IgG antibody refers to an antibody having a KD of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target binding partner molecule. However, "high affinity" binding can vary for other antibody isotypes. For example, "high affinity" binding for an IgM isotype refers to an antibody having a KD of $10^{-6}$M or less, more preferably $10^{-7}$M or less, even more preferably $10^{-8}$M or less.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Generation of Anti-Renalase Antibodies

The invention provides compositions that bind to renalase. The renalase molecules disclosed herein are a class of molecules that include those having high and/or significant sequence identity with other polypeptides disclosed herein. More specifically, the putative renalase will share at least about 40% sequence identity with a nucleic acid having the sequence SEQ ID NO: 49 or 51. More preferably, a nucleic acid encoding renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO:49 or 51 disclosed herein. Even more preferably, the nucleic acid is SEQ ID NO:49 or 51 or 93 or 95. The term "renalase" also includes renalase isoforms. The renalase gene contains 9 exons spanning 310188 bp in chromosome 10 of human genome. The renalase clone (SEQ ID NO: 49, GenBank accession number: BC005364) disclosed herein is the gene containing exons 1, 2, 3, 4, 5, 6, 8. There are at least two additional alternatively-spliced forms of renalase protein as shown in the human genome database. One alternatively spliced form contains exons 1, 2, 3, 4, 5, 6, 9, identified by clones in the human genome database as GenBank accession number AK002080 and NMJ)18363, the sequences of which are expressly incorporated herein by reference. The other alternatively spliced form contains exons 5, 6, 7, 8, identified by clones in the human genome database as GenBank accession number BX648154, the sequence of which is expressly incorporated herein by reference. Unless otherwise indicated, "renalase" encompasses all known renalases (e.g., rat renalase, and human renalase), and renalases to be discovered, including but not limited to, human renalase and chimpanzee renalase, having the characteristics and/or physical features of the renalase disclosed herein.

In addition, the putative renalase share at least about 60% sequence identity with a polypeptide having the sequence SEQ ID NO:8 or 50. More preferably, renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO:8 or 50 disclosed herein. Even more preferably, the renalase polypeptide has the amino acid sequence of SEQ ID NO:8 or 50 or 92 or 94.

In one embodiment, the antibodies of the invention can be generated by using a peptide derived from the sequence of renalase to immunize an animal whereby the animal produces antibodies directed against the immunogen. Exemplary immunogens include peptide derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in Table 1 (SEQ ID NOs: 1-7).

Anti-renalase antibodies of the present invention can be optionally produced by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse or rabbit or other species immunized with polypeptide or peptide of the invention with myeloma cells and then screening the hybridomas resulting from the fusion for hybridoma clones that secrete an antibody able to bind a polypeptide of the invention. Briefly, mice can be immunized with a renalase polypeptide or peptide thereof. In a preferred embodiment, the renalase polypeptide or peptide thereof is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Alternatively, rabbits can be immunized with a renalase polypeptide or peptide thereof. In this embodiment, either full length renalase proteins or peptides derived from renalase can be used as immunogens.

Renalase used in the invention can take a variety of forms. For example, they can include purified renalase proteins or fragments thereof, recombinantly produced renalase or fragments thereof. In some embodiments, the renalase is human renalase. When recombinant renalase is used, it can be produced in eukaryotic or prokaryotic cells as is known in the art. Additional immunogens include peptides derived from renalase. That is, peptides having fragments of the renalase sequence can be used in the inventions. Peptides can be produced in a variety of ways, including expression as recombinant peptides, expression as larger polypeptides and cleaved enzymatically or chemically. Alternatively, they may be produced synthetically as is known in the art. Preferred peptides as used to generate affinity reagents of the present invention are found in Table 1 (SEQ ID NOs: 1-7). The full-length amino acid sequence of human renalase is depicted in SEQ ID NO:8, where a known polymorphism is possible as indicated (compare to SEQ ID NO. 92). The amino acid sequence of renalase-2 is found in SEQ ID NO:50, again where a known polymorphism is possible as indicated (compare to SEQ ID NO. 94). It is appreciated that other polymorphisms exist. These also are included in the definition of renalase. In some embodiments, the renalase binding molecules of the invention specifically bind to at least one of SEQ ID NOS:1-7, 8, 50, 92, 94, and fragments thereof.

The anti-renalase antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-renalase antibody can be isolated from such animals and immortalized using suitable methods, such as the methods described herein. Alternatively, the antibody coding sequences may be cloned, introduced into a suitable vector, and used to transfect a host cell for expression and isolation of the antibody by methods taught herein and those known in the art.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. No. 5,569,825, U.S. Pat. No. 6,300,129 and 1994, Nature 368:856-9; Green, L. et al., 1994, Nature Genet. 7:13-21; Green, L. & Jakobovits, 1998, Exp. Med. 188:483-95; Lonberg, N. and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Bruggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies such as Abgenix, Inc. (Freemont, Calif.) and Medarex (San Jose, Calif.) can be engaged to provide human antibodies directed against a selected target binding partner molecule (e.g., antigen, etc.) using technology as described elsewhere herein.

In another embodiment, the human antibody is selected from a phage library, where that phage comprises human immunoglobulin genes and the library expresses human antibody binding domains as, for example, single chain antibodies (scFv), as Fab, or some other construct exhibiting paired or unpaired antibody variable regions (Vaughan et lo al. Nature Biotechnology 14:309-314 (1996): Sheets et al. PITAS (USA) 95:6157-6162 (1998)); Hoogenboom and Winter, J. Mol. Biol., 227:381 (1991); Marks et al. J. Mol. Biol., 222:581 (1991)). Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired binding fragment, and expressed in any desired host, including mammalian cells, insect cells, plant cells, yeast, and bacteria.

Humanized Antibodies

The invention further provides humanized immunoglobulins (or antibodies) which bind human renalase. The humanized forms of immunoglobulins have variable framework region(s) substantially from a human immunoglobulin (termed an acceptor immunoglobulin) and CDRs substantially from a non-human mAbs which specifically binds renalase. The constant region(s), if present, are also substantially from a human immunoglobulin. The humanized antibodies exhibit $K_D$ for renalase of at least about $10^{-6}$M (1 microM), about $10^{-7}$M (100 nM), or less. The binding affinity of the humanized antibodies may be greater or less than that of the mouse antibody from which they were derived. To affect a change in affinity, improve affinity, of the humanized antibody for renalase substitutions in either the CDR residues or the human residues may be made.

The source for production of humanized antibody which binds to renalase is preferably the 1D-28-4, 1D-37-10, 1F-26-1, 1F42-7 or 3A-5-2 mouse antibodies whose generation, isolation and characterization are described in the Examples provided herein, although other mouse antibodies, which compete with the 1D-28-4, 1D-37-10, 1F-26-1, 1F42-7 or 3A-5-2 mouse antibodies for binding to renalase can also be used. The identified CDRs set forth in the sequece listing can be a starting point of the humanization process. For example, any one or more of the following amino acid sequences (and corresponding nucleic acid sequences thereof) can be a starting point of the humanization process: (a) a heavy chain variable region CDR1 comprising an amino acid sequence selected from the group consisting of SEQ ID NOs: 11, 19, 27, 35, and 43; (b) a heavy chain variable region CDR2 comprising an amino acid sequence selected from the group consisting of SEQ ID NOs: 12, 20, 28, 36, and 44; (c) a heavy chain variable region CDR3 comprising an amino acid sequence selected from the group consisting of SEQ ID NOs: 13, 21, 29, 37, and 45; (d) a light chain variable region CDR1 comprising an amino acid sequence selected from the group consisting of SEQ ID NOs: 14, 22, 30, 38, and 46; (e) a light chain variable region CDR2 comprising an amino acid sequence selected from the group consisting of SEQ ID NOs: 15, 23, 31, 39 and 47; and (f) a light chain variable region CDR3 comprising an amino acid sequence selected from the group consisting of SEQ ID NOs: 16, 24, 32, 40 and 48.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies, be derived from human germline immunoglobulin sequences, or can be consensus sequences of several human antibody and/or germline sequences.

Suitable human antibody sequences are identified by computer comparisons of the amino acid sequences of the mouse variable regions with the sequences of known human antibodies. The comparison is performed separately for heavy and light chains but the principles are similar for each.

In one example, the amino acid sequence of anti-renalase mAb is used to query a human antibody database compiled from public antibody sequence databases. The heavy chain variable region can be used to find the human variable region with the highest sequence identity. The variable region of the light chain can, similarly, be used to find the human variable region with the highest sequence identity. A DNA construct in which the regions coding for the CDRs of one of the heavy chain variable regions from the murine mAbs donor are transferred into the selected human heavy chain variable sequence, replacing the CDRs of the human variable region is prepared for each murine variable region.

The unnatural juxtaposition of murine CDR regions with human variable framework region can result in unnatural conformational restraints, which, unless corrected by substitution of certain amino acid residues, lead to loss of binding affinity. As noted supra, the humanized antibodies of the invention comprise variable framework region(s) substantially from a human immunoglobulin and CDRs substantially from a mouse immunoglobulin. Having identified the CDRs of mouse antibodies and appropriate human acceptor immunoglobulin sequences, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to the target binding partner molecule. Investigation of such possible influences can be done by modeling, examination of the characteristics of the amino acids at particular locations, or empirical observation of the effects of substitution or mutagenesis of particular amino acids. With regard to the empirical method, it has been found to be particularly convenient to create a library of variant sequences that can be screened for the desired activity, binding affinity or specificity. One format for creation of such a library of variants is a phage display vector. Alternatively, variants can be generated using other methods for varigation of a nucleic acid sequence encoding the targeted residues within the variable domain.

Another method of determining whether further substitutions are required, and the selection of amino acid residues for substitution, can be accomplished using computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

Usually the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Because of the degeneracy of the code, a variety of nucleic acid sequences will encode each immunoglobulin amino acid sequence. The desired nucleic acid sequences can be produced by de nova solid-phase DNA synthesis or by PCR mutagenesis of an earlier prepared variant of the desired polynucleotide. All nucleic acids encoding the antibodies described in this application are expressly included in the invention.

The variable segments of humanized antibodies produced as described supra are typically linked to at least a portion of a human immunoglobulin constant region. The antibody will contain both light chain and heavy chain constant regions. The heavy chain constant region usually includes CH1, hinge, CH2, CH3, and, sometimes, CH4 domains. The humanized antibodies may comprise any type of constant domains from any class of antibody, including IgM, IgG, IgD, IgA and IgE, and any subclass (isotype), including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86, 10029 (1989); WO 90/07861; Co et al., J. Immunol. 148, 1149 (1992), which are incorporated herein by reference in their entirety for all purposes).

Methods of Using the Renalase Binding Molecules

Given the properties of the renalase binding molecules (e.g., antibodies, etc.) of the present invention, the renalase binding molecules are suitable as diagnostic, therapeutic and prophylactic agents for diagnosing, treating or preventing renalase-associated conditions in humans and animals.

In general, use comprises administering a therapeutically or prophylactically effective amount of one or more monoclonal antibodies or binding fragments of the present invention to a susceptible subject or one exhibiting a condition in which renalase activity is known to have pathological sequelae, such as tumor growth and metastasis. Any active form of the renalase binding molecule can be administered, including antibody Fab and F(ab')2 fragments.

Preferably, the renalase binding molecule used is compatible with the recipient species such that the immune response to the renalase binding molecule does not result in an unacceptably short circulating half-life or induce an immune response to the renalase binding molecule in the subject. Preferably, the renalase binding molecule administered exhibits some secondary functions such as binding to Fc receptors of the subject and activation of ADCC mechanisms.

Treatment of individuals may comprise the administration of a therapeutically effective amount of the renalase binding molecules of the present invention. The renalase binding molecules can be provided in a kit as described below. The renalase binding molecules can be used or administered as a mixture, for example in equal amounts, or individually, provided in sequence, or administered all at once. In providing a patient with renalase binding molecule, the dosage of administered agent will vary depending upon such factors as the patient's age, weight, height, sex, general medical condition, previous medical history, etc.

In general, if administering a systemic dose of a renalase binding molecule, it is desirable to provide the recipient with a dosage of a renalase binding molecule which is in the range of from about 1 ng/kg-100 ng/kg, 100 ng/kg-500 ng/kg, 500 ng/kg-1 µg/kg, 1 µg/kg-100 µg/kg, 100 µg/kg-500 µg/kg, 500 µg/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the renalase binding molecule may be given which is not based upon the weight of the patient such as an amount in the range of 1 µg-100 µg, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, ophthalmic, or transdermal means.

The renalase binding molecule composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or ophthalmically such as, but not limited to, eye drops; or for the treatment of dental disease; or transdermally such as not limited to a gel, ointment, lotion, suspension or patch delivery system with chemical enhancers such as dimethyl sulfoxide to either modify the skin structure or to increase the drug concentration in the transdermal patch, or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402).

In a similar approach, another therapeutic use of the renalase binding molecule of the present invention is the active immunization of a patient using an anti-idiotypic antibody raised against one of the present monoclonal antibodies. Immunization with an anti-idiotype which mimics the structure of the epitope could elicit an active anti-renalase response (Linthicum, D. S, and Farid, N. R., Anti-Idiotypes, Receptors, and Molecular Mimicry (1988), pp 1-5 and 285-300).

The renalase binding molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect of the present invention is a kit for detecting renalase in a biological sample. The kit includes a container holding one or more renalase binding molecules which binds an epitope of renalase and instructions for using the renalase binding molecule for the purpose of binding to renalase to form complex and detecting the formation of the complex such that the presence or absence of the complex correlates with presence or absence of renalase in the sample. Examples of containers include multiwell plates which allow simultaneous detection of renalase in multiple samples.

Combination Therapy

The renalase binding molecule compositions of the invention can be used in combination with another therapeutic treatment or agent to treat the disease or disorder. For example, the renalase binding molecule of the invention may be administered alone, or in combination with one or more therapeutically effective agents or treatments. The other therapeutically effective agent may be conjugated to the renalase binding molecule of the invention, incorporated into the same composition as the renalase binding molecule of the invention, or may be administered as a separate composition. The other therapeutically agent or treatment may be administered prior to, during and/or after the administration of the antibody of the invention or related compound.

In certain embodiments, the renalase binding molecule of the invention is co-administered with one or more other therapeutic agents or treatments. In other embodiments, the renalase binding molecule of the invention is administered independently from the administration of one or more other therapeutic agents or treatments. For example, the renalase binding molecule of the invention is administered first, followed by the administration of one or more other therapeutic agents or treatments. Alternatively, one or more other therapeutic agents are administered first, followed by the administration of a renalase binding molecule of the invention. As another example, a treatment (e.g., a surgery, radiation, etc.) is carried out first, followed by the administration of the renalase binding molecule of the invention.

Other therapeutically effective agents/treatments include surgery, anti-neoplastics (including chemotherapeutic agents and radiation), anti-angiogenesis agents, antibodies to other targets, small molecules, photodynamic therapy, immunotherapy, immunity enhancing therapy, cytotoxic agents, cytokines, chemokines, growth inhibitory agents, anti-hormonal agents, kinase inhibitors, cardioprotectants, immunostimulatory agents, immunosuppressive agents, and agents that promote proliferation of hematological cells.

In one embodiment, the "another therapeutic agent," as used herein, are second, distinct therapeutic agents or anti-cancer agents, i.e., therapeutic agents or anti-cancer agents "other than" the renalase binding molecule of the invention. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would administer to an animal or patient a renalase binding molecule of the invention in combination with another, i.e., a second, distinct anti-cancer agent in a manner effective to result in their combined anti-tumor actions within the animal or patient. The agents would therefore be provided in amounts effective and for periods of time effective to result in their combined, or concurrent, presence within the tumor or tumor vasculature and their combined actions in the tumor environment. To achieve this goal, the renalase binding molecule of the invention and the second, distinct anti-cancer agents may be administered to the animal substantially simultaneously, either in a single composition, or as two distinct compositions using different administration routes.

Alternatively, the renalase binding molecule of the invention may precede, or follow, the second, distinct anti-cancer agent by, e.g., intervals ranging from minutes to weeks. In certain embodiments where the renalase binding molecule of the invention and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed elsewhere herein. However, a preference for selecting one or more second, distinct anti-cancer agents for prior or subsequent administration does not preclude their use in substantially simultaneous administration if desired. Second, distinct anti-cancer agents selected for administration "prior to" the primary therapeutic agents of the present invention, and designed to achieve increased and potentially synergistic effects.

Second, distinct anti-cancer agents selected for administration "subsequent to" the primary therapeutic agents of the present invention, and designed to achieve increased and potentially synergistic effects, include agents that benefit from the effects of the primary therapeutic agent. Accordingly, effective second, distinct anti-cancer agents for subsequent administration include anti-angiogenic agents, which inhibit metastasis; agents targeting necrotic tumor cells, such as antibodies specific for intracellular binding partner molecules that become accessible from malignant cells in vivo (U.S. Pat. Nos. 5,019,368, 4,861,581 and 5,882,626, each specifically incorporated herein by reference); chemotherapeutic agents; and anti-tumor cell immunoconjugates, which attack any tumor cells.

The renalase binding molecule of the invention can also be administered in combination with a cancer immunotherapy. The cancer immunotherapy can be one designed to elicit a humoral immune response against the subject's cancer cells, or a cell-mediated immune response against the subject's cancer cells, or a combination of a humoral response and a cell-mediated response against the subject's cancer cells. Non-limiting examples of cancer immunotherapy useful in combination with the renalase binding molecules of the invention include a cancer vaccine, a DNA cancer vaccine, adoptive cellular therapy, adoptive immunotherapy, CAR T-cell therapy, antibodies, immunity enhancing compounds, cytokines, interleukins (e.g., IL-2, etc.), interferons (IFN-α, etc.), and checkpoint inhibitors (e.g., PD-1 inhibitor, CTLA-4 inhibitor, etc.).

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the renalase binding molecule of the invention or the second, distinct anti-cancer agent will be utilized. The renalase binding molecule of the invention and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Chemotherapeutic drugs can be used in combination with the renalase inhibitors of the invention. Chemotherapeutic drugs can kill proliferating tumor cells, enhancing the necrotic areas created by the overall treatment.

One aspect of the invention provides a method of treating or preventing cancer using a renalase inhibitor of the invention. The skilled artisan will understand that treating or preventing cancer in a patient includes, by way of non-limiting examples, killing and destroying a cancer cell, as well as reducing the proliferation of or cell division rate of a cancer cell. The skilled artisan will also understand that a cancer cell can be, by way of non-limiting examples, a primary cancer cell, a cancer stem cell, a metastatic cancer cell. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Paraganglioma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer comprising treating the subject prior to, concurrently with, or subsequently to the administration of the renalase binding molecule of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The renalase binding molecule of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; albumin-bound paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+ myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; imilimumab; mirtazapine; BrUOG 278; BrUOG 292; RAD0001; CT-011; folfirinox; tipifarnib; R115777; LDE225; calcitriol; AZD6244; AMG 655; AMG 479; BKM120; mFOLFOX6; NC-6004; cetuximab; IM-C225; LGX818; MEK162; BBI608; MEDI4736; vemurafenib; ipilimumab; ivolumab; nivolumab; panobinostat; leflunomide; CEP-32496; alemtuzumab; bevacizumab; ofatumumab; panitumumab; pembrolizumab; rituximab; trastuzumab; STAT3 inhibitors (e.g., STA-21, LLL-3, LLL12, XZH-5, S31-201, SF-1066, SF-1087, STX-0119, cryptotanshinone, curcumin, diferuloylmethane, FLLL11, FLLL12, FLLL32, FLLL62, C3, C30, C188, C188-9, LYS, OPB-31121, pyrimethamine, OPB-51602, AZD9150, etc.); hypoxia inducing factor 1 (HIF-1) inhibitors (e.g., LW6, digoxin, laurenditerpenol, PX-478, RX-0047, vitexin, KC7F2, YC-1, etc.) and zinostatin stimalamer. In one embodiment, the anti-cancer drug is 5-fluorouracil, taxol, or leucovorin.

Methods of Diagnosis

In some embodiments, an increase in the level of renalase, or a renalase fragment, in a subject's cell, tissue, or bodily fluid, compared with a comparator is used in the methods of the invention as marker for the diagnosis of a disease or disorder, assessing the severity of a disease or disorder, and for monitoring the effect or effectiveness of a treatment of a disease or disorder. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder.

In one embodiment, the invention is a method of diagnosing a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or the renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of diagnosing includes a further step of treating the patient for the diagnosed disease or disorder.

In another embodiment, the invention is a method of assessing the severity of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of assessing the severity includes a further step of treating the patient for the disease or disorder.

In another embodiment, the invention is a method of monitoring the effect of a treatment of a disease or disorder of a subject by assessing the level of renalase, or a renalase fragment, in a biological sample of the subject. In one embodiment, the biological sample of the subject is a cell, tissue, or bodily fluid. Non-limiting examples of bodily fluids in which the level of renalase, or a renalase fragment, can be assessed include, but are not limited to, blood, serum, plasma and urine. In various embodiments, the level of renalase, or a renalase fragment, in the biological sample of the subject is compared with the renalase, or a renalase fragment, level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is acute renal failure (i.e., acute tubular necrosis, or ATN, an ischemic condition in the kidney), a cardiovascular disease or disorder (e.g., hypertension, pulmonary hypertension, systolic hypertension, diabetic hypertension, asymptomatic left ventricular dysfunction, chronic congestive heart failure, myocardial infarction, cardiac rhythm disturbance, atherosclerosis, etc.), cancer, heart disease or disorder, a kidney disease or disorder, a gastrointestinal disease or disorder, a liver disease or disorder, a lung disease or disorder, a pancreas disease or disorder (e.g., pancreatitis), mental disease or disorder (e.g., depression, anxiety, etc.), or a neurological disease or disorder. In some embodiments, the method of monitoring the effect of a treatment includes a further step of treating the patient for the disease or disorder.

In various embodiments, the subject is a human subject, and may be of any race, sex and age. Representative subjects include those who are suspected of having experienced a disease or disorder, those who have been diagnosed as having experienced a disease or disorder, those who have been diagnosed as having a disease or disorder, and those who are at risk of developing a disease or disorder.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of renalase, or a renalase fragment, contained therein. In one embodiment, the biological sample is a sample containing at least a fragment of a renalase polypeptide useful in the methods described herein.

In other various embodiments of the methods of the invention, the level of renalase is determined to be increased when the level of renalase, or a renalase fragment, is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, by at least 1000%, when compared to with a comparator control. In various embodiments, an increased level of renalase, or a renalase fragment, is indicative of a disease or disorder. In various embodiments, the disease or disorder is acute renal failure (i.e., acute tubular necrosis, or ATN, an ischemic condition in the kidney), cardiovascular disease, and cancer.

In the methods of the invention, a biological sample from a subject is assessed for the level of renalase, or a renalase fragment, in the biological sample obtained from the patient. The level of renalase, or a renalase fragment, in the biological sample can be determined by assessing the amount of renalase polypeptide, or a fragment, in the biological sample, the amount of renalase mRNA, or a fragment, in the biological sample, the amount of renalase activity (e.g., enzymatic activity, substrate binding activity, receptor binding activity, etc.) in the biological sample, or a combination thereof. In some embodiments, the level of renalase in the biological sample is determined in an assay using at least one of the renalase binding molecules of the invention described elsewhere herein.

In various embodiments of the methods of the invention, methods of measuring renalase levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007). In some embodiments, the level of renalase in the biological sample is measure with an assay that uses at least one of the renalase binding molecules of the invention that are described elsewhere herein.

Kits

The invention also includes a kit comprising a renalase binding molecule (e.g., antibody, etc.), or combinations thereof, of the invention and an instructional material which describes, for instance, administering the renalase binding molecule, or a combination thereof, to an individual as a therapeutic treatment or a non-treatment use as described elsewhere herein. In an embodiment, this kit further comprises a (preferably sterile) pharmaceutically acceptable carrier suitable for dissolving or suspending the therapeutic composition, comprising a renalase binding molecule, or combinations thereof, of the invention, for instance, prior to administering the renalase binding molecule of the invention to an individual. Optionally, the kit comprises an applicator for administering the renalase binding molecule.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Development of Renalase Antibodies

Figure 4:
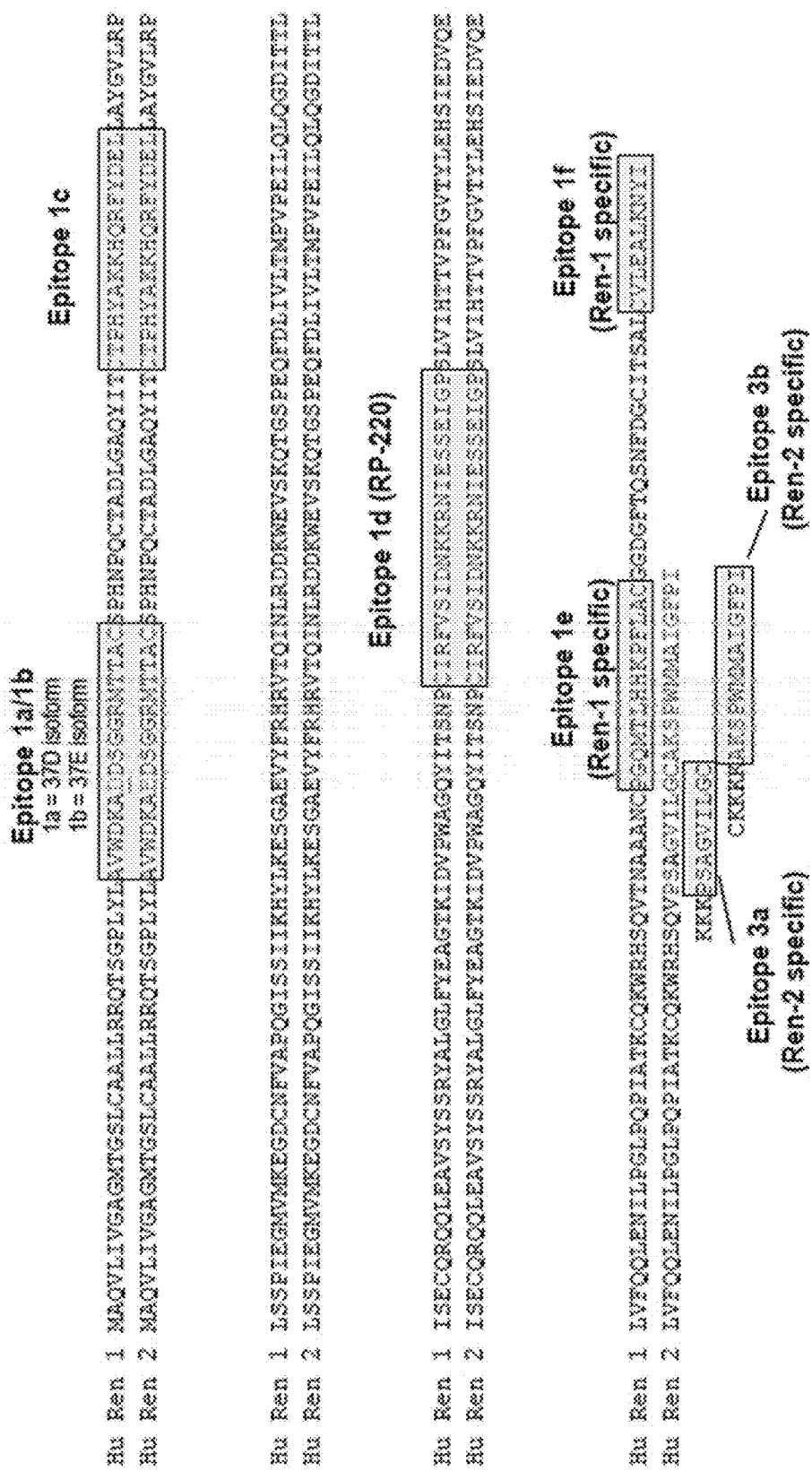
FIG. 4 is an image showing sequence alignments of the peptides in Table 1 and where these peptides correspond to the renalase-1 or 2 sequences.

Peptides were used as immunogens. The peptides generated ranged from 9 to 21 amino acids and corresponded to regions of the renalase-1 and renalase-2 proteins. All of the peptides had an N or C terminal cysteine residue. The sequence of the peptides can be seen in Table 1 and where these peptides correspond to the renalase-1 or 2 sequences is demonstrated in the sequence alignment of FIG. 4. As can be seen, the renalase-1 specific peptides are labeled 1A-F and the renalase-2 specific peptide is labeled 3A5. Each peptide was conjugated to the adjuvant KLH via the cysteine and used to immunize 6 rabbits. Antiserum collected from each animal was screened for anti-renalase antibody titer by ELISA assay using both the relevant peptide (BSA-conjugate) or full length renalase-1 or 2. The antisera were also tested for their ability to detect endogenous renalase in tissue lysates by western blot. Using these screening criteria the animals producing antibodies with the preferred characteristics were selected. In some examples and for some peptides, several animals produced antibodies with the required specificity. In these cases one animal had a final antisera bleed for polyclonal antibody production and one or in some examples two other animals were used to harvest spleen lymphocytes. In other examples a single animal had a terminal bleed and a splenectomy. Polyclonal antibodies raised against all of the peptides were generated by purification of total IgG from terminal bleeds by protein G chromatography followed by further purification on peptide affinity chromatography. Further and using standard procedures, lymphocytes from the spleens of selected animals were fused to myeloma cells for hybridoma generation. The hybridoma supernatants were screened for binding to both the peptides against which they were raised and secondarily screened against whole renalase protein. Selected hybridomas were sub-cloned and expanded for antibody purification. The monoclonal antibodies were purified from conditioned hybridoma culture supernatant by protein A affinity chromatography.

TABLE 1

Sequence of renalase peptides used to generate anti-renalase antibodies

| Antigen Code | Antigen Sequence | Specificity | poly-clonal | Mono-clonal | Monoclonal Name |
|---|---|---|---|---|---|
| 1A | AVWDKADDSGG RMTTAC | R1, R2 | Yes | | |
| 1B | AVWDKAEDSGG RMTTAC | R1, R2 | Yes | | |
| 1C | CTPHYAKKHQR FYDEL | R1, R2 | Yes | Yes | 1C-22-1 |
| 1D | CIRFVSIDNKK RNIESSEIGP | R1, R2 | Yes | Yes | 1D-28-4 1D-37-10 |
| 1E | PGQMTLHHKPF LAC | R1, R2 | Yes | | |
| 1F | CVLEALKNYI | R1 | Yes | Yes | 1F-26-1 1F-42-7 |
| 3A | PSAGVILGC | R2 | Yes | Yes | 3A-5-2 |

Antibody Affinity determined by Biocore

Binding studies were performed using a Biacore T100. Binding studies were performed at 25° C. using 25 mM Tris pH 8, 150 mM NaCl, 1 mM EDTA, 10% glycerol, 0.005% Tween-20 and 0.1 mg/mL BSA as the running buffer. The biotinylated antibodies were captured on individual streptavidin sensor chip flow cells as shown below. Because the study took two sensor chips, the analysis of two of the mAbs on the second sensor chip was repeated to gather more data. Renalase-1 was tested at 50 nM as the highest concentration in a three-fold dilution series. Each of 5 concentrations was tested in duplicate. Bound complexes were regenerated with a short pulse of 1/1000 phosphoric acid. Data sets were global fit to extract estimates of the binding constants summarized in Table 2.

TABLE 2

Affinity of renalase monoclonal antibodies as determined by Biocore

| IgG | ka (M−1s−1) | kd (s−1) | KD (nM) |
|---|---|---|---|
| BiO-1D 28-4 | 6.467(4)e4 | 2.04(3)e−5 | 0.316(5) |
| BiO-1F 42-7 | 3.928(5)e4 | 9.47(6)e−5 | 2.41(2) |
| BiO-1D 37-10 | 1.749(5)e4 | 4.67(4)e−5 | 2.67(3) |
| BiO-1F 26-1 | 4.526(8)e4 | 1.020(9)e−4 | 2.25(2) |

1D28-4 has highest affinity and was used in the inhibition studies

The Nucleotide and Amino Acid Sequence of Anti-Renalase Antibodies

The monoclonal antibodies 1D-28-4, 1D-37-10, 1F-26-1, 1F-42-7 and 3A-5-2 were selected for their renalase binding specificity and high affinity. Using standard polymerase chain reaction procedures and degenerate primer sets, the cDNA of the antibody heavy and light chain variable regions for these antibodies were amplified from the subcloned hybridomas. The variable region nucleotide and amino acid sequences of 1D-28-4 (RP-220) are shown in FIG. 5. In this way the composition of antibodies with preferred characteristics is exemplified.

Figure 6:
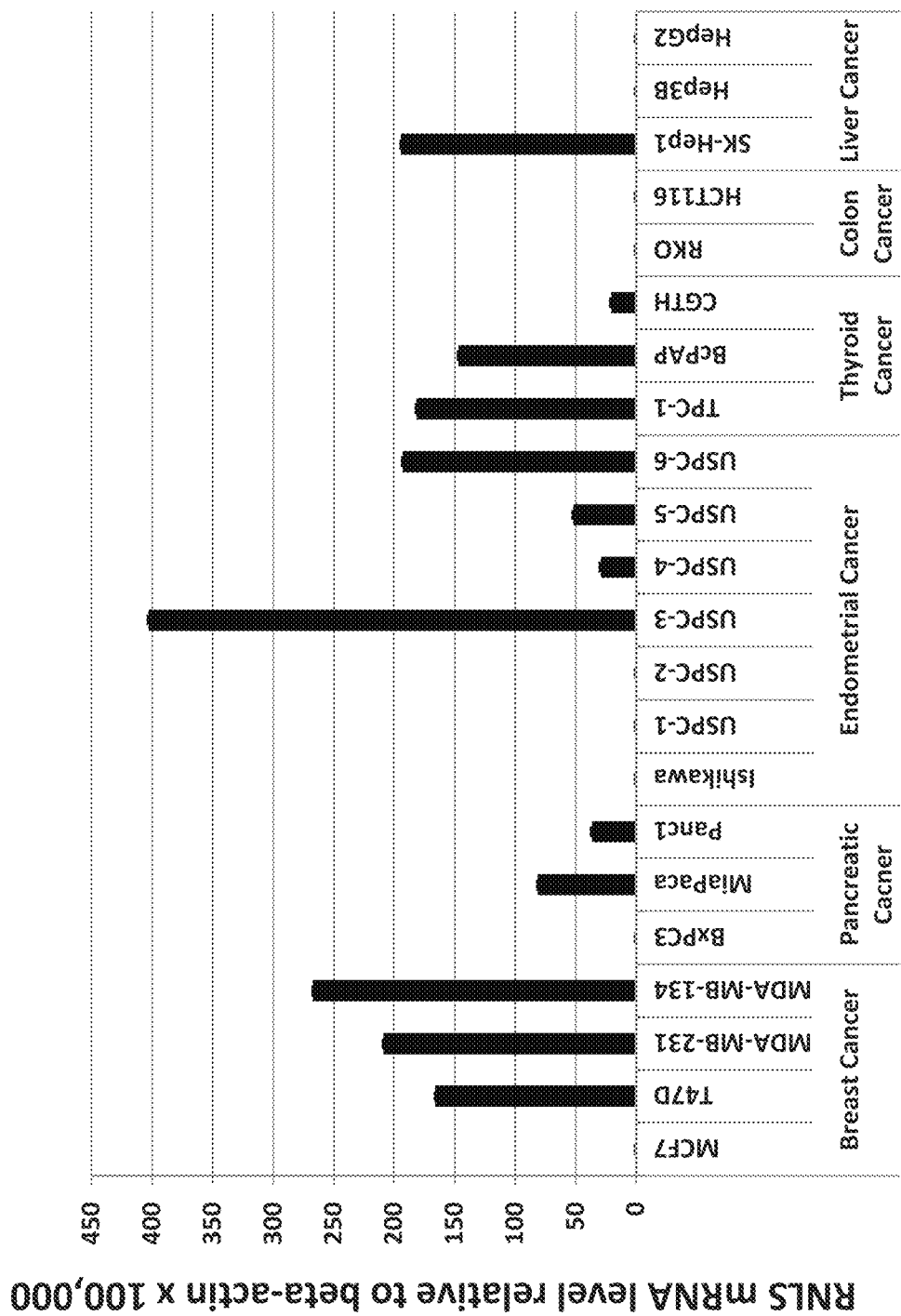
FIG. 6 is a chart showing renalase expression in cancer cell lines: expression determined by quantitative PCR and normalized to actin expression.
Figure 7:
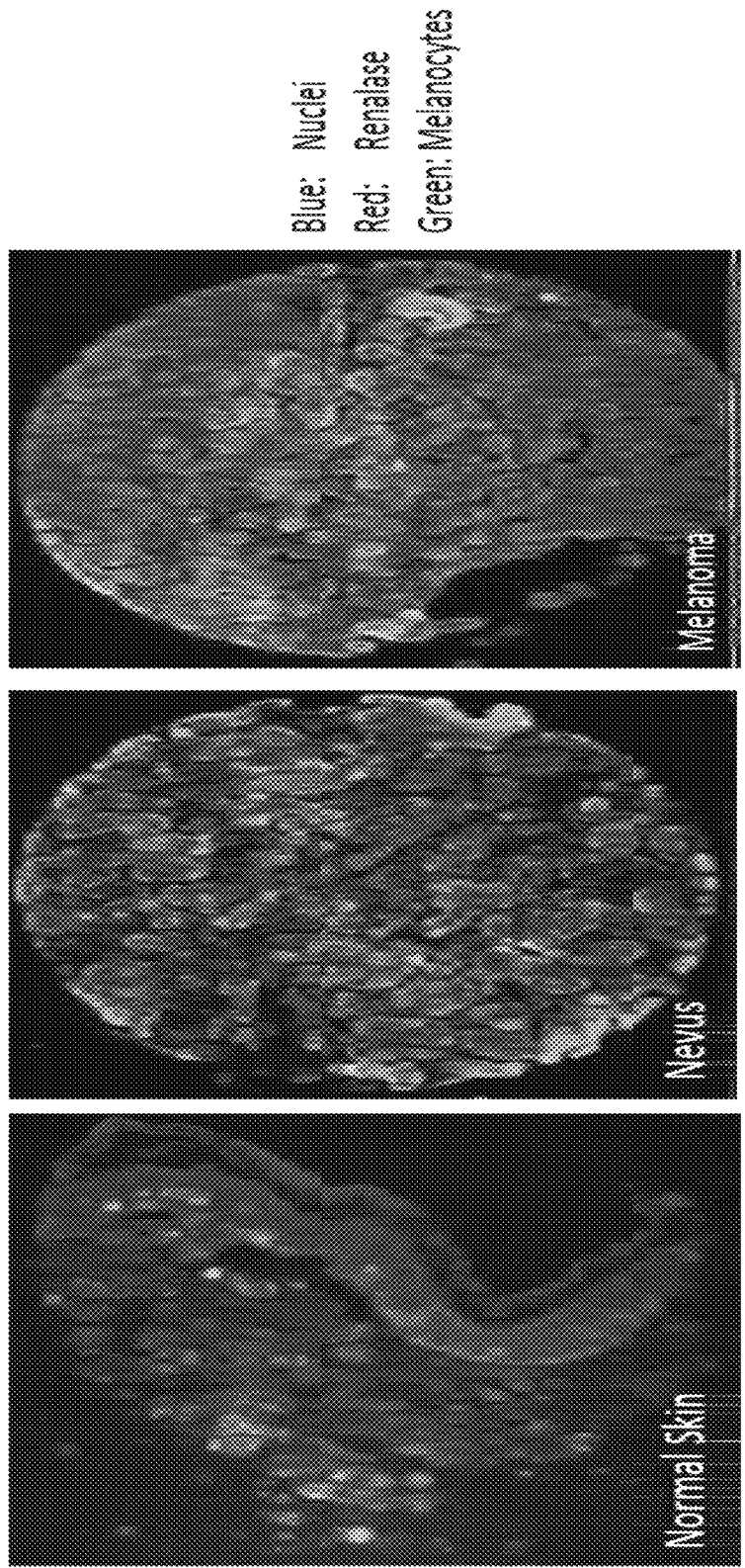
FIG. 7 is an image showing renalase expression in melanocytes: marked increased in renalase expression in nevus and melanoma compared to normal skin.
Figure 8:
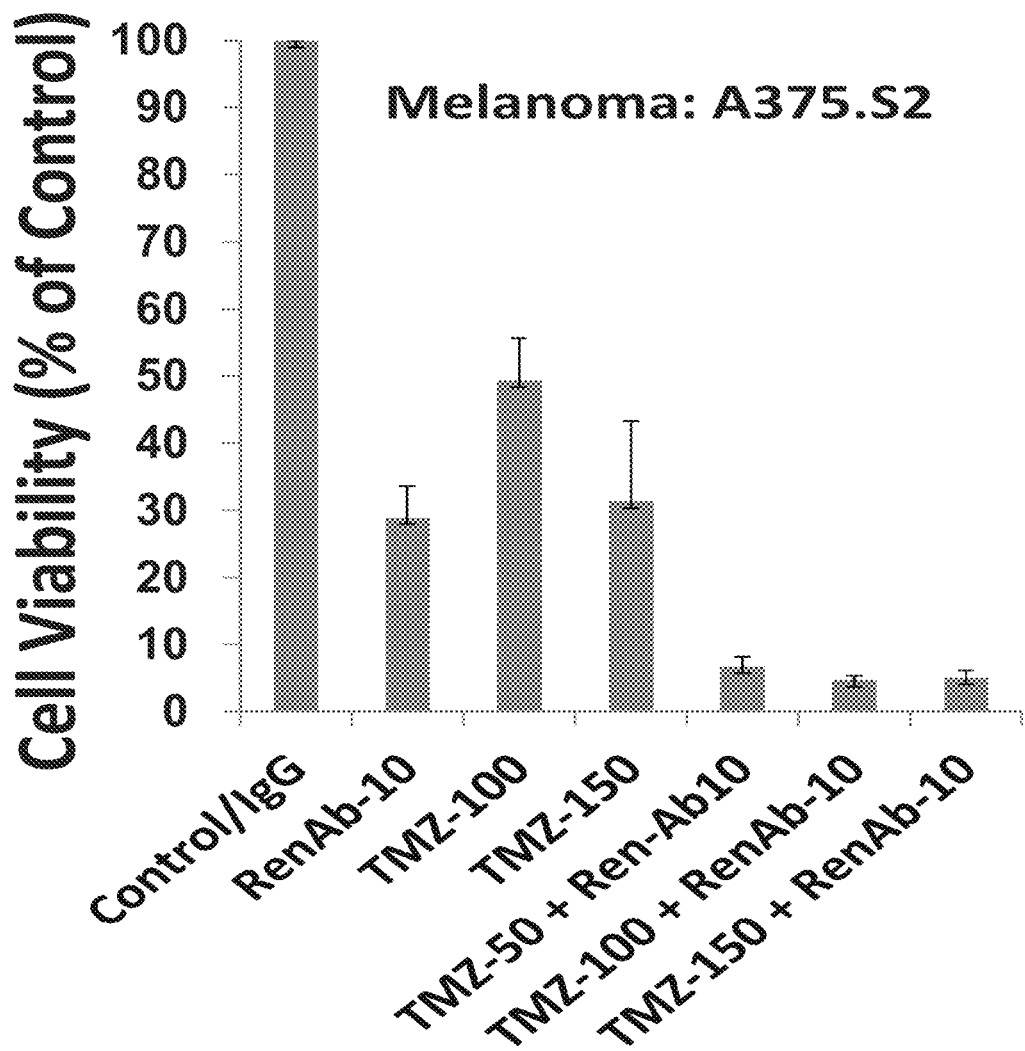
FIG. 8 is a chart showing that anti-renalase monoclonal inhibits A375.S2 melanoma cells in culture and shows synergism with temozolamide: Cell viability measured by the WST-1 methods at 72 hrs post treatment; RenAb-10: renalase monoclonal, 10 µ/ml; TMZ: temozolamide, 100 or 150 µg/ml.
Figure 9:
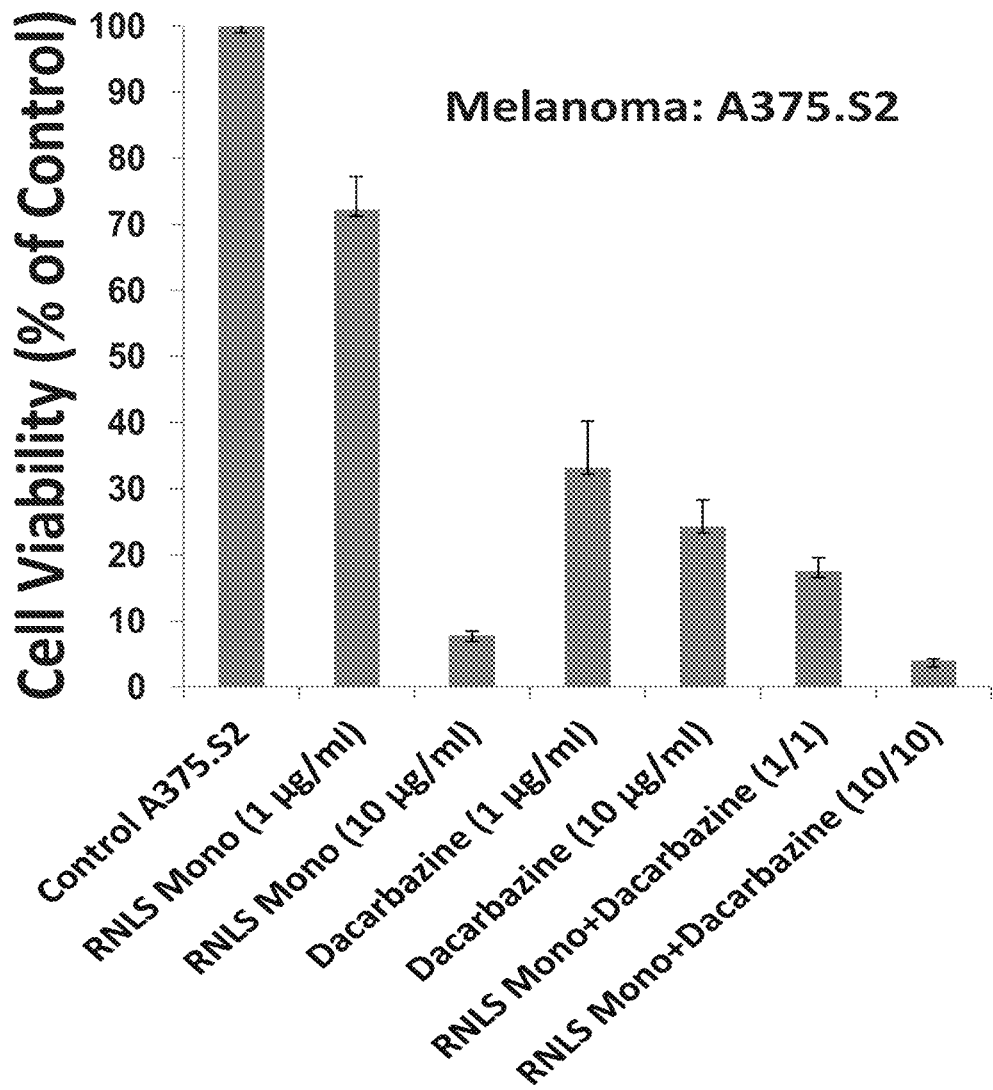
FIG. 9 is a chart showing that anti-renalase monoclonal inhibits A375.S2 melanoma cells in culture and shows synergism with dacarbazine: Cell viability measured by the WST-1 methods at 72 hrs post treatment; RNLSMono: renalase monoclonal.
Figure 10:
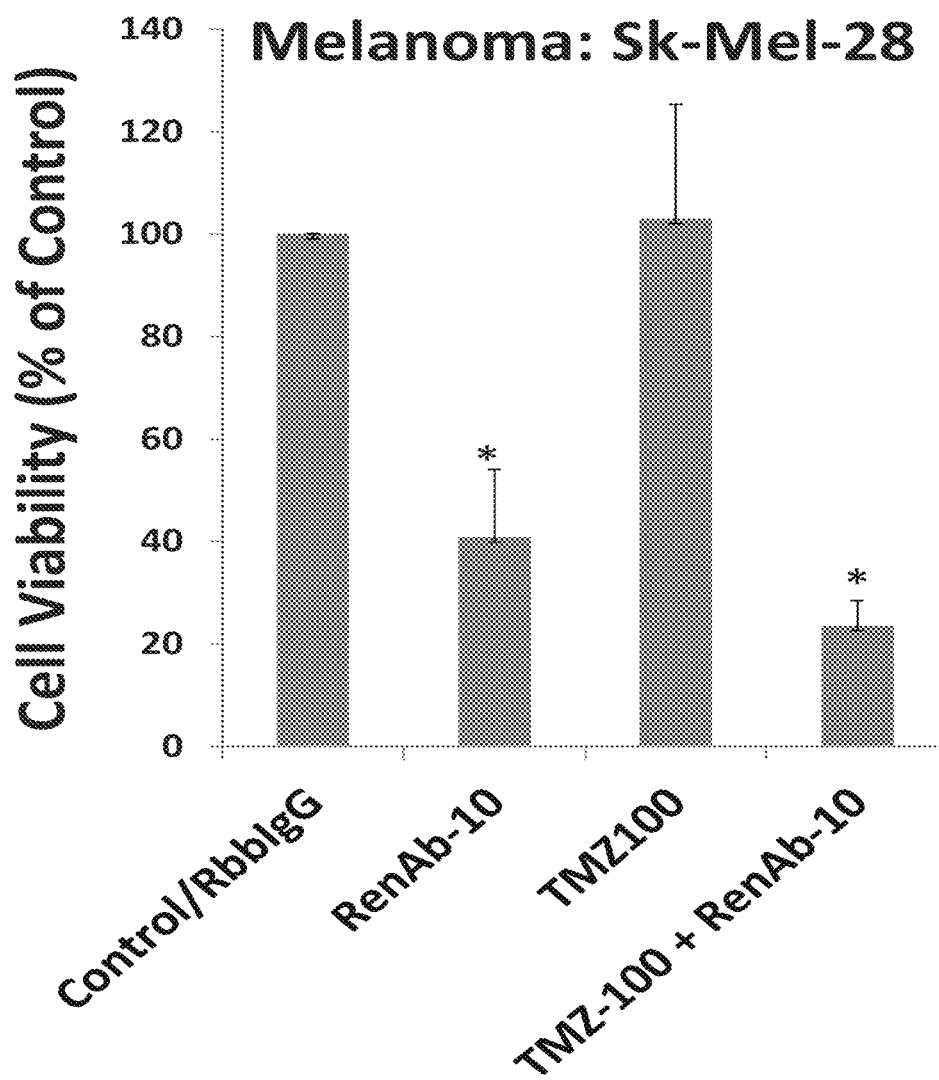
FIG. 10 is a chart showing that anti-renalase monoclonal inhibits Sk-Mel-28 melanoma cells in culture and shows synergism with temozolamide: Cell viability measured by the WST-1 methods at 72 hrs post treatment; RenAb-10: renalase monoclonal, 10 µ/ml, TMZ100: temozolamide, 100 µg/ml.

Inhibition of Renalase Signaling by Antibodies Decreases the Survival of Cancer Cells Since renalase expression is up-regulated in several cancer cell lines (FIG. 6), experiments were performed to determine whether renalase provided a survival advantage to cancer cells. It was found that renalase expression increased markedly in nevi, and metastatic melanoma compared to normal skin (FIG. 7), suggesting that renalase provided a survival advantage to melanocytes. In addition, RenMonoAb1 (monoclonal raised against RP-220) was highly effective at reducing the viability of A375.S2 (melanoma cell line with mutant B-Raf (V600E)), and displayed synergism with two alkylating agents active against melanoma: temozolomide, (FIG. 8) and dacarbazine (FIG. 9). RenMonoAb1 was also effective at reducing the viability of the melanoma cell line Sk-Mel-28 (expresses mutant B-Raf (V600E) and wild type N-Ras) and showed synergism with temozolomide (FIG. 10).

Figure 11:
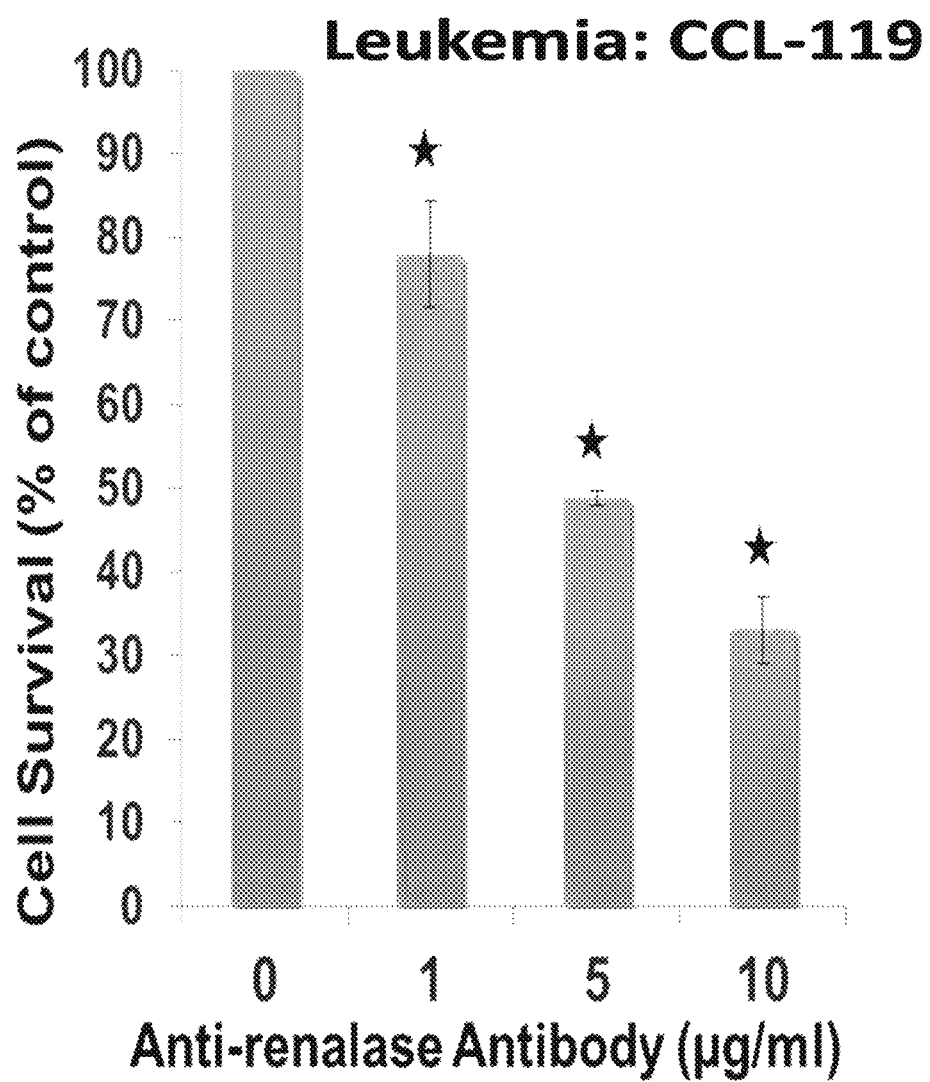
FIG. 11 is a chart showing that anti-renalase monoclonal inhibits leukemic cell line in culture: CCL-119 cells in culture treated with antirenalase monoclonal antibody for 24 hours; cell survival measured by the WST-1 method (n=3, *P,0.05).
Figure 12:
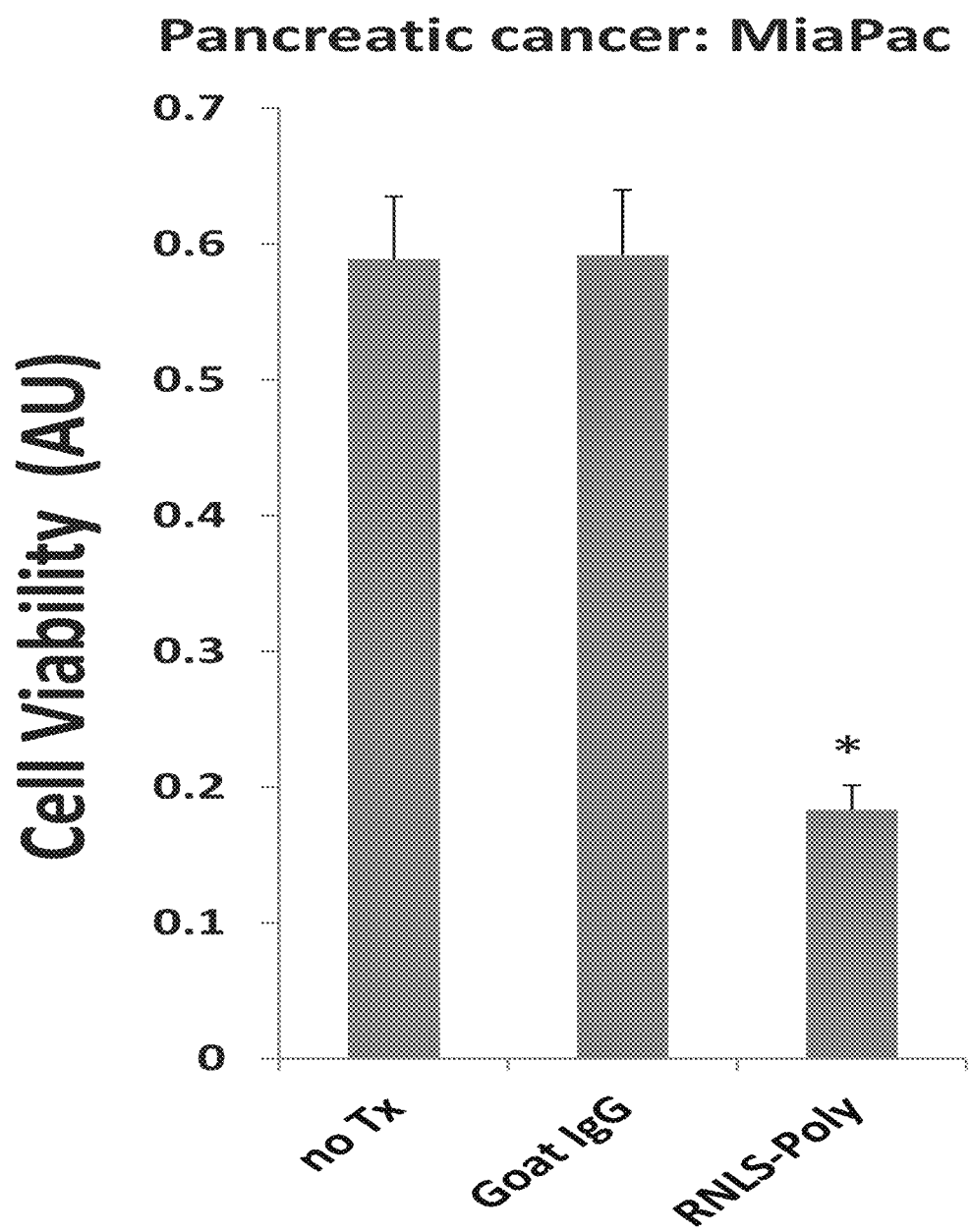
FIG. 12 is a chart showing that anti-renalase polyclonal inhibits pancreatic cancer cell line MiaPac.
Figure 13:
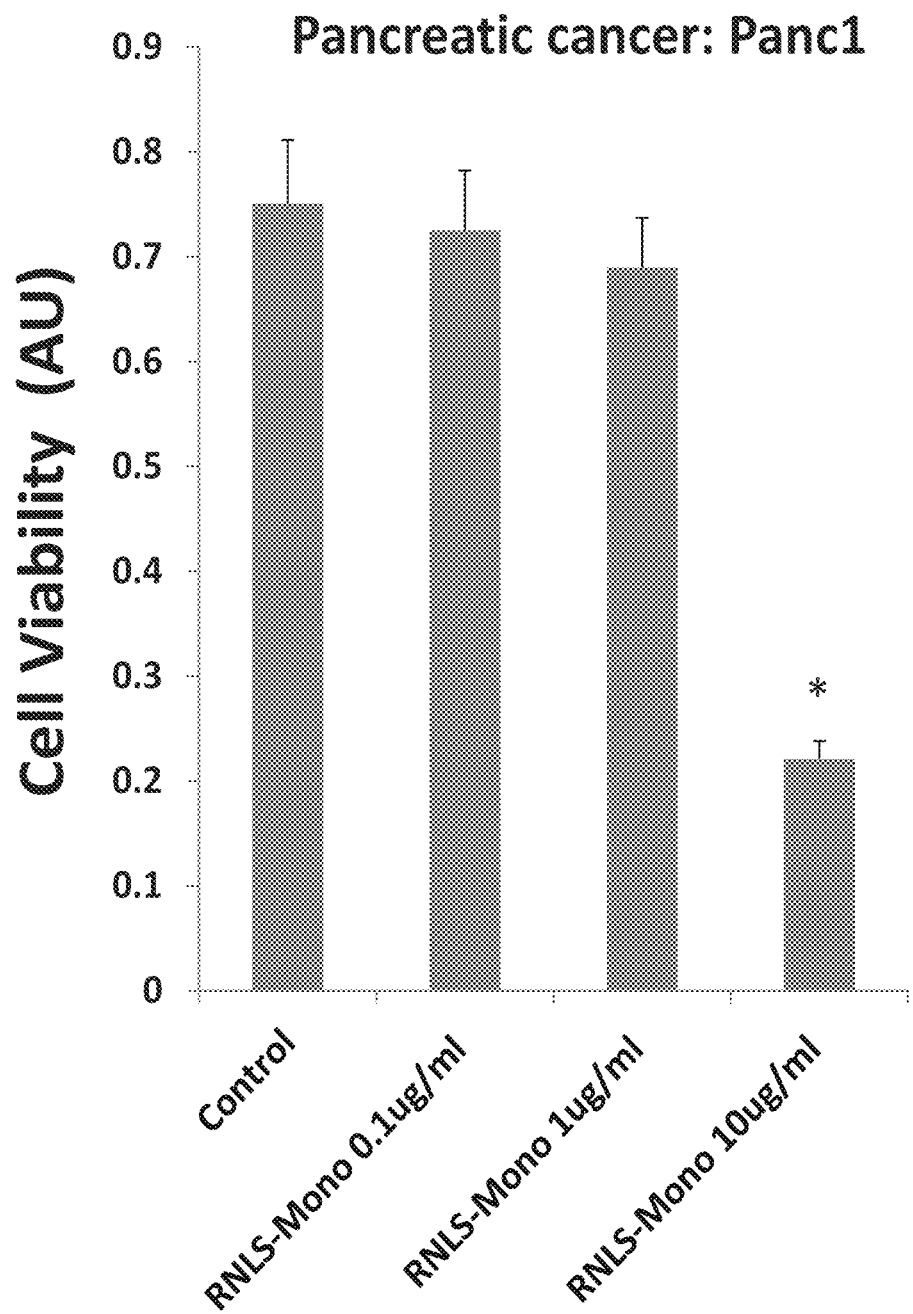
FIG. 13 is a chart showing anti-renalase monoclonal inhibits pancreatic cancer cell line Panc1.
Figure 14:
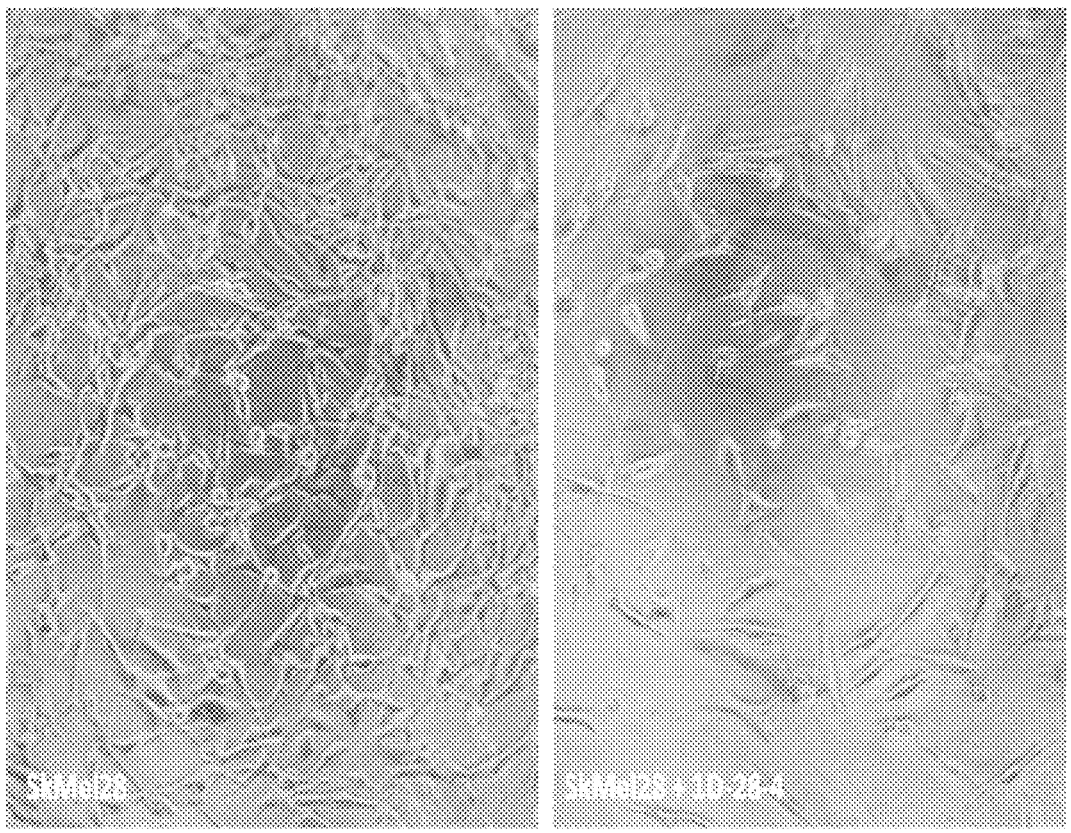
FIG. 14 is a photomicrograph comparing melanoma cells in culture with and without a renalase monoclonal. The renalase antibody markedly decreases the number of live cells.
Figure 15:
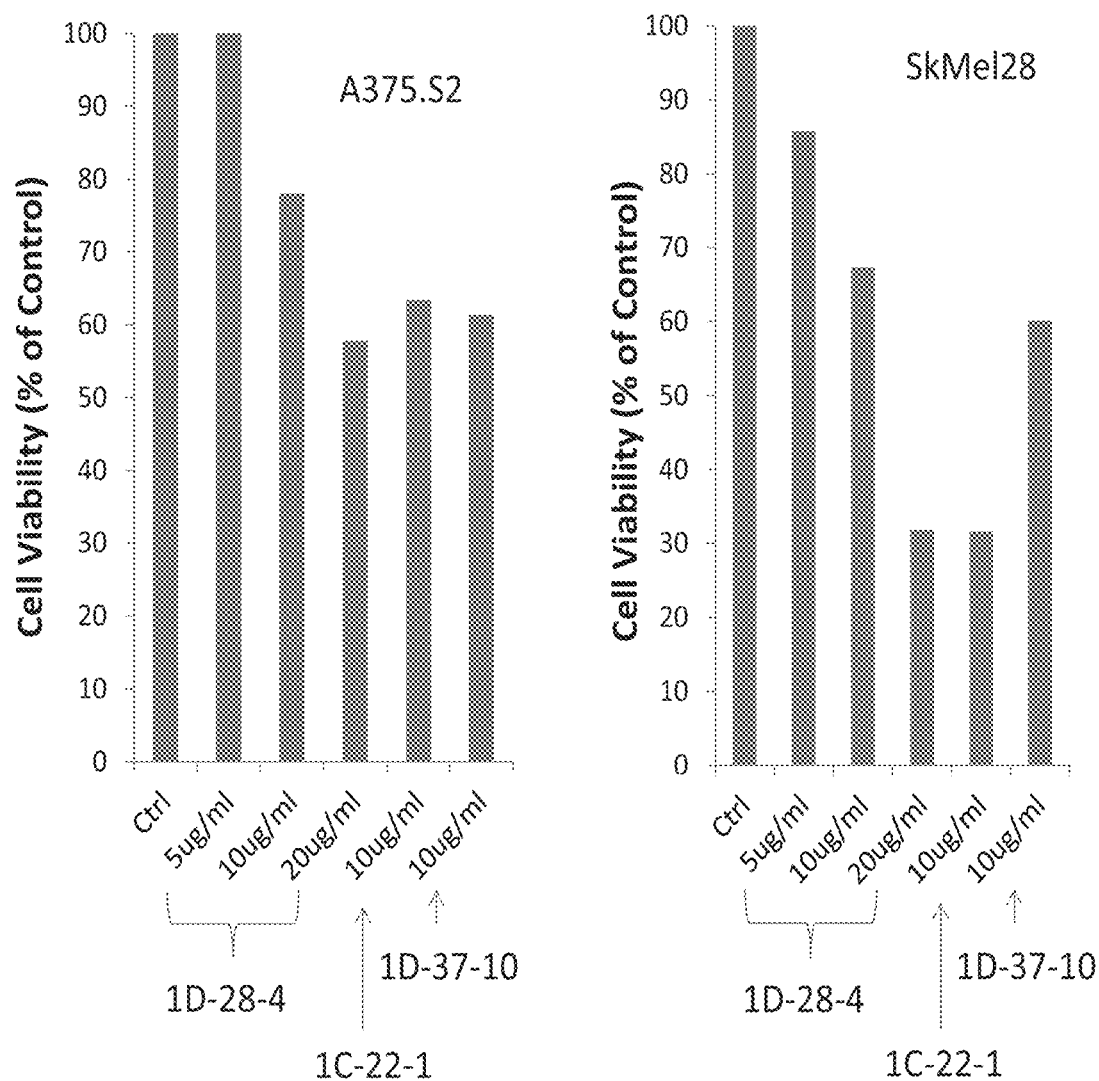
FIG. 15 is a chart demonstrating that renalase monoclonal antibodies 1C-22-1 and 1D-37-10 inhibit melanoma cells in culture.

Next, experiments were performed to determine whether the inhibitory action of RenMonoAb1 was specific to melanoma, or whether it affected a broader range of tumor cells. CCL-119 cells (CCF-MEC, acute lymphoblastic leukemic cell line; American Type Culture Collection) divide rapidly and express a high level of renalase, approximately 3.8-fold over mean (microarray data from BioGPS.org) among the cells making up the NCI-60 panel. RenMonoAb1 significantly decreased the viability of CCL-119 cells in culture (FIG. 11). Similarly, RenMonoAb1 also inhibited the growth of two pancreatic cancer cell lines, MiaPac and Panc1 (FIGS. 12-13). FIG. 14 is a photomicrogarph depicting the effect of renalase monoclonal antibody on melanoma cell number and morphology. It was observed that renalase monoclonal (e.g., 1D-28-4) inhibits melanoma cells in culture. FIG. 15 shows that two additional, 1C-22-1 and D-37-10 renalase monoclonal antibodies also inhibit melanoma cell growth. These data indicate that renalase inhibition could be a useful therapeutic option in several cancers.

Renalase Overexpression Associated with Poor Outcome in Melanoma Patients

Figure 16:
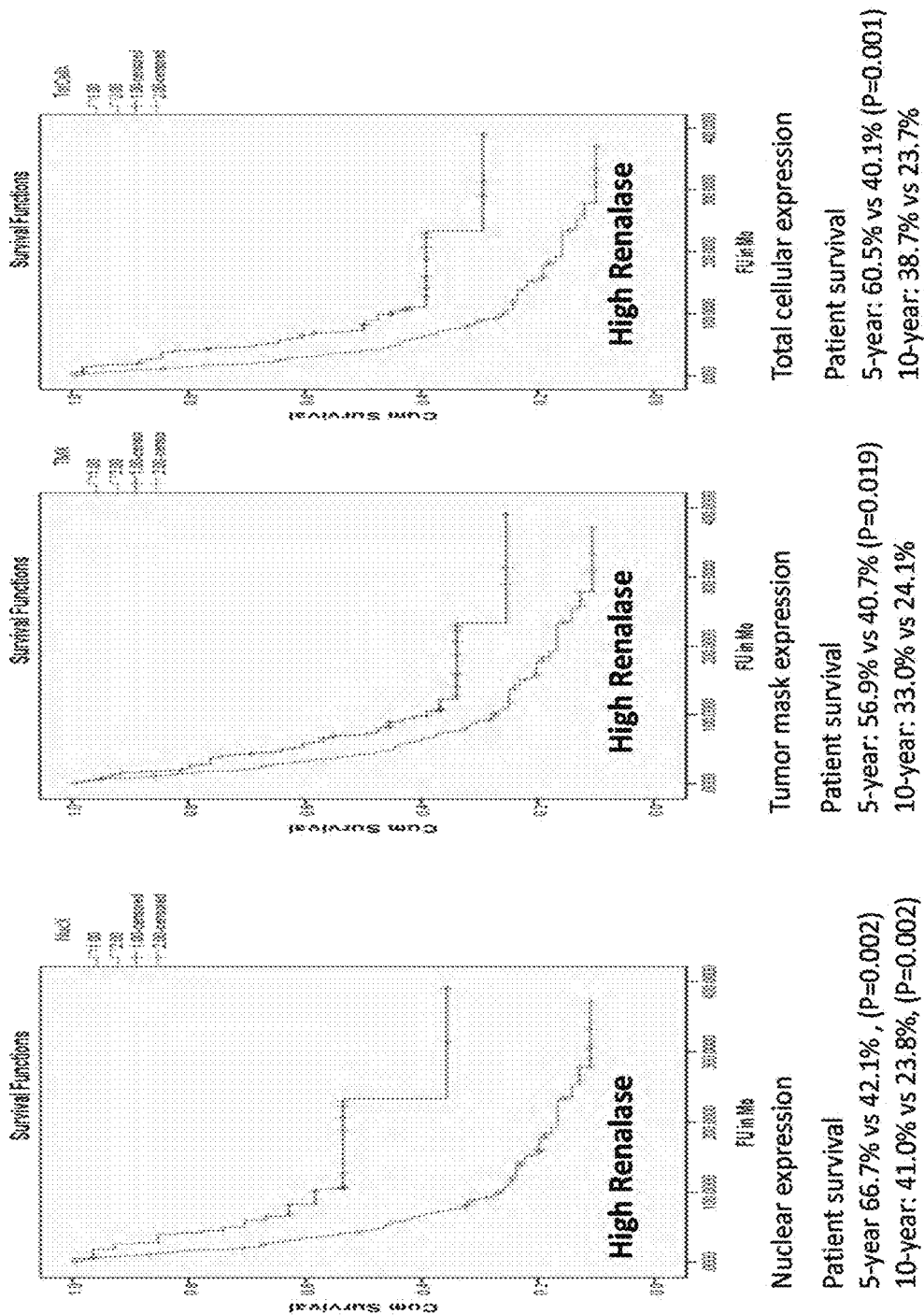
FIG. 16 is a series of images showing increased mortality in patient with melanomas expressing high renalase levels: renalase expression measured by AQUA in biopsy specimens from 263 patients with melanomas; tumor mask obtained using antibodies against S-100 and gp100; Follow up period on x axis in months; % cumulative survival shown on Y axis.

The expression of renalase in primary and metastatic tumor samples obtained from Yale discovery and metastatic series (263 patients followed for up to 30 years) was examined. Fluorescence-based immuno-histochemical staining was performed using the automated quantitative analysis (AQUA) technology (Gould et al., 2009 Journal of Clinical Oncology, 27:5772-5780), a method by which target antigen expression is determined within a compartment defined by labeling with both anti S-100 and anti gp100. It was found that elevated renalase expression in melanoma tissue was associated with a significant increase in disease-specific mortality (FIG. 16), suggesting that inhibition of renalase's action may be a useful therapeutic option in this disease.

Example 2: Renalase Expression by Alternatively Activated, Tumor Associated Macrophages Promotes Melanoma Growth Through a STAT3 Mediated Mechanism Since RNLS functions as a survival factor that engages the MAPK and PI3K pathways, and because its expression is regulated by STAT3 (Sonawane et al., 2014 Biochemistry. 53(44):6878-6892), the question is whether RNLS expression and signaling provides a survival advantage to cancer cells. The focus is on melanoma, a disorder in which the MAPK, PI3K and JAK/STAT pathways are regulated abnormally, and for which additional therapeutic targets would be desirable.

RNLS expression is markedly increased in melanoma cell lines and tumor samples. In patients with metastatic melanoma, RNLS expression is inversely correlated with disease-specific survival. Examination of the pattern of expression of RNLS in melanoma suggests that up-regulation predominantly occurs in the cellular components of tumor-associated stroma, specifically in CD163+ macrophages. Experimental data indicate that alternatively activated macrophages (M2-like, CD163$^+$) recruited into the tumors suppress the immune response against the tumor, increase angiogenesis, and facilitate tumor cell migration, invasion and dissemination (Ruhrberg et al., 2010 Nat Med. 16:861-2; Pollard et al., 2004 Nat Rev Cancer. 4:71-8; Hao et al., 2012 Clinical and Developmental Immunology. 2012:11). TAMs account for a significant percentage of the tumor mass in human melanoma, and also in the xenograft model described in this work.

Figure 22A:
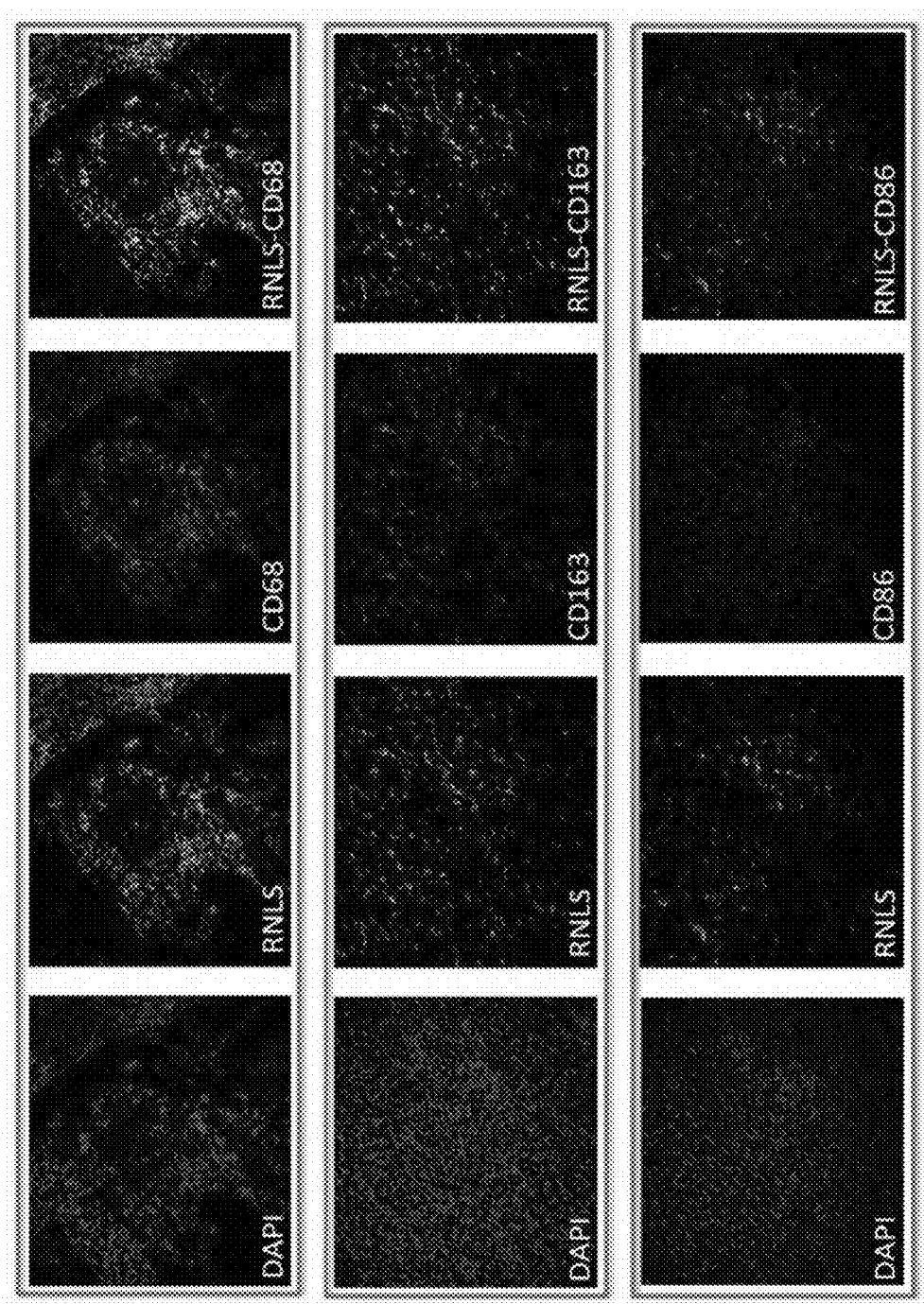
FIGS. 22A through 22C, is a series of images and charts showing that RNLS is expressed in CD163+ TAMs in melanoma.
Figure 22B:
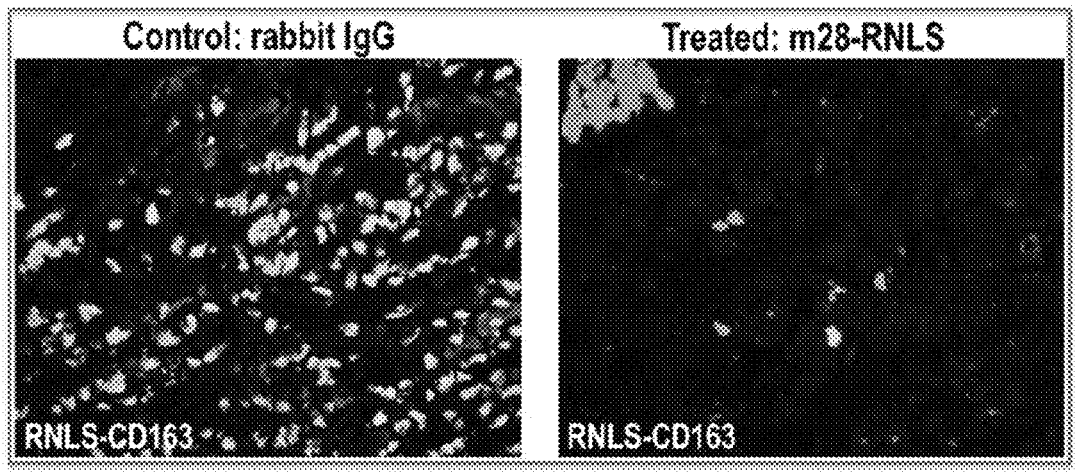
Figure 22C:
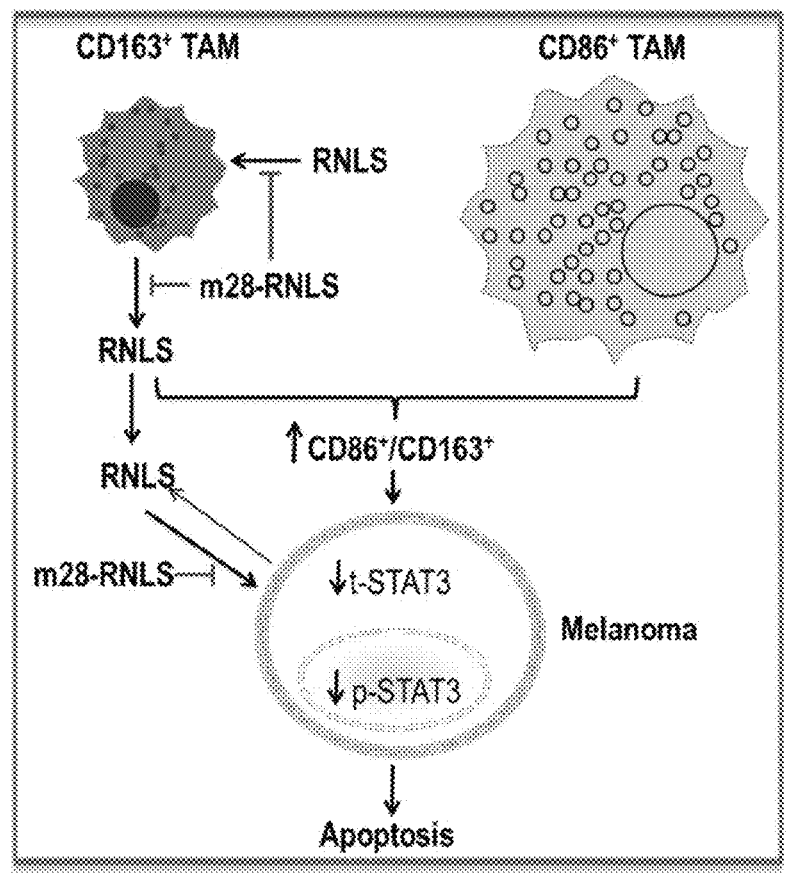

RNLS is preferentially expressed in CD162$^+$ TAMs, suggesting that M2-like TAMs could facilitate tumor progression by secreting RNLS. FIG. 22C illustrates a working model that incorporates the key mechanisms that underlie the anti-tumor effects observed with inhibition of RNLS signaling. Inhibition of RNLS signaling by the RNLS monoclonal m28-RNLS increases the ratio of CD86$^+$ to CD163$^+$ TAMs, and decreases RNLS secretion by CD163$^+$ TAMs. In addition, m28-RNLS inhibits RNLS signaling in melanoma cells. The net result is a dramatic fall in total and phosphorylated STAT3, leading to apoptosis.

The regulatory promoter elements and transcription factors that regulate RNLS gene expression have been recently investigated (Sonawane et al., 2014 Biochemistry. 53(44): 6878-6892) and these data point to a key role for STAT3. The results suggest the existence of a feedforward loop between RNLS and STAT3, in which signals that upregulate STAT3 increase RNLS gene expression, which in turn increases STAT3 activity. The existence of such an interaction between RNLS and STAT3 has important implications regarding the role of RNLS signaling in the pathogenesis of cancer. Indeed, there are extensive data pointing to a key role for the STAT family proteins, particularly STAT3, in the induction and maintenance of an inflammatory microenvironment that facilitates malignant transformation and cancer progression (Yu et al., 2009 Nat Rev Cancer. 9:798-809).

STAT3 signaling is often persistently activated in malignant cells, and such activation not only drives tumor cell proliferation, but also increases the production of a large number of genes that sustain inflammation in the tumor microenvironment. A STAT3 feedforward loop between cancer cells and non-transformed and stromal cells has been documented in cancer (Catlett-Falcone et al., 1999 Immunity. 10:105-15; Yu et al., 2007 Nat Rev Immunol. 7:41-51; Ara et al., 2009 Cancer Res. 69:329-37). For instance, STAT3 is constitutively activated in multiple myeloma patients. In the IL-6-dependent human myeloma cell line U266, IL-6 signals through Janus kinases to activate STAT3, which in turn up-regulates anti-apoptotic factors, and promotes the survival of tumor cells (Catlett-Falcone et al., 1999 Immunity. 10:105-15). Through various mechanisms, STAT3 has also been found to be constitutively activated in a majority of melanomas leading to increases in tumor cell survival, proliferation, metastasis, angiogenesis, and decreases in tumor immune response (Lesinski et al., 2013 Future oncology. 9:925-7; Kortylewski et al., 2005 Cancer metastasis reviews. 24:315-27; Emeagi et al., 2013 Gene therapy. 20:1085-92; Yang et al., 2010 International journal of interferon, cytokine and mediator research: IJIM. 2010:1-7).

RNLS mediates cytoprotection by increasing the anti-apoptotic factor Bcl2, and preventing the activation of effector caspases (Wang et al., 2014 Journal of the American Society of Nephrology DOI:10.1681/asn.2013060665). Inhibition of RNLS signaling in A375.S2 cells is associated with sustained activation of p38 MAPK, followed by activation of the apoptotic factor Bax, and apoptosis. The MAPK p38 is a stress-activated protein kinase that has been implicated in inflammation, cell differentiation, cell cycle regulation and apoptosis (Ono et al., 2000 Cellular Signalling. 12:1-13). For instance, nerve growth factor withdrawal was shown to cause apoptosis following sustained activation of JNK and p38, and down-regulation of ERK (Xia et al., 1995 Science. 270:1326-31). However, since under certain conditions inhibition of p38 can block apoptosis (Ono et al., 2000 Cellular Signalling. 12:1-130, p38's role in apoptosis is clearly context dependent. The data suggests that in A375.S2 cells, RNLS dependent activation of p38 causes apoptosis.

Inhibition of RNLS signaling markedly decreases the expression of Ki-67 in xenographs of melanoma. Since Ki-67 is a well-defined marker of cellular proliferation that has been used extensively to evaluate the proliferative capacity of tumors, the data is interpreted as indicating that RNLS signaling is a key driver of tumor proliferation, and that RNLS inhibition decreases the proliferative rate of tumors. Many of the key factors that determine cell cycle progression have been identified, and include a set of cyclin dependent kinases (CDKs) along with two classes of CDK inhibitors, namely the inhibitor of cyclin dependent kinase 4 (INK4) and the CDK interacting protein/kinase inhibitor protein (CIP/KIP) families (Jung et al., 2010 Cellular Signalling. 22:1003-12). The expression of p21, a CDK inhibitor belonging to the CIP/KIP family, is regulated by RNLS signaling. Inhibition of RNLS signaling is associated with a marked increase in p21 expression. p21 is a negative regulator of cell cycle that can maintain cells in G0, block G1/S transition, and cause G1 or inter-S phase arrest (Jung et al., 2010 Cellular Signalling. 22:1003-12). Therefore, the increase in p21 expression could account for the decrease in cell proliferation observed in tumors treated with an anti RNLS antibody. In addition, p38 has also been shown to affect cell cycle progression (Ono et al., 2000 Cellular Signalling. 12:1-13), and activation of p38 by anti RNLS treatment could also contribute to cell cycle arrest.

These findings identify RNLS as a secreted protein that can promote the survival and growth of cancer cells, and provide a framework to further investigate the use of anti RNLS therapy for the treatment of malignant melanoma, alone or in conjunction with other TAM- or melanoma-inhibiting drugs, such as CSF-1R inhibitors or MAPK pathway inhibitors, respectively. Because there are multiple mechanisms for regulating MAPK and PI3K and JAK/STAT3 and since there is crosstalk between pathways, cell fate depends on the dynamic balance and integration of multiple signals, and the data suggests that RNLS inhibition will tilt the balance toward cancer cell death.

The materials and methods used in this example are now described.

Reagents

Human melanoma cell lines A375.S2, SkMe128, SkMe15, MeWo, and WM266-4 were obtained from the American Type Culture Collection and maintained as recommended. Recombinant human RNLS was expressed, purified, concentrated, and dialyzed against PBS as described (Desir et al., Journal of the American Heart Association. 2012; 1:e002634). RNLS peptides RP220 and mutated peptide RP220A were synthesized at United Peptide. Rabbit anti-RNLS monoclonal antibody (AB178700), goat polyclonal anti-RNLS antibody (AB31291), goat IgG and rabbit IgG were purchased from Abcam.

Synthesis of Anti-RNLS Monoclonal Antibodies m28-RNLS (Also Known as 1D-28-4), m37-RNLS (also known as 1D-37-10)

RNLS peptide RP-220 was conjugated to KLH and used to immunize 6 rabbits, and lymphocytes from the spleens of selected animals were fused to myeloma cells for hybridoma generation. Hybridoma supernatants were screened against rRNLS and selected hybridomas were cloned and expanded for antibody purification. The monoclonal antibodies were purified from conditioned hybridoma culture supernatant by protein A affinity chromatography.

Two clones, m28-RNLS (also known as 1D-28-4), m37-RNLS (also known as 1D-37-10), were selected based on their high binding affinity (KD of 0.316 and 2.67 nM, respectively) as determined using a Biacore T100 system. The m28-RNLS' nucleotide sequence was determined by PCR, synthesized and cloned it into a mammalian expression vector. m28-RNLS, synthesized by transient expression into 293-F cells, was purified by protein A chromatography.

Tissue Specimens

Human melanoma cDNA arrays I and II were obtained from OriGene Technologies (Rockville, Md., USA). The relevant pathology reports are available online: http://www.origene.com/assets/documents/TissueScan. Human melanoma and normal skin tissue samples obtained from US Biomax (Rockville, Md., USA) were used for immunohistochemistry or immunofluorescence.

Quantitative RT-PCR

Relative expression levels of various genes were assessed by qRT-PCR, as described previously (Lee et al., 2013 J Am Soc Nephrol. 24:445-55). The mRNA level of RNLS, 2'-5'-oligoadenylate synthetase 1 (OAS1), β-actin and 18s rRNA was assessed using the TaqMan Gene Expression real-time PCR assays (Applied Biosystems, Carlsbad, Calif., USA). The results were expressed as the threshold cycle (Ct). The relative quantification of the target transcripts normalized to the endogenous control 18s rRNA or β-actin was determined by the comparative Ct method (ΔCt) and the 2-ΔΔCt method was used to analyze the relative changes in gene expression between the tested cell lines according to the manufacturer's protocol (User Bulletin No. 2, Applied Biosystems).

Immunohistochemical Staining and Western Blot Analysis

Immunohistochemistry was performed as described previously (Guo et al., 2012 Cancer science. 103:1474-80). Briefly, tumor tissues were formalin-fixed, paraffin-embedded and cut into 5-μm sections on glass slides. The slides were de-paraffinized and hydrated, followed by antigen retrieval in a pressure cooker containing 10 mM sodium citrate, pH6 buffer. The sections were blocked in 3% hydrogen peroxide for 30 min and 2.5% normal horse serum in PBS/0.1% Tween20 for 1 h followed by incubation with primary antibody and isotype control IgG overnight at 4° C. The following antibodies were used in this study: m28-RNLS at 500 ng/ml; goat polyclonal anti-RNLS at 250 ng/ml (Abcam, ab31291); rabbit monoclonal anti-CD68 (BDBioscience, 1:100); rabbit monoclonal anti-CD163 (AbD Serotec, 1:100); rabbit monoclonal anti-CD86 (Abcam, 1:100); rabbit monoclonal anti-Ki67 (Vector Lab, VP-RM04, 1:100); rabbit monoclonal anti-p21, phspho-$Tyr^{705}$-Stat3, and total Stat3 (Cell Signaling Technologies, #2947, 1:100, #9145, 1:400, and #4904, 1:400, respectively). ImmPRESS peroxidase-anti-rabbit IgG (Vector Laboratories, Burlingame, Calif., USA) was used to detect primary antibodies. The color was developed using a Vector DAB substrate kit and counterstained with hematoxylin (Vector Laboratories). Slides were observed and photographed using an Olympus BX41 microscope and camera (Olympus America Inc, Center Valley, PA, USA).

Western blot analysis was carried out as previously described (Wang et al., 2014 Journal of the American Society of Nephrology DOI:10.1681/asn.2013060665).

Tissue Microarray

Melanoma tissue microarrays were purchased from US BioMax, Inc. and Yale tissue pathology services. This study was approved by the Human Investigation Committee of Yale University School of Medicine (HIC protocol No. 1003006479). The Yale melanoma tissue microarray was constructed as previously described (Berger et al., 2003 Cancer research. 63:8103-7; Rimm et al., 2001 Cancer journal. 7:24-31). A total of 570 tissue cores representing 542 total melanoma cases and a small series of controls measuring 0.6 mm were spaced 0.8 mm apart on a single glass slide. The cohort was constructed from formalin-fixed, paraffin-embedded tissue blocks obtained from the archives of the Department of Pathology at Yale University School of Medicine. A pathologist examined each case to select the region for inclusion in the tissue microarray. Core biopsies from the specimens were placed on the tissue microarray with a Tissue Micorarrayer (Beecher Instruments, Sun Prairie, Wis.). The tissue microarrays were then cut to 5-um sections and placed on glass slides with the adhesive tape transfer system (Instumedics, Inc., Hackensack, N.J.) with UV cross-linking. The specimens were all drawn from archives of tumors resected between 1959 and 1994, with a follow-up range of 2 months and 38 years (median follow-up time, 60 months). The cohort characteristics are described previously (Berger et al., 2004 Cancer research. 64:8767-72).

The tissue microarray slide was stained as described previously (Berger et al., 2004 Cancer research. 64:8767-72; Nicholson et al., 2014 Journal of the American College of Surgeons. 219:977-87). The slides were deparaffinized, rehydrated, unmasked, and blocked in the same way as processed for immunohistochemistry described above. The melanoma tissue arrays were stained with a cocktail of m28-RNLS plus anti-S100 mouse monoclonal (1:100, Millipore, Temecula, Calif., USA) and anti-HMB45 mouse monoclonal (1:100, Thermo Scientific, Fremont, Calif., USA) diluted in BSA/TBS at 4° C. overnight. The secondary antibodies Alexa 488-conjugated goat anti-mouse (1:100, Molecular Probes, Eugene, Oreg.) plus Envision anti-rabbit (DAKO) diluted in BSA/TBS were applied for 1 hour at room temperature. The slide was washed with TBST (three times for 5 minutes each) and then incubated with Cy5-tyramide (Perkin-Elmer Life Science Products, Boston, Mass.) and activated by horseradish peroxidase, resulting in the deposition of numerous covalently associated Cy5 dyes immediately adjacent to the horseradish peroxidase-conjugated secondary antibody. Cy5 was used because its emission peak (red) is well outside of the green-orange spectrum of tissue autofluorescence. The slides were sealed with coverslips with Prolong Gold anti-fade reagent containing 4',6-Diamidino-2-phenylindole to visualize nuclei.

Cell Viability Assays

Total cell number and percentage of live cells were assessed by trypan blue exclusion, and cells were counted using a BioRad TC10 automated cell counter. For additional studies, cell viability was determined using WST-1 reagent (Roche Diagnostics, Indianapolis, Ind., USA) according to the manufacturers' instruction. Absorbances were read using a microplate reader (Power Waves XS, BioTek Instruments, Winooski, Vt., USA).

RNA Interference

Four individual siRNAs and a siRNA SMART pool targeting RNLS were purchased from Dharmacon (Lafayette, Colo., USA). Cells were transfected with RNLS siRNA or a universal negative control small interfering RNA (control siRNA, Dharmacon) using DharmaFECT 4 reagent (Dharmacon) as instructed by the manufacturer. Knockdown efficiency was determined by qPCR.

Mouse Tumor Model

Female athymic, 18-20 g nude mice (nu/nu) were obtained from Charles River (Willimantic, Conn.) and housed in microisolator cages, with autoclaved bedding in a specific pathogen-free facility, with a 12-h light/dark cycle. Animals received water and food ad libitum, and were observed for signs of tumor growth, activity, feeding and pain, in accordance with the study protocol approved by the VACHS IACUC.

Xenograft tumors were established by subcutaneous injection of A375.S2 cells ($2 \times 10^6$ in 100 μl of PBS, pH 7.6). When the tumors reached a volume of 50-100 mm³, the mice were divided into a control group (n=14 treated with rabbit IgG, 40 μg by intraperitoneal injection (IP) once weekly, and 40 ug subcutaneously (SQ) around the tumor site every 3 days), and an experimental group (n=14) that received m28-RNLS (40 μg IP, once weekly, and 40 ug SQ, every 3 days). Tumor size was measured with digital calipers and volume was calculated according to the formula (length× width)×π/2.

At the end of the study, the mice were sacrificed, the tumors were excised and immediately snap-frozen in liquid nitrogen and stored at −80° C. Apoptosis was examined using the TUNEL assay (Roche in situ Apoptosis Detection System), according to the manufacturer's instructions. Sections were examined by light microscopy and the apoptosis index was determined by counting≥1000 cells in 10 randomly selected high-power fields (×200 magnification).

Statistical Analyses

The Wilcoxon rank sum test and the Mann-Whitney U test were used for paired and unpaired data, respectively. When appropriate for nonparametric repeated-measures, ANOVA (Friedman test) was used to evaluate statistical significance.

When the Friedman test revealed statistical significance, Dunn's test was used for pairwise comparisons. A Kaplan-Meier survival analysis and multivariate Cox regression analysis were also carried out. All data are mean±standard error of the mean (mean±SEM), and values of P<0.05 were accepted as a statistically significant difference. Statistical analyses of tissue array data were performed using SPSS® software, version 21.0 (SPSS Inc., Chicago, Ill., USA).

The results of this example are now described.

RNLS Overexpression in Melanoma

In order to determine if RNLS expression differed between normal human skin and malignant melanoma, tissue microarrays (TMAs; Yale Tissue Microarray Facility and US Biomax, Inc.) spanning the progression of normal skin to benign nevus to primary and metastatic melanoma were examined. The Yale TMAs contained formalin-fixed, paraffin-embedded specimens obtained from a cohort of 192 primary melanomas collected during 1959 to 1994, a cohort of 246 serial primary and metastatic melanomas collected from 1997 to 2004, a cohort of 295 patients with benign nevi, and matched normal skin specimens from 15 patients. The demographics and clinical characteristics for these tissue microarrays have been described previously (Gould Rothberg et al., 2009 Journal of clinical oncology: official journal of the American Society of Clinical Oncology. 27:5772-80). The US Biomax array contained 74 specimens, including 35 primary melanomas, 11 metastatic lesions, 14 benign nevi, and 14 normal samples. Examination of approximately 600 histospots for RNLS protein expression using a quantitative, automated immunofluorescence (IF) microscopy system (AQUA), revealed that progression from normal skin to benign nevi to primary malignant melanoma to metastatic melanoma was accompanied by a significant increase in RNLS expression (p=0.009, p=0.0003, and p<0.001, respectively, FIG. 17A-C).

The question is whether dysregulated RNLS expression and signaling could facilitate melanoma growth, and, therefore, serve as a prognostic marker. Each primary melanoma from a cohort of 246 serial primary and metastatic samples collected from 1997 to 2004 were examined. One hundred nineteen patients had histospots that were suitable for evaluation by AQUA technology. In this group, the outcome of patients whose tumors expressed high RNLS levels (RNLS AQUA score>median AQUA score 75,764.45) were compared to those with low RNLS expression. High RNLS expression was associated with increased melanoma-specific death: 5-year and 10-year disease-specific survival rates of 55% versus 69% and 39.7% versus 58.5%, respectively, p=0.008, (FIG. 17D). Following multivariate analysis of this cohort, RNLS levels were found to be independently predictive of survival in melanoma (p=0.004, HR=3.130). Stage of disease at diagnosis (p=0.05, HR=3.940), Clark level (p=0.015, HR=1.687), and ulceration of the primary tumor (p=0.001, HR=2.54) were also found to independently predict survival in melanoma. These findings suggest that RNLS expression may serve as a useful prognostic marker in melanoma, and may help identify a subset of patients with a more aggressive phenotype.

RNLS Overexpression Favors Cancer Cell Survival

Figure 18A:
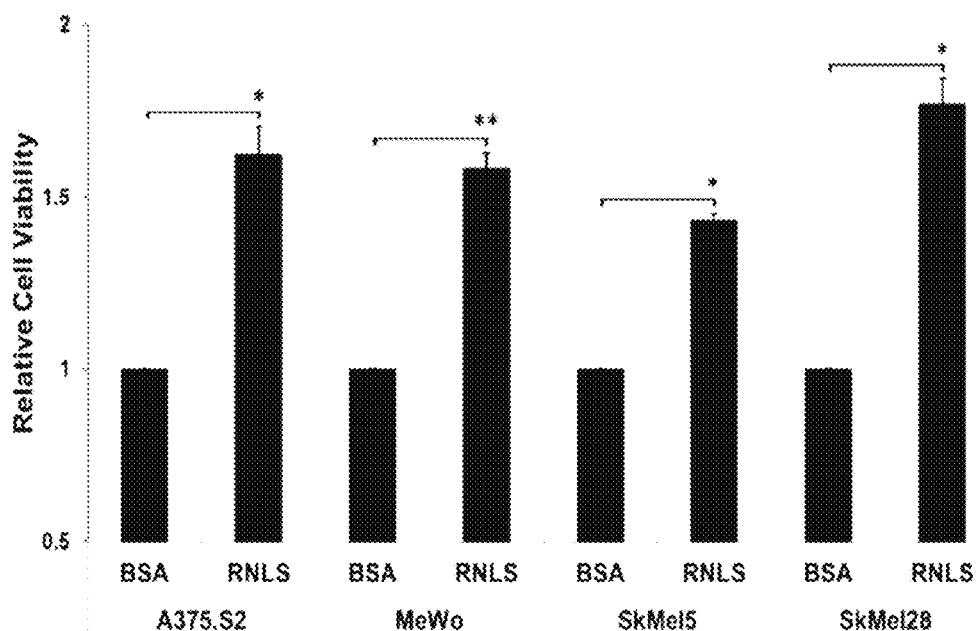
FIGS. 18A and 18B, is two charts showing that RNLS overexpression favors cancer cell survival.
Figure 18B:
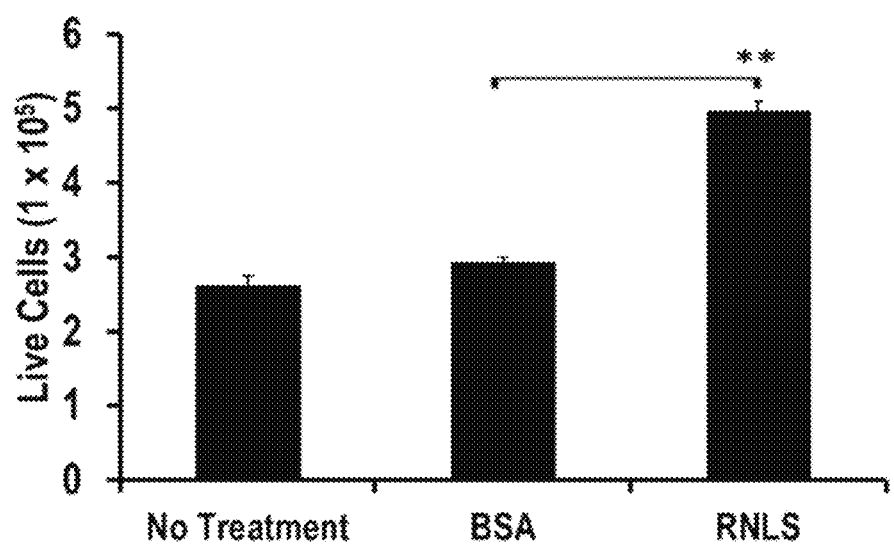

RNLS-mediated signaling is anti-apoptotic, and protects normal cells exposed to toxic stress from apoptotic death (Wang et al., 2014 J Am Soc Nephrol.; Lee et al., 2013 J Am Soc Nephrol. 24:445-55). To explore if RNLS signaling favored the survival of cancer cells, either recombinant RNLS (rRNLS) or bovine serum albumin (BSA) was added to serum-starved melanoma cells (A375.S2, MeWo, SkMe15, and SkMe128) in culture, and cell viability was determined. Compared to BSA, RNLS markedly increased the survival of serum-starved cells, and caused an apparent increase in the proliferative rate as measured by the WST-1 assay (n=6, p<0.05, FIG. 18A). The total cell number and percentage of live cells of those treated with RNLS were counted to determine if the apparent increase in proliferative rate was due an increase in cell proliferation or to a decrease in the rate of apoptosis. As shown in FIG. 18B, treatment with RNLS showed increased cell counts, and increased percentage of live cells compared to those treated with BSA, suggesting that RNLS functions as an anti-apoptotic, survival factor.

Inhibition of RNLS Signaling is Cytotoxic to Melanoma Cells In Vitro

Figure 19A:
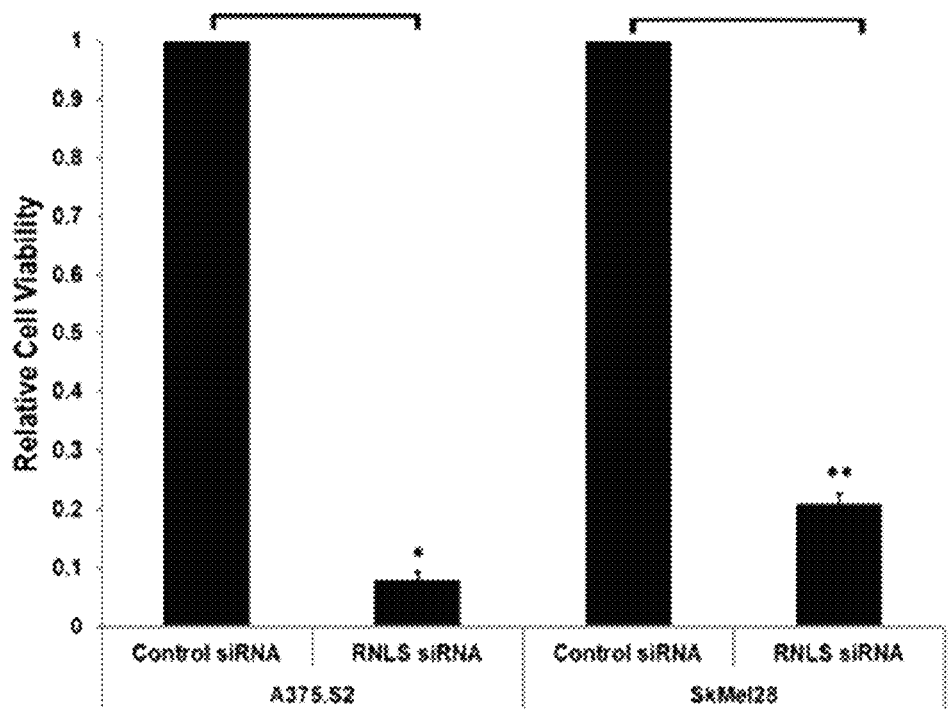
FIGS. 19A through 19D, is a series of images and charts showing that inhibition of RNLS signaling is cytotoxic to melanoma cells in vitro.
Figure 19B:
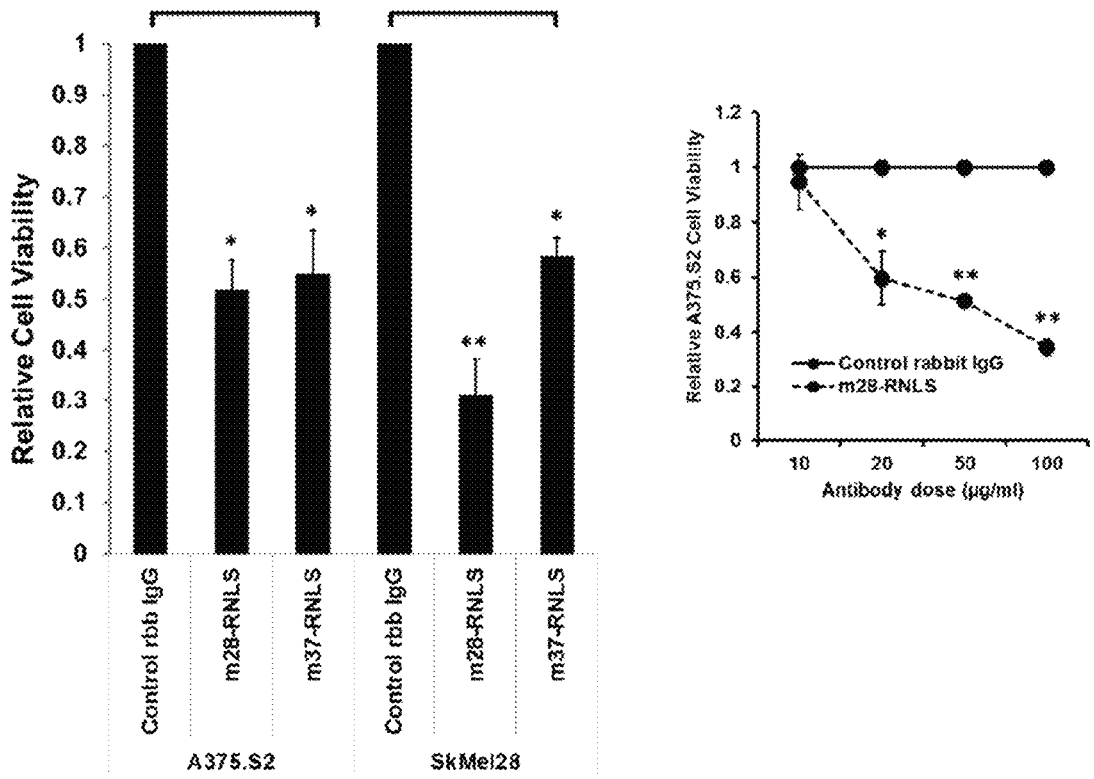
Figure 19D:
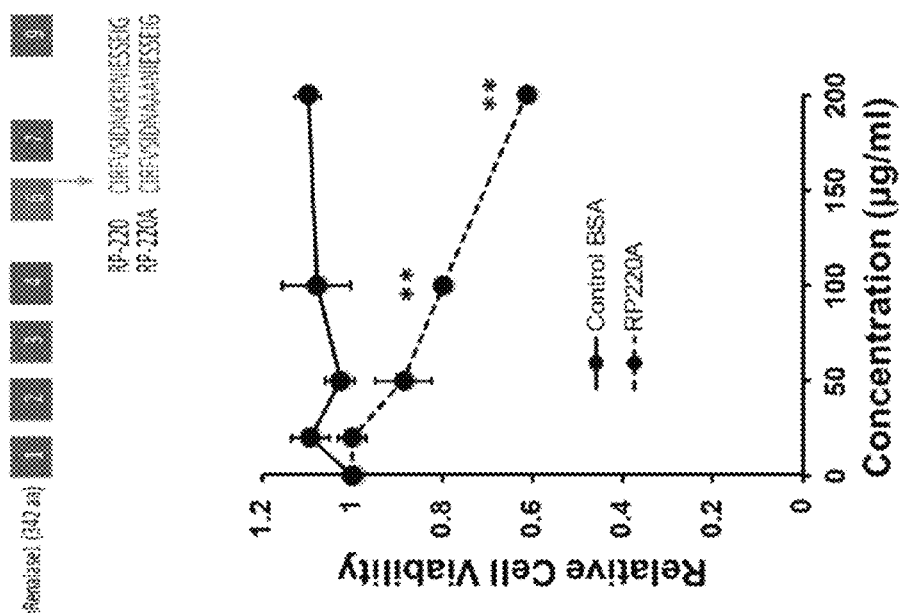
Figure 19C:
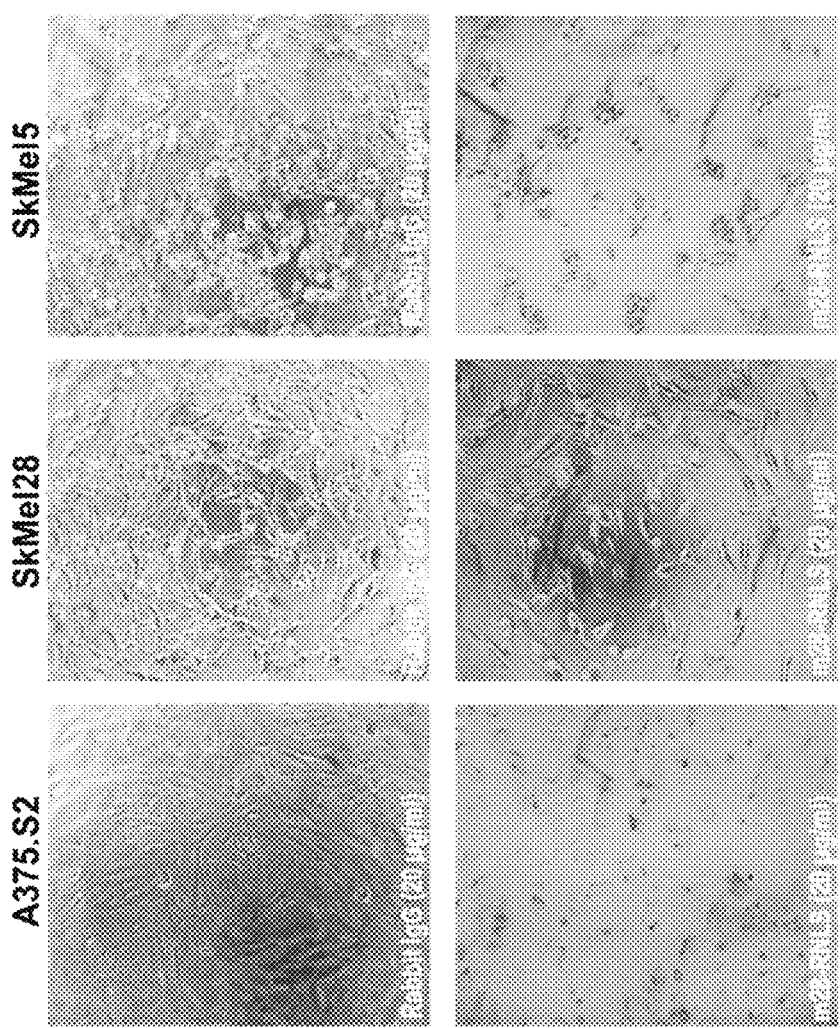

Three approaches to determine the functional consequences of inhibiting RNLS expression and signaling in melanoma were used. First, the effect of decreasing RNLS expression on cell viability was evaluated. RNLS knockdown by siRNA markedly reduced the viability of the melanoma cell lines A375.S2 and SkMe128 (p=0.03 and p=0.003, respectively, FIG. 19A). Second, since the RNLS peptide RP-220 mimics the protective effect and signaling properties of rRNLS, it has been reasoned that it likely interacts with a critical region of the receptor for extracellular RNLS and that antibodies directed against it could have inhibitory properties. Therefore, a panel of monoclonal antibodies against RP-220 was developed, and their effect on cancer cell survival was tested. Two monoclonal antibodies generated against RNLS, [clones #28-4 (m28-RNLS), 37-10 (m37-RNLS)] decreased the viability of all (total of 5) melanoma cell lines tested, and representative examples are shown in FIGS. 19B-C. m28-RNLS demonstrated increasing levels of cytotoxicity in correlation with increasing treatment concentrations (p<0.05, FIG. 19B). Third, a peptide antagonist (RP-220A) was generated by decreasing RP-220's net charge (3 Lysine/arginine changed to alanine FIG. 19D). RP220A does not mediate RNLS dependent signaling, but binds to PMCA4b and antagonizes the action of endogenous RNLS (Wang et al., 2015 PLoS ONE. 10:e0122932). RP-220A proved to be cytotoxic in increasing doses to melanoma cells in culture (p<0.005, FIG. 19D).

Inhibition of RNLS Signaling Blocks Tumor Growth In Vivo

Figure 20A:
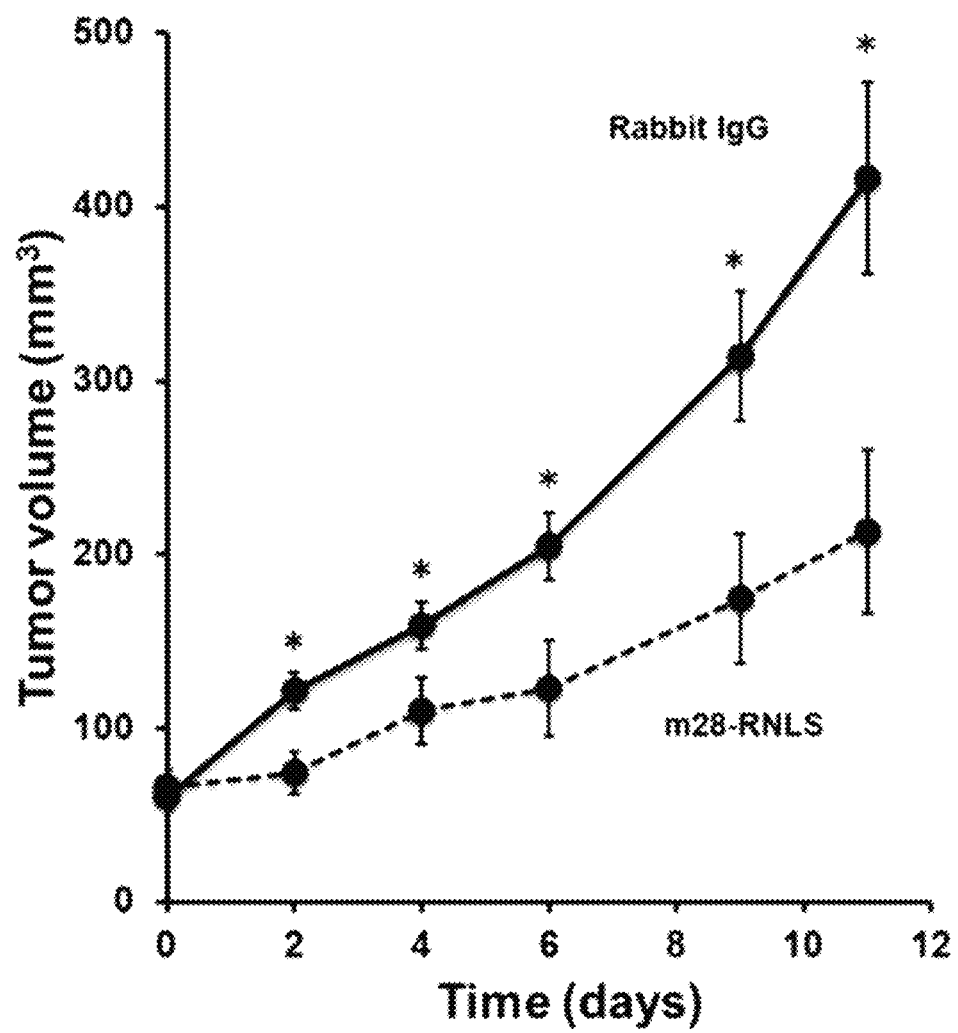
FIG. 20A is a chart showing tumor volume increase in nude athymic mice xenografted with A375.S2 cells, tumor size measured prior to treatment every 3 days with 2 mg/kg of either rabbit IgG as a negative control or with RNLS monoclonal Ab, m28-RNLS; n=14 per group; daily tumor growth rate is computed as change in tumor size from previous measurement; *indicates p<0.05.
Figure 20B:
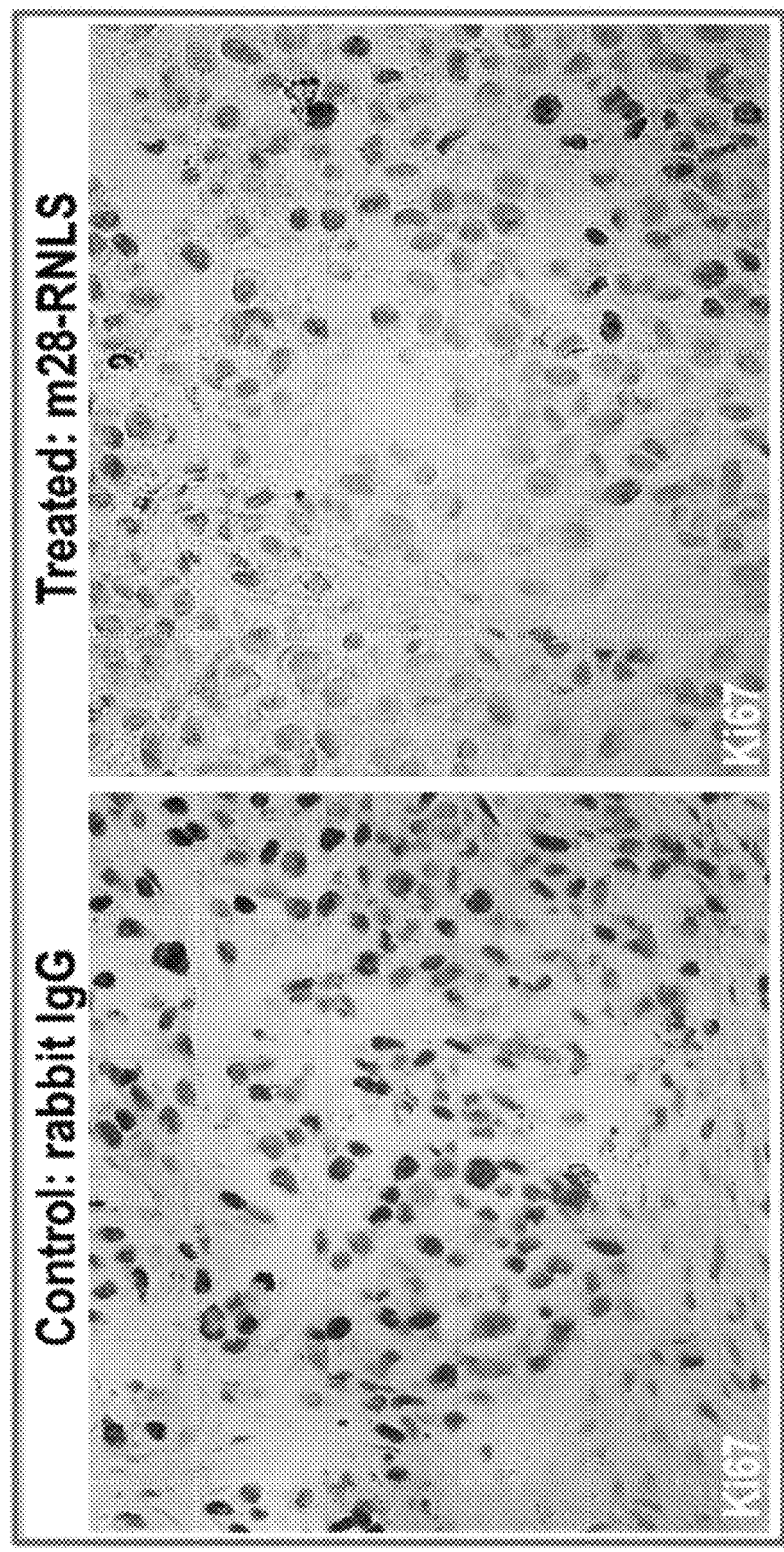
FIG. 20B comprises representative images of IHC staining of sections from A375.S2 xenografted tumors (n=14 each) treated with m28-RNLS or control rabbit IgG for cell proliferation marker Ki67; brown color: Ki67 positive cells.

A375.S2 (human melanoma) cells were injected subcutaneously into athymic nude mice to generate tumors. Once the tumors reached a volume of ~50 mm$^3$, the animals were then treated with either control rabbit IgG or a RNLS neutralizing monoclonal antibody, m28-RNLS. As overall animal health and activity was maintained throughout the study, the antibody treatment did not appear to be toxic. Tumor size was measured every other day, and treatment with m28-RNLS decreased tumor volume at all points tested (p<0.05, FIG. 20A). The animals were sacrificed at day 11 due to overall tumor size and ulceration in some animals. IHC staining of sections from the xenografted tumors with the cellular proliferation marker Ki67 revealed a significant decrease in cellular proliferation within the tumors treated with the anti-RNLS antibody versus to those treated with rabbit IgG: of 35.1±2.3 positive cells/high power field in the control group vs. 13.4±3.0 in the RNLS Ab treated group, n=14, p=0.0004 (FIG. 20B).

Figure 21A:
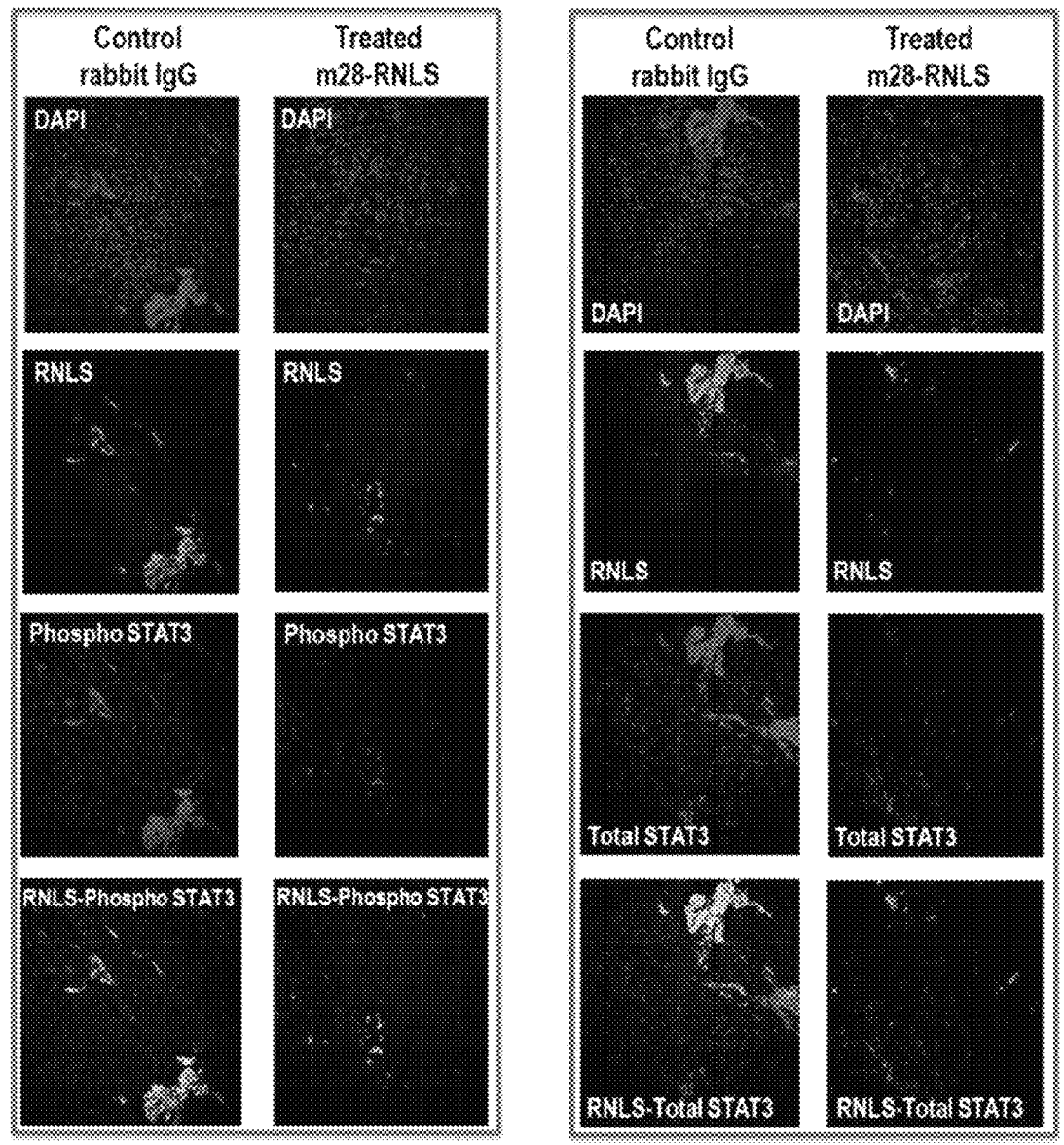
FIGS. 21A through 21F, is a series of images and charts showing that inhibition of RNLS signaling blocks RNLS expression and STAT3 activation and induces apoptosis and cell cycle arrest.
Figure 21B:
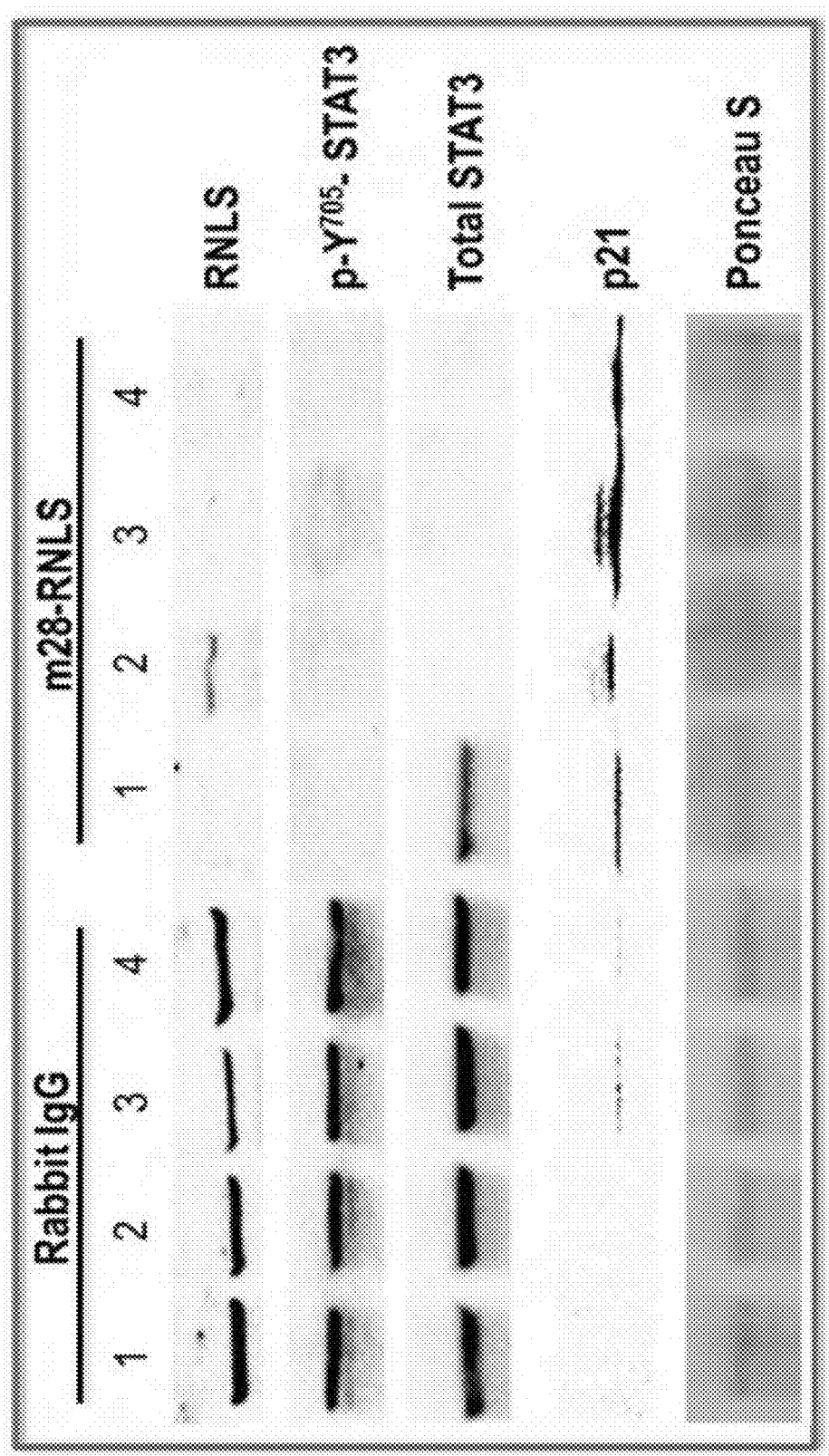
Figure 21C:
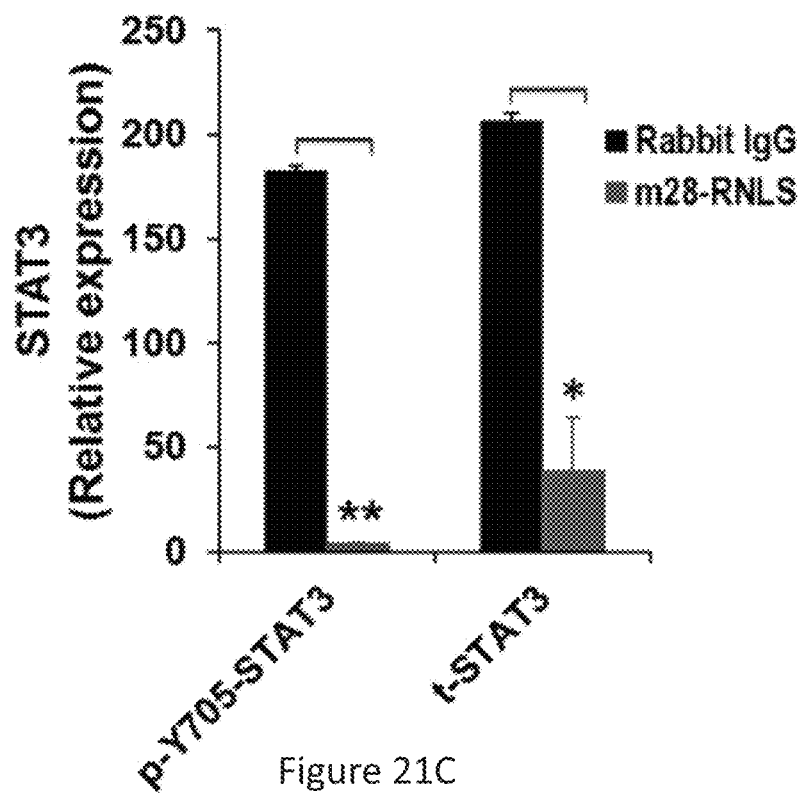

Inhibition of RNLS Signaling Blocks Endogenous RNLS Expression and STAT3 Activation and Induces Apoptosis and Cell Cycle Arrest STAT3 is known to bind to the promoter region of the RNLS gene and increase its expression, and a positive RNLS-STAT3 feedback loop has been suggested (Sonawane et al., 2014 Biochemistry. 53(44):6878-6892). This relationship was further investigated through immunofluorescent tissue staining and study of the cell lysates from the xenografted tumors treated with control IgG and m28-RNLS. Significant coexpression of RNLS with phosphorylated and total STAT3 was noted in the tumor samples (FIG. 21A) as assessed by IF. Treatment with m28-RNLS caused a dramatic reduction in RNLS protein expression, and in both total and phosphorylated STAT3 (FIG. 21A). Changes in protein expression were confirmed by western blot as shown in FIGS. 21B-C. In tumors treated with m28-RNLS, STAT3 phosphorylation at tyrosine 705 (p-$Y^{705}$-STAT3), and total STAT3 were significantly decreased (n=8, p<0.005, FIG. 21B-C).

Figure 21D:
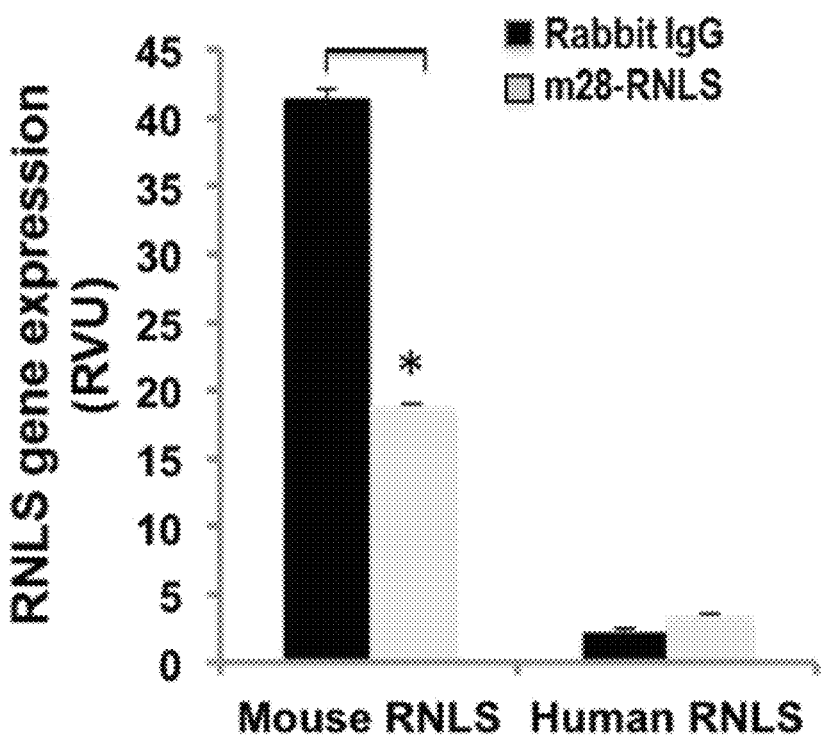

To test if the significant decrease in RNLS expression was primarily occurring in the melanoma cells, human and mouse specific primers were used to amplify tumor (human) and endogenous (mouse) RNLS in the tumor mass. As depicted in FIG. 21D, treatment with m28-RNLS causes a significant reduction in mouse RNLS expression, without affecting human (tumor) expression, suggesting that tumor-infiltrating cells play a key role in RNLS production and secretion.

Figure 21E:
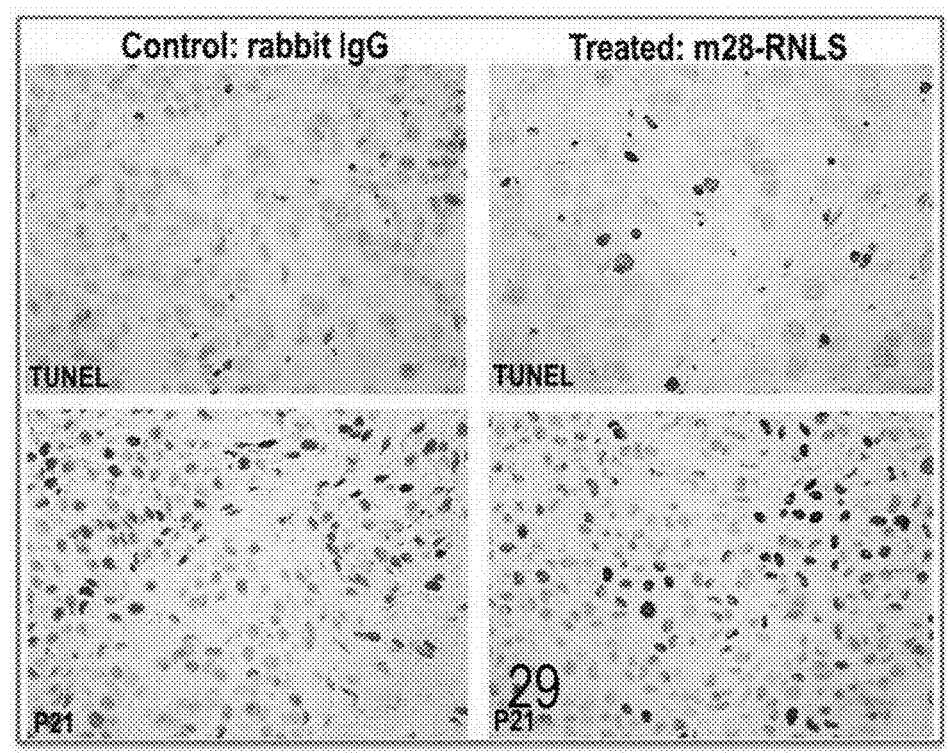
Figure 21F:
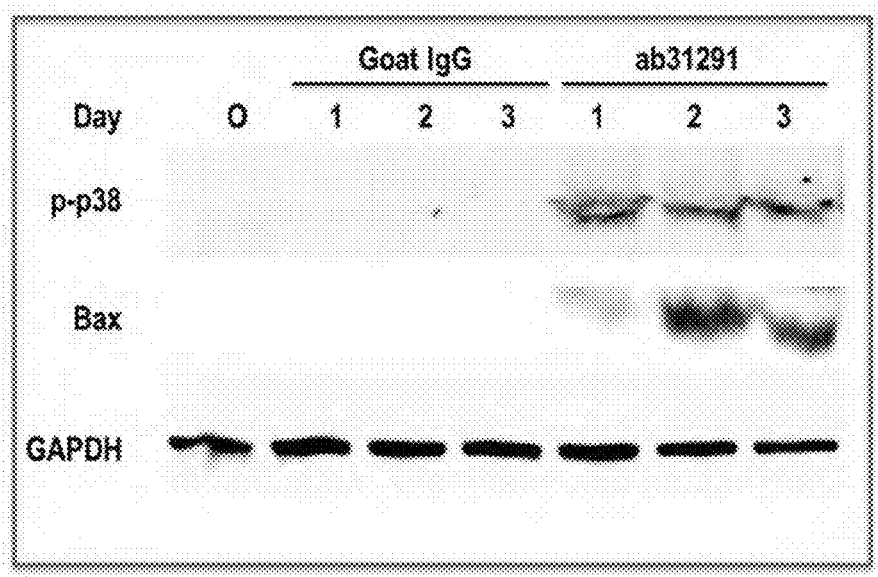

In addition, increased expression of the cell cycle inhibitor p21 was noted. Antibody treatment markedly increased the expression of the cell cycle regulator p21 in the tumor samples: 24.2±2.4 positive cells in the antibody treated group vs. 12.2±1.0 in the control group, n=14, p=0.009 (FIG. 21E). Terminal deoxynucleotidyl transferase dUTP nick end labeling (TUNEL) staining revealed a significant increase in the average number of cells undergoing apoptosis in the antibody-treated tumors over the control group with an average of 13.3±0.6 positive cells vs. 4.3±0.2, n=14, p<0.001, (FIG. 21E). The increase in apoptosis was temporally related to phosphorylation of p38 MAPK, and subsequent activation of the B-cell lymphoma 2 related protein Bax (FIG. 21F). These data indicate that treatment with anti-RNLS antibody causes a marked reduction in total and phosphorylated STAT3, decreases cell proliferation, and increases apoptosis in tumor cells.

Inhibition of RNLS Signaling Increases the Ratio of CD86+ to CD163+ TAMs

Figure 17A:
FIGS. 17A through 17D, is a series of images and charts showing RNLS overexpression in melanoma, and association with poor patient outcome.
Figure 17B:
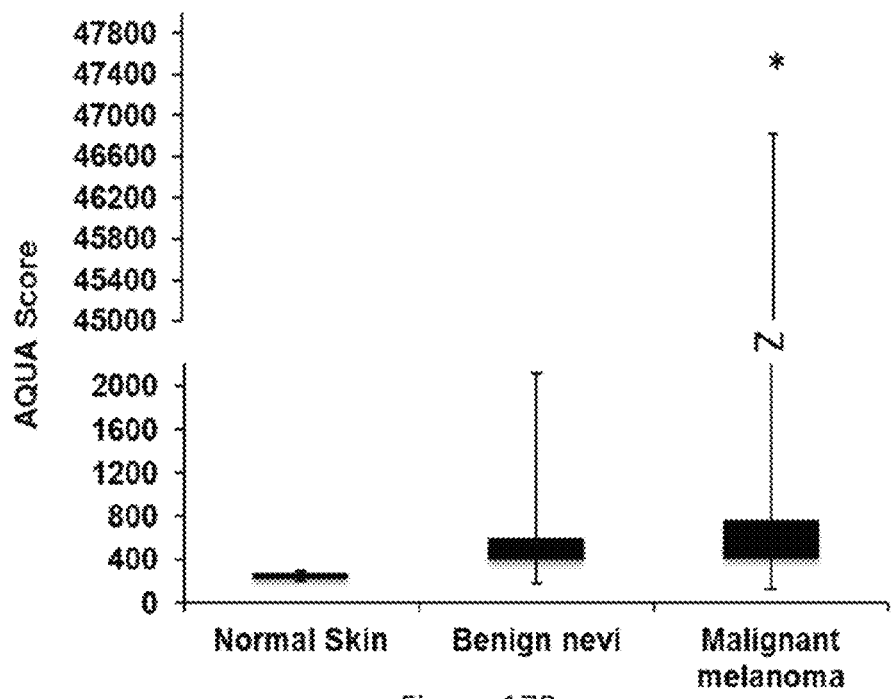
Figure 17C:
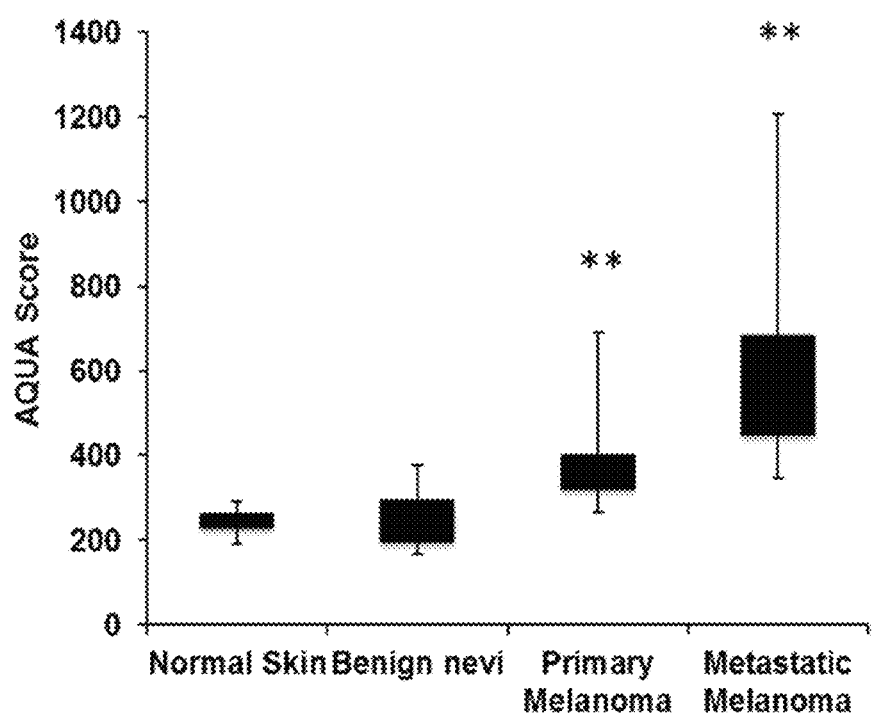
Figure 17D:
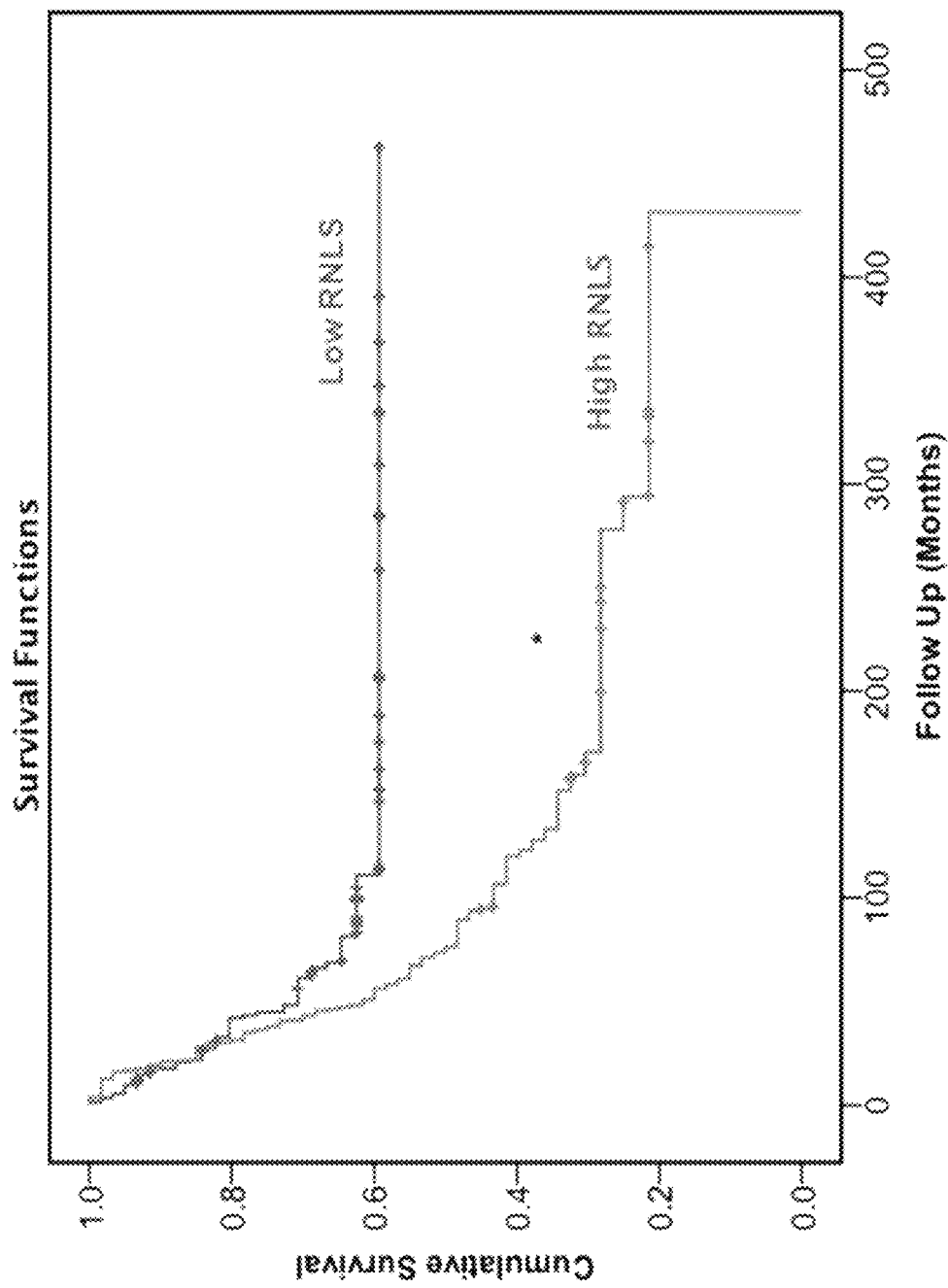

The melanocytes did not appear to be the main source of the RNLS in the melanoma histospots, as there was minimal overlap noted between RNLS and melanocyte staining (FIG. 17A). Melanomas often have significant infiltration of immune cells, including macrophages. The infiltrating macrophages appeared to contribute the majority of the tumoral RNLS as a substantial component of the RNLS staining noted in each histospot overlapped significantly with the pan-macrophage marker CD68 (FIG. 22A top panel). Upon further investigation, it was determined that RNLS was coexpressed predominantly with CD163+(M2-like) TAMs (FIG. 22A, middle panel). Coexpression of RNLS with CD86+(M1-like) macrophages was minimal (FIG. 22A, bottom panel). M2-like (CD163+) macrophages are associated with immune escape and shown to promote cancer development and spread, while M1-like (CD86+) macrophages are typically pro-inflammatory, and inhibit tumor growth (Biswas et al., 2010 Nat Immunol. 11:889-96; Mantovani et al., Trends in Immunology. 23:549-55). Treatment of the xenografts with m28-RNLS antibody led to a considerable decrease in the number of CD163+ TMAs, and the remaining cells did not express detectable levels of RNLS (FIG. 22B).

Example 3: Sustained Renalase Signaling Through the Plasma Membrane Calcium ATPase PMCA4b Promotes Pancreatic Cancer Growth Since RNLS functions as a survival factor that engages the MAPK and PI3K pathways that are disordered in pancreatic cancer, and because its expression is regulated by the signal transducer and activator of transcription STAT3 (Sonawane et al., 2014 Biochemistry. 53(44):6878-6892), it has been postulated that abnormal regulation of RNLS expression and signaling could provide a survival advantage to cancer cells, and promote tumor formation (Guo et al., 2014 Curr Opin Nephrol Hypertens. 23(5):513-8).

It is shown herein that RNLS expression is increased in several types of cancers, and in a cohort of patients with pancreatic ductal adenocarcinoma (PDAC), overall survival was inversely correlated with RNLS expression in the tumor, suggesting a pathogenic role for RNLS. Inhibition of RNLS expression using siRNA, or inhibitory anti-RNLS antibodies decreased cultured PDAC cells viability. In a xenograft mouse model, the RNLS monoclonal antibody m28-RNLS inhibited PDAC growth, and caused apoptosis and cell cycle arrest by down-regulating STAT3, and up-regulating in p21, and p38. Down-regulation of RNLS expression in tumor cells led to an equivalent decrease in PMCA4b (RNLS receptor) expression and resulted in a reduction in tumor size similar to that observed with inhibitory anti-RNLS antibodies. These results reveal a previously unrecognized pro-survival function of the RNLS pathway in cancer, show that RNLS expression may serve as a prognostic marker, and identify novel therapeutic targets for the management of pancreatic cancer.

Evidence is provided here for both a pathogenic role of increased RNLS expression in PDAC, and for the therapeutic utility of inhibiting RNLS signaling. In addition, the molecular mechanisms that mediate the observed antitumor activity of inhibitors of RNLS signaling are being explored.

Taken together, these findings indicate that upregulated RNLS-mediated signaling plays a pathogenic role in PDAC. It is being shown here that high RNLS tumor expression is associated with a two-fold increase in overall 3-year mortality, supporting the use of RNLS as a diagnostic or prognostic marker. Furthermore, since RNLS is a secreted protein, it can be used as a biomarker for the primary detection of tumors, or as a surrogate marker for treatment response or recurrence.

A primary mechanism of RNLS mediated cyto-protection appears to be its ability to activate AKT, ERK and STAT, to increase the anti-apoptotic factor Bcl2, and to prevent the activation of effector caspases (Wang et al., 2014 Journal of the American Society of Nephrology. DOI:10.1681/asn.2013060665). Inhibition of RNLS signaling in Panc1 cells is associated with sustained activation of p38 MAPK, and apoptosis. p38 is a stress-activated kinase that has been implicated in inflammation, cell differentiation, cell cycle regulation and apoptosis (Ono et al., 2000 Cellular Signalling. 12(1):1-13). For example, nerve growth factor withdrawal causes apoptosis along with sustained activation of JNK and p38, and down-regulation of ERK (Xia et al., 1995 Science. 270(5240):1326-31). However, since under certain conditions inhibition of p38 can block apoptosis (Ono et al., 2000 Cellular Signalling. 12(1):1-13), p38's role in the apoptotic process is clearly context dependent. The data described herein are consistent with the explanation that in Panc1 cells, m28-RNLS dependent activation of p38 is associated with apoptosis.

Inhibition of RNLS signaling markedly decreases the expression of Ki-67 in xenografts of pancreatic cancer. Since Ki-67 is used to evaluate levels of cell division, the data is consistent with the explanation that RNLS inhibition decreases the proliferative rate of tumors. Many of the key factors that determine cell cycle progression have been identified, and include cyclin dependent kinases (CDK) and two classes of endogenous CKD inhibitors, namely the inhibitor of cyclin dependent kinase 4 (INK4) and the CDK interacting proteins/kinase inhibitor (CIP/KIP) protein families (Jung et al., 2010 Cellular Signalling. 22(7):1003-12). The data reveal that the expression of p21, a CKD inhibitor belonging to the CIP/KIP family, is regulated by RNLS signaling. Inhibition of RNLS signaling is associated with a marked increase in p21 expression. Since p21 is a negative regulator of cell cycle that can maintain cells in G0, block G1/S transition and cause G1 or inter-s phase arrest (Jung et al., 2010 Cellular Signalling. 22(7):1003-12), its upregulation could account for the decrease in cell proliferation observed in tumors treated with m28-RNLS. In addition, p38 has also been shown to affect cell cycle progression (Ono et al., 2000 Cellular Signalling. 12(1):1-13), and its activation by anti-RNLS treatment could also contribute to cell cycle arrest.

The regulatory promoter elements and transcription factors that regulate RNLS gene expression have been recently investigated (Sonawane et al., 2014 Biochemistry. 53(44): 6878-6892), and these data point to a key role for STAT3. The results suggest a feedforward loop between RNLS and STAT3: signals that upregulate STAT3 increase RNLS gene expression, and RNLS, in turn, increases STAT3 activity. Such an interaction between RNLS and STAT3 has important implications regarding the role of RNLS signaling in the pathogenesis of cancer. STAT family proteins, particularly STAT3, are firmly implicated in the induction and maintenance of an inflammatory microenvironment that facilitates malignant transformation and cancer progression (Yu et al., 2009 Nat Rev Cancer. 9(11):798-809). STAT3 signaling is often persistently activated in cancer cells, and such activation not only drives tumor cell proliferation, but also increases the production of a large number of genes that sustain inflammation in the tumor microenvironment. A STAT3 feedforward loop between cancer cells and non-transformed and stromal cells has been documented in cancer (Catlett-Falcone et al., 1999 Immunity. 10(1):105-15; Yu et al., 2007 Nat Rev Immunol. 7(1):41-51; Ara et al., 2009 Cancer Res. 69(1):329-37). For instance, STAT3 is constitutively activated in multiple myeloma patients. In the IL-6-dependent human myeloma cell line U266, IL-6 signals through Janus kinases to the activate STAT3, which in turn up-regulates anti-apoptotic factors, and promotes the survival of tumor cells (Catlett-Falcone et al., 1999 Immunity. 10(1):105-15). Likewise, STAT3 is constitutively activated in the majority of pancreatic ductal adenocarcinomas, and appears to be required for the initiation and progression of KRAS-induced pancreatic tumorigenesis (Corcoran et al., 2011 Cancer Res. 71(14):5020-9).

The STAT3 pathway and RNLS may also have a role in promoting the most common and important environmental factor in PDAC development, cigarette smoking (Muscat et al., 1997 Cancer epidemiology, biomarkers & prevention: a publication of the American Association for Cancer Research, cosponsored by the American Society of Preventive Oncology. 6(1):15-9; Boyle et al., 1996 International journal of cancer Journal international du cancer. 67(1):63-71; Fuchs et al., 1996 Archives of internal medicine. 156 (19):2255-60). Nicotine, a key constituent of cigarette smoke, has been shown to enhance the rate of proliferation and angiogenesis in cancers (Heeschen et al., 2002 J Clin Invest. 110(4):527-36; Heeschen et al., 2001 Nat Med. 7(7):833-9). Nicotine's action of tumor growth and metastases is believed to be mediated by its interaction with acetylcholine receptor alpha-7nACHR resulting in JAK-STAT3 and MEK-ERK1-2 downstream signaling cascades (Momi et al., 2013 Oncogene. 32(11):1384-95). In this context, nicotine increases RNLS promoter activity through the synergistic action of Sp1 and STAT3 (Sonawane et al., 2014 Biochemistry. 53(44):6878-6892).

PMCA4b has previously been characterized as a plasma membrane ATPase involved in cell signaling, cardiac hypertrophy, and cancer (Cartwright et al., 2007 Annals of the New York Academy of Sciences. 1099(1):247-53; Pinton et al., 2001 EMBO J. 20(11): 2690-2701; Oceandy et al., 2011 Biochimica et Biophysica Acta (BBA)—Molecular Cell Research. 1813(5):974-8). It transports $Ca^{2+}$ from the cytosol to the external environment, and appears to regulate local calcium concentration. In addition to its role in regulating cytoplasmic $Ca^{2+}$, PMCA4b is central to a macromolecular complex that can also signal through Ras and the MAPKs (Ara et al., 2009 Cancer Res. 69(1):329-37; Corcoran et al., 2011 Cancer Res. 71(14):5020-9; Muscat et al., 1997 Cancer epidemiology, biomarkers & prevention: a publication of the American Association for Cancer Research, cosponsored by the American Society of Preventive Oncology. 6(1):15-9). For example, it modulates Ras signaling and ERK activation through its interaction with the tumor suppressor RASSF1 (Armesilla et al., 2004 Journal of Biological Chemistry. 279(30):31318-28). The data indicate that RNLS signals though PMCA4b, that down-regulation of PMCA4b expression or inhibition of its enzymatic function is cytotoxic to pancreatic adenocarcinoma cells. These findings suggest that PMCA4b represent a therapeutic target in the management of PDAC.

Figure 27A:
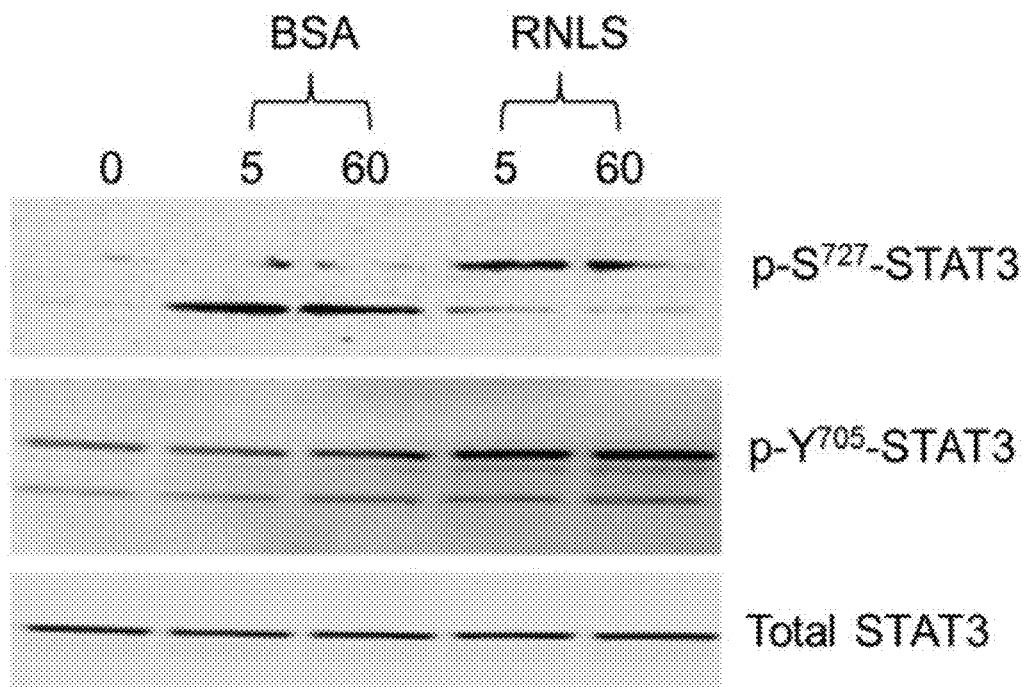
FIGS. 27A through 27E, is a series of images and charts showing the interaction between RNLS and STAT3, and the mechanistic model of inhibition by m28-RNLS.
Figure 27B:
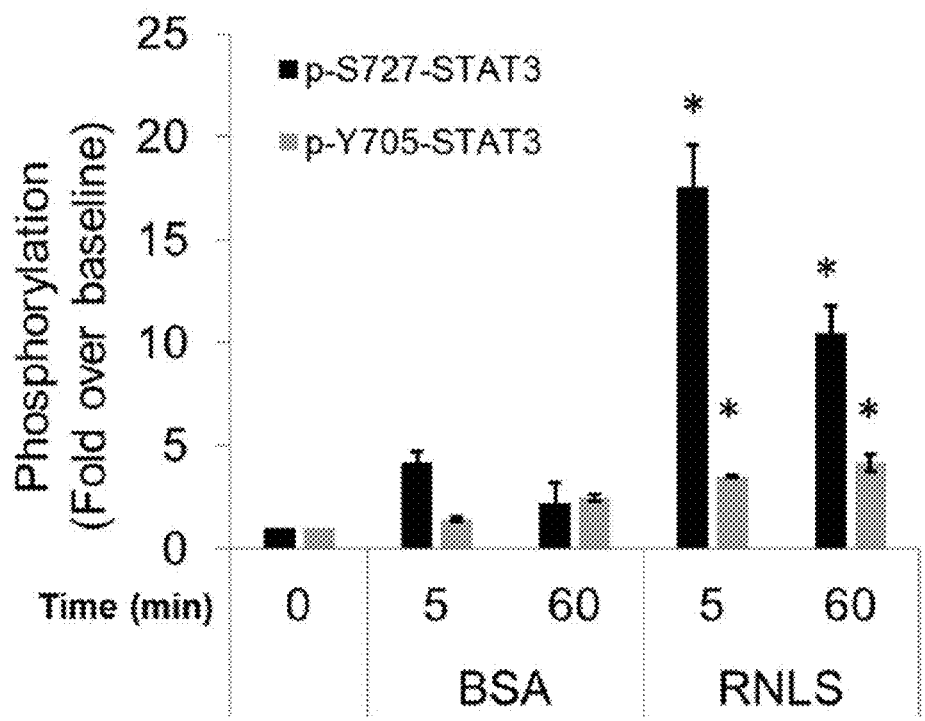
Figure 27C:
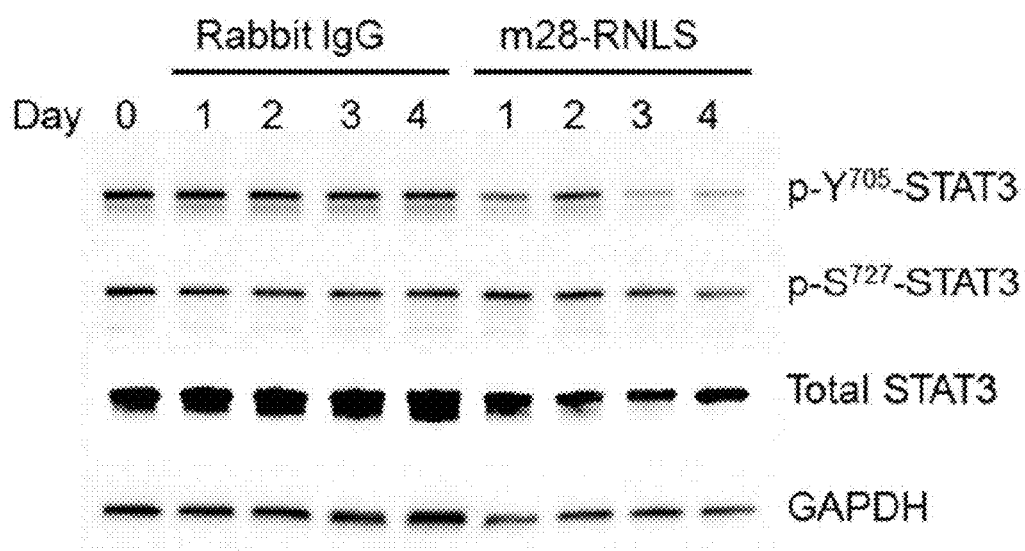
Figure 27D:
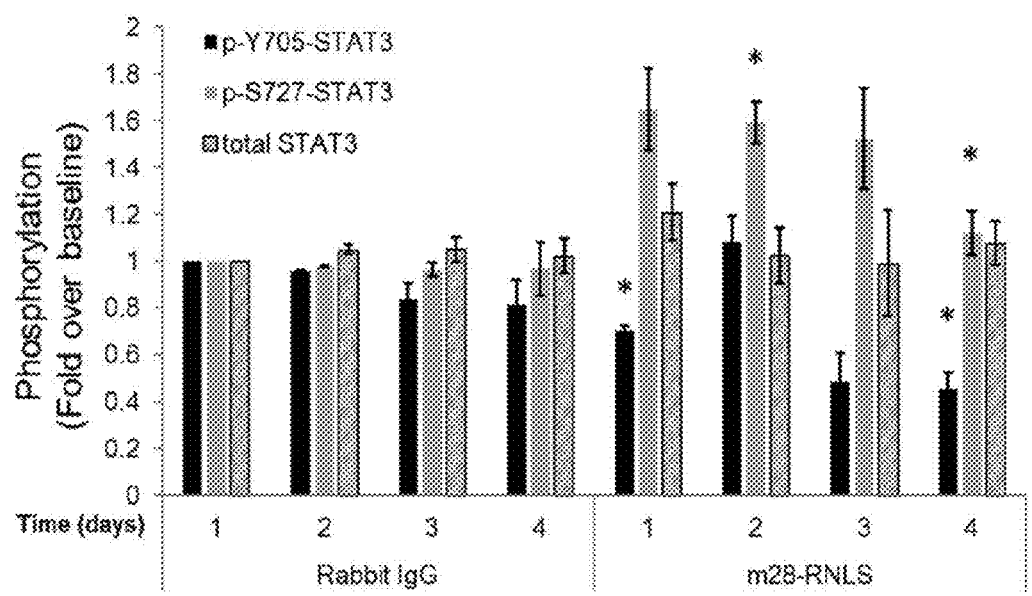
Figure 27E:
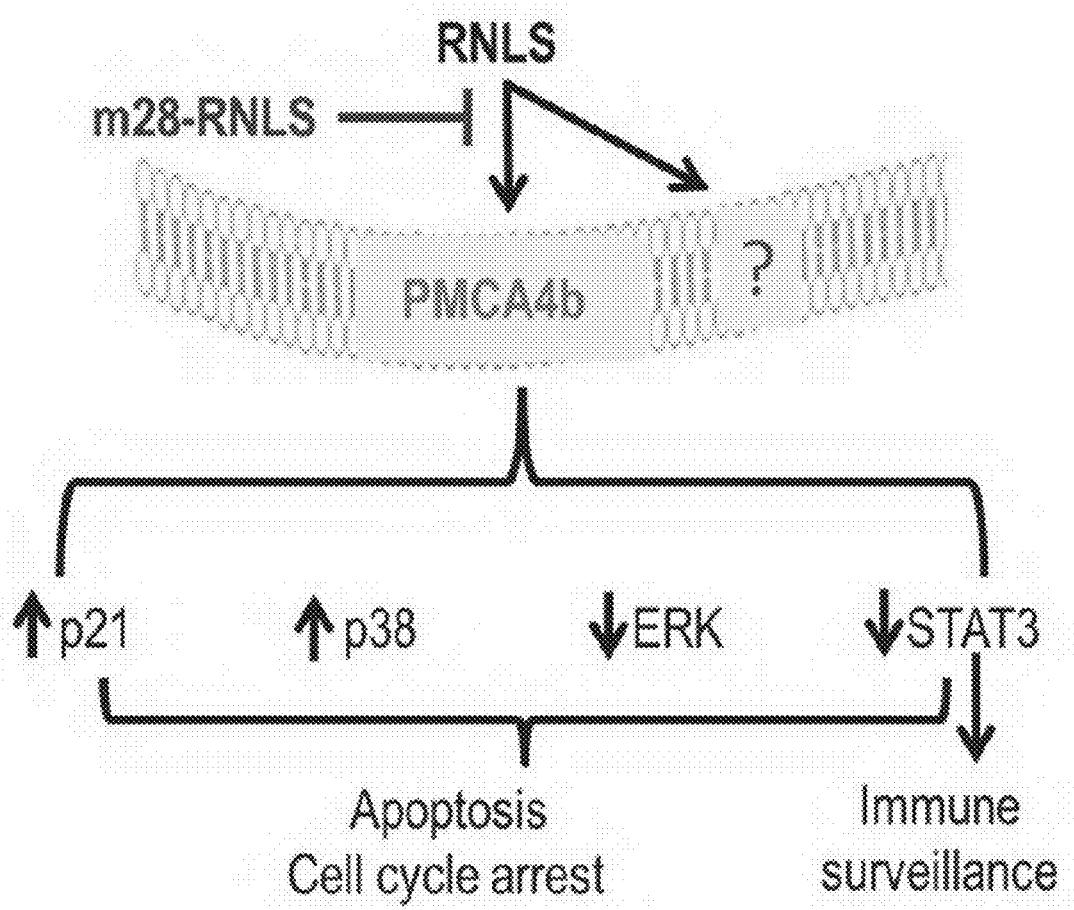

In summary, these findings demonstrate that RNLS is a secreted protein that can promote the survival and growth of PDACs. This provides a framework to further investigate the use of therapies that inhibit RNLS for the treatment of cancer. In this context, that RNLS modulates the multiple inter-related signals that mediate MAPK, PI3K and JAK-STAT3 are active in cancer, the molecule might be a particularly attractive therapeutic target (FIG. 27E). The materials and methods used in this example are now described.

Reagents

The human ductal pancreatic adenocarcinoma cell lines BxPC-3, Panc1 and MiaPaCa-2 were obtained from the American Type Culture Collection (ATCC) (Manassas, Va., USA) and maintained as recommended. The p38 and STAT3 blockers SB203580 and Stattic were purchased from Abcam (Cambridge, UK). The JNK inhibitor SP600125 and the ERK inhibitor U0126 were obtained from Sigma Aldrich (St. Louis, Mo., USA), and Cell Signaling Technologies (Beverly Mass., USA), respectively. Recombinant human RNLS (rRNLS) was expressed, purified, concentrated, and dialyzed against PBS as previously described (Desir et al., 2012 J Am Heart Assoc. 1(4):e002634). Rabbit anti-RNLS monoclonal (AB178700), goat polyclonal anti-RNLS (AB31291), goat IgG and rabbit IgG were purchased from Abcam.

Synthesis of Anti-RNLS Monoclonal Antibodies m28-RNLS (Also Known as 1D-28-4), m37-RNLS (Also Known as 1D-37-10)

RNLS peptide RP-220 was conjugated to KLH and used to immunize 6 rabbits, and lymphocytes from the spleens of selected animals were fused to myeloma cells for hybridoma generation. Hybridoma supernatants were screened against rRNLS and selected hybridomas were cloned and expanded for antibody purification. The monoclonal antibodies were purified from conditioned hybridoma culture supernatant by protein A affinity chromatography.

Two clones, m28-RNLS, m37-RNLS, were selected based on their high binding affinity (KD of 0.316 and 2.67 nM respectively) as determined using a Biacore T100 system. The m28-RNLS' nucleotide sequence was determined by PCR, synthesized and cloned it into a mammalian expression vector. m28-RNLS, synthesized by transient expression into 293-F cells, was purified by protein A chromatography.

Tissue Specimens

Human cancer cDNA arrays (Screen cDNA Arrays I and II, pancreatic cancer cDNA array) were obtained from OriGene Technologies (Rockville, Md., USA). The relevant pathology reports are available online: www.origene.com/assets/documents/TissueScan. Human pancreas cancer and normal tissue samples obtained from US Biomax (Rockville, Md., USA) were used for immunohistochemistry or immunofluorescence.

Quantitative PCR

Relative expression levels of various genes were assessed by qPCR. The mRNA level of RNLS, 2'-5'-oligoadenylate synthetase 1 (OAS1), β-actin and 18s rRNA was assessed using the TaqMan Gene Expression real-time PCR assays (Applied Biosystems, Carlsbad, Calif., USA). The results were expressed as the threshold cycle (Ct). The relative quantification of the target transcripts normalized to the endogenous control 18s rRNA or β-actin was determined by the comparative Ct method ($\Delta$Ct) and the 2-$\Delta\Delta$Ct method was used to analyze the relative changes in gene expression between the tested cell lines according to the manufacturer's protocol (User Bulletin No. 2, Applied Biosystems).

Immunohistochemistry and Western Blot Analysis

Immunohistochemistry was performed as described previously (Guo et al., 2012 Cancer Science. 103(8):1474-80). Briefly tumor tissues were formalin-fixed, paraffin-embedded and cut into 5 μm sections on glass slides. The slides were de-paraffinized and hydrated, followed by antigen retrieval in a pressure cooker containing 10 mM sodium citrate, pH6 buffer. The sections were blocked in 3% hydrogen peroxide for 30 min and 2.5% normal horse serum in PBS/0.1% Tween20 for 1 h followed by incubation with primary antibody and isotype control IgG overnight at 4° C. The following antibodies were used in this study: m28-RNLS at 500 ng/ml; goat polyclonal anti-RNLS at 250 ng/ml (Abcam, AB31291); rabbit monoclonal anti Ki67 (Vector Lab, VP-RM04, 1:100); rabbit monoclonal anti p21 and phspho-Tyr$^{705}$-Stat3 (Cell Signaling Technologies, #2947, 1:100 and #9145, 1:400, respectively). ImmPRESS peroxidase-anti-rabbit IgG (Vector Laboratories, Burlingame, Calif., USA) was used to detect primary antibodies. The color was developed using a Vector DAB substrate kit and counterstained with hematoxylin (Vector Laboratories). Slides were observed and photographed using an Olympus BX41 microscope and camera (Olympus America Inc, Center Valley, Pa., USA).

Western blot analysis was carried out as previously described (Wang et al., 2014 Journal of the American Society of Nephrology. DOI: 10.1681/asn.2013060665).

Tissue Microarray

Pancreas tissue microarrays were purchased from US BioMax. Tissue microarray slides were stained as described previously (Nicholson et al., 2014 Journal of the American College of Surgeons. 219(5):977-87). In brief, specimens were co-stained with m28-RNLS and mouse monoclonal pan-cytokeratin antibodies (1:100, DAKO M3515) at 4° C. overnight. The secondary antibodies Alexa 488-conjugated goat anti-mouse (1:100, Molecular Probes, Eugene, Oreg.) and Envision anti-rabbit (DAKO) were applied for 1 hour at room temperature. The slides were washed with Tris-buffered saline (three times for 5 minutes), and incubated with Cy5-tyramide (Perkin-Elmer Life Science Products, Boston, Mass.) and activated by horseradish peroxidase. Cy5 was used because its emission peak (red) is outside of the green-orange spectrum of tissue auto-fluorescence. The slides were sealed with coverslips with Prolong Gold anti-fade reagent containing 4',6-Diamidino-2-phenylindole to facilitate the visualization of nuclei.

Cell Viability Assays

Cell viability was assessed by trypan blue exclusion, and cells were counted using a BioRad TC10 automated counter. For some studies, cell viability was determined using the WST-1 reagent (Roche Diagnostics, Indianapolis, Ind., USA) as previously described (Wang et al., 2014 Journal of the American Society of Nephrology. DOI:10.1681/asn.2013060665).

Apoptosis and Cell Cycle Analysis

For cell cycle analysis, cultured cells were dissociated using 10 mM EDTA, fixed with ice-cold 70% ethanol, digested with RNAse A, and stained with propidium iodide. Propidium staining was detected using a BD FACSCalibur flow cytometer (BD Biosciences, San Jose, Calif., USA), and analyzed using CellQuest software.

Apoptosis was detected and quantified as previously done (Guo et al., 2012 Cancer Science. 103(8):1474-80). In brief, cells were stained with FITC-labeled Annexin-V and propidium iodide according to the manufacturer's instructions (Bender MedSystems, Burlingame, Calif., USA). At least 20,000 events were collected on a BD FACSCalibur flow cytometer (BD Biosciences, San Jose, Calif., USA) and analyzed using CellQuest software.

RNA Interference

Four individual siRNAs and a siRNA SMART pool targeting RNLS were purchased from Dharmacon (Lafayette, Colo., USA). Cells were transfected with RNLS siRNA or a universal negative control siRNA (control siRNA, Dharmacon) using DharmaFECT 4 reagent (Dharmacon) as suggested by the manufacturer.

To generate a stably transfected Panc1 cell line, cells were transduced with lentivirus (Santa Cruz) carrying either RNLS shRNA (sh-RNLS) or control shRNA (sh-Control) according to the manufacturer's protocol. Cells were transduced twice to increase shRNA copy number and stable clones were established after selection in 80 μg/ml puromycin for 10 days. Knock-down efficiency was determined by qPCR.

Mouse Xenograft Tumor Model

Female athymic, 18-20 g nude mice (nu/nu) were obtained from Charles River (Willimantic, Conn.) and housed in microisolator cages, with autoclaved bedding in a specific pathogen-free facility, with a 12-h light/dark cycle. Animals received water and food ad libitum, and were observed for signs of tumor growth, activity, feeding and pain, in accordance with the study protocol approved by the VACHS IACUC.

Xenograft tumors were established by subcutaneous injection of BxPC3 cells (2×10$^6$ in 100 μl of PBS, pH 7.6). When the tumors reached a volume of 50-100 mm$^3$, the mice were divided a control group (n=14 treated with rabbit IgG, 40 μg by intraperitoneal injection (IP)), and an experimental group (n=14) that received m28-RNLS (40 μg IP, every 3 days). Tumor size was measured with digital calipers and volume was calculated according to the formula (length×width)×π/2. In another group of animals (n=6 each) sh-RNLS or sh-Control Panc1 cells (2×10$^6$ in 100 µl of PBS, pH 7.6) were injected subcutaneously. These animals received no further treatments, and tumor size and volume were measured for up to 30 days.

At the end of the study, the mice were sacrificed, the tumors were excised and immediately snap-frozen in liquid nitrogen and stored at −80° C. Apoptosis was examined using the TUNEL assay (Roche in situ Apoptosis Detection System), according to the manufacturer's instructions. Sections were examined by light microscopy and the apoptosis index was determined by counting≥1000 cells in 5 randomly selected high-power fields (×200 magnification).

Statistical Analyses

The Wilcoxon rank test and the Mann-Whitney test were used for paired and unpaired data, respectively. When appropriate, nonparametric repeated-measures ANOVA (Friedman test) was used to evaluate statistical significance. When the Friedman test revealed statistical significance, Dunn's test was used for pairwise comparisons. All data are mean±standard error of the mean (mean±SEM), and values of $P<0.05$ were accepted as a statistically significant difference. Statistical analyses of tissue array data were performed using SPSS® software, version 21.0 (SPSS Inc., Chicago, Ill., USA).

The results of this example are now described.

RNLS Overexpression in PDAC and Association with Decreased Survival

Figure 23A:
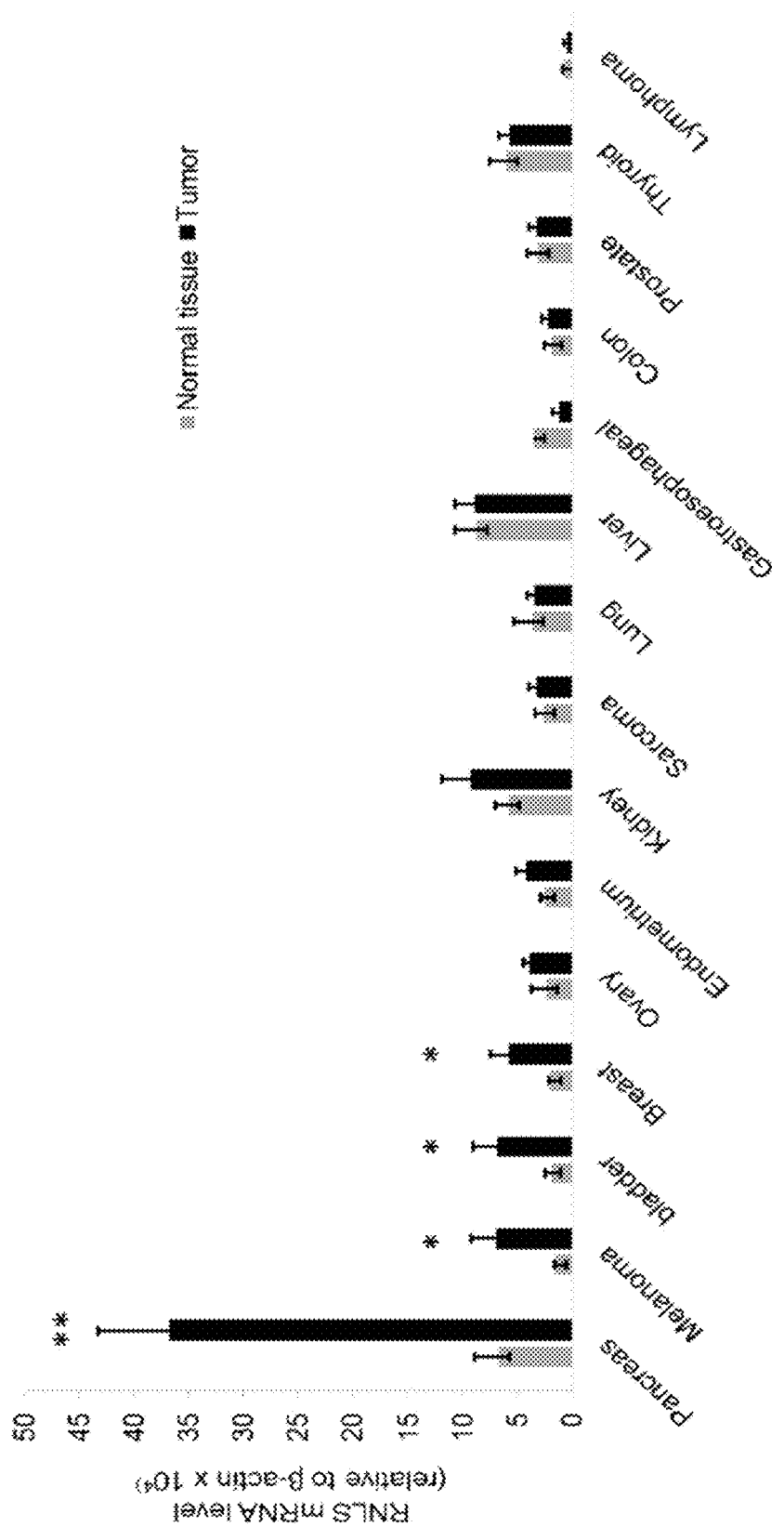
Figure 23B:
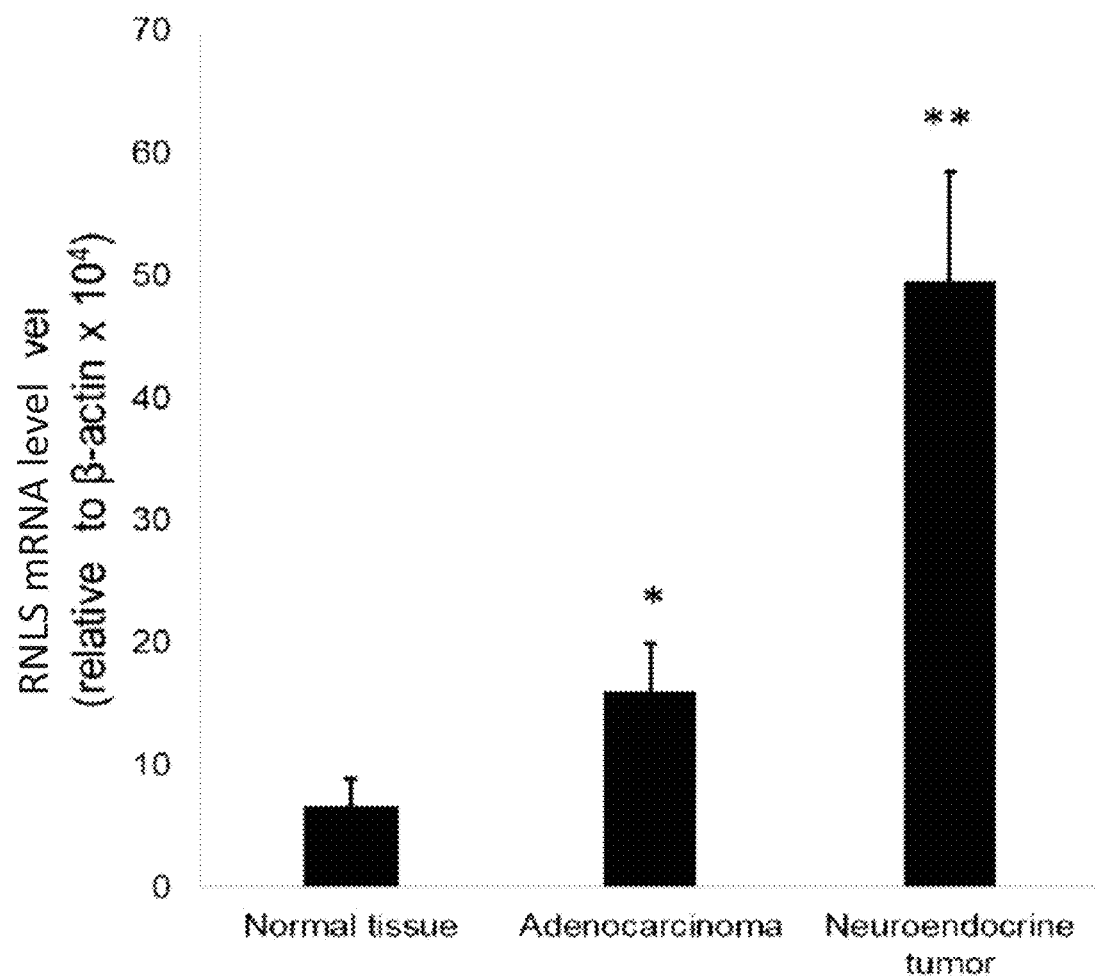
Figure 28:
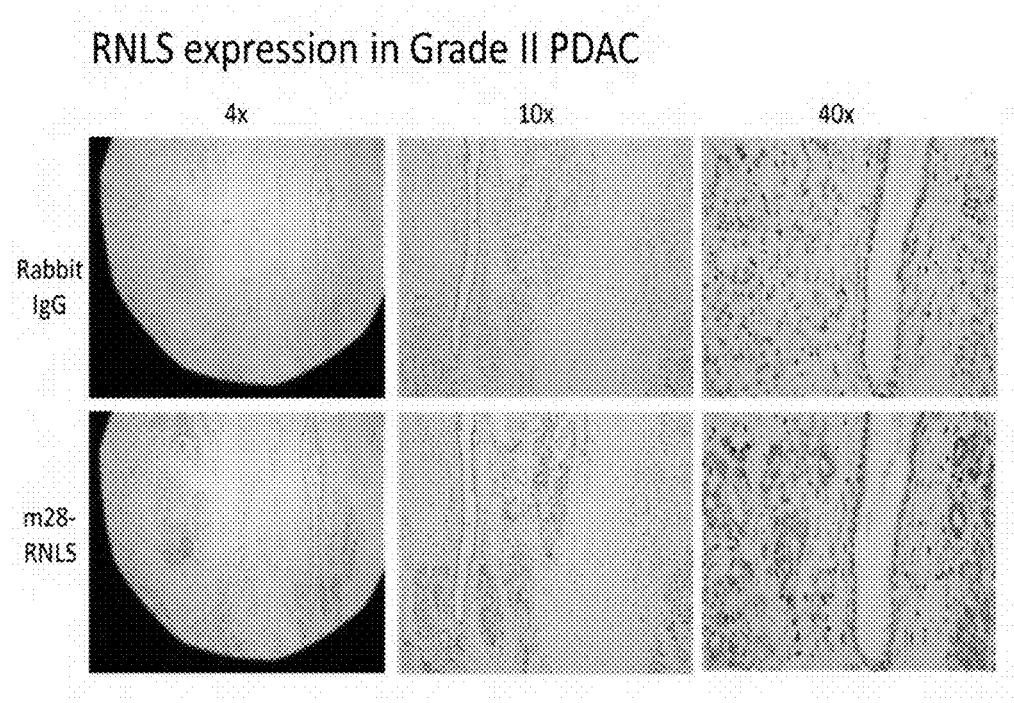
FIG. 28 comprises images depicting that RNLS expression was present in PDAC grade 1-4 and was predominantly localized to cancer cells.
Figure 29:
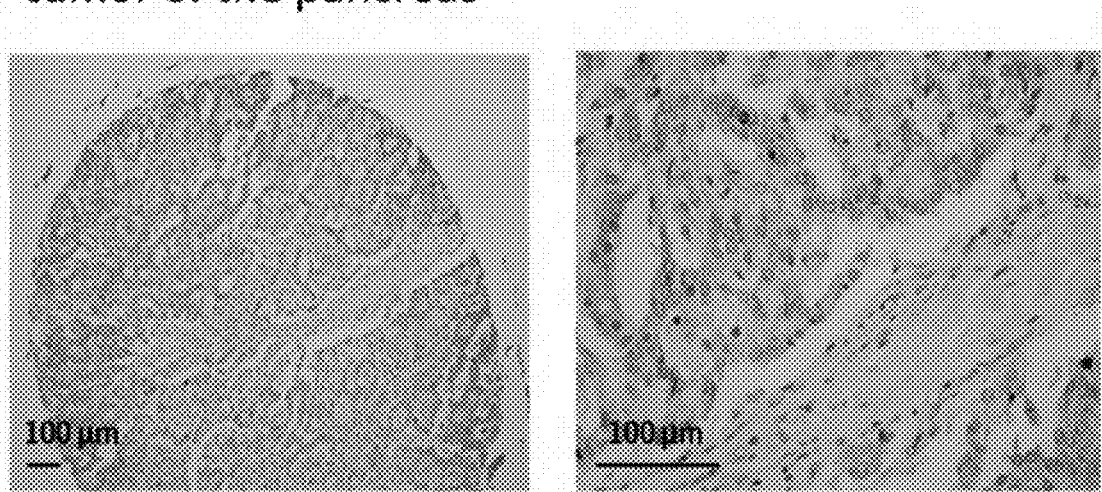
FIG. 29 comprises images showing RNLS expression in neuroendocrine tumor of the pancreas, and showing that RNLS was expressed in cells throughout the tumor.
Figure 30:
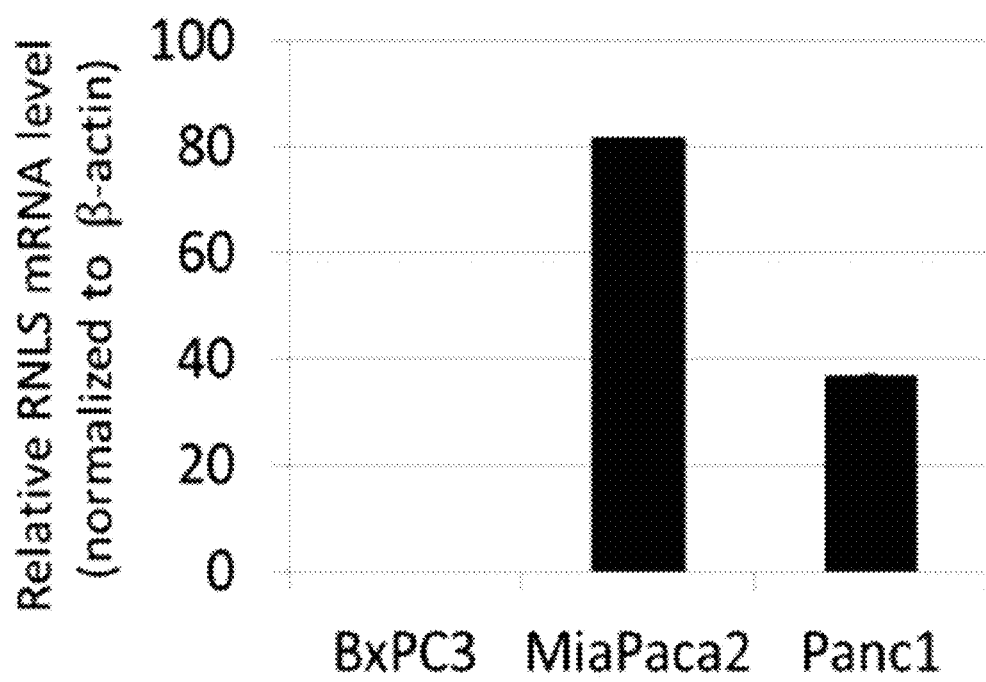
FIG. 30 is a chart depicting the relative RNLS mRNA levels normalized to β-actin, showing that RNLS gene expression was greater in pancreatic ductal adenocarcinoma cell (PDACC) lines with KRAS mutations (MiaPaCa2 and Panc1) than those with wild type KRAS, such as BxPC3.

To determine if RNLS expression differed between normal and cancer tissue, fifteen different types of cancer were examined by screening commercially available human tissue cDNA arrays using quantitative PCR (qPCR). RNLS expression was significantly increased in cancers of the pancreas, bladder and breast and in melanoma (FIG. 23A). Because of their particularly poor survival and limited therapeutic options, the focus was on pancreatic neoplasms. RNLS expression was elevated in both PDAC (~3 fold) and pancreatic neuroendocrine (8 fold) tumors (FIG. 23B). Immunocytochemical studies using the anti-RNLS monoclonal m28-RNLS showed that RNLS expression was present in PDAC grade 1-4 and was predominantly localized to cancer cells, as shown in FIGS. 23C and 28). Most RNLS appeared to have a cytoplasmic distribution in cancer cells; it was present in all tumor grades, but was most evident in more-differentiated cancers (Grades In neuroendocrine tumors of the pancreas, RNLS was expressed in cells throughout the tumor (FIG. 29). RNLS gene expression was greater in pancreatic ductal adenocarcinoma cell (PDACC) lines with KRAS mutations (MiaPaCa2 and Panc1) than those with wild type KRAS, such as BxPC3 (FIG. 30).

RNLS expression in 69 patients with PDAC was characterized using tissue microarrays (TMA) consisting of formalin-fixed, paraffin-embedded tumor cores with matched adjacent normal tissue. The demographics and clinical characteristics of the individuals from whom the samples were obtained are shown in Table 3. Examination of 138 histospots from paired PDAC tumors and their non-tumor adjacent tissues for RNLS protein expression, using an unbiased, quantitative, automated immunofluorescence microscopy system (AQUA) (Gould Rothberg et al., 2009 Journal of Clinical Oncology. 27(34):5772-80), showed that overall RNLS levels were more than 2-fold greater in PDAC tumors than in their adjacent non-tumor pancreatic tissue (p<0.001, FIG. 23D).

TABLE 3

Characteristics of patient cohort with PDAC

| Characteristics | Number/Total number |
|---|---|
| Gender | |
| Female | 24/69 (34.8%) |
| Male | 45/69 (65.2%) |
| Age (years) | |
| Median | 61 (36-85) |
| 36-50 | 14/69 (20.3%) |
| 51-69 | 39/69 (56.5%) |
| 70-85 | 16/69 (23.2%) |
| Tumor Grade | |
| 1 | 1/69 (1.4%) |
| 2 | 48/69 (69.6%) |
| 3 | 15/69 (21.7%) |
| 4 | 1/69 (1.4%) |
| Unknown | 4/69 (5.8%) |
| Survival (Months) | |
| 0-12 | 29/69 (42%) |
| 13-24 | 9/69 (13%) |
| 25-48 | 18/69 (26%) |
| 49-87 | 13/69 (19%) |

Figure 23E:
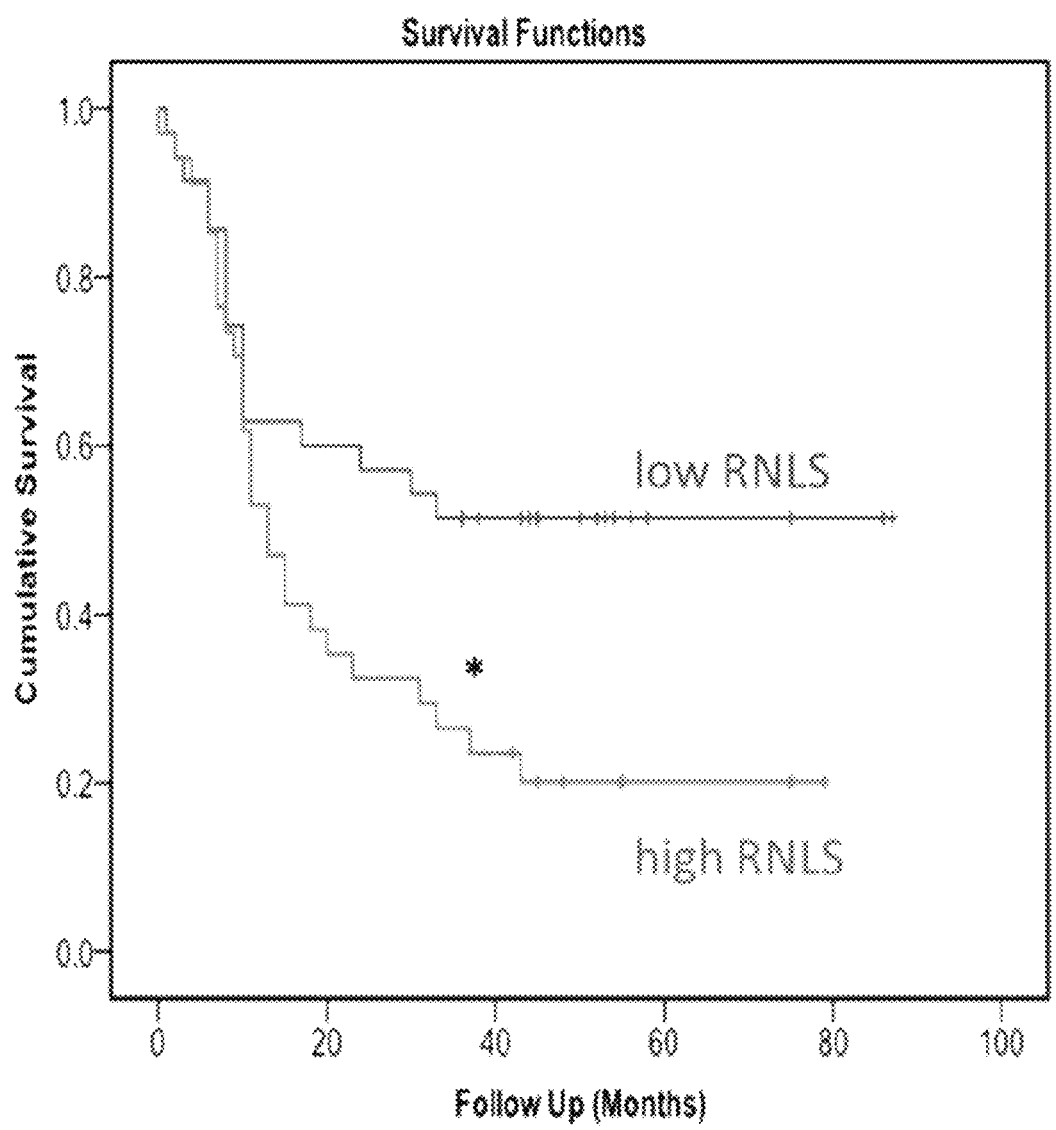

To determine whether enhanced RNLS expression might affect PDAC's clinical behavior, the question was asked whether the level of expression affected prognosis. Individuals whose tumors expressed high RNLS levels (n=34 with RNLS AQUA score>median) had a dramatically reduced 3-year survival rate (24% versus 49%, p=0.024, FIG. 23E). These findings indicate that tumor levels of RNLS expression may be useful prognostic markers in PDAC, and help identify a subset of patients with a more aggressive phenotype.

Figure 24A:
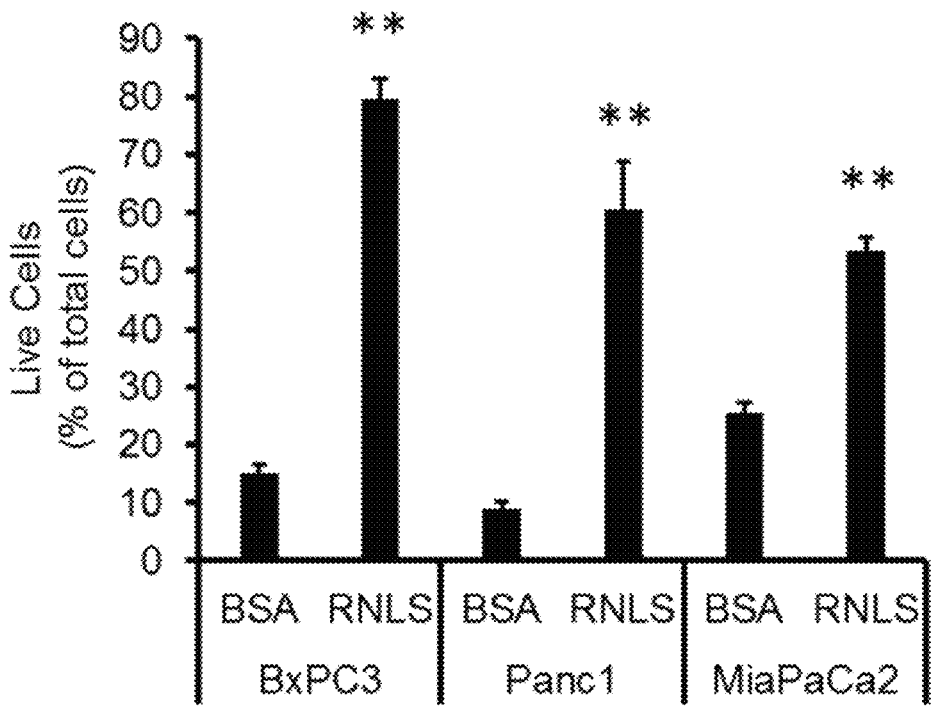
FIGS. 24A through 24D, is a series of charts showing that RNLS overexpression favors cancer cell survival.

RNLS Signals Through PMCA4b and Functions as a Survival Factor for Pancreatic Cancer Cells RNLS-mediated signaling protects HK-2 cells exposed to toxic stress from apoptosis (Lee et al., 2013 J Am Soc Nephrol. 24(3):445-55; Wang et al., 2014 Journal of the American Society of Nephrology. DOI:10.1681/asn.2013060665). To explore if RNLS signaling provided a survival advantage to pancreatic ductal adenocarcinoma cells (PDACC) exposed to stress, serum was withdrawn from cultured BxPC3, Panc1, and MiaPaCa2 cells for 48 hours, and either recombinant RNLS (rRNLS) or bovine serum albumin (BSA) was added to the culture medium for an additional 72 hrs; total and live (trypan blue exclusion) cell counts were determined. Compared to BSA, rRNLS increased PDACC survival rate by 2 to 5 fold (FIG. 24A).

Figure 24B:
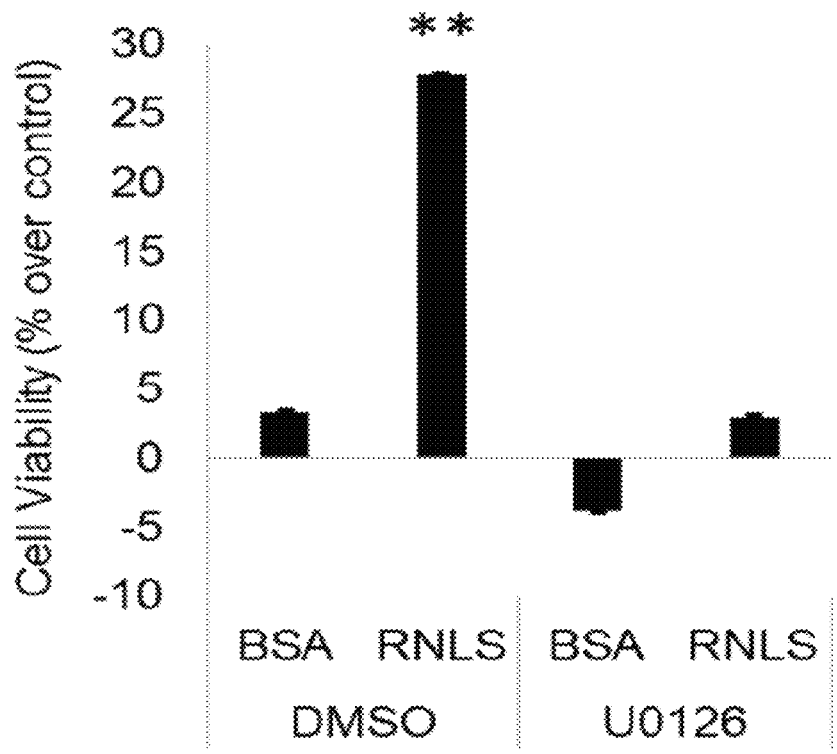

It has been shown that the cytoprotection afforded by the addition of rRNLS to HK-2 cells exposed to hydrogen peroxide or cisplatin injury was dependent on ERK activation (Lee et al., 2013 J Am Soc Nephrol. 24(3):445-55; Wang et al., 2014 Journal of the American Society of Nephrology. DOI: 10.1681/asn.2013060665). The results shown in FIG. 24B indicate that rRNLS also improves PDACC survival in an ERK-dependent manner since pretreating with U0126 an inhibitor of the MAPK kinase MEK1 abrogated rRNLS' protective effect.

Figure 24C:
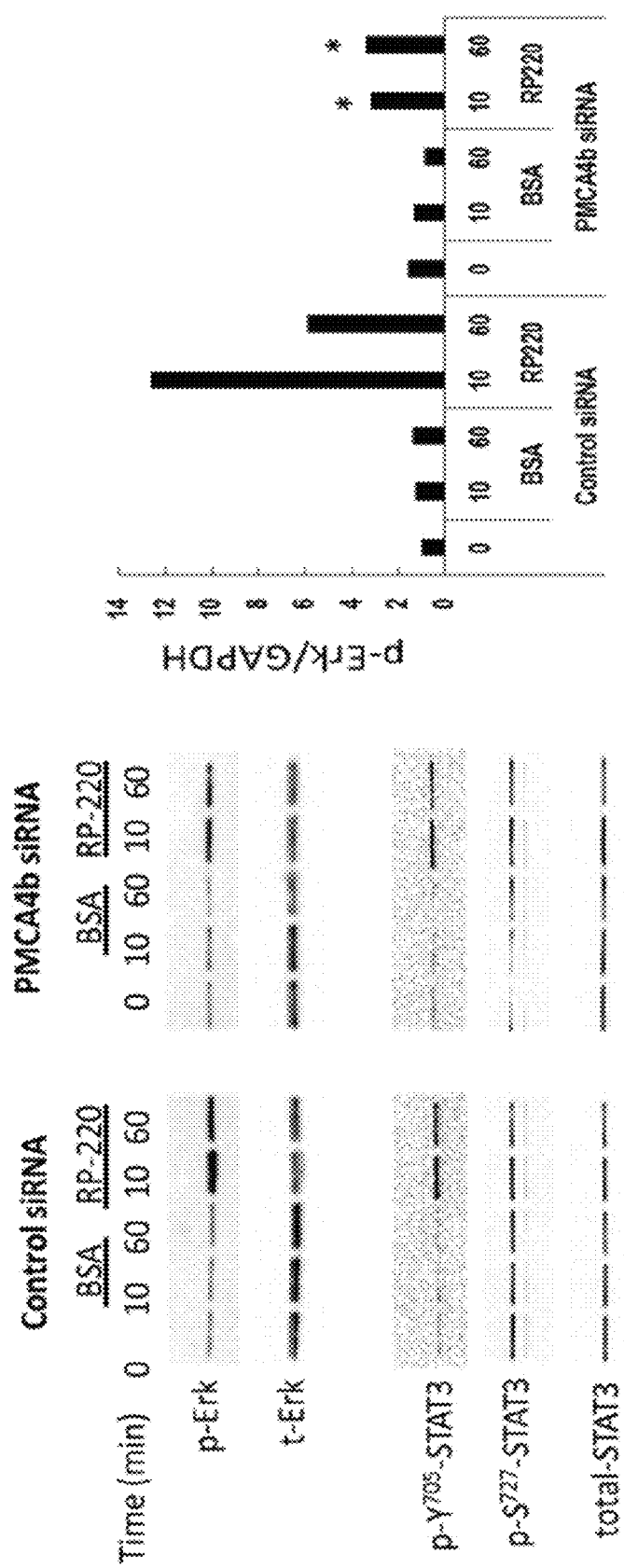

Evidence regarding PMCA4b's role in RNLS dependent signaling in pancreatic cancer was obtained by specifically down-regulating PMCA4b expression using siRNA. In control studies, non-targeting siRNAs affected neither PMCA4b gene expression nor RNLS-mediated ERK phosphorylation (FIG. 24C). In contrast, PMCA4b-targeting siRNAs decreased gene expression by more than 90%, and reduced RNLS dependent ERK phosphorylation by ~70% (FIG. 24C). PMCA4b inhibition had no discernable effect on RNLS mediated STAT3 phosphorylation suggesting the existence of an additional RNLS receptor(s).

Figure 24D:
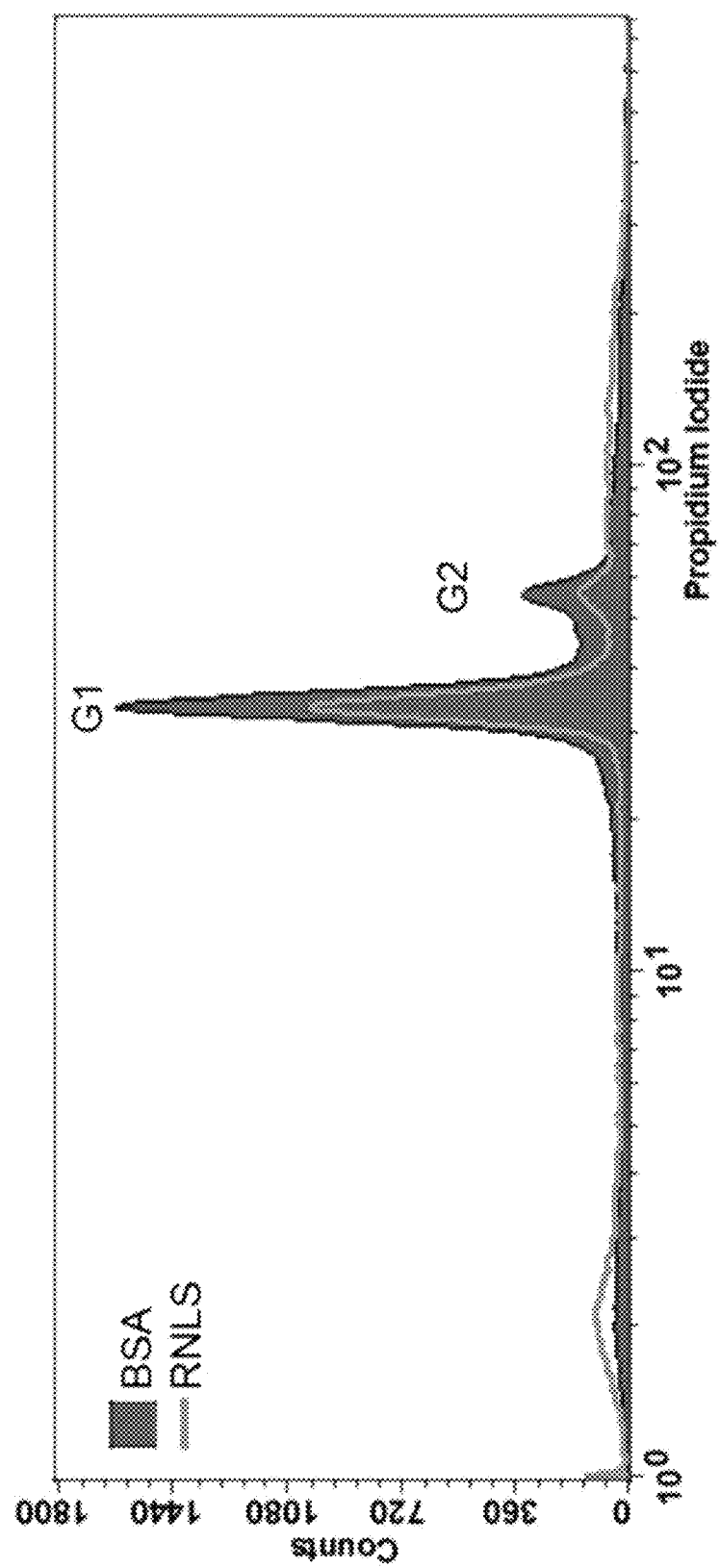

The observed increase in PDAC cell number in the presence of rRNLS is consistent with RNLS signaling either preventing cell death and/or increasing cell proliferation. The effect of RNLS on cell cycle was examined by fluorescence activated cell sorting (FACS) analysis to determine if the apparent increase in PDACC viability was due to increased cell proliferation or to a decrease in the rate of cell death. As shown in FIG. 24D, compared to treatment with BSA, rRNLS had no effect on cell cycle progression, indicating that RNLS does not affect proliferation programs, but rather prevents cells death, and functions as a survival factor.

Inhibitors of RNLS Signaling Block Pancreatic Cancer Growth

Figure 25A:
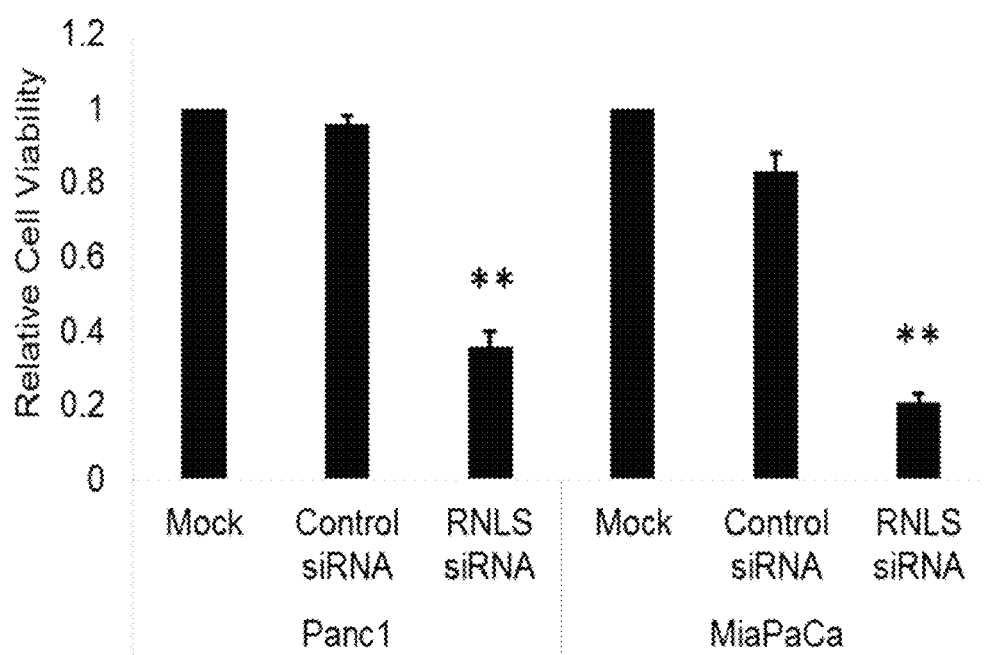
FIGS. 25A through 25E, is a series of charts and images showing that inhibition of RNLS signaling is cytotoxic to cancer cells in vitro and in vivo.
Figure 25B:
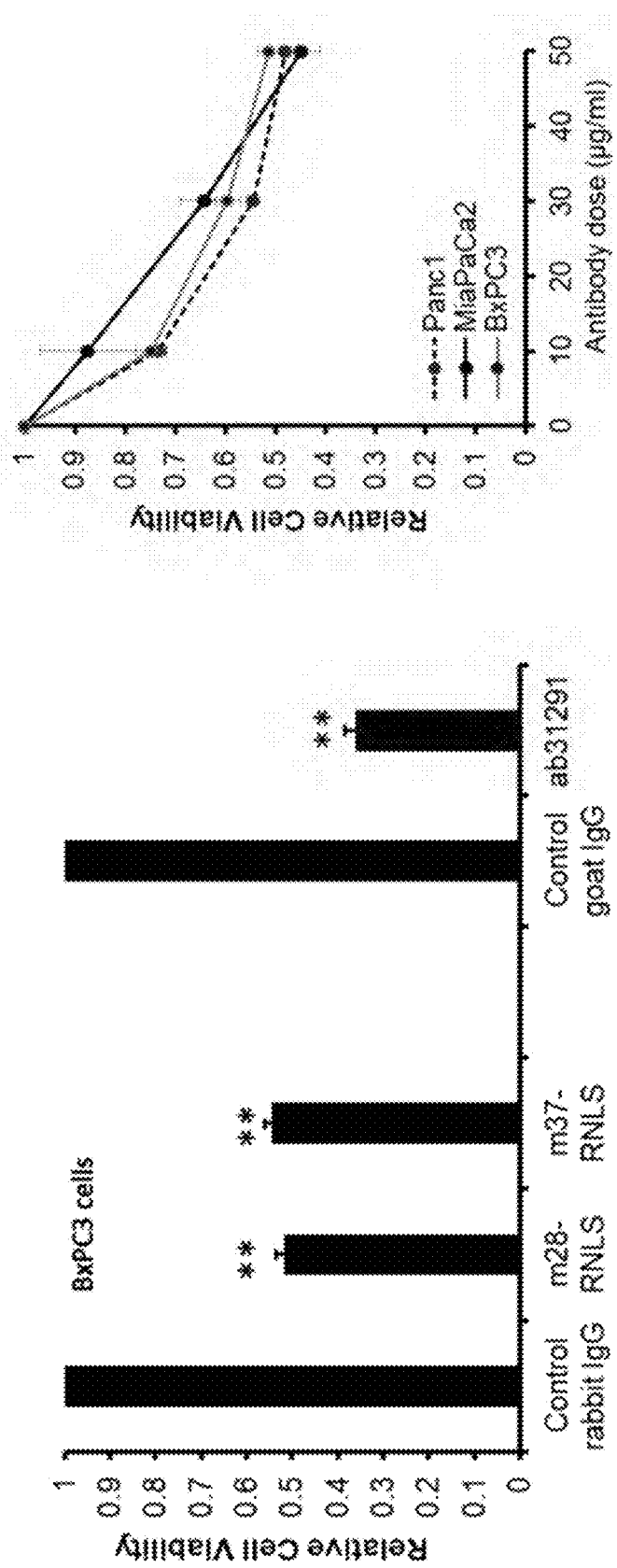
Figure 25C:
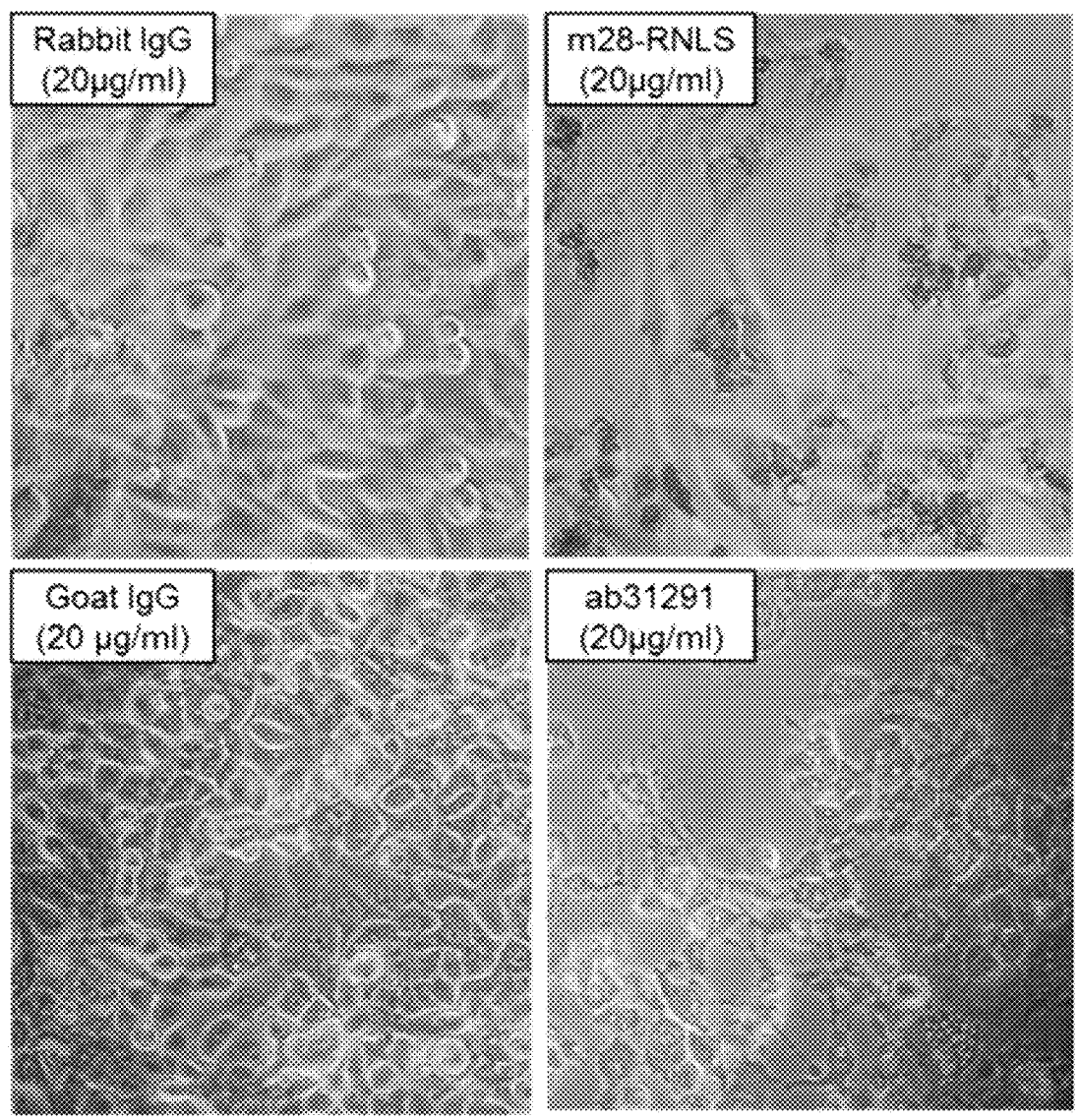
Figure 31:
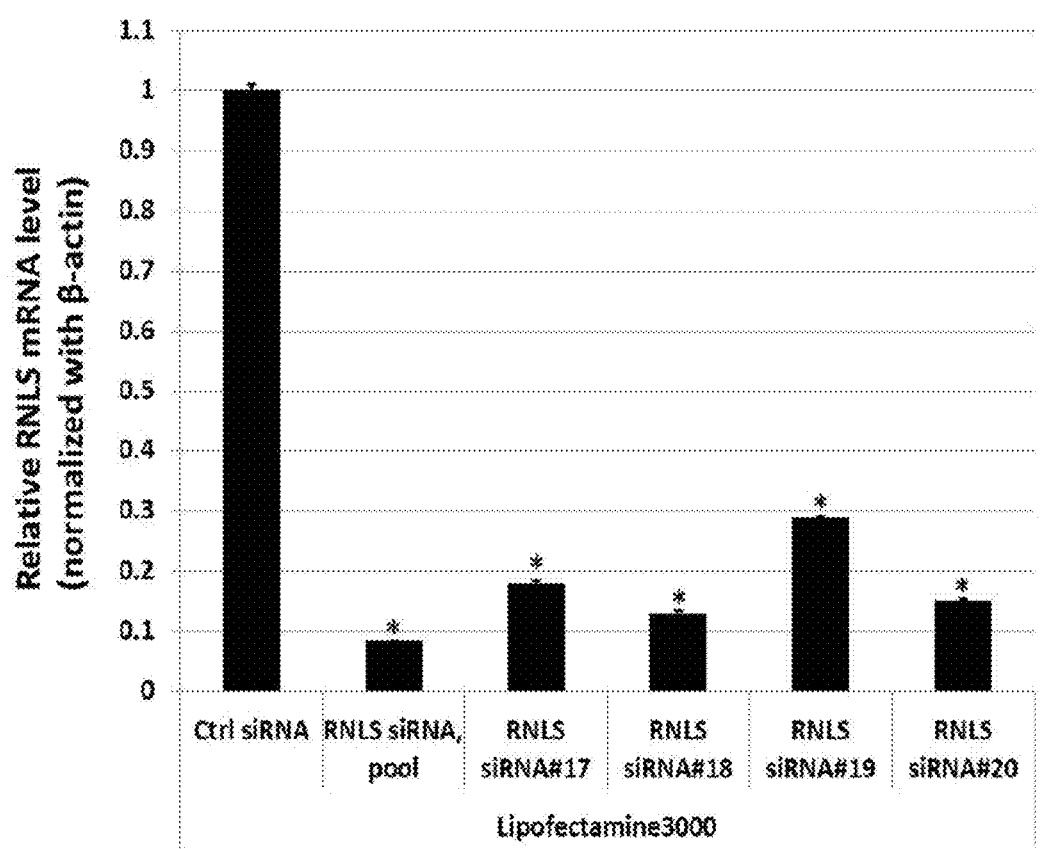
FIG. 31 is a chart depicting the relative RNLS mRNA levels normalized with β-actin, showing the effect of decreasing RNLS expression on cell viability in vitro, evaluated by RNLS knockdown by siRNA; this treatment markedly reduced the viability of the PDACC lines Panc1 and MiaPaCa2.

To determine the functional consequences of inhibiting RNLS expression and signaling in pancreatic cancer cells, the effect of decreasing RNLS expression on cell viability in vitro was evaluated by RNLS knockdown by siRNA. This treatment markedly reduced the viability of the PDACC lines Panc1 and MiaPaCa2 (FIGS. 25A and 31). Since the RNLS peptide RP-220 mimics the protective effect and signaling properties of rRNLS, it has been reasoned that it likely interacts with a critical region of the receptor for extracellular RNLS, and that antibodies generated against it could be inhibitory. From a panel of monoclonal antibodies generated in rabbit against RP-220, two clones, m28-RNLS, m37-RNLS, were selected based on their high binding affinity (KD of 0.316 and 2.67 nM respectively). The inhibitory effects of m28-RNLS, m37-RNLS and of a commercially available polyclonal (against a partial sequence of RP-220) on PDACC growth are shown by the representative examples depicted in FIGS. 25B and 25C. These studies in cultured cells suggest that RNLS can act through an autocrine/paracrine pathway to stimulate PDACC growth.

Figure 25D:
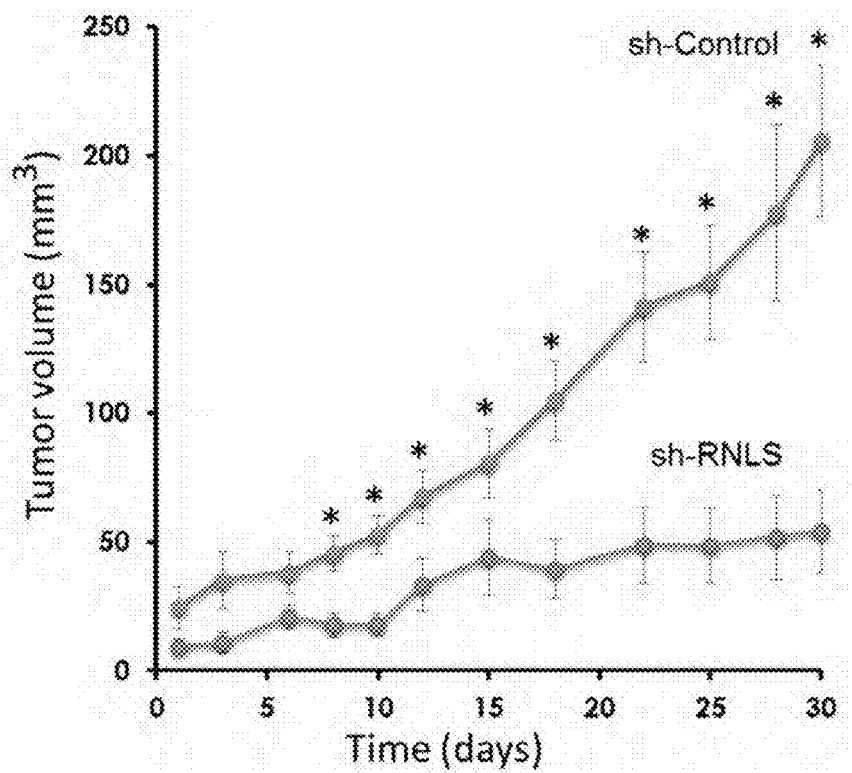
Figure 32:
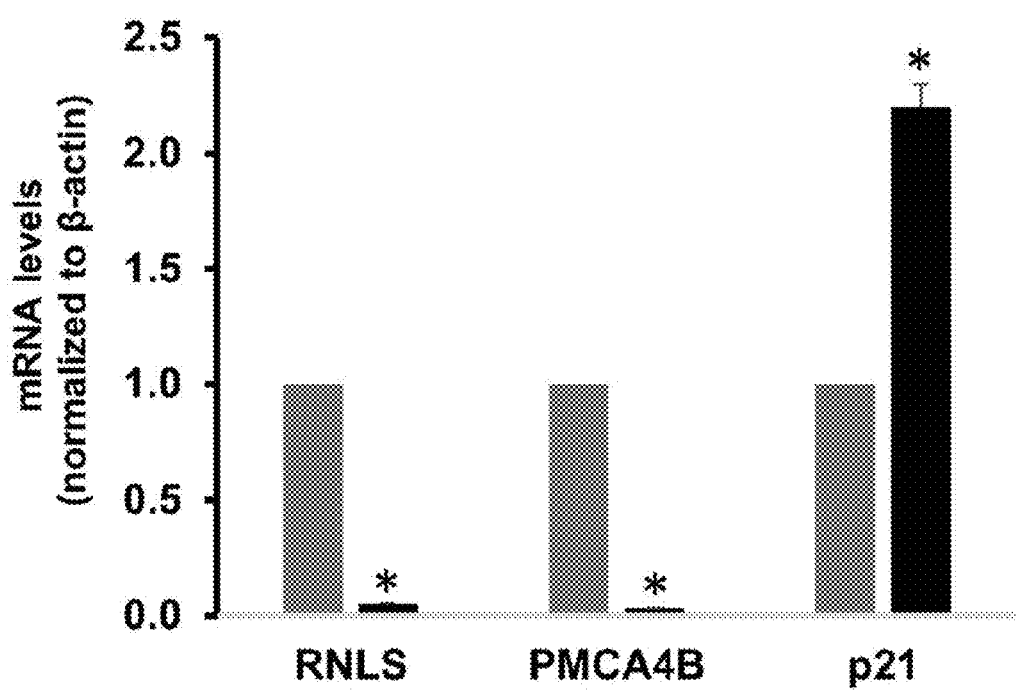
FIG. 32 is a chart showing that inhibition of RNLS expression by RNLS-targeting shRNA resulted in a marked reduction in the expression of its receptor PMCA4b, suggesting RNLS and PMCA4b expression are co-regulated.

To determine if inhibition of RNLS signaling affected tumor growth in vivo, shRNA was used to generate two stably transfected Panc1 cell lines: one containing non-targeting shRNA (sh-Control), and another with RNLS-targeting shRNA (sh-RNLS). RNLS expression in sh-RNLS cells was decreased by more than 90%, as assessed by qPCR (FIG. 31). Surprisingly, inhibition of RNLS expression by RNLS-targeting shRNA resulted in a marked reduction in the expression of its receptor PMCA4b, suggesting RNLS and PMCA4b expression are co-regulated (FIG. 32). The transfected cells were injected subcutaneously into athymic nude mice and tumor size was assessed over a 30 day period. The tumor volume generated by sh-RNLS cells was significantly smaller than that of sh-Control cells from day 8 until day 30 when the animals were sacrificed (FIG. 25D). Since RNLS production and secretion by the host mouse were unaffected, these results indicate that sh-RNLS tumor cells were unresponsive to circulating RNLS because of the concomitant inhibition the RNLS receptor PMCA4b.

Figure 25E:
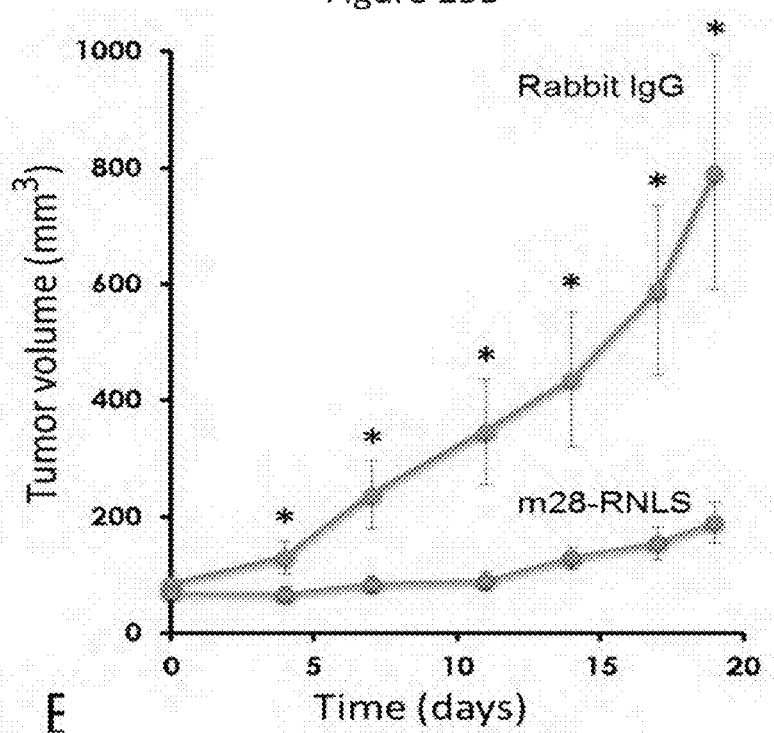

To evaluate the therapeutic potential of inhibitory antibodies, BxPC3 cells were subcutaneously injected into athymic, nude mice, which were treated with either control rabbit IgG, or m28-RNLS, and tumor volume was measured for up to 3 weeks. As shown in FIG. 25E, compared to rabbit IgG, m28-RNLS treatment caused a significant decrease in tumor volume. Together these studies in cultured PDACC cells and in an in vivo model of PDACC provide compelling evidence that the RNLS pathway modulates pancreatic cancer growth and might serve as a therapeutic target.

Induction of Apoptosis and Cell Cycle Arrest in Tumor Cells by m28-RNLS

Figure 26A:
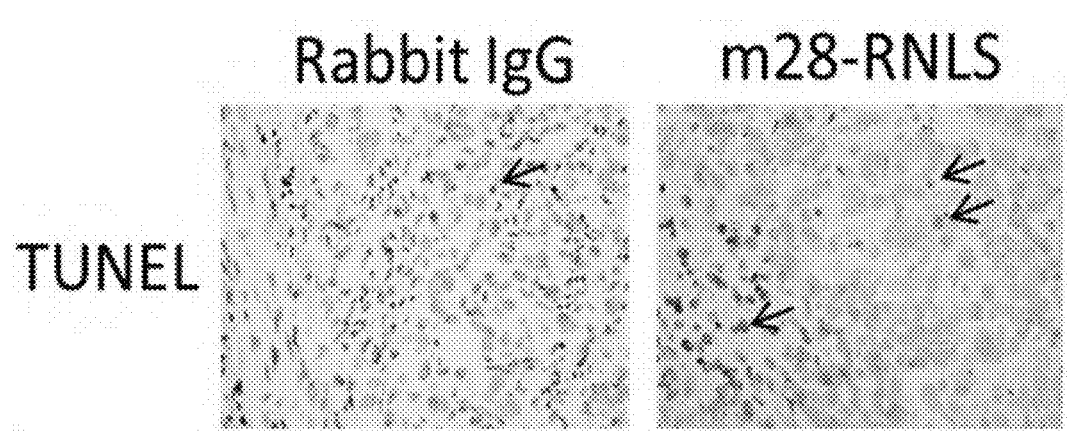
FIGS. 26A through 26E, is a series of images and charts showing that inhibition of RNLS signaling induces apoptosis and cell cycle arrest.
Figure 26B:
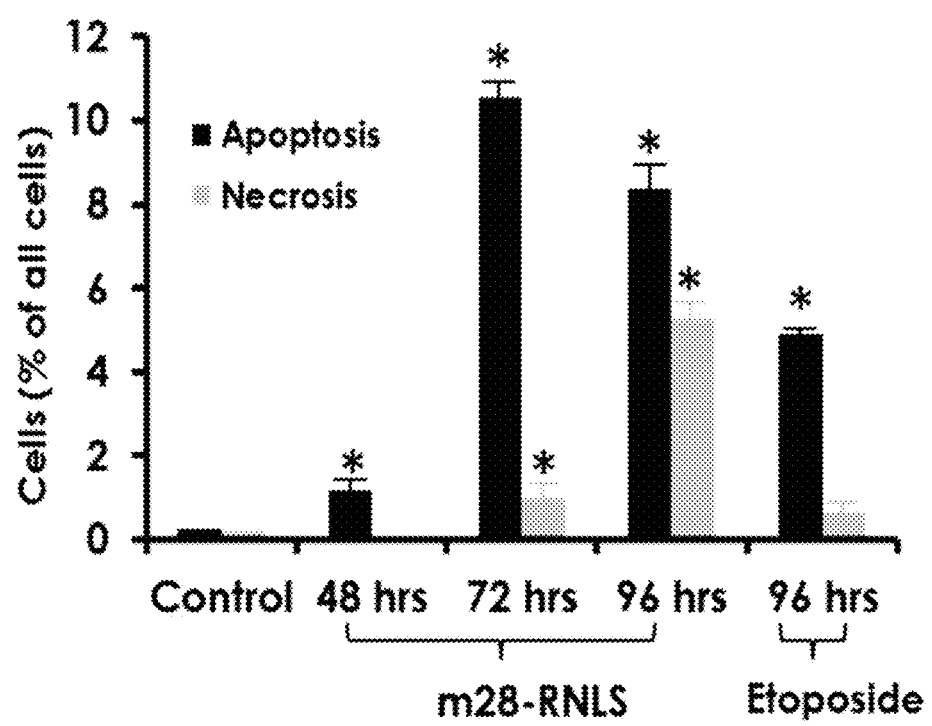
Figure 26C:
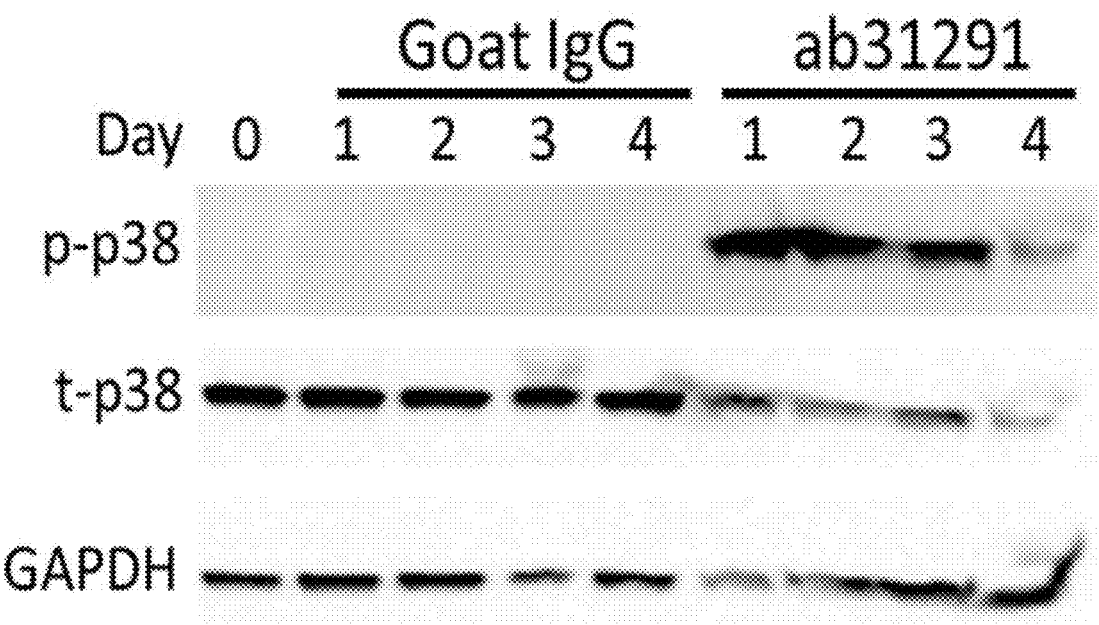
Figure 33:
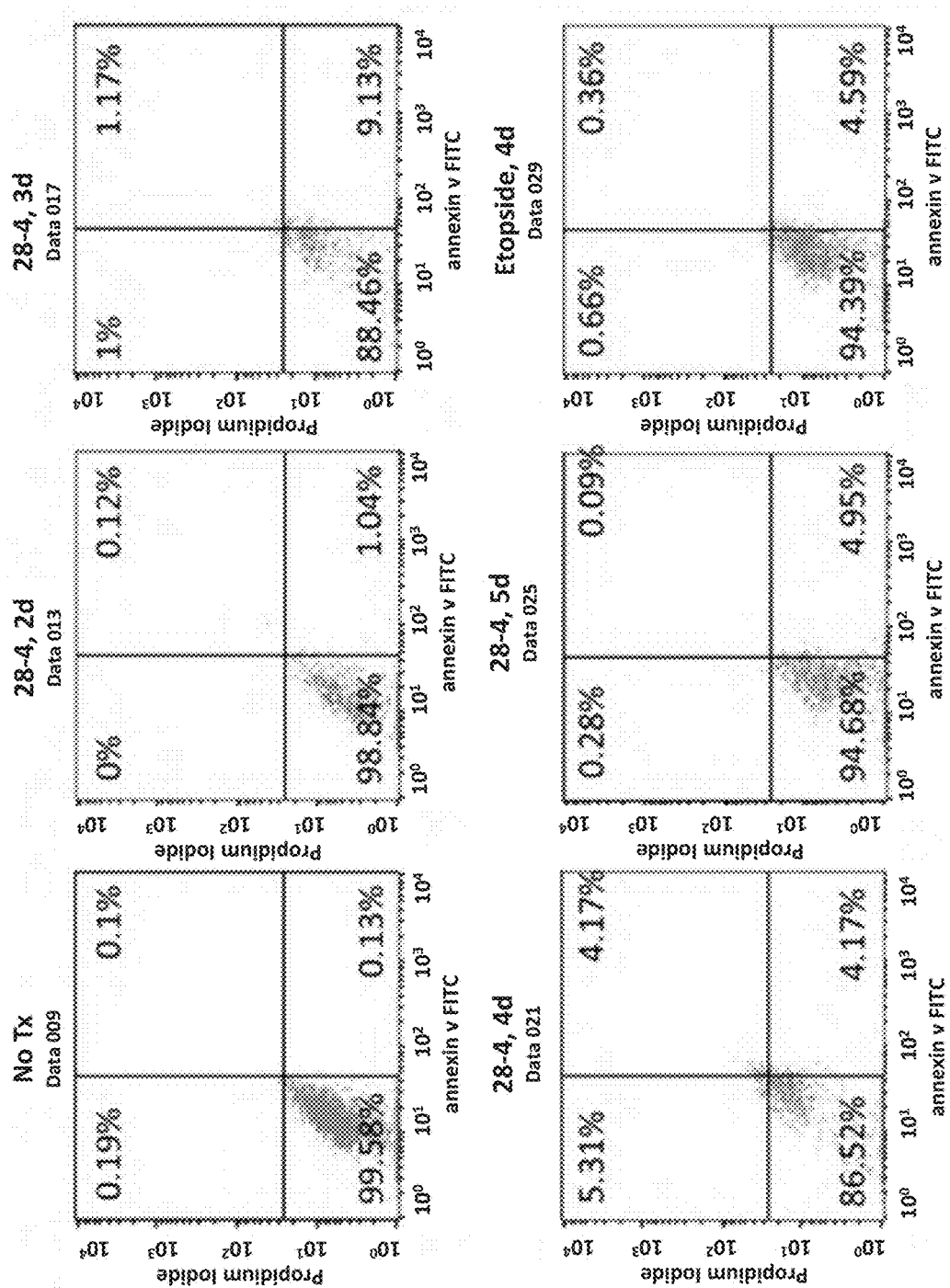
FIG. 33 is a series of charts depicting FACS analysis of Panc1 cells in culture, which confirmed m28-RNLS caused apoptosis.

Sections of BxPC3 xenografted tumors from mice treated with either rabbit IgG or m28-RNLS to reduce RNLS levels revealed a ~2-fold increase in apoptosis (TUNEL staining) (FIG. 26A) in the antibody-treated tumors: m28-RNLS vs IgG; 28.4±3.3 positive cells/high power field vs. IgG-14.8±2.3, n=14, p=0.002. FACS analysis of Panc1 cells in culture confirmed m28-RNLS caused apoptosis (FIGS. 26B and 33). Treatment with m28-RNLS antibody caused sustained phosphorylation of p38 MAPK beginning at day 1 post treatment (FIG. 26C).

Figure 26D:
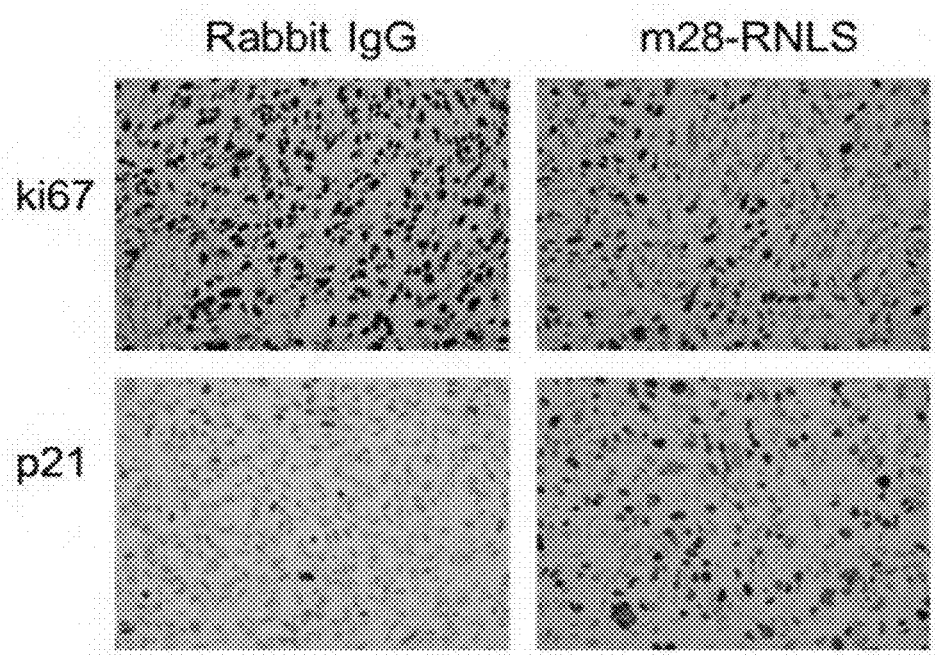
Figure 26E:
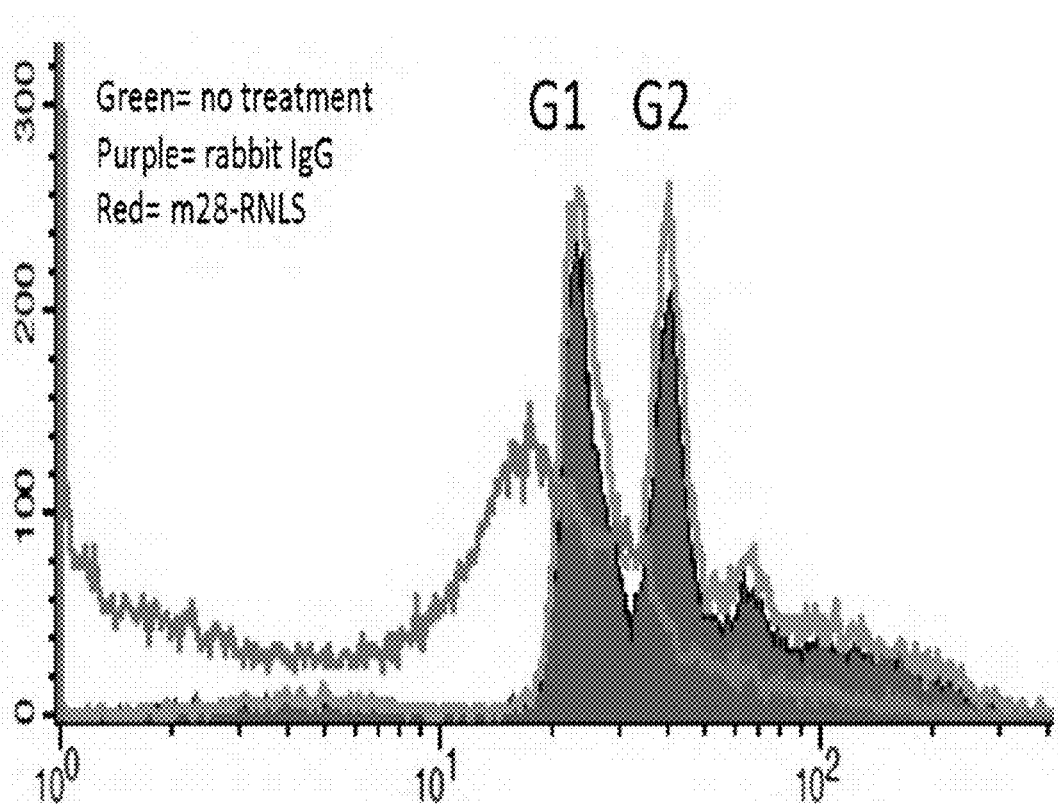

The m28-RNLS treatment of BxPC3 tumors also led to a 2.5-fold decrease in the expression of a cellular proliferation marker Ki67 (m28-RNLS vs IgG: IgG, 137.1±14.9 vs 340.2±11.9 positive cells/high power field, n=14, p=1.4× $10^{-8}$) (FIG. 26D, top panel), and to a ~4-fold increase in the expression of the cell cycle regulator p21 expression (m28-RNLS vs IgG: IgG, 178.1±11.4 vs 42.2±4.7.6 positive cells/high power field, n=14, p=1.6×$10^{-10}$) (FIG. 26D, bottom panel). FACS analysis of Panc1 cells was performed to examine the effect of RNLS signaling inhibition on the cell cycle. The data shown in FIG. 26E confirm that RNLS inhibition caused apoptosis, as evidenced by the appearance of a large pre-G1 peak. They also reveal a marked decrease in G2 indicating that inhibition of RNLS signaling by m28-RNLS causes a pre-G2 cell cycle arrest.

Figure 34:
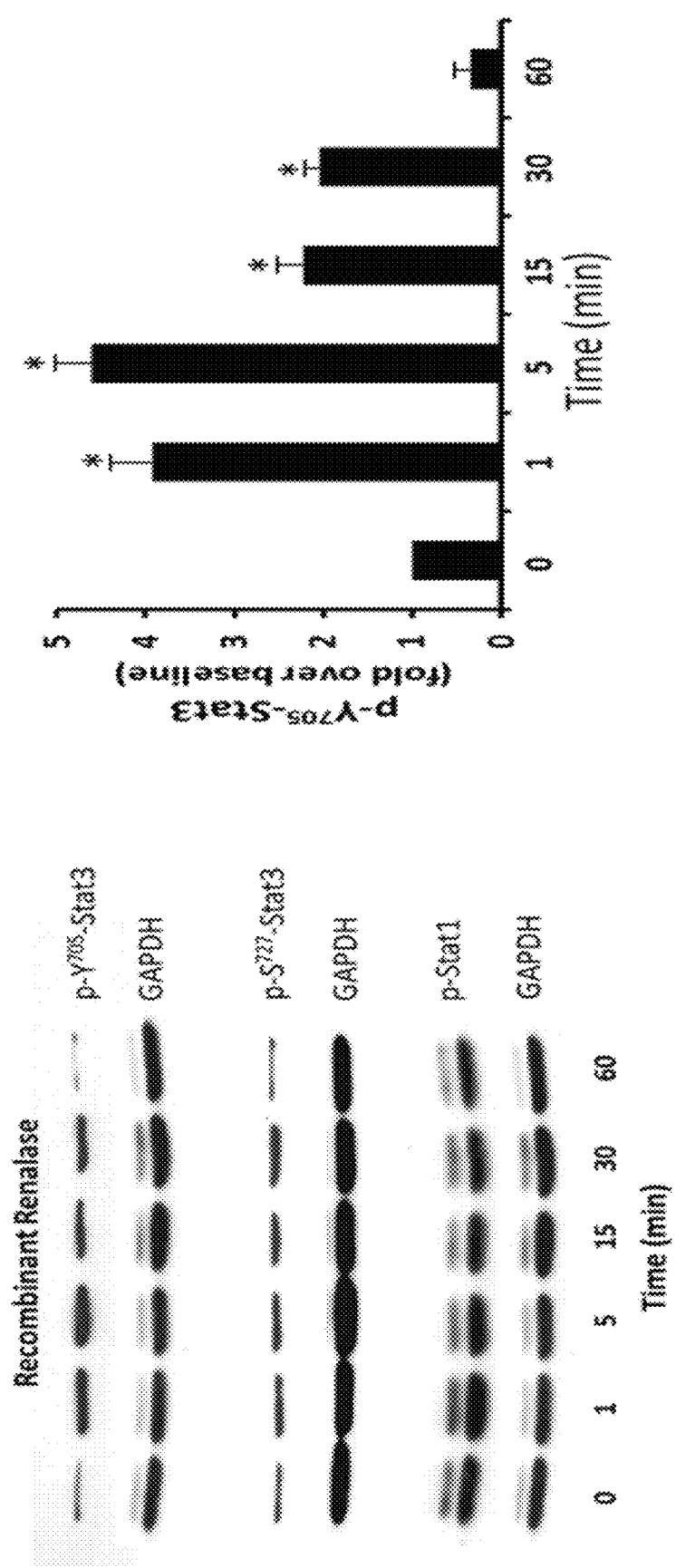
FIG. 34 comprises an image and a chart, showing that a positive RNLS-STAT3 feedback loop is suggested by the observation that in HK-2 cells treated with RNLS, STAT3 phosphorylation at serine 727 (p-Ser$^{727}$-STAT3) and tyrosine 705 (p-Y$^{705}$-STAT3) increases 2 and 4 fold respectively, but STAT1 is unaffected.

Presence of a Positive RNLS-STAT3 Feedback Loop and its Interruption by m28-RNLS STAT3 binds to the promoter region of the RNLS gene and increases its expression (Sonawane et al., 2014 Biochemistry. 53(44):6878-6892). A positive RNLS-STAT3 feedback loop is suggested by the observation that in HK-2 cells treated with RNLS, STAT3 phosphorylation at serine 727 (p-Ser$^{727}$-STAT3) and tyrosine 705 (p-Y$^{705}$-STAT3) increases 2 and 4 fold respectively, but STAT1 is unaffected (FIG. 34). As depicted in FIGS. 27A-B, the addition of RNLS to the PDACC line Panc1 caused a rapid increase in phosphorylated STAT3 (p-Ser$^{727}$-STAT3 and p-Y$^{705}$-STAT3). Additional support for a RNLS-STAT3 feedback loop is provided by the finding that inhibition of RNLS signaling in Panc1 by m28-RNLS leads to a long-lasting and sustained decrease in p-Y$^{705}$-STAT3 (FIG. 27C-D).

SEQUENCES

<SEQ ID NO: 1-antigenseq1a;PRT;homo sapiens>
AVWDKADDSGGRMTTAC

<SEQ ID NO: 2-antigenseq1b;PRT;homo sapiens>
AVWDKAEDSGGRMTTAC

<SEQ ID NO: 3-antigenseq1c;PRT;homo sapiens>
CTPHYAKKHQRFYDEL

<SEQ ID NO: 4-antigenseq1d;PRT;homo sapiens>
CIRFVSIDNKKRNIESSEIGP

<SEQ ID NO: 5-antigenseq1e;PRT;homo sapiens>
PGQMTLHHKPFLAC

<SEQ ID NO: 6-antigenseq1f;PRT;homo sapiens>
CVLEALKNYI

SEQUENCES

<SEQ ID NO: 7-antigenseq3a;PRT;*homo sapiens*>
PSAGVILGC

<SEQ ID NO: 8-HuRenalase-1 protein(polymorphism resulting in the glutamate amino acid at position 37);PRT;*homo sapiens*>
MAQVLIVGAGMTGSLCAALLRRQTSGPLYLAVWDKAEDSGGRMTTACSP

HNPQCTADLGAQYITCTPHYAKKHQRFYDELLAYGVLRPLSSPIEGMVM

KEGDCNFVAPQGISSIIKHYLKESGAEVYFRHRVTQINLRDDKWEVSKQ

TGSPEQFDLIVLTMPVPEILQLQGDITTLISECQRQQLEAVSYSSRYAL

GLFYEAGTKIDVPWAGQYITSNPCIRFVSIDNKKRNIESSEIGPSLVIH

TTVPFGVTYLEHSIEDVQELVFQQLENILPGLPQPIATKCQKWRHSQVT

NAAANCPGQMTLHHKPFLACGGDGFTQSNFDGCITSALCVLEALKNYI

<SEQ ID NO: 9-1D-28-4 full length heavy chain amino acid;PRT;*oryctolagus cuniculus*>
METGLRWLLLVAVLKGVQCQSVEESGGRLVTPGTPLTLTCTVSGFSLSS

FAVGWVRQAPGKGLEYIGIISSVGITRYASWAAGRFTISKTSTTVDLKI

TSPTTEDTATYFCARYGYSGDVNRLDLWGQGTLVTVSSGQPKAPSVFPL

APCCGDTPSSTVTLGCLVKGYLPEPVTVTWNSGTLTNGVRTFPSVRQSS

GLYSLSSVVSVTSSSQPVTCNVAHPATNTKVDKTVAPSTCSKPTCPPPE

LLGGPSVFIFPPKPKDTLMISRTPEVTCVVVDVSQDDPEVQFTWYINNE

QVRTARPPLREQQFNSTIRVVSTLPIAHQDWLRGKEFKCKVHNKALPAP

IEKTISKARGQPLEPKVYTMGPPREELSSRSVSLTCMINGFYPSDISVE

WEKNGKAEDNYKTTPAVLDSDGSYFLYSKLSVPTSEWQRGDVFTCSVMH

EALHNHYTQKSISRSPGK

<SEQ ID NO: 10-1D-28-4 full length light chain amino acid;PRT;*oryctolagus cuniculus*>
MDTRAPTQLLGLLLLWLPGATFAQVLTQTASPVSAAVGGTVTINCQASQ

SVYDNNNLAWYQQKPGQPPKQLIYGASTLASGVSSRFKGSGSGTQFTLT

ISGVQCDDAATYYCLGEFSCSSADCFAFGGGTEVVVKGDPVAPTVLIFP

PSADLVATGTVTIVCVANKYFPDVTVTWEVDGTTQTTGIENSKTPQNSA

DCTYNLSSTLTLTSTQYNSHKEYTCKVTQGTTSVVQSFNRGDC

<SEQ ID NO: 11-1D-28-4 heavy chain CDR1 amino acid;PRT;*oryctolagus cuniculus*>
LSSFAVG <SEQ ID NO: 12-1D-28-4 heavy chain CDR2 amino acid;PRT;*oryctolagus cuniculus*>
ITSSVGITRYASWAAG <SEQ ID NO: 13-1D-28-4 heavy chain CDR3 amino acid;PRT;*oryctolagus cuniculus*>
YGYSGDVNRLDL <SEQ ID NO: 14-1D-28-4 light chain CDR1 amino acid;PRT;*oryctolagus cuniculus*>
SQSVYDNNNLA <SEQ ID NO: 15-1D-28-4 light chain CDR2 amino acid;PRT;*oryctolagus cuniculus*>
GASTLAS <SEQ ID NO: 16-1D-28-4 light chain CDR3 amino acid;PRT;*oryctolagus cuniculus*>
LGEFSCSSADCFA <SEQ ID NO: 17-1D-37-10 full length heavy chain amino acid;PRT;*oryctolagus cuniculus*>
METGLRWLLLVAVLKGVQCQSVEESGGRLVTPGGSLTLTCTVSGFSLSD

YAIIWVRQAPGKGLEYIAIIGSSGDTFYATWAKGRFTISKTSTTVDLKM

TSLTAADTATYFCAPRYAGTTDYHDAFDPWGPGTLVTVSSGQPKAPSVF

PLAPCCGDTPSSTVTLGCLVKGYLPEPVTVTWNSGTLTNGVRTFPSVRQ

SSGLYSLSSVVSVTSSSQPVTCNVAHPATNTKVDKTVAPSTCSKPTCPP

PELLGGPSVFIFPPKPKDTLMISRTPEVTCVVVDVSQDDPEVQFTWYIN

NEQVRTARPPLREQQFNSTIRVVSTLPIAHQDWLRGKEFKCKVHNKALP

APIEKTISKARGQPLEPKVYTMGPPREELSSRSVSLTCMINGFYPSDIS

VEWEKNGKAEDNYKTTPAVLDSDGSYFLYSKLSVPTSEWQRGDVFTCSV

MHEALHNHYTQKSISRSPGK

<SEQ ID NO: 18-1D-37-10 full length light chain amino acid;PRT;*oryctolagus cuniculus*>
MDTRAPTQLLGLLLLWLPGARCAEVVMTQTPASMEAPMGGTVTIKCQAS

QNIYNYLSWYQQKPGQPPKLLVYKASTLTSGVPSRFKGSGSGTQFTLTI

SDLECADAATYYCQINYSIYNHYNIIFGGGTEVVVKGDPVAPTVLIFPP

SADLVATGTVTIVCVANKYFPDVTVTWEVDGTTQTTGIENSKTPQNSAD

CTYNLSSTLTLTSTQYNSHKEYTCKVTQGTTSVVQSFNRGDC

<SEQ ID NO: 19-1D-37-10 heavy chain CDR1 amino acid;PRT;*oryctolagus cuniculus*>
LSDYAII <SEQ ID NO: 20-1D-37-10 heavy chain CDR2 amino acid;PRT;*oryctolagus cuniculus*>
IIGSSGDTFYATWAKG <SEQ ID NO: 21-1D-37-10 heavy chain CDR3 amino acid;PRT;*oryctolagus cuniculus*>
RYAGTTDYHDAFDP <SEQ ID NO: 22-1D-37-10 light chain CDR1 amino acid;PRT;*oryctolagus cuniculus*>
SQNIYNYLS <SEQ ID NO: 23-1D-37-10 light chain CDR2 amino acid;PRT;*oryctolagus cuniculus*>
KASTLTS <SEQ ID NO: 24-1D-37-10 light chain CDR3 amino acid;PRT;*oryctolagus cuniculus*>
QINYSIYNHYNII <SEQ ID NO: 25-1F-26-1 full length heavy chain amino acid;PRT;*oryctolagus cuniculus*>
METGLRWLLLVAVLKGVQCQSVKESGGGLFKPTDTLTLTCTVSGFSLSS

YGVTWVRQAPGNGLEWIGLIGDRGTTFYASWAKSRSTITRNTNLNTVTL

KMTRLTAADTATYFCARGSGYGARIWGPGTLVTVSSWQPKAPSVFPLAP

CCGDTPSSTVTLGCLVKGYLPEPVTVTWNSGTLTNGVRTFPSVRQSSGL

YSLSSVVSVTSSSQPVTCNVAHPATNTKVDKTVAPSTCSKPTCPPPELL

GGPSVFIFPPKPKDTLMISRTPEVTCVVVDVSQDDPEVQFTWYINNEQV

RTARPPLREQQFNSTIRVVSTLPIAHQDWLRGKEFKCKVHNKALPAPIE

KTISKARGQPLEPKVYTMGPPREELSSRSVSLTCMINGFYPSDISVEWE

KNGKAEDNYKTTPAVLDSDGSYFLYSKLSVPTSEWQRGDVFTCSVMHEA

LHNHYTQKSISRSPGK

<SEQ ID NO: 26-1F-26-1 full length light chain
amino acid;PRT;*oryctolagus cuniculus*>
MDTRAPTQLLGLLLLWLPGATFAQVLTQTPSPVSAAVGGTVTINCQSSQ

SVYKNNYLAWYQQKPGQPPKLLIYETSKLASGVPPRFSGSGSGTQFTLT

ISSVQCDDAATYYCQGGYSGVDFMAFGGGTEVVVKGDPVAPTVLIFPPS

ADLVATGTVTIVCVANKYFPDVTVTWEVDGTTQTTGIENSKTPQNSADC

TYNLSSTLTLTSTQYNSHKEYTCKVTQGTTSVVQSFNRGDC

<SEQ ID NO: 27-1F-26-1 heavy chain CDR1 amino
acid;PRT;*oryctolagus cuniculus*>
LSSYGVT <SEQ ID NO: 28-1F-26-1 heavy chain CDR2 amino
acid;PRT;*oryctolagus cuniculus*>
LIGDRGTTFYASWAKS <SEQ ID NO: 29-1F-26-1 heavy chain CDR3 amino
acid;PRT;*oryctolagus cuniculus*>
GSGYGARI <SEQ ID NO: 30-1F-26-1 light chain CDR1 amino
acid;PRT;*oryctolagus cuniculus*>
SQSVYKNNYLA <SEQ ID NO: 31-1F-26-1 light chain CDR2 amino
acid;PRT;*oryctolagus cuniculus*>
ETSKLAS <SEQ ID NO: 32-1F-26-1 light chain CDR3 amino
acid;PRT;*oryctolagus cuniculus*>
QGGYSGVDFMA <SEQ ID NO: 33-1F-42-7 full length heavy chain
amino acid;PRT;*oryctolagus cuniculus*>
METGLRWLLLVAVLKGVQCQSVKESEGGLFKPTDTLTLTCTVSGFSLTT

YGVTWVRQAPGNGLEWIGLIGDRGTTYYASWVNGRSTITRNTNLNTVTL

KMTRLTAADTATYFCARGSGYGARIWGPGTLVTVASWQPKAPSVFPLAP

CCGDTPSSTVTLGCLVKGYLPEPVTVTWNSGTLTNGVRTFPSVRQSSGL

YSLSSVVSVTSSSQPVTCNVAHPATNTKVDKTVAPSTCSKPTCPPPELL

GGPSVFIFPPKPKDTLMISRTPEVTCVVVDVSQDDPEVQFTWYINNEQV

RTARPPLREQQFNSTIRVVSTLPIAHQDWLRGKEFKCKVHNKALPAPIE

KTISKARGQPLEPKVYTMGPPREELSSRSVSLTCMINGFYPSDISVEWE

KNGKAEDNYKTTPAVLDSDGSYFLYSKLSVPTSEWQRGDVFTCSVMHEA

LHNHYTQKSISRSPGK

<SEQ ID NO: 34-1F-42-7 full length light chain
amino acid;PRT;*oryctolagus cuniculus*>
MDTRAPTQLLGLLLLWLPGATFAQVLTQTPSPMSAALGGTVTINCQSSQ

TVYNNYLSWYQQKPGQPPKLLIYETSKLSSGVPPRFSGSGSGTQFTLT

ISSVQCDDAATYYCQGGYSGVDFMAFGGGTEVVVKGDPVAPTVLIFPPS

ADLVATGTVTIVCVANKYFPDVTVTWEVDGTTQTTGIENSKTPQNSADC

TYNLSSTLTLTSTQYNSHKEYTCKVTQGTTSVVQSFNRGDC

<SEQ ID NO: 35-1F-42-7 heavy chain CDR1 amino
acid;PRT;*oryctolagus cuniculus*>
LTTYGVT <SEQ ID NO: 36-1F-42-7 heavy chain CDR2 amino
acid;PRT;*oryctolagus cuniculus*>
LIGDRGTTYYASWVNG <SEQ ID NO: 37-1F-42-7 heavy chain CDR3 amino
acid;PRT;*oryctolagus cuniculus*>
GSGYGARI <SEQ ID NO: 38-1F-42-7 light chain CDR1 amino
acid;PRT;*oryctolagus cuniculus*>
SQTVYNNNYLS <SEQ ID NO: 39-1F-42-7 light chain CDR2 amino
acid;PRT;*oryctolagus cuniculus*>
ETSKLSS <SEQ ID NO: 40-1F-42-7 light chain CDR3 amino
acid;PRT;*oryctolagus cuniculus*>
QGGYSGVDFM <SEQ ID NO: 41-3A-5-2 full length heavy chain
amino acid;PRT;*oryctolagus cuniculus*>
METGLRWLLLVAVLKGVQCQSLEESGGRLVTPGTPLTLTCTVSGFSLNN

YHIYWVRQAPGKGLEYIGIIFNGGTYYARWTKGRFTISKTSTTVDLKMT

SLTTEDTATYFCARGDGIWGPGTLVTVSLGQPKAPSVFPLAPCCGDTPS

STVTLGCLVKGYLPEPVTVTWNSGTLTNGVRTFPSVRQSSGLYSLSSVV

SVTSSSQPVTCNVAHPATNTKVDKTVAPSTCSKPTCPPPELLGGPSVFI

FPPKPKDTLMISRTPEVTCVVVDVSQDDPEVQFTWYINNEQVRTARPPL

REQQFNSTIRVVSTLPIAHQDWLRGKEFKCKVHNKALPAPIEKTISKAR

GQPLEPKVYTMGPPREELSSRSVSLTCMINGFYPSDISVEWEKNGKAED

NYKTTPAVLDSDGSYFLYSKLSVPTSEWQRGDVFTCSVMHEALHNHYTQ

KSISRSPGK

<SEQ ID NO: 42-3A-5-2 full length light chain
amino acid;PRT;*oryctolagus cuniculus*>
MDTRAPTQLLGLLLLWLPGATFAQVLTQTPASVSAAVGGTVTINCQASQ

SVFNNNYLAWYQQKPGQPPKRLIYSASTLASGVSSRFKGSGSGTEFTLT

MSGVECDDAATYYCAGSFDCNSGDCVAFGGGTEVVVKGDPVAPTVLIFP

PAADQVATGTVTIVCVANKYFPDVTVTWEVDGTTQTTGIENSKTPQNSA

DCTYNLSSTLTLTSTQYNSHKEYTCKVTQGTTSVVQSFNRGDC

<SEQ ID NO: 43-3A-5-2 heavy chain CDR1 amino
acid;PRT;*oryctolagus cuniculus*>
LNNYHIY <SEQ ID NO: 44-3A-5-2 heavy chain CDR2 amino
acid;PRT;*oryctolagus cuniculus*>
IIFNGGTYYARWTKG <SEQ ID NO: 45-3A-5-2 heavy chain CDR3 amino
acid;PRT;*oryctolagus cuniculus*>
GDGI <SEQ ID NO: 46-3A-5-2 light chain CDR1 amino
acid;PRT;*oryctolagus cuniculus*>
SQSVFNNNYLA <SEQ ID NO: 47-3A-5-2 light chain CDR2 amino
acid;PRT;*oryctolagus cuniculus*>
SASTLAS <SEQ ID NO: 48-3A-5-2 light chain CDR3 amino
acid;PRT;*oryctolagus cuniculus*>
AGSFDCNSGDCVA <SEQ ID NO: 49-Human Renalase-1 nucleic acid sequence (possible polymorphism at nucleotide position 111);DNA;homo sapiens>
ATGGCGCAGGTGCTGATCGTGGGCGCCGGGATGACAGGAAGCTTGTGCG

CTGCGCTGCTGAGGAGGCAGACGTCCGGTCCCTTGTACCTTGCTGTGTG

GGACAAGGCTGAGGACTCAGGGGGAAGAATGACTACAGCCTGCAGTCCT

CATAATCCTCAGTGCACAGCTGACTTGGGTGCTCAGTACATCACCTGCA

CTCCTCATTATGCCAAAAAACACCAACGTTTTTATGATGAACTGTTAGC

CTATGGCGTTTTGAGGCCTCTAAGCTCGCCTATTGAAGGAATGGTGATG

AAAGAAGGAGACTGTAACTTTGTGGCACCTCAAGGAATTTCTTCAATTA

TTAAGCATTACTTGAAAGAATCAGGTGCAGAAGTCTACTTCAGACATCG

TGTGACACAGATCAACCTAAGAGATGACAAATGGGAAGTATCCAAACAA

ACAGGCTCCCCTGAGCAGTTTGATCTTATTGTTCTCACAATGCCAGTTC

CTGAGATTCTGCAGCTTCAAGGTGACATCACCACCTTAATTAGTGAATG

CCAAAGGCAGCAACTGGAGGCTGTGAGCTACTCCTCTCGATATGCTCTG

GGCCTCTTTTATGAAGCTGGTACGAAGATTGATGTCCCTTGGGCTGGGC

AGTACATCACCAGTAATCCCTGCATACGCTTCGTCTCCATTGATAATAA

GAAGCGCAATATAGAGTCATCAGAAATTGGGCCTTCCCTCGTGATTCAC

ACCACTGTCCCATTTGGAGTTACATACTTGGAACACAGCATTGAGGATG

TGCAAGAGTTAGTCTTCCAGCAGCTGGAAAACATTTTGCCGGGTTTGCC

TCAGCCAATTGCTACCAAATGCCAAAAATGGAGACATTCACAGGTTACA

AATGCTGCTGCCAACTGTCCTGGCCAAATGACTCTGCATCACAAACCTT

TCCTTGCATGTGGAGGGGATGGATTTACTCAGTCCAACTTTGATGGCTG

CATCACTTCTGCCCTATGTGTTCTGGAAGCTTTAAAGAATTATATTTAA

<SEQ ID NO: 50-Human Renalase-2 amino acid sequence (polymorphism resulting in the glutamate amino acid at position 37;PRT; homo sapiens>
MAQVLIVGAGMTGSLCAALLRRQTSGPLYLAVWDKAEDSGGRMTTACSP

HNPQCTADLGAQYITCTPHYAKKHQRFYDELLAYGVLRPLSSPIEGMVM

KEGDCNFVAPQGISSIIKHYLKESGAEVYFRHRVTQINLRDDKWEVSKQ

TGSPEQFDLIVLTMPVPEILQLQGDITTLISECQRQQLEAVSYSSRYAL

GLFYEAGTKIDVPWAGQYITSNPCIRFVSIDNKKRNIESSEIGPSLVIH

TTVPFGVTYLEHSIEDVQELVFQQLENILPGLPQPIATKCQKWRHSQVP

SAGVILGCAKSPWMMAIGFPI

<SEQ ID NO: 51-Human Renalase-2 nucleic acid sequence (possible polymorphism at nucleotide position 111);DNA;homo sapiens>
ATGGCGCAGGTGCTGATCGTGGGCGCCGGGATGACAGGAAGCTTGTGCG

CTGCGCTGCTGAGGAGGCAGACGTCCGGTCCCTTGTACCTTGCTGTGTG

GGACAAGGCTGAGGACTCAGGGGGAAGAATGACTACAGCCTGCAGTCCT

CATAATCCTCAGTGCACAGCTGACTTGGGTGCTCAGTACATCACCTGCA

CTCCTCATTATGCCAAAAAACACCAACGTTTTTATGATGAACTGTTAGC

CTATGGCGTTTTGAGGCCTCTAAGCTCGCCTATTGAAGGAATGGTGATG

AAAGAAGGAGACTGTAACTTTGTGGCACCTCAAGGAATTTCTTCAATTA

TTAAGCATTACTTGAAAGAATCAGGTGCAGAAGTCTACTTCAGACATCG

TGTGACACAGATCAACCTAAGAGATGACAAATGGGAAGTATCCAAACAA

ACAGGCTCCCCTGAGCAGTTTGATCTTATTGTTCTCACAATGCCAGTTC

CTGAGATTCTGCAGCTTCAAGGTGACATCACCACCTTAATTAGTGAATG

CCAAAGGCAGCAACTGGAGGCTGTGAGCTACTCCTCTCGATATGCTCTG

GGCCTCTTTTATGAAGCTGGTACGAAGATTGATGTCCCTTGGGCTGGGC

AGTACATCACCAGTAATCCCTGCATACGCTTCGTCTCCATTGATAATAA

GAAGCGCAATATAGAGTCATCAGAAATTGGGCCTTCCCTCGTGATTCAC

ACCACTGTCCCATTTGGAGTTACATACTTGGAACACAGCATTGAGGATG

TGCAAGAGTTAGTCTTCCAGCAGCTGGAAAACATTTTGCCGGGTTTGCC

TCAGCCAATTGCTACCAAATGCCAAAAATGGAGACATTCACAGGTACCA

AGTGCTGGTGTGATTCTAGGATGTGCGAAGAGCCCCTGGATGATGGCGA

TTGGATTTCCCATC

<SEQ ID NO: 52-1D-28-4 full length heavy chain nucleic acid;DNA;oryctolagus cuniculus>
ATGGAGACTGGGCTGCGCTGGCTTCTCCTGGTCGCTGTGCTCAAAGGTG

TCCAGTGTCAGTCGGTGGAGGAGTCCGGGGGTCGCCTGGTCACGCCTGG

GACACCCCTGACACTCACCTGCACAGTCTCTGGATTCTCCCTCAGTAGT

TTTGCAGTGGGCTGGGTCCGCCAGGCTCCAGGGAAGGGGCTGGAATACA

TCGGAATCATTAGTAGTGTTGGTATTACACGCTACGCGAGCTGGGCGGC

CGGCCGATTCACCATCTCCAAAACCTCGACCACGGTGGATCTGAAAATC

ACCAGTCCGACAACCGAGGACACGGCCACCTATTTTTGTGCCAGATATG

GTTATAGTGGTGATGTTAATCGGTTGGATCTCTGGGGCCAGGGCACCCT

GGTCACCGTCTCCTCAGGGCAACCTAAGGCTCCATCAGTCTTCCCACTG

GCCCCCTGCTGCGGGGACACACCCAGCTCCACGGTGACCCTGGGCTGCC

TGGTCAAAGGGTACCTCCCGGAGCCAGTGACCGTGACCTGGAACTCGGG

CACCCTCACCAATGGGGTACGCACCTTCCCGTCCGTCCGGCAGTCCTCA

GGCCTCTACTCGCTGAGCAGCGTGGTGAGCGTGACCTCAAGCAGCCAGC

CCGTCACCTGCAACGTGGCCCACCCAGCCACCAACACCAAAGTGGACAA

GACCGTTGCGCCCTCGACATGCAGCAAGCCCACGTGCCCACCCCCTGAA

CTCCTGGGGGGACCGTCGTCTTCATCTTCCCCCCAAAACCCAAGGACA

CCCTCATGATCTCACGCACCCCCGAGGTCACATGCGTGGTGGTGGACGT

GAGCCAGGATGACCCCGAGGTGCAGTTCACATGGTACATAAACAACGAG

CAGGTGCGCACCGCCCGGCCGCCGCTACGGGAGCAGCAGTTCAACAGCA

CGATCCGCGTGGTCAGCACCCTCCCCATCGCGCACCAGGACTGGCTGAG

GGGCAAGGAGTTCAAGTGCAAAGTCCACAACAAGGCACTCCCGGCCCCC

ATCGAGAAAACCATCTCCAAAGCCAGAGGGCAGCCCCTGGAGCCGAAGG

TCTACACCATGGGCCCTCCCCGGGAGGAGCTGAGCAGCAGGTCGGTCAG

CCTGACCTGCATGATCAACGGCTTCTACCCTTCCGACATCTCGGTGGAG

| SEQUENCES |
|---|
| TGGGAGAAGAACGGGAAGGCAGAGGACAACTACAAGACCACGCCGGCCG |
| TGCTGGACAGCGACGGCTCCTACTTCCTCTACAGCAAGCTCTCAGTGCC |
| CACGAGTGAGTGGCAGCGGGGCGACGTCTTCACCTGCTCCGTGATGCAC |
| GAGGCCTTGCACAACCACTACACGCAGAAGTCCATCTCCCGCTCTCCGG |
| GTAAATGA |
| <SEQ ID NO: 53-1D-28-4 full length light chain nucleic acid;DNA;*oryctolagus cuniculus*> |
| ATGGACACGAGGGCCCCCACTCAGCTGCTGGGGCTCCTGCTGCTCTGGC |
| TCCCAGGTGCCACATTTGCCCAAGTGCTGACCCAGACTGCATCGCCCGT |
| GTCTGCAGCTGTGGGAGGCACAGTCACCATCAATTGCCAGGCCAGTCAG |
| AGTGTTTATGATAACAACAACTTAGCCTGGTATCAGCAGAAACCAGGGC |
| AGCCTCCCAAGCAACTGATCTATGGTGCATCCACTCTGGCATCTGGGGT |
| CTCATCGCGGTTCAAAGGCAGTGGATCTGGGACACAGTTCACTCTCACC |
| ATCAGCGGCGTGCAGTGTGACGATGCTGCCACTTACTACTGTCTAGGCG |
| AATTTAGTTGTAGTAGTGCTGATTGTTTTGCTTTCGGCGGAGGGACCGA |
| GGTGGTCGTCAAAGGTGATCCAGTTGCACCTACTGTCCTCATCTTCCCA |
| CCATCTGCTGATCTTGTGGCAACTGGAACAGTCACCATCGTGTGTGTGG |
| CGAATAAATACTTTCCCGATGTCACCGTCACCTGGGAGGTGGATGGCAC |
| CACCCAAACAACTGGCATCGAGAACAGTAAAACACCGCAGAATTCTGCA |
| GATTGTACCTACAACCTCAGCAGCACTCTGACACTGACCAGCACACAGT |
| ACAACAGCCACAAAGAGTACACCTGCAAGGTGACCCAGGGCACGACCTC |
| AGTCGTCCAGAGCTTCAATAGGGGTGACTGTTAG |
| <SEQ ID NO: 54-1D-28-4 heavy chain CDR1 nucleic acid;DNA;*oryctolagus cuniculus*> |
| ctcagtagttttgcagtgggc |
| <SEQ ID NO: 55-1D-28-4 heavy chain CDR2 nucleic acid;DNA;*oryctolagus cuniculus*> |
| atcattagtagtgttggtattacacgctacgcgagctgggcggccggc |
| <SEQ ID NO: 56-1D-28-4 heavy chain CDR3 nucleic acid;DNA;*oryctolagus cuniculus*> |
| tatggttatagtggtgatgttaatcggttggatctc |
| <SEQ ID NO: 57-1D-28-4 light chain CDR1 nucleic acid;DNA;*oryctolagus cuniculus*> |
| agtcagagtgtttatgataacaacaacttagcc |
| <SEQ ID NO: 58-1D-28-4 light chain CDR2 nucleic acid;DNA;*oryctolagus cuniculus*> |
| ggtgcatccactctggcatct |
| <SEQ ID NO: 59-1D-28-4 light chain CDR3 nucleic acid;DNA;*oryctolagus cuniculus*> |
| ctaggcgaatttagttgtagtagtgctgattgttttgct |
| <SEQ ID NO: 60-1D-37-10 full length heavy chain nucleic acid;DNA;*oryctolagus cuniculus*> |
| ATGGAGACTGGGCTGCGCTGGCTTCTCCTGGTCGCTGTGCTCAAAGGTG |
| TCCAGTGTCAGTCGGTGGAGGAGTCCGGGGGTCGCCTGGTCACGCCTGG |
| AGGATCCCTGACACTCACCTGCACAGTCTCTGGATTCTCCCTCAGTGAC |
| TATGCAATAATCTGGGTCCGCCAGGCTCCAGGGAAGGGGCTGGAATACA |
| TCGCAATTATTGGTAGTAGTGGTGACACATTCTACGCGACCTGGGCGAA |
| AGGCCGATTCACCATCTCCAAAACCTCGACCACGGTGGATCTGAAAATG |
| ACCAGTCTGACAGCCGCGGACACGGCCACCTATTTCTGTGCCCCACGTT |
| ATGCTGGTACTACTGATTATCATGATGCTTTTGATCCCTGGGGCCCAGG |
| CACTTTGGTCACCGTCTCCTCAGGGCAACCTAAGGCTCCATCAGTCTTC |
| CCACTGGCCCCTGCTGCGGGACACACCCAGCTCCACGGTGACCCTGG |
| GCTGCCTGGTCAAAGGGTACCTCCCGGAGCCAGTGACCGTGACCTGGAA |
| CTCGGGCACCCTCACCAATGGGGTACGCACCTTCCCGTCCGTCCGGCAG |
| TCCTCAGGCCTCTACTCGCTGAGCAGCGTGGTGAGCGTGACCTCAAGCA |
| GCCAGCCCGTCACCTGCAACGTGGCCCACCCAGCCACCAACACCAAAGT |
| GGACAAGACCGTTGCGCCCTCGACATGCAGCAAGCCCACGTGCCCACCC |
| CCTGAACTCCTGGGGGGACCGTCTGTCTTCATCTTCCCCCCAAAACCCA |
| AGGACACCCTCATGATCTCACGCACCCCCGAGGTCACATGCGTGGTGGT |
| GGACGTGAGCCAGGATGACCCCGAGGTGCAGTTCACATGGTACATAAAC |
| AACGAGCAGGTGCGCACCGCCCGGCCGCCGCTACGGGAGCAGCAGTTCA |
| ACAGCACGATCCGCGTGGTCAGCACCCTCCCCATCGCGCACCAGGACTG |
| GCTGAGGGGCAAGGAGTTCAAGTGCAAAGTCCACAACAAGGCACTCCCG |
| GCCCCCATCGAGAAAACCATCTCCAAAGCCAGAGGGCAGCCCCTGGAGC |
| CGAAGGTCTACACCATGGGCCCTCCCCGGGAGGAGCTGAGCAGCAGGTC |
| GGTCAGCCTGACCTGCATGATCAACGGCTTCTACCCTTCCGACATCTCG |
| GTGGAGTGGGAGAAGAACGGGAAGGCAGAGGACAACTACAAGACCACGC |
| CGGCCGTGCTGGACAGCGACGGCTCCTACTTCCTCTACAGCAAGCTCTC |
| AGTGCCCACGAGTGAGTGGCAGCGGGGCGACGTCTTCACCTGCTCCGTG |
| ATGCACGAGGCCTTGCACAACCACTACACGCAGAAGTCCATCTCCCGCT |
| CTCCGGGTAAATGA |
| <SEQ ID NO: 61-1D-37-10 full length light chain nucleic acid;DNA;*oryctolagus cuniculus*> |
| ATGGACACGAGGGCCCCCACTCAGCTGCTGGGGCTCCTGCTGCTCTGGC |
| TCCCAGGTGCCAGATGTGCCGAAGTAGTGATGACCCAGACTCCAGCCTC |
| CATGGAGGCACCTATGGGAGGCACAGTCACCATCAAGTGCCAGGCCAGT |
| CAGAACATTTACAACTACTTATCCTGGTATCAGCAGAAACCAGGGCAGC |
| CTCCCAAGCTCCTAGTCTACAAGGCCTCCACTCTGACTTCTGGGGTCCC |
| GTCGCGCTTCAAAGGCAGTGGATCTGGGACACAGTTCACTCTCACCATC |
| AGCGACCTGGAGTGTGCCGATGCTGCCACTTACTACTGTCAAATCAATT |
| ACTCTATTTATAATCATTATAATATTATTTTTGGCGGAGGGACCGAGGT |
| GGTCGTCAAGGGTGATCCAGTTGCACCTACTGTCCTCATCTTCCCACCA |
| TCTGCTGATCTTGTGGCAACTGGAACAGTCACCATCGTGTGTGTGGCGA |
| ATAAATACTTTCCCGATGTCACCGTCACCTGGGAGGTGGATGGCACCAC |
| CCAAACAACTGGCATCGAGAACAGTAAAACACCGCAGAATTCTGCAGAT |
| TGTACCTACAACCTCAGCAGCACTCTGACACTGACCAGCACACAGTACA |

| SEQUENCES |
|---|
| ACAGCCACAAAGAGTACACCTGCAAGGTGACCCAGGGCACGACCTCAGT |
| CGTCCAGAGCTTCAATAGGGGTGACTGTTAG |
| <SEQ ID NO: 62-1D-37-10 heavy chain CDR1 nucleic acid;DNA;*oryctolagus cuniculus*> ctcagtgactatgcaataatc |
| <SEQ ID NO: 63-1D-37-10 heavy chain CDR2 nucleic acid;DNA;*oryctolagus cuniculus*> attattggtagtagtggtgacacattctacgcgacctgggcgaaaggc |
| <SEQ ID NO: 64-1D-37-10 heavy chain CDR3 nucleic acid;DNA;*oryctolagus cuniculus*> cgttatgctggtactactgattatcatgatgcttttgatccc |
| <SEQ ID NO: 65-1D-37-10 light chain CDR1 nucleic acid;DNA;*oryctolagus cuniculus*> agtcagaacatttacaactacttatcc |
| <SEQ ID NO: 66-1D-37-10 light chain CDR2 nucleic acid;DNA;*oryctolagus cuniculus*> aaggcctccactctgacttct |
| <SEQ ID NO: 67-1D-37-10 light chain CDR3 nucleic acid;DNA;*oryctolagus cuniculus*> caaatcaattactctatttataatcattataatattatt |
| <SEQ ID NO: 68-1F-26-1 full length heavy chain nucleic acid;DNA;*oryctolagus cuniculus*> ATGGAGACTGGGCTGCGCTGGCTTCTCCTGGTCGCTGTGCTCAAAGGTG |
| TCCAGTGTCAGTCGGTGAAGGAGTCCGAGGGAGGTCTCTTCAAGCCAAC |
| GGATACCCTGACACTCACCTGCACAGTCTCTGGATTCTCCCTCAGTAGC |
| TATGGAGTGACCTGGGTCCGCCAGGCTCCAGGGAACGGGCTGGAGTGGA |
| TCGGATTGATTGGTGATCGTGGTACTACGTTCTACGCGAGCTGGGCGAA |
| AAGCCGATCCACCATCACCAGAAACACCAACCTGAACACGGTGACTCTG |
| AAAATGACCAGGCTGACAGCCGCGGACACGGCCACCTATTTCTGTGCGA |
| GGGGGAGTGGGTATGGTGCTCGCATCTGGGGCCCAGGCACCCTGGTCAC |
| CGTCTCCTCATGGCAACCTAAGGCTCCATCAGTCTTCCCACTGGCCCCC |
| TGCTGCGGGACACACCCAGCTCCACGGTGACCCTGGGCTGCCTGGTCA |
| AAGGGTACCTCCCCGGAGCCAGTGACCGTGACCTGGAACTCGGGCACCCT |
| CACCAATGGGGTACGCACCTTCCCGTCCGTCCGGCAGTCCTCAGGCCTC |
| TACTCGCTGAGCAGCGTGGTGAGCGTGACCTCAAGCAGCCAGCCCGTCA |
| CCTGCAACGTGGCCCACCCAGCCACCAACACCAAAGTGGACAAGACCGT |
| TGCGCCCTCGACATGCAGCAAGCCCACGTGCCCACCCCCTGAACTCCTG |
| GGGGGACCGTCTGTCTTCATCTTCCCCCCAAAACCCAAGGACACCCTCA |
| TGATCTCACGCACCCCCGAGGTCACATGCGTGGTGGTGGACGTGAGCCA |
| GGATGACCCCGAGGTGCAGTTCACATGGTACATAAACAACGAGCAGGTG |
| CGCACCGCCCGGCCGCCGCTACGGGAGCAGCAGTTCAACAGCACGATCC |
| GCGTGGTCAGCACCCTCCCCATCGCGCACCAGGACTGGCTGAGGGGCAA |
| GGAGTTCAAGTGCAAAGTCCACAACAAGGCACTCCCGGCCCCCATCGAG |
| AAAACCATCTCCAAAGCCAGAGGGCAGCCCCTGGAGCCGAAGGTCTACA |
| CCATGGGCCCTCCCCGGGAGGAGCTGAGCAGCAGGTCGGTCAGCCTGAC |
| CTGCATGATCAACGGCTTCTACCCTTCCGACATCTCGGTGGAGTGGGAG |
| AAGAACGGGAAGGCAGAGGACAACTACAAGACCACGCCGGCCGTGCTGG |
| ACAGCGACGGCTCCTACTTCCTCTACAGCAAGCTCTCAGTGCCCACGAG |
| TGAGTGGCAGCGGGGCGACGTCTTCACCTGCTCCGTGATGCACGAGGCC |
| TTGCACAACCACTACACGCAGAAGTCCATCTCCCGCTCTCCGGGTAAAT |
| GA |
| <SEQ ID NO: 69-1F-26-1 full length light chain nucleic acid;DNA;*oryctolagus cuniculus*> ATGGACACGAGGGCCCCCACTCAGCTCCTGGGGCTCCTGCTGCTCTGGC |
| TCCCAGGTGCCACATTTGCCCAAGTGCTGACCCAGACTCCATCGCCTGT |
| GTCTGCAGCTGTGGGAGGCACAGTCACCATCAATTGCCAGTCCAGTCAG |
| AGTGTTTATAAGAACAACTACTTAGCCTGGTATCAGCAGAAACCAGGGC |
| AGCCTCCCAAGCTCCTTATCTACGAAACATCCAAACTGGCATCTGGGGT |
| CCCACCGCGGTTCAGCGGCAGTGGGTCTGGGACAGTTCACTCTCACC |
| ATCAGCAGCGTGCAGTGTGACGATGCTGCCACTTACTACTGTCAAGGCG |
| GTTATAGTGGTGTTGATTTTATGGCTTTCGGCGGAGGGACCGAGGTGGT |
| CGTCAAAGGTGATCCAGTTGCACCTACTGTCCTCATCTTCCCACCATCT |
| GCTGATCTTGTGGCAACTGGAACAGTCACCATCGTGTGTGTGGCGAATA |
| AATACTTTCCCGATGTCACCGTCACCTGGGAGGTGGATGGCACCACCCA |
| AACAACTGGCATCGAGAACAGTAAAACACCGCAGAATTCTGCAGATTGT |
| ACCTACAACCTCAGCAGCACTCTGACACTGACCAGCACACAGTACAACA |
| GCCACAAAGAGTACACCTGCAAGGTGACCCAGGGCACGACCTCAGTCGT |
| CCAGAGCTTCAATAGGGGTGACTGTTAG |
| <SEQ ID NO: 70-1F-26-1 heavy chain CDR1 nucleic acid;DNA;*oryctolagus cuniculus*> ctcagtagctatggagtgacc |
| <SEQ ID NO: 71-1F-26-1 heavy chain CDR2 nucleic acid;DNA;*oryctolagus cuniculus*> ttgattggtgatcgtggtactacgttctacgcgagctgggcgaaaagc |
| <SEQ ID NO: 72-1F-26-1 heavy chain CDR3 nucleic acid;DNA;*oryctolagus cuniculus*> Gggagtgggtatggtgctcgcatc |
| <SEQ ID NO: 73-1F-26-1 light chain CDR1 nucleic acid;DNA;*oryctolagus cuniculus*> agtcagagtgtttataagaacaactacttagcc |
| <SEQ ID NO: 74-1F-26-1 light chain CDR2 nucleic acid;DNA;*oryctolagus cuniculus*> gaaacatccaaactggcatct |
| <SEQ ID NO: 75-1F-26-1 light chain CDR3 nucleic acid;DNA;*oryctolagus cuniculus*> caaggcggttatagtggtgttgattttatggct |
| <SEQ ID NO: 76-1F-42-7 full length heavy chain nucleic acid;DNA;*oryctolagus cuniculus*> ATGGAGACTGGGCTGCGCTGGCTTCTCCTGGTCGCTGTGCTCAAAGGTG |
| TCCAGTGTCAGTCGGTGAAGGAGTCCGAGGGAGGTCTCTTCAAGCCAAC |
| GGATACCCTGACACTCACCTGCACAGTCTCTGGATTCTCCCTCACTACC |
| TATGGAGTGACCTGGGTCCGCCAGGCTCCAGGGAATGGGCTGGAGTGGA |

| SEQUENCES |
|---|
| TCGGATTGATTGGTGATCGCGGTACCACTTACTACGCGAGCTGGGTGAA |
| TGGCCGATCCACCATCACCAGAAACACCAACCTGAACACGGTGACTCTG |
| AAAATGACCAGGCTGACAGCCGCGGACACGGCCACCTATTTCTGTGCGA |
| GGGGGAGTGGATATGGTGCTCGCATCTGGGGCCCAGGCACCCTGGTCAC |
| CGTCGCCTCATGGCAACCTAAGGCTCCATCAGTCTTCCCACTGGCCCCC |
| TGCTGCGGGACACACCCAGCTCCACGGTGACCCTGGGCTGCCTGGTCA |
| AAGGGTACCTCCCGGAGCCAGTGACCGTGACCTGGAACTCGGGCACCCT |
| CACCAATGGGGTACGCACCTTCCCGTCCGTCCGGCAGTCCTCAGGCCTC |
| TACTCGCTGAGCAGCGTGGTGAGCGTGACCTCAAGCAGCCAGCCCGTCA |
| CCTGCAACGTGGCCCACCCAGCCACCAACACCAAAGTGGACAAGACCGT |
| TGCGCCCTCGACATGCAGCAAGCCCACGTGCCCACCCCCTGAACTCCTG |
| GGGGGACCGTCTGTCTTCATCTTCCCCCCAAAACCCAAGGACACCCTCA |
| TGATCTCACGCACCCCCGAGGTCACATGCGTGGTGGTGGACGTGAGCCA |
| GGATGACCCCGAGGTGCAGTTCACATGGTACATAAACAACGAGCAGGTG |
| CGCACCGCCCGGCCGCCGCTACGGGAGCAGCAGTTCAACAGCACGATCC |
| GCGTGGTCAGCACCCTCCCCATCGCGCACCAGGACTGGCTGAGGGGCAA |
| GGAGTTCAAGTGCAAAGTCCACAACAAGGCACTCCCGGCCCCCATCGAG |
| AAAACCATCTCCAAAGCCAGAGGGCAGCCCCTGGAGCCGAAGGTCTACA |
| CCATGGGCCCTCCCCGGGAGGAGCTGAGCAGCAGGTCGGTCAGCCTGAC |
| CTGCATGATCAACGGCTTCTACCCTTCCGACATCTCGGTGGAGTGGGAG |
| AAGAACGGGAAGGCAGAGGACAACTACAAGACCACGCCGGCCGTGCTGG |
| ACAGCGACGGCTCCTACTTCCTCTACAGCAAGCTCTCAGTGCCCACGAG |
| TGAGTGGCAGCGGGGCGACGTCTTCACCTGCTCCGTGATGCACGAGGCC |
| TTGCACAACCACTACACGCAGAAGTCCATCTCCCGCTCTCCGGGTAAAT |
| GA |
| <SEQ ID NO: 77-1F-42-7 full length light chain nucleic acid;DNA;*oryctolagus cuniculus*> ATGGACACGAGGGCCCCCACTCAGCTCCTGGGGCTCCTGCTGCTCTGGC |
| TCCCAGGTGCCACATTTGCCCAAGTGCTGACCCAGACTCCATCCCCCAT |
| GTCTGCAGCTCTGGGAGGCACAGTCACCATCAATTGCCAGTCCAGTCAG |
| ACTGTTTATAACAATAACTACTTATCCTGGTATCAGCAGAAACCAGGGC |
| AGCCTCCCAAGCTCCTTATCTACGAAACATCCAAACTGTCATCTGGGGT |
| CCCACCGCGGTTCAGCGGCAGTGGGTCTGGGACACAGTTCACTCTCACC |
| ATCAGCAGCGTGCAGTGTGACGATGCTGCCACTTACTACTGTCAAGGCG |
| GTTATAGTGGTGTTGATTTTATGGCTTTCGGCGGAGGGACCGAGGTGGT |
| CGTCAAAGGTGATCCAGTTGCACCTACTGTCCTCATCTTCCCACCATCT |
| GCTGATCTTGTGGCAACTGGAACAGTCACCATCGTGTGTGTGGCGAATA |
| AATACTTTCCCGATGTCACCGTCACCTGGGAGGTGGATGGCACCACCCA |
| AACAACTGGCATCGAGAACAGTAAAACACCGCAGAATTCTGCAGATTGT |
| ACCTACAACCTCAGCAGCACTCTGACACTGACCAGCACACAGTACAACA |
| GCCACAAAGAGTACACCTGCAAGGTGACCCAGGGCACGACCTCAGTCGT |
| CCAGAGCTTCAATAGGGGTGACTGTTAG |
| <SEQ ID NO: 78-1F-42-7 heavy chain CDR1 nucleic acid;DNA;*oryctolagus cuniculus*> ctcactacctatggagtgacc |
| <SEQ ID NO: 79-1F-42-7 heavy chain CDR2 nucleic acid;DNA;*oryctolagus cuniculus*> ttgattggtgatcgcggtaccacttactacgcgagctgggtgaatggc |
| <SEQ ID NO: 80-1F-42-7 heavy chain CDR3 nucleic acid;DNA;*oryctolagus cuniculus*> gggagtggatatggtgctcgcatc |
| <SEQ ID NO: 81-1F-42-7 light chain CDR1 nucleic acid;DNA;*oryctolagus cuniculus*> agtcagactgtttataacaataactacttatcc |
| <SEQ ID NO: 82-1F-42-7 light chain CDR2 nucleic acid;DNA;*oryctolagus cuniculus*> gaaacatccaaactgtcatct |
| <SEQ ID NO: 83-1F-42-7 light chain CDR3 nucleic acid;DNA;*oryctolagus cuniculus*> ggcggttatagtggtgttgattttatggct |
| <SEQ ID NO: 84-3A-5-2 full length heavy chain nucleic acid;DNA;*oryctolagus cuniculus*> ATGGAGACTGGGCTGCGCTGGCTTCTCCTGGTCGCTGTGCTCAAAGGTG |
| TCCAGTGTCAGTCGCTGGAGGAGTCCGGGGGTCGCCTGGTCACGCCTGG |
| GACACCCCTGACACTCACCTGCACAGTCTCTGGATTCTCCCTCAATAAC |
| TACCACATATACTGGGTCCGCCAGGCTCCAGGAAAGGGGCTGGAATACA |
| TCGGAATCATTTTCAATGGTGGCACATATTACGCGAGATGGACAAAAGG |
| CCGATTCACCATCTCCAAAACCTCGACCACGGTGGATCTGAAAATGACC |
| AGTCTGACAACCGAGGACACGGCCACCTATTTCTGTGCCAGAGGGGACG |
| GCATCTGGGCCCAGGCACCCTGGTCACCGTCTCCTTAGGGCAACCTAA |
| GGCTCCATCAGTCTTCCCACTGGCCCCCTGCTGCGGGGACACACCCAGC |
| TCCACGGTGACCCTGGGCTGCCTGGTCAAAGGGTACCTCCCGGAGCCAG |
| TGACCGTGACCTGGAACTCGGGCACCCTCACCAATGGGGTACGCACCTT |
| CCCGTCCGTCCGGCAGTCCTCAGGCCTCTACTCGCTGAGCAGCGTGGTG |
| AGCGTGACCTCAAGCAGCCAGCCCGTCACCTGCAACGTGGCCCACCCAG |
| CCACCAACACCAAAGTGGACAAGACCGTTGCGCCCTCGACATGCAGCAA |
| GCCCACGTGCCCACCCCCTGAACTCCTGGGGGGACCGTCTGTCTTCATC |
| TTCCCCCCAAAACCCAAGGACACCCTCATGATCTCACGCACCCCCGAGG |
| TCACATGCGTGGTGGTGGACGTGAGCCAGGATGACCCCGAGGTGCAGTT |
| CACATGGTACATAAACAACGAGCAGGTGCGCACCGCCCGGCCGCCGCTA |
| CGGGAGCAGCAGTTCAACAGCACGATCCGCGTGGTCAGCACCCTCCCCA |
| TCGCGCACCAGGACTGGCTGAGGGGCAAGGAGTTCAAGTGCAAAGTCCA |
| CAACAAGGCACTCCCGGCCCCCATCGAGAAAACCATCTCCAAAGCCAGA |
| GGGCAGCCCCTGGAGCCGAAGGTCTACACCATGGGCCCTCCCCGGGAGG |
| AGCTGAGCAGCAGGTCGGTCAGCCTGACCTGCATGATCAACGGCTTCTA |
| CCCTTCCGACATCTCGGTGGAGTGGGAGAAGAACGGGAAGGCAGAGGAC |

AACTACAAGACCACGCCGGCCGTGCTGGACAGCGACGGCTCCTACTTCC

TCTACAGCAAGCTCTCAGTGCCCACGAGTGAGTGGCAGCGGGGCGACGT

CTTCACCTGCTCCGTGATGCACGAGGCCTTGCACAACCACTACACGCAG

AAGTCCATCTCCCGCTCTCCGGGTAAATGA

<SEQ ID NO: 85-3A-5-2 full length light chain
nucleic acid;DNA;*oryctolagus cuniculus*>
ATGGACACGAGGGCCCCCACTCAGCTGCTGGGGCTCCTGCTGCTCTGGC

TCCCAGGTGCCACATTTGCCCAAGTGCTGACCCAGACTCCAGCCTCCGT

GTCTGCAGCTGTGGGAGGCACAGTCACCATCAATTGCCAGGCCAGTCAG

AGTGTTTTTAATAACAACTATTTAGCCTGGTATCAGCAGAAACCAGGGC

AGCCTCCCAAGCGCCTGATCTATTCTGCATCCACTCTGGCGTCTGGGGT

CTCATCGCGGTTCAAAGGCAGTGGATCTGGGACAGAATTCACTCTGACC

ATGAGTGGCGTGGAGTGTGACGATGCTGCCACTTACTACTGTGCAGGCA

GTTTTGATTGTAATAGTGGTGATTGTGTTGCTTTCGGCGGAGGGACCGA

GGTGGTGGTCAAGGGTGATCCAGTTGCACCTACTGTCCTCATCTTCCCA

CCAGCTGCTGATCAGGTGGCAACTGGAACAGTCACCATCGTGTGTGTGG

CGAATAAATACTTTCCCGATGTCACCGTCACCTGGGAGGTGGATGGCAC

CACCCAAACAACTGGCATCGAGAACAGTAAAACACCGCAGAATTCTGCA

GATTGTACCTACAACCTCAGCAGCACTCTGACACTGACCAGCACACAGT

ACAACAGCCACAAAGAGTACACCTGCAAGGTGACCCAGGGCACGACCTC

AGTCGTCCAGAGCTTCAATAGGGGTGACTGTTAG

<SEQ ID NO: 86-3A-5-2 heavy chain CDR1 nucleic
acid;DNA;*oryctolagus cuniculus*>
ctcaataactaccacatatac <SEQ ID NO: 87-3A-5-2 heavy chain CDR2 nucleic
acid;DNA;*oryctolagus cuniculus*>
atcattttcaatggtggcacatattacgcgagatggacaaaaggc <SEQ ID NO: 88-3A-5-2 heavy chain CDR3 nucleic
acid;DNA;*oryctolagus cuniculus*>
ggggacggcatc <SEQ ID NO: 89-3A-5-2 light chain CDR1 nucleic
acid;DNA;*oryctolagus cuniculus*>
agtcagagtgtttttaataacaactatttagcc <SEQ ID NO: 90-3A-5-2 light chain CDR2 nucleic
acid;DNA;*oryctolagus cuniculus*>
tctgcatccactctggcgtct <SEQ ID NO: 91-3A-5-2 light chain CDR3 nucleic
acid;DNA;*oryctolagus cuniculus*>
Gcaggcagttttgattgtaatagtggtgattgtgttgct <SEQ ID NO: 92-alternative Human Renalase-1
protein (polymorphism resulting in the
aspartate amino acid at position 37;PRT;
*homo sapiens*>
MAQVLIVGAGMTGSLCAALLRRQTSGPLYLAVWDKADDSGGRMTTACSP

HNPQCTADLGAQYITCTPHYAKKHQRFYDELLAYGVLRPLSSPIEGMVM

KEGDCNFVAPQGISSIIKHYLKESGAEVYFRHRVTQINLRDDKWEVSKQ

TGSPEQFDLIVLTMPVPEILQLQGDITTLISECQRQQLEAVSYSSRYAL

GLFYEAGTKIDVPWAGQYITSNPCIRFVSIDNKKRNIESSEIGPSLVIH

TTVPFGVTYLEHSIEDVQELVFQQLENILPGLPQPIATKCQKWRHSQVT

NAAANCPGQMTLHHKPFLACGGDGFTQSNFDGCITSALCVLEALKNYI

<SEQ ID NO: 93-alternative Human Renalase-1
nucleic acid sequence (note possible
polymorphism at nucleotide position 111;
DNA;*homo sapiens*>
ATGGCGCAGGTGCTGATCGTGGGCGCCGGGATGACAGGAAGCTTGTGCG

CTGCGCTGCTGACGAGGCAGACGTCCGGTCCCTTGTACCTTGCTGTGTG

GGACAAGGCTGAGGACTCAGGGGGAAGAATGACTACAGCCTGCAGTCCT

CATAATCCTCAGTGCACAGCTGACTTGGGTGCTCAGTACATCACCTGCA

CTCCTCATTATGCCAAAAAACACCAACGTTTTTATGATGAACTGTTAGC

CTATGGCGTTTTGAGGCCTCTAAGCTCGCCTATTGAAGGAATGGTGATG

AAAGAAGGAGACTGTAACTTTGTGGCACCTCAAGGAATTTCTTCAATTA

TTAAGCATTACTTGAAAGAATCAGGTGCAGAAGTCTACTTCAGACATCG

TGTGACACAGATCAACCTAAGAGATGACAAATGGGAAGTATCCAAACAA

ACAGGCTCCCCTGAGCAGTTTGATCTTATTGTTCTCACAATGCCAGTTC

CTGAGATTCTGCAGCTTCAAGGTGACATCACCACCTTAATTAGTGAATG

CCAAAGGCAGCAACTGGAGGCTGTGAGCTACTCCTCTCGATATGCTCTG

GGCCTCTTTTATGAAGCTGGTACGAAGATTGATGTCCCTTGGGCTGGGC

AGTACATCACCAGTAATCCCTGCATACGCTTCGTCTCCATTGATAATAA

GAAGCGCAATATAGAGTCATCAGAAATTGGGCCTTCCCTCGTGATTCAC

ACCACTGTCCCATTTGGAGTTACATACTTGGAACACAGCATTGAGGATG

TGCAAGAGTTAGTCTTCCAGCAGCTGGAAAACATTTTGCCGGGTTTGCC

TCAGCCAATTGCTACCAAATGCCAAAAATGGAGACATTCACAGGTTACA

AATGCTGCTGCCAACTGTCCTGGCCAAATGACTCTGCATCACAAACCTT

TCCTTGCATGTGGAGGGGATGGATTTACTCAGTCCAACTTTGATGGCTG

CATCACTTCTGCCCTATGTGTTCTGGAAGCTTTAAAGAATTATATTTAA

<SEQ ID NO: 94-alternative Human Renalase-2 amino
acid sequence (polymorphism resulting in the
aspartate amino acid at position 37;PRT;
*homo sapiens*>
MAQVLIVGAGMTGSLCAALLRRQTSGPLYLAVWDKADDSGGRMTTACSP

HNPQCTADLGAQYITCTPHYAKKHQRFYDELLAYGVLRPLSSPIEGMVM

KEGDCNFVAPQGISSIIKHYLKESGAEVYFRHRVTQINLRDDKWEVSKQ

TGSPEQFDLIVLTMPVPEILQLQGDITTLISECQRQQLEAVSYSSRYAL

GLFYEAGTKIDVPWAGQYITSNPCIRFVSIDNKKRNIESSEIGPSLVIH

TTVPFGVTYLEHSIEDVQELVFQQLENILPGLPQPIATKCQKWRHSQVP

SAGVILGCAKSPWMMAIGFPI

<SEQ ID NO: 95-alternative Human Renalase-2
nucleic acid sequence (note possible
polymorphism at nucleotide position 111;
DNA;*homo sapiens*>
ATGGCGCAGGTGCTGATCGTGGGCGCCGGGATGACAGGAAGCTTGTGCG

CTGCGCTGCTGACGAGGCAGACGTCCGGTCCCTTGTACCTTGCTGTGTG

GGACAAGGCTGAGGACTCAGGGGGAAGAATGACTACAGCCTGCAGTCCT

SEQUENCES

CATAATCCTCAGTGCACAGCTGACTTGGGTGCTCAGTACATCACCTGCA

CTCCTCATTATGCCAAAAAACACCAACGTTTTTATGATGAACTGTTAGC

CTATGGCGTTTTGAGGCCTCTAAGCTCGCCTATTGAAGGAATGGTGATG

AAAGAAGGAGACTGTAACTTTGTGGCACCTCAAGGAATTTCTTCAATTA

TTAAGCATTACTTGAAAGAATCAGGTGCAGAAGTCTACTTCAGACATCG

TGTGACACAGATCAACCTAAGAGATGACAAATGGGAAGTATCCAAACAA

ACAGGCTCCCCTGAGCAGTTTGATCTTATTGTTCTCACAATGCCAGTTC

CTGAGATTCTGCAGCTTCAAGGTGACATCACCACCTTAATTAGTGAATG

CCAAAGGCAGCAACTGGAGGCTGTGAGCTACTCCTCTCGATATGCTCTG

GGCCTCTTTTATGAAGCTGGTACGAAGATTGATGTCCCTTGGGCTGGGC

AGTACATCACCAGTAATCCCTGCATACGCTTCGTCTCCATTGATAATAA

GAAGCGCAATATAGAGTCATCAGAAATTGGGCCTTCCCTCGTGATTCAC

SEQUENCES

ACCACTGTCCCATTTGGAGTTACATACTTGGAACACAGCATTGAGGATG

TGCAAGAGTTAGTCTTCCAGCAGCTGGAAAACATTTTGCCGGGTTTGCC

TCAGCCAATTGCTACCAAATGCCAAAAATGGAGACATTCACAGGTACCA

AGTGCTGGTGTGATTCTAGGATGTGCGAAGAGCCCCTGGATGATGGCGA

TTGGATTTCCCATC

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an isolated monoclonal antibody, wherein the antibody comprises: a) the heavy chain CDR1 sequence of SEQ ID NO:11; b) the heavy chain CDR2 sequence of SEQ ID NO:12; c) the heavy chain CDR3 sequence of SEQ ID NO:13; d) the light chain CDR1 sequence of SEQ ID NO:14; e) the light chain CDR2 sequence of SEQ ID NO:15; and f) the light chain CDR3 sequence of SEQ ID NO:16.

2. The composition of claim 1, wherein the antibody specifically binds to renalase with an affinity of at least $10^{-6}$ M.

3. The composition of claim 1, wherein the antibody specifically binds a peptide sequence as set forth in SEQ ID NO:4.

4. The composition of claim 1, wherein the antibody is selected from the group consisting of an immunoconjugate, a defucosylated antibody, and a bispecific antibody.

5. The composition of claim 4, wherein the immunoconjugate comprises a therapeutic agent or a detection moiety.

6. The composition of claim 1, wherein the antibody is selected from the group consisting of a humanized antibody, a chimeric antibody, a fully human antibody, and an antibody mimetic.

7. The composition of claim 1, wherein the antibody comprises a heavy chain sequence as set forth in SEQ ID NO:9.

8. The composition of claim 1, wherein the antibody comprises a light chain sequence as set forth in SEQ ID NO:10.

* * * * *